(12) United States Patent
Agoulnik et al.

(10) Patent No.: US 8,937,056 B2
(45) Date of Patent: Jan. 20, 2015

(54) MULTIKINASE INHIBITORS FOR USE IN THE TREATMENT OF CANCER

(71) Applicant: Eisai R&D Management Co., Ltd., Tokyo (JP)

(72) Inventors: Sergei Agoulnik, Wilmington, MA (US); Bruce Decosta, Salem, NH (US); Hong Du, North Andover, MA (US); Yimin Jiang, Londonberry, NH (US); Xiang-Yi Li, Andover, MA (US); Kenichi Nomoto, Belmont, MA (US); John (Yuan) Wang, Andover, MA (US); Huiming Zhang, Andover, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/794,635

(22) Filed: Mar. 11, 2013

(65) Prior Publication Data
US 2013/0303489 A1    Nov. 14, 2013

Related U.S. Application Data

(63) Continuation of application No. 12/180,408, filed on Jul. 25, 2008, now Pat. No. 8,609,640.

(60) Provisional application No. 60/951,901, filed on Jul. 25, 2007, provisional application No. 60/951,906, filed on Jul. 25, 2007, provisional application No. 61/029,196, filed on Feb. 15, 2008.

(51) Int. Cl.
| | |
|---|---|
| *A01N 57/00* | (2006.01) |
| *A61K 31/665* | (2006.01) |
| *A01N 43/02* | (2006.01) |
| *A61K 31/335* | (2006.01) |
| *A01N 43/76* | (2006.01) |
| *A61K 31/42* | (2006.01) |
| *A61K 31/415* | (2006.01) |
| *A61K 31/497* | (2006.01) |
| *A61K 31/535* | (2006.01) |
| *A61K 31/4178* | (2006.01) |
| *A61K 31/365* | (2006.01) |
| *A61K 31/422* | (2006.01) |
| *A61K 31/5377* | (2006.01) |
| *A61K 45/06* | (2006.01) |
| *A61K 31/496* | (2006.01) |
| *A61K 31/4025* | (2006.01) |
| *A61K 31/4523* | (2006.01) |

(52) U.S. Cl.
CPC .......... *A61K 31/365* (2013.01); *A61K 31/4178* (2013.01); *A61K 31/422* (2013.01); *A61K 31/5377* (2013.01); *A61K 45/06* (2013.01); *A61K 31/496* (2013.01); *A61K 31/4025* (2013.01); *A61K 31/4523* (2013.01); *A61K 31/665* (2013.01)

USPC .............. 514/100; 514/233.5; 514/254.1; 514/376; 514/385; 514/450

(58) Field of Classification Search
None
See application file for complete search history.

(56) References Cited

U.S. PATENT DOCUMENTS

| | | | |
|---|---|---|---|
| 5,674,892 A | 10/1997 | Giese et al. | |
| 5,728,726 A | 3/1998 | Giese et al. | |
| 5,795,910 A | 8/1998 | Giese et al. | |
| 6,265,603 B1 | 7/2001 | Lewis et al. | |
| 6,962,789 B2 | 11/2005 | Bacus | |
| 7,071,164 B2 | 7/2006 | Quirk et al. | |
| 7,799,827 B2 | 9/2010 | Boivin et al. | |

(Continued)

FOREIGN PATENT DOCUMENTS

| | | |
|---|---|---|
| EP | 0606044 A1 | 11/1993 |
| GB | 2323845 A | 10/1998 |

(Continued)

OTHER PUBLICATIONS

Wang, John (Yuan) et al., "Recent Advances of MEK Inhibitors and Their Clinical Progress," Current Topics in Medicinal Chemistry, vol. 7:1364-1378 (2007).

Winssinger, Nicolas et al., "Chemistry and biology of resorcylic acid lactones," Chem. Commun., pp. 22-36 (2007).

Zhao, Annie et al., "Resorcylic Acid Lactones: Naturally Occurring Potent and Selective Inhibitors of MEK," The Journal of Antibiotics, vol. 52(12):1086-1094 (1999).

(Continued)

*Primary Examiner* — Anna Pagonakis
(74) *Attorney, Agent, or Firm* — Lathrop & Gage LLP; James H. Velema

(57) ABSTRACT

The present invention provides compounds, pharmaceutical compositions and methods for the treatment of specific cancers. Such compositions may generally comprise a compound of formula (I):

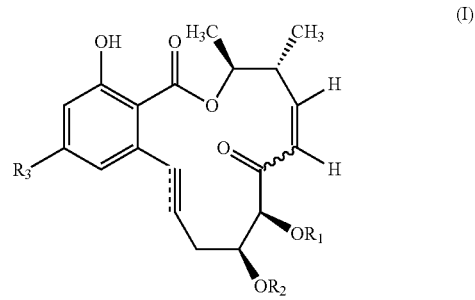

wherein $R_1$-$R_3$ are as defined herein, or pharmaceutically acceptable salts or esters thereof; and a pharmaceutically acceptable carrier.

14 Claims, 12 Drawing Sheets

(56) References Cited

U.S. PATENT DOCUMENTS

| | | | |
|---|---|---|---|
| 7,915,306 | B2 | 3/2011 | Chiba et al. |
| 2002/0015974 | A1 | 2/2002 | Bacus et al. |
| 2003/0045451 | A1 | 3/2003 | Bacus |
| 2004/0096855 | A1 | 5/2004 | Stratton et al. |
| 2005/0038080 | A1 | 2/2005 | Boyer et al. |
| 2005/0186584 | A1 | 8/2005 | Stratton et al. |
| 2005/0214325 | A1 | 9/2005 | David |
| 2005/0222163 | A1 | 10/2005 | Eck et al. |
| 2005/0267060 | A1 | 12/2005 | Robertson et al. |
| 2005/0272755 | A1 | 12/2005 | Denis et al. |
| 2006/0079494 | A1 | 4/2006 | Santi et al. |
| 2006/0216288 | A1 | 9/2006 | Chang |
| 2008/0131885 | A1 | 6/2008 | Pratilas et al. |
| 2009/0082313 | A1 | 3/2009 | Agoulnik |
| 2011/0046398 | A1 | 2/2011 | Fang |
| 2011/0237805 | A1 | 9/2011 | Boivin |

FOREIGN PATENT DOCUMENTS

| | | |
|---|---|---|
| JP | 6-228122 | 8/1994 |
| JP | 840893 | 2/1996 |
| JP | 10-508024 | 8/1998 |
| JP | 2001-294527 | 10/2001 |
| JP | 2004-292314 | 10/2004 |
| JP | 2004-292315 | 10/2004 |
| WO | WO9613259 A2 | 5/1996 |
| WO | WO00/38674 A1 | 7/2000 |
| WO | WO00/39314 A1 | 7/2000 |
| WO | WO01/36003 A2 | 5/2001 |
| WO | WO02/48135 A1 | 6/2002 |
| WO | WO02/48136 A1 | 6/2002 |
| WO | WO03/076424 A1 | 9/2003 |
| WO | WO2005/047542 A1 | 5/2005 |
| WO | 2006/036941 A2 | 4/2006 |
| WO | WO2009/015368 A2 | 1/2009 |

OTHER PUBLICATIONS

International Search Report for Application No. PCT/US2008/071256, dated Jan. 21, 2009.
Folkman. Role of angiogenesis in tumor growth and metastasis. Semin. Oncol. 29 (Suppl. 16): 15-18, 2002.
Panka et al. Targeting the mitogen-activated protein kinase pathway in the treatment of malignant melanoma. Clin. Cancer Res. 2006; 2371s-2375s. Published online Apr. 11, 2006.
Deling Li et al., Rays and arrays: the transcriptional program in the response of human epidermal keratinocytes to UVB illumination; The FASEB Journal; Nov. 2001, vol. 15, pp. 2533-2535.
Sebolt-Leopold, Judith S. et al., "Targeting the Mitogen-Activated Protein Kinase Cascade to Treat Cancer," Nature Reviews Cancer, vol. 4:937-947 (2004).
Solit, David B. et al., "BRAF mutation predicts sensitivity to MEK inhibition," Nature, vol. 439:358-362 (2006).
Partial European Search Report for Application No. 12154122.1, 6 pages, dated Mar. 27, 2012.
International Search Report for Application No. PCT/US2008/081646, dated Sep. 2, 2009.
U.S. Office Action for related Application No. 101507,067, dated Jun. 23, 2009.
Cancer [online], (retrieved Jul. 6, 2007) URL: <http://www.nlm.nih.gov/medlineplus/cancer.html.
Golub et al., Science (1999), vol. 286, 531-37.
"Cancer" [online], (retrieved Jul. 6, 2007) URL: <http://en.wikipedia.org/wiki/Cancer.
Protein Kinase [online], (retrieved Sep. 8, 2008) URL: <http://en.wikipedia.org/wiki/Protein_Kinase.
Lala et al., Cancer and Metastasis Reviews (1998), 17(1), 91-106.
Partial file history of USSN 101657,910 (documents dating from Dec. 1, 2003 through Jan. 7, 2009).
International Preliminary Report on Patentability and Written Opinion for Application No. PCT/US2008/081646, dated May 4, 2010.
Fernandes, Darren J. et al., "Contribution of the p38MAPK signalling pathway to proliferation in human cultured airway smooth muscle cells is mitogen-specific," British Journal of Pharmacology, vol. 142:1182-1190 (2004).
Rawlins, Philip et al., "Inhibition of endotoxin-induced TNF-a production in macrophages by 5Z-7-oxo-zeaenol and other fungal resorcylic acid lactones," International Journal of Immunopharmacology, vol. 21:799-814 (1999).
Invitation to Pay Additional Fees for Application No. PCT/US2008/081646, dated Jun. 24, 2009.
Andersson, Patiyan et al., "PIK3CA, HRAS and KRAS Gene Mutations in Human Penile Cancer," The Journal of Urology, vol. 179:2030-2034 (2008).
Gray-Schopfer, Vanessa C. et al., "The role of B-RAF in melanoma," Cancer and Metastasis Reviews, vol. 24:165-183 (2005).
Japanese Office Action for Application No. 2003-574642, dated Jul. 15, 2009.
Partial file history of related U.S. Appl. No. 10/657,910 (documents dating from May 6, 2009 through Sep. 14, 2009).
Vranic, Semir et al., "PIK3CA and PTEN mutations in adenoid cystic carcinoma of the breast metastatic to kidney," Human Pathology, vol. 38:1425-1431 (2007).
Yamamoto, et al., "Therapeutic potential of inhibition of the NF-KB Pathway in the treatment of inflammation and cancer", J. Clin_ Investigation, 107(2), 135-142, 2001.
Invitation to Pay Additional Fees for Application No. PCT/US2008/081646, dated Feb. 5, 2009.
Davies, Helen et al., "Mutations of the BRAFgene in human cancer," Nature, vol. 417:949-954 (2002).
Guanti, Ginevra et al., "Involvement of PTEN mutations in the genetic pathways of colorectal cancerogenesis," Human Molecular Genetics, vol. 9(2):283-287 (2000).
Katso, Roy et al., "Cellular Function of Phosphoinositide 3-Kinases: Implications for Development, Immunity, Homeostasis, and Cancer," Annu. Rev. Cell Dev. Biol., vol. 17:615- 675 (2001).
Kolch, Walter, "Meaningful relationships: the regulation of the Ras/Raf/MEK/ERK pathway by protein interactions," Biochem. J., vol. 351:289-305 (2000).
Kopini, B.P., "Targets of Oncogenes and Tumor Suppressors: Key for Understanding Basic Mechanisms of Carcinogenesis," Biochemistry (Moscow), vol. 65(1):2-27 (2000).
Rodriguez-Viciana, Pablo et al., "Germline Mutations in Genes Within the MAPK Pathway Cause Cardio-facio-cutaneous Syndrome," Science, vol. 311 :1287-1290 (2006).
Tatsuta, et al., "The First Total Synthesis of a Macrocyclic Antiprotozoan, LL-Z16040-2", Chem. Lett., vol. 2, 172-173, 2001.
"Sun Exposure and Skin Cancer" [online], p. 1, (retrieved Sep. 8, 2008) URL: <http:/www.medicinenet.com/script/main/art.asp?Ii=USA&articlekey=43077&page=1.
Agatsuma, et al., "Revised Structure and Stereochemistry of Hypothemycin", Chem.Pharm.Bull.; 41(2):373-375 1993.
Chen, et al., "Activation of p38 MAP kinase and ERK are required for ultraviolet-B induced c-fos gene expression gene expression in human keratinocytes", Oncogene, 18: 7649-7476, 1999.
Dombrowski, et al., "Production of a Family of Kinase-inhibiting Lactones from Fungal Dermentations", J. Antibiot_, 52 (12): 1077-1085, 1999.
Ellestad, et al_, "New Zearalenone Related Macrolides and Isocoumarins from an Unidentified Fungus", J. Org. Chem., 43(12)2339-2343, 1978.
Wallace, Eli M. et al., "Progress Towards Therapeutic Small Molecule MEK Inhibitors for Use in Cancer Therapy," Current Topics in Medicinal Chemistry, vol. 5:215-229 (2005).
Kastelic, et al., "Induction of Rapid IL=16 mRNA Degradaton in THP-1 Cells Mediated Through the AU-Rich Region in the 3'UTR by a Radicocol Analogue", Cytokine 8(10): 751-761, 1996.
Matsuoka, et al., "Inhibition of HgC12-induced mitogen-activated protein kinase activation by LL-Z1640-2 in CCRF-CEM cells", Eur. J. Pharmacol., 409(2): 155-158, 2000.
Tak, et al., "NF-KB pathway in the treatment of inflammation and cancer", J. Clin.Investigation, 107(2), 135-142, 2001.

(56) References Cited

OTHER PUBLICATIONS

Takehana, et al., "A radicicol-Related Macrocyclic Nonaketide Compound, Antibiotic LL-Z1640-2, Inhibits the JNK/p38 Pathways in Signal-Specific Manner", Biochem. Biophys. Res. Commun., 257(1): 19-23, 1999.

International Search Report for PCT/US03/07377.

Johnson, David B.R., Sawicki, Carol, Widholz, T.B. and Patchett, A.A., Synthesis of Dideoxyzearalanone and Hydroxyl Derivatives, J. Med. Chem., 13(5): 941-44 (1970).

Patani, George & Lavoie, Edmond J., Bioisosterism: A Rational Approach in Drug Design, Chem. Rev. 96:3147-76 (1996).

"Sun Exposure and Skin Cancer" [online], p. 2 (retrieved Sep. 8, 2008) URL: <http:/www.medicinetnet.com/script/main/art.asp?Ii=USA&articlekey=43077&page=2>.

Partial file history of USSN 101507,067, documents dating from Sep. 8, 2004 through Mar. 10, 2009.

Byron, Sara et al., Sensitivity to the MEK inhibitor, E6201, is associated with mutant BRAF status and is inversely correlated with pAKT expression levels in melanoma cell lines, Translational Genomics Research Institute, AZ, US, Eisai Inc., MA, U.S.

Byron, Sara et al., Abstract B93: Sensitivity to the MEK inhibitor, E6201, is associated with mutant BRAF status and is inversely correlated with pAKT expression levels in melanoma cell lines, Molecular Cancer Therapeutics: Dec. 2009; vol. 8, Issue 12, Supplement 1, Boston, MA.

Roberts, P.J. et al., "Targeting the Raf-MEK-ERK mitogen-activated protein kinase cascade for the treatment of cancer," Oncogene, vol. 26:3291-3310 (2007).

Schirmer, Andreas et al., "Targeted covalent inactivation of protein kinases by resorcylic acid lactone polyketides," PNAS, vol. 103(11):4234-4239 (2006).

Biochemical MEK1 Assays

| Compound | Biochemical MEK1 inhibition (IC50; nM) | |
|---|---|---|
| | 10 μM ATP | 100 μM ATP |
| 091 | 10 | 70 |

| Compound | IC$_{50}$(nM) | | Compound | IC$_{50}$(nM) | |
|---|---|---|---|---|---|
| Compound 013 | 120 | | Compound 054 | >330 | |
| Compound 014 | 471 946 | | Compound 065 | 187 | |
| Compound 015 | 91 101 | | Compound 069 | 37 9.5 | |
| Compound 016 | 356 640 | | Compound 076 | 657 | |
| Compound 018 | - | | Compound 091 | 34 37 22 10.9 24 2.8 | 24.4 51 33 113 73 71 |
| Compound 019 | 658 | | Compound 092 | 27 4.8 | 14.8 715 |
| Compound 022 | 846 | | Compound 106 | 107 13 172 | 45 71 |
| Compound 024 | 187 | | Compound 114 | 56 101 | |
| Compound 025 | 484 | | Compound 122 | 356 | |
| Compound 029 | 91  182 198 | | Compound 127 | >330 | |
| Compound 034 | 172 | | Compound 137 | 182 | |
| Compound 041 | 756 | | Compound 144 | 75 163 | 104 117 |
| Compound 045 | 318 | | Compound 155 | 433 421 | |
| Compound 046 | 657 | | Compound 156 | 79 | |
| Compound 047 | 99  310 310 | | Compound 157 | 240 421 | |
| Compound 048 | 366 | | Compound 158 | 145 | |

*Fig. 2A*

Kinase inhibition

| Kinase | Class | Importance in cancer | Compound 091 IC50 (nM) |
|---|---|---|---|
| Abl | TK | Leukemia | 214 |
| c-Src | Src TK family | Colon, Pancreatic | 91 |
| Flt3 | Receptor TK | Leukemia | 91 |
| Fyn | Src TK family | Leukemia | 47 |
| Lyn | Src TK family | Leukemia | 35 |
| TrkB | Receptor TK | Prostate, Pancreatic Glioma | 26 |
| MEK1 | MAPKK | Proliferation | 10 |
| MEKK1 | MAPKKK | Antiapoptosis MM/Lymphoma | 46* |
| KDR | Receptor TK | Angiogenesis | 500* |

* Result from separate study

Percent Kinase Activity Remaining

| Kinase | Compound 091 | | Compound 106 | |
|---|---|---|---|---|
| | 0.1 µM | 1 µM | 0.1 µM | 1 µM |
| Abl | 69 | 22 | 51 | 15 |
| cSRC | 47 | 5 | 31 | 1 |
| Flt3 | 48 | 8 | 33 | 6 |
| Fyn | 25 | 2 | 24 | 0 |
| Lck | 38 | 3 | 27 | 0 |
| Lyn | 15 | 2 | 45 | 2 |
| MEK1 | 30 | 4 | -- | -- |
| TrkB | 15 | 4 | 24 | 4 |
| Yes | 46 | 7 | 54 | 8 |

*Fig. 2B*

*Inhibition of B-RAF Mutated Cancer Cell Growth*

| Cell line | Description | K-ras mutation | B-RAF mutation | Mean IC$_{50}$, nmol/L | |
|---|---|---|---|---|---|
| | | | | Cpd 106 | Cpd 091 |
| AU-565 | breast cancer | | WT | >10000 | >10000 |
| MCF-7 | | | WT | >10000 | >10000 |
| MDA-MB-231 | | G13D | WT | 156 | 119 |
| MDA-MB-435 | | | V600E | 71 | 50 |
| DU4475 | | | V600E | 52 | 30 |
| SK-MEL-2 | melanoma | Q61R (N-ras) | WT | 135 | 113 |
| SK-MEL-3 | | | V600E | 24 | 19 |
| SK-MEL-24 | | | V600E | 66 | 53 |
| SK-MEL-31 | | | V600E | 225 | 209 |
| HCT-116 | colon cancer | G13D | WT | 423 | 257 |
| DLD-1 | | G13D | WT | 649 | 466 |
| LoVo | | G13D | WT | 132 | 90 |
| SW-620 | | G12V | WT | 282 | 207 |
| COLO205 | | WT | V600E | 43 | 27 |
| HT-29 | | WT | V600E | 84 | 65 |
| Mia PaCa-2 | pancreatic cancer | G12C | WT | 734 | 582 |
| PANC-1 | | G12D | WT | >10000 | >10000 |
| BxPC-3 | | WT | WT | — | 412 |
| MES-SA | sarcoma | | WT | 7490 | 5780 |
| MES-SA/ Dx5-Rx1 | sarcoma (P-glycoprotein overex.) | | WT | 1590 | 908 |
| IMR-90 | Non-dividing fibroblast | | | — | >10000 |

"WT" = wild type; "—" = not tested

*Fig. 3*

*Inhibition of B-cell Driven Hematological Malignant Cancer Cell Growth*

| Cell line | Type | Compound 091 IC$_{50}$ (µM) | Compound 106 IC$_{50}$ (µM) |
|---|---|---|---|
| HL-60 | Acute Promyelocytic Leukemia | 0.05 ± 0.001 | 0.06 ± 0.004 |
| THP-1 | Acute Monocytic Leukemia | 0.09 ± 0.012 | 0.12 ± 0.008 |
| K562 | Chronic Myelogenous Leukemia | 1.43 ± 0.20 | 1.80 ± 0.09 |
| U266 | MM | 1.00 ± 0.58 | 0.95 ± 0.22 |
| RPMI-8226 | MM | >4.83 ± 2.65 | >7.05 ± 2.95 |
| RL | Non-Hodgkin's Lymphoma (B-lymphoblast) | 1.62 ± 0.34 | 1.65 ± 0.37 |
| NALM-6 | Non-Hodgkin's Lymphoma (Pre-B lymphoma) | 0.65 ± 0.20 | 0.62 ± 0.11 |

*Fig. 7*

*Penetration of Blood Brain Barrier*

Penetration of compound 091 into the brain tissue, as measured by the brain/plasma $AUC_{0-t}$ ratio, is as follows:

| Species | Compound | Dose | Brain penetration ratio ($AUC_{0-t}$brain/$AUC_{0-t}$plasma) |
|---|---|---|---|
| Mouse (n=10) | 091 | 20 mg/kg, i.v. | 3.170 ± 1.289 |

*Fig. 9*

MULTIKINASE INHIBITORS FOR USE IN THE TREATMENT OF CANCER

RELATED APPLICATIONS

This application claims priority to U.S. patent application Ser. No. 12/180,408, filed on Jul. 25, 2008; U.S. Provisional Patent Application No. 60/951,901, filed on Jul. 25, 2007; U.S. Provisional Patent Application No. 60/956,901, filed on Jul. 25, 2007; and U.S. Provisional Patent Application No. 61/029,196, filed on Feb. 15, 2008. The entire contents of each of these applications are hereby incorporated herein by reference.

BACKGROUND OF THE INVENTION

F152 (LL-Z1640-2), a zearalenone-like macrolide, was first isolated from shake flask fermentation, crude extracts of which inhibited the ciliated protozoan *Tetrahymena pyriformis* (see, McGahren et al. *J. Org. Chem.* 1978, 43, 2339). Although initial biological

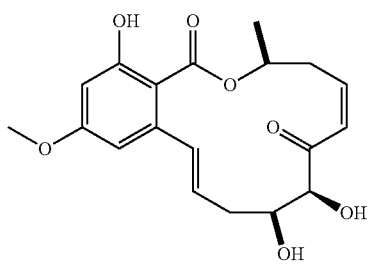

F152 studies using this natural product failed to yield any particularly interesting activities, the possibility of preparing additional derivatives and/or further exploring their biological activity was undertaken. For example, F152 and certain isomers thereof inhibit the phosphorylating enzyme Map/Erk kinase (MEK) and may be useful for the treatment of certain MEK-related cancers and other diseases characterized by the formation of neoangiogenesis (see, e.g., GB 323 845). Derivatives of F152 have also been shown to have activity as tyrosine kinase inhibitors, which are useful, for example, for the treatment of cancer and inflammatory disorders (see, e.g., EP 606 044; WO 00/38674; JP 8-40893; WO 96/13259; U.S. Pat. No. 5,728,726; U.S. Pat. No. 5,674,892; U.S. Pat. No. 5,795,910). Often, however, F152 and derivatives thereof are obtained by fermentation techniques and modifications to the natural product and thus were limited in the number and types of derivatives that could be prepared and evaluated for biological activity. Additionally, although F152 and certain derivatives thereof have demonstrated potent in vitro activities, these compounds may be biologically unstable (for example, they are susceptible to enone isomerization in mouse and human plasma), thereby limiting the development of these compounds as therapeutics for the treatment of humans or other animals.

Recently, F152 analogues have been shown to be inhibitors of NF-κB activation, and MEK1 (See, e.g., U.S. application Ser. No. 10/507,067 and U.S. Application Publication No.: US 2004/0224936). The compounds were also reported to inhibit AP-1 activation and some protein kinases (for example, MEKK, PDGFr, VEGFr). Based on these mechanisms of action, it was suggested that the compounds inhibit the production of various pro-inflammatory and/or immunologic cytokines such as TNFα, IL-1, IL-6, IL-8, IL-2 etc, and also inhibit the production of various pro-inflammatory molecules under the regulation of NF-κB pathway such as prostaglandins produced from COX-2, ICAM-1 and MMP-1 and 3 etc. Also, it was reported that the compounds have the ability to inhibit cell proliferation under the regulation of AP-1 pathway through the inhibition of MEK1. In addition, it was reported that the compounds have ability to inhibit angiogenesis, likely based on the inhibitory activity on VEGFr kinase and weak inhibitory activity on PDGFr kinase.

SUMMARY OF THE INVENTION

The present invention is based, at least in part, on the discovery that the compounds of formula (I) or (II) have unique multikinase inhibition profiles, which can be useful against specific cancers selected based upon the unique multikinase inhibition profile of the compounds. Generally, chemotherapeutic drugs often lack of specificity and have unwanted side effects associated therewith. Accordingly, it is an object of the present invention to provide cancer-specific agents for targeted cancer therapy and targeted methods for treating and/or preventing cancer which may circumvent adverse side effects often associated with chemotherapeutics.

Accordingly, in some aspects, the present invention provides methods for treating a SrcTK/MEK associated cancer in a subject in need thereof. The methods generally include administering to the subject a composition comprising a SrcTK/MEK inhibitor in an amount effective to treat the SrcTK/MEK associated cancer. In some aspects, the present invention also relates to the use of a SrcTK/MEK inhibitor in the manufacture of a medicament for the treatment of a SrcTK/MEK associated cancer.

In some embodiments, the SrcTK/MEK inhibitor inhibits the activity of at least one member of the Src tyrosine kinase family by at least about 75% at a concentration of about 0.1 μM. The members of the Src tyrosine kinase family can be any member of the Src family including cSrc, Fyn, Lyn, Lck, Yes, Fgr, Hck and Blk. In some embodiments, the SrcTK/MEK inhibitor inhibits the activity of at least five members of the Src tyrosine kinase family by at least about 50% at a concentration of about 0.1 μM. In some embodiments, the SrcTK/MEK inhibitor inhibits the activity of MEK1 by at least about 50% at a concentration of about 0.1 μM.

In some embodiments, the SrcTK/MEK inhibitor is a compound of formula (I):

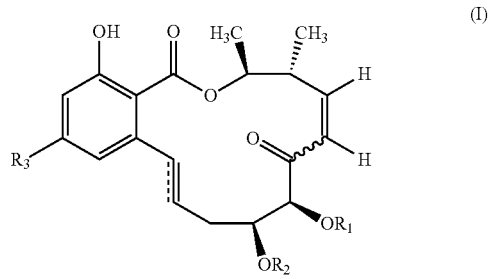

(I)

wherein:

$R_1$ is H $R_2$ is a moiety selected from the group consisting of H and trifluoromethylcarbonyl; or $R_1$ and $R_2$ are taken together with the core structure to form a heterocyclydiyl moiety of formula (a):

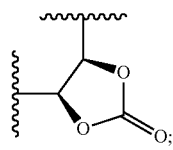

$R_3$ is a moiety selected from the group consisting of —$OR_a$ and —$NR_bR_c$;

$R_a$ is a $C_{1-4}$ alkyl group optionally substituted with an imidazolyl;

$R_b$ is a moiety selected from the group consisting of a $C_{1-4}$ alkyl group and a $C_{1-4}$ alkoxy group, wherein $R_b$ is substituted with 0, 1 or 2 groups each independently selected from the group consisting of —$OCH_3$, —$C(O)OH$, —$C(O)NR'R''$, —$NH(C_{1-3}$ alkyl), —$NH(CH_2CH_2O)_nCH_3$, wherein n is 2-4, piperazinyl, N-methylpiperazinyl, piperidinyl, N-methylpiperidinyl, N-morpholinyl, imidazolyl, pyrrolidinyl, —$OPO_3H_2$ and hydroxyl; wherein the —$NH(C_{1-3}$ alkyl) group is substituted with 0, 1 or 2 hydroxyl moieties and wherein R' and R'' are each independently selected from —H or —$CH_3$; and $R_c$ is H, or $R_b$ and $R_c$ are taken together with the nitrogen to which they are attached to form a heterocyclyl moiety selected from the group consisting of formula (b) and formula (c):

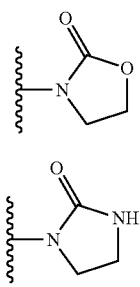

or a pharmaceutically acceptable salt or ester thereof.

In some embodiments, the SrcTK/MEK associated cancer is chronic myeloid leukemia or colorectal cancer. In some embodiments, the SrcTK/MEK inhibitor also inhibits the activity of Bcr-Abl, and the SrcTK/MEK associated cancer is leukemia. In some embodiments, the SrcTK/MEK inhibitor also inhibits the activity of TrkB. In some embodiments, the SrcTK/MEK inhibitor also inhibits the activity of TrkB at least to the extent described further herein, e.g., by at least about 75% at a concentration of about 0.1 µM.

In some aspects, the present invention is directed to methods for treating a TrkB/MEK associated cancer in a subject in need thereof. The methods generally include administering to the subject a composition comprising a TrkB/MEK inhibitor in an amount effective to treat the TrkB/MEK associated cancer. In some aspects, the present invention also relates to the use of a TrkB/MEK inhibitor in the manufacture of a medicament for the treatment of a TrkB/MEK associated cancer.

In some embodiments, the TrkB/MEK inhibitor inhibits the activity of TrkB by at least about 75% at a concentration of about 0.1 µM. In some embodiments, the TrkB/MEK inhibitor inhibits the activity of MEK1 by at least about 50% at a concentration of about 0.1 µM.

In some embodiments, the TrkB/MEK inhibitor is a compound of formula (I):

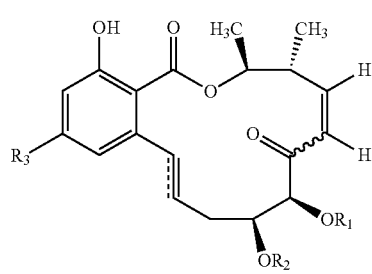

wherein:

$R_1$ is H $R_2$ is a moiety selected from the group consisting of H and trifluoromethylcarbonyl; or $R_1$ and $R_2$ are taken together with the core structure to form a heterocyclydiyl moiety of formula (a):

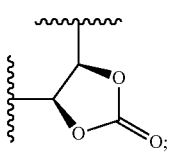

$R_3$ is a moiety selected from the group consisting of —$OR_a$ and —$NR_bR_c$;

$R_a$ is a $C_{1-4}$ alkyl group optionally substituted with an imidazolyl;

$R_b$ is a moiety selected from the group consisting of a $C_{1-4}$ alkyl group and a $C_{1-4}$ alkoxy group, wherein $R_b$ is substituted with 0, 1 or 2 groups each independently selected from the group consisting of —$OCH_3$, —$C(O)OH$, —$C(O)NR'R''$, —$NH(C_{1-3}$ alkyl), —$NH(CH_2CH_2O)_nCH_3$, wherein n is 2-4, piperazinyl, N-methylpiperazinyl, piperidinyl, N-methylpiperidinyl, N-morpholinyl, imidazolyl, pyrrolidinyl, —$OPO_3H_2$ and hydroxyl; wherein the —$NH(C_{1-3}$ alkyl) group is substituted with 0, 1 or 2 hydroxyl moieties and wherein R' and R'' are each independently selected from —H or —$CH_3$; and $R_c$ is H, or $R_b$ and $R_c$ are taken together with the nitrogen to which they are attached to form a heterocyclyl moiety selected from the group consisting of formula (b) and formula (c):

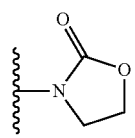

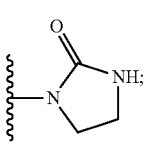

or a pharmaceutically acceptable salt or ester thereof.

In one embodiment, compound (I) is a compound of formula (II):

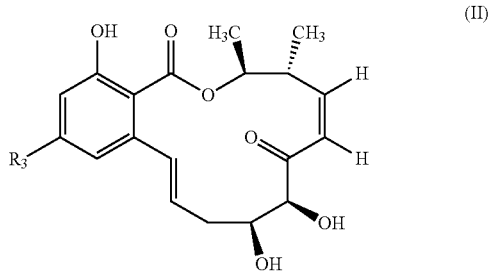

wherein

R$_3$ is —NHR$_b$, and R$_b$ is C$_1$-C$_3$ alkyl substituted with 0, 1, or 2 hydroxyl moieties; or a pharmaceutically acceptable salt or ester thereof.

Reference herein to compounds of formula (I) or (II) (or compositions comprising the same) includes pharmaceutically acceptable salts and esters of the compounds (or the compositions comprising the same).

In some embodiments, the TrkB/MEK associated cancer is pancreatic cancer, neural cancer, glioma, neuroblastoma or retinoblastoma. In some embodiments, the TrkB/MEK inhibitor also inhibits the activity of at least one member of the Src tyrosine kinase family. In some embodiments, the TrkB/MEK inhibitor also inhibits the activity of at least one member of the Src tyrosine kinase family at least to the extent described further herein, e.g., by at least about 75% at a concentration of about 0.1 µM.

In some aspects, the present invention provides methods for treating at least one cancer selected from the group consisting of chronic myeloid leukemia, pancreatic cancer, neural cancer, glioma, neuroblastoma, retinoblastoma, ovarian cancer, thyroid cancer, colorectal cancer and melanoma, in a subject in need thereof. The methods generally include administering to the subject a composition comprising a compound of formula (I), (II), or a pharmaceutically acceptable salt or ester thereof, in an amount effective for treating the cancer. The compound of formula (I) or (II) can be any of the compounds of formula (I) or (II) as described herein.

In some aspects, the present invention also relates to the use of a compound of formula (I) or (II) in the manufacture of a medicament for the treatment of chronic myeloid leukemia, pancreatic cancer, neural cancer, glioma, neuroblastoma, retinoblastoma, ovarian cancer, thyroid cancer, colorectal cancer or melanoma. In some aspects, the present invention provides methods for inhibition of a metastatic process in a subject in need thereof. The methods generally include administering to the subject a composition comprising a compound of formula (I) or (II) or a pharmaceutically acceptable salt or ester thereof, in an amount effective for inhibiting the metastatic process. The compound of formula (I) or (II) can be any of the compounds of formula (I) or (II) as described herein.

In other aspects, the present invention provides methods for treating a B-RAF mutated cancer in a subject in need thereof. The methods generally include administering to the subject a composition comprising at least one compound of formula (I) or (II) or a pharmaceutically acceptable salt or ester thereof; in an amount effective for treating the B-RAF mutated cancer. The compound of formula (I) or (II) can be any of the compounds of formula (I) or (II) as described herein. In some embodiments, the B-RAF mutated cancer is a B-RAF V600E mutated cancer. In some embodiments, the B-RAF mutated cancer is ovarian cancer, thyroid cancer, colorectal cancer or melanoma.

In other aspects, the present invention provides methods for treating a FLT3 mutated cancer in a subject in need thereof. For example, the method can comprise administration of a compound of formula (I) or (II) or a pharmaceutically acceptable salt or ester thereof (or a composition comprising same) to the subject in an amount effective for treating the FLT3 mutated cancer. In certain embodiments of the method, the FLT3 mutated cancer carries a mutation of residue D835 and/or a mutation of residue I836, for example, a D835Y mutation. In some embodiments, the FLT3 mutated cancer is acute myeloid leukemia (AML).

In other aspects, the present invention provides methods for treating a central nervous system tumor in a subject in need thereof. The methods generally include administering to the subject a composition comprising a compound of formula (I) or (II) or a pharmaceutically acceptable salt or ester thereof; an amount effective for treating the tumor, such that at least 20% of the compound of formula (I) or (II) penetrates the blood brain barrier. The compound of formula (I) or (II) can be any of the compounds of formula (I) or (II) as described herein. In some embodiments, at least about 65% of the compound of formula (I) or (II) penetrates the blood brain barrier, based upon a ratio of amount of a compound of formula (I) or (II) in the brain to amount of a compound of formula (I) or (II) in the plasma. In some embodiments, the central nervous system tumor is a brain tumor, a glioma or a neuroblastoma.

In some embodiments,

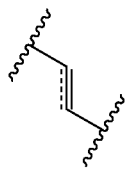

in formula (I) represents a double bond. In some embodiments,

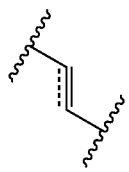

represents a triple bond. In some embodiments, R$_3$ is —NR$_b$R$_c$, R$_c$ is H and R$_b$ is an unsubstituted C$_{1-4}$ alkyl. In some embodiments, R$_c$ is H and R$_b$ is methyl or ethyl. For example, compounds of formula (I) include the following compounds:

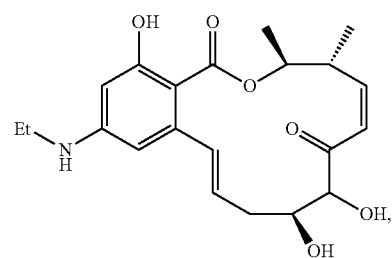

-continued

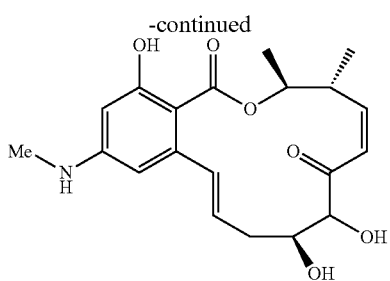

and pharmaceutically acceptable salts and esters thereof.

In some embodiments, any of the methods of the present invention include intravenous administration of the compositions described herein. In some embodiments, any of the methods of the present invention include administration of a dosage between about 0.10 mg/kg to about 25 mg/kg of body weight of the compositions described herein.

In some aspects, the present invention is directed to the following compounds:

(Compound 013)

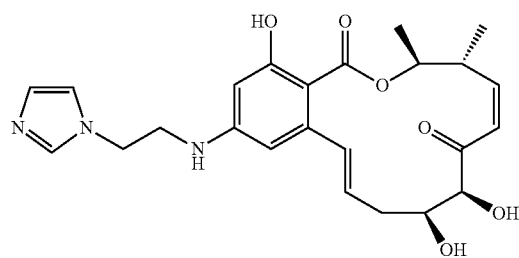

(Compound 014)

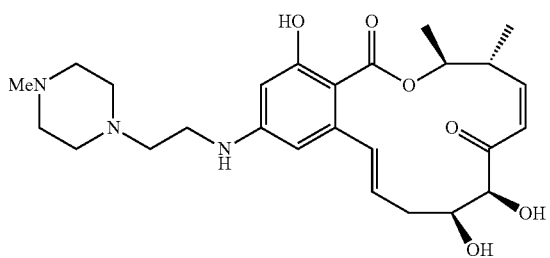

(Compound 015)

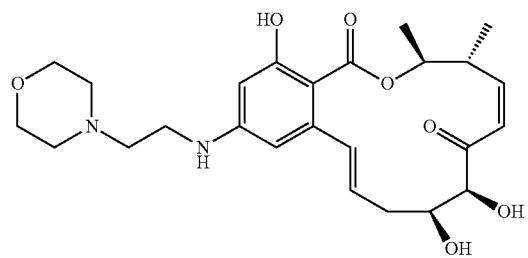

(Compound 016)

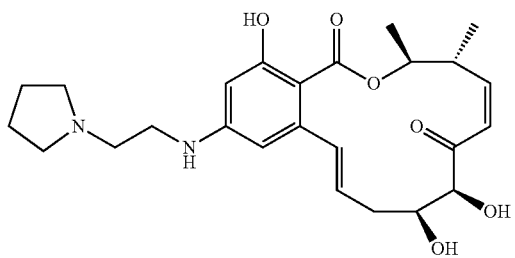

(Compound 018)

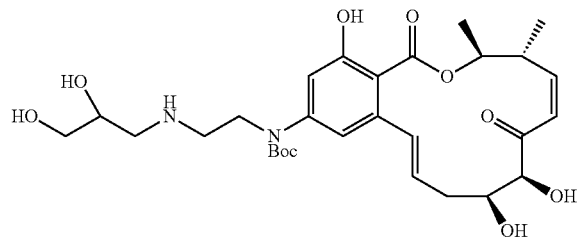

(Compound 019)

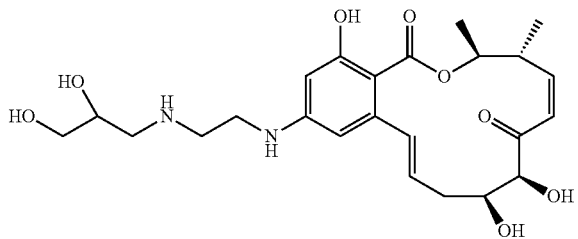

(Compound 022)

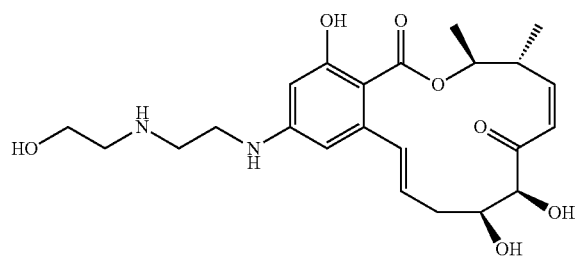

(Compound 024)

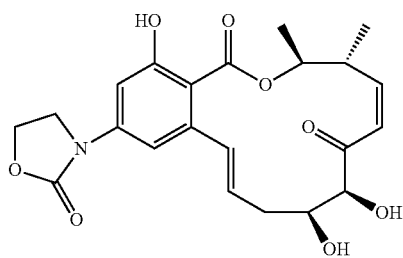

-continued
(Compound 025)
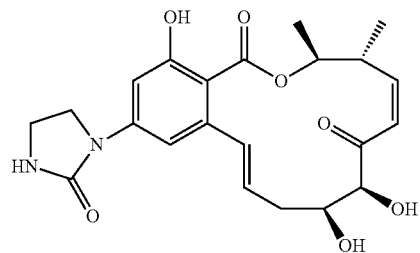
(Compound 034)
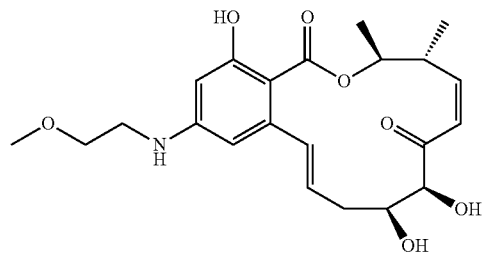
(Compound 041)
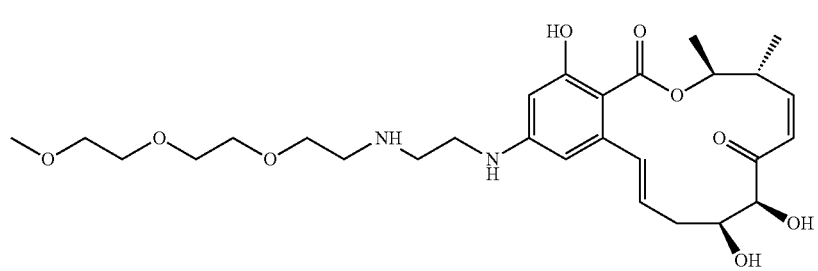
(Compound 045)
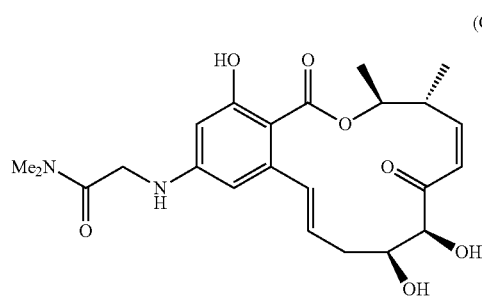
(Compound 046)
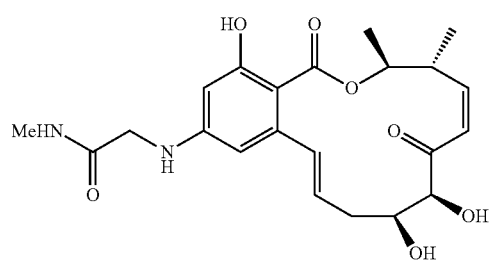
(Compound 047)
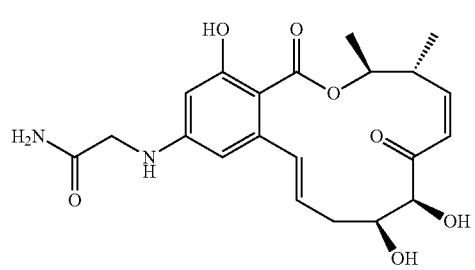
(Compound 048)
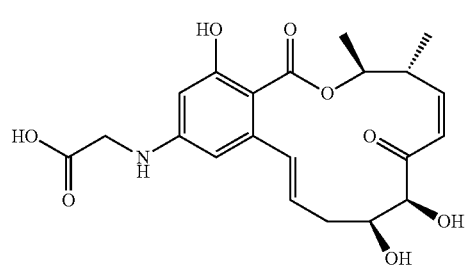
(Compound 054)
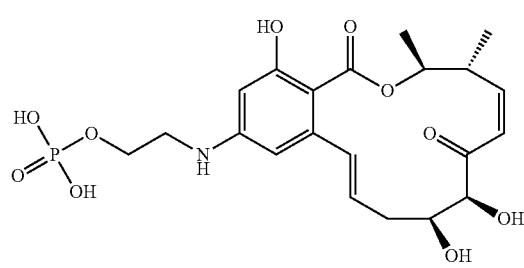
(Compound 065)
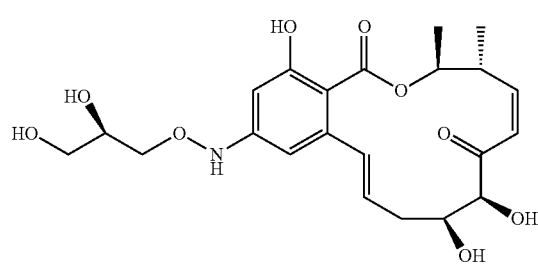

-continued (Compound 076)
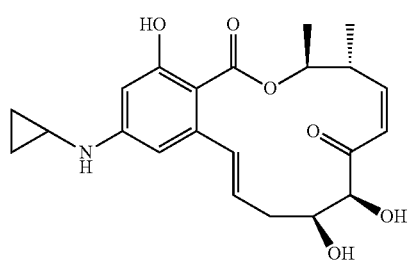

(Compound 114)
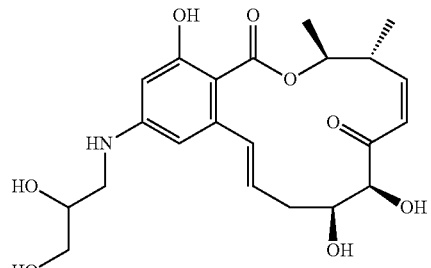

(Compound 122)
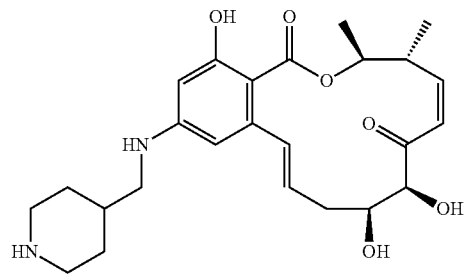

(Compound 127)
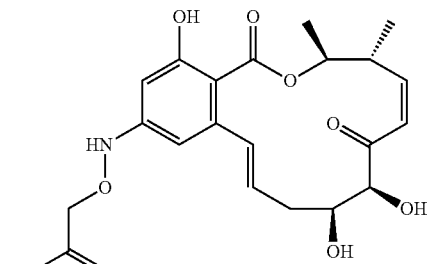

(Compound 137)
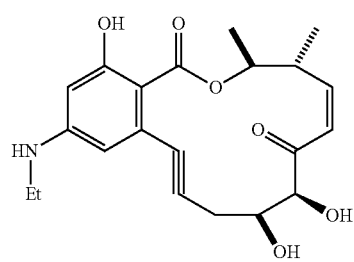

(Compound 144)
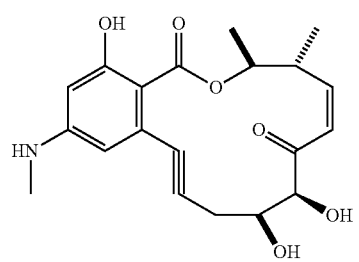

(Compound 155)
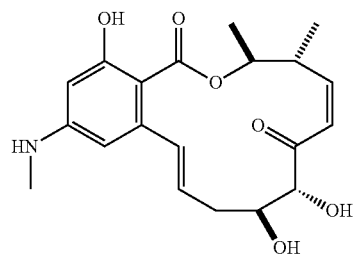

(Compound 156)
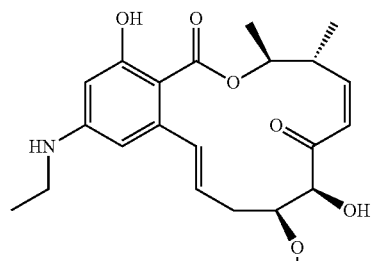

(Compound 157)
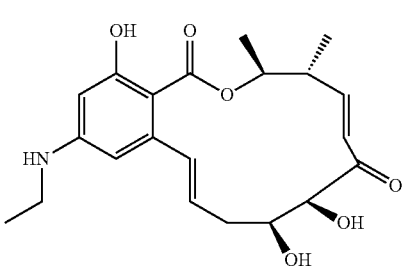

(Compound 158)

and pharmaceutically acceptable salts and esters thereof.

With regard to compounds of formula (II), in some embodiments, $R_3$ is an unsubstituted $C_{1-3}$ alkylamino. In some embodiments, $R_3$ is a group selected from the group consisting of methylamino and ethylamino. In some embodiments, $R_3$ is a group selected from the group consisting of 2-hydroxyethylamino and 2,3-dihydroxypropylamino. For example, compounds of formula (II) include, but are not limited to, the following compounds:

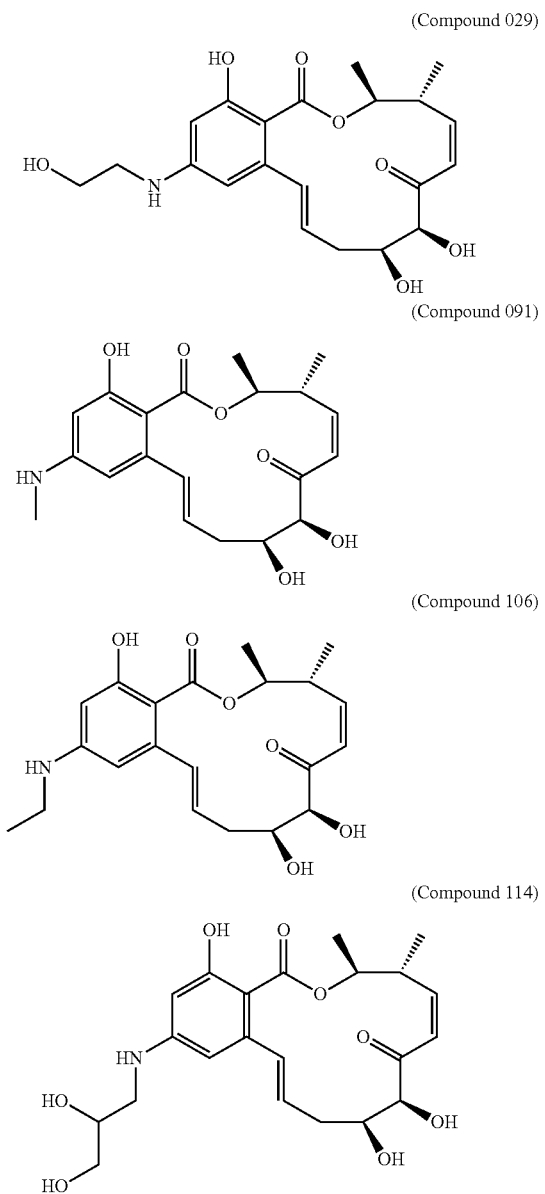

(Compound 029)
(Compound 091)
(Compound 106)
(Compound 114)

and pharmaceutically acceptable salts and esters thereof.

In some embodiments, any of the methods of the present invention include administration of a second chemotherapeutic drug.

BRIEF DESCRIPTION OF THE DRAWINGS

FIG. 2A describes results of exemplary compounds of formula (I) or (II) in biochemical and cell based MEK1 assays.

FIG. 2B describes exemplary kinase inhibition results of a compound.

FIG. 3 describes results of exemplary compounds of formula (I) or (II) in cell growth inhibition assays in a variety of cancer cell lines.

FIG. 7 describes effects of a compound on B-cell driven hematological malignant cancer cell growth.

FIG. 9 describes blood brain barrier (BBB) experiments of a compound.

DETAILED DESCRIPTION OF THE INVENTION

Figure 1:
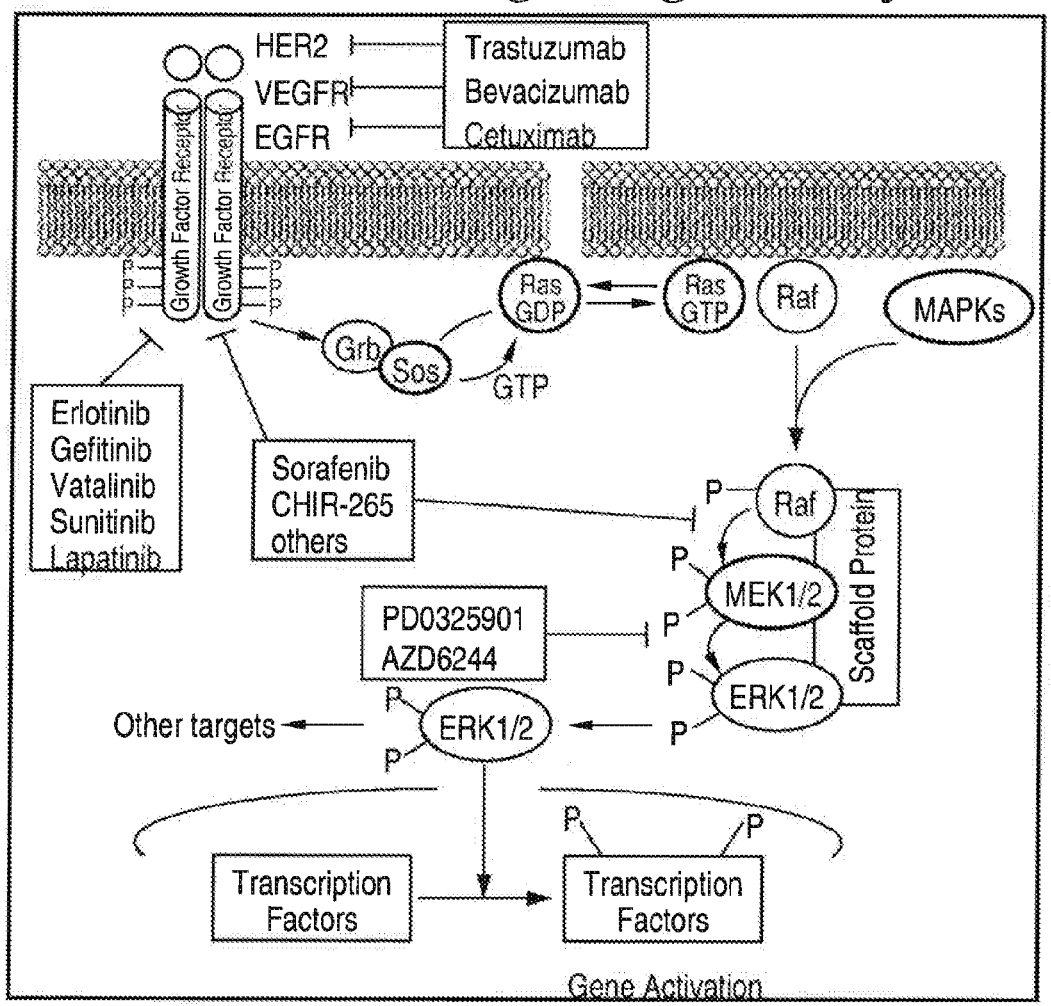
FIG. 1 depicts a schematic representation of the RAS-MAPK signaling pathway.

As discussed in WO 05/023792 and WO 03/076424, certain analogs of F152 have been reported to have inhibitory activity against MEK1, have demonstrated increased stability and are potent inhibitors of NF-κB activation, AP-1 activation and protein kinases (for example, MEKK, MEK1, PDGFr, VEGFr). The present invention is based, at least in part, on the discovery that certain F152 macrolide analogs also have unique multikinase inhibition profiles. That is, compounds of formula (I) or (II) are effective as inhibitors of multiple, specific kinases as discussed in further detail herein. Certain multikinases have previously been shown to be effective against cancer. It has recently been discovered, for example, that imatinib mesylate (STI571, GLEEVEC), an inhibitor of the Bcr-Abl kinase, has been successful in the treatment of chronic myeloid leukemia. This success is attributed, at least in part, to the multikinase activity of imatinib mesylate. Accordingly, without wishing to be bound to any particular theory, it is believed that compounds with these unique multikinase inhibition profiles, e.g., F152 macrolide analogs of formula (I) or (II), have a broader therapeutic spectrum than selective MEK1 inhibitors. For example, it is believed that compounds having this unique multikinase inhibition profile can be used in the treatment and/or prevention of specific cancers.

DEFINITIONS

In order to more clearly and concisely describe the subject matter of the claims, the following definitions are intended to provide guidance as to the meaning of specific terms used herein.

It is to be noted that the singular forms "a," "an," and "the" as used herein include "at least one" and "one or more" unless stated otherwise. Thus, for example, reference to "a pharmacologically acceptable carrier" includes mixtures of two or more carriers as well as a single carrier, and the like.

As used herein, the term "SrcTK/MEK inhibitor" refers to a single compound that inhibits both MEK1 and at least one member of the Src tyrosine kinase family. Exemplary members of the Src tyrosine kinase family include cSrc, Fyn, Lyn, Lck, Yes, Fgr, Hck and Blk. In some embodiments, the term "SrcTK/MEK inhibitor" refers to a single compound that inhibits both MEK1 and from 1 to 5 members of the Src tyrosine kinase family, e.g., 1, 2, 3, 4, or 5 members of the Src tyrosine kinase family.

As used herein, the term "TrkB/MEK inhibitor" refers to a single compound that inhibits both MEK1 and TrkB.

When used herein, a specific protein kinase is referred to by a specific name, e.g., Src, TrkB, and other kinases mentioned specifically herein, but may have a number of synonyms known in the art. For example, Src protein kinase may also be referred to as ASV, c-Src, p60-Src, pp60c-src, Proto-oncogene tyrosine-protein kinase Src, SRC1, AW259666, Neuronal proto-oncogene tyrosine-protein kinase, fc54g04, wu:fc54g0 and/or SDR. Additionally, TrkB can also be referred to as BDNF/NT-3 growth factors receptor precursor, GP145-TrkB, Neurotrophic tyrosine kinase receptor type 2, Trk-B, TrkB tyrosine kinase, AI848316, C030027L06Rik, GP145-TrkB/GP95-TrkB and/or Tkrb. Yes may also be referred to as c-Yes, HsT441, p61-Yes, Proto-oncogene tyrosine-protein kinase Yes, Yes, AI323763, p61-Yes, Tyrosine-protein kinase Yes, MGC94936 and/or p60c-yes. Lck may also be referred to as LSK, Lymphocyte cell-specific protein-tyrosine kinase, p56-LCK, Proto-oncogene tyrosine-protein kinase LCK, T cell-specific protein-tyrosine kinase, Hck-3 and/or Lsk-t. Fyn may also be referred to as MGC45350, p59-Fyn, Protooncogene Syn, Proto-oncogene tyrosine-protein kinase Fyn, SLK, SYN, AI448320, AW552119, MGC115870, MGC132140, MGC52878, Src Kinase p59, c-fyn and/or zgc:86720. Lyn may also be referred to as FLJ26625, JTK8, Tyrosine-protein kinase Lyn, AA407514, Hck-2, Lyncein and/or TBC1 domain family member 1. It is well within the capability of the skilled artisan to determine whether a name is a synonym for the protein kinases recited herein using, e.g., searchable protein databases.

When used herein, a specific protein kinase includes not only the naturally occurring kinase, e.g., Src, TrkB, and other kinases mentioned specifically herein, but also modified kinases. Accordingly, in some embodiments, the compounds of formula (I) or (II) inhibit kinases which share at least 90% sequence identity with naturally occurring counterparts. In other embodiments, the compounds of formula (I) or (II) inhibit kinases which share at least 95% sequence identity with naturally occurring counterparts. In still other embodiments, the compounds of formula (I) or (II) inhibit kinases which share at least 97% sequence identity with naturally occurring counterparts. In yet other embodiments, the compounds of formula (I) or (II) inhibit kinases which share at least 99% sequence identity with naturally occurring counterparts. Kinases which share sequence identity with naturally occurring counterparts can be naturally occurring or synthetic. The term "sequence identity" generally refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. In some embodiments, the window size is at least 20 nucleotide positions, for example, at least 25-50 nucleotides. In other embodiments, the window size is greater than 50 nucleotides. In some embodiments, the window size is the entire naturally occurring protein kinase. In other embodiments, the window size is the sequence which corresponds at least to the ATP binding site on the naturally occurring protein kinase.

As used herein, the term "SrcTK/MEK associated cancer" refers to cancers that are associated with or otherwise affected by the activity or function of MEK1 and at least one member of the Src tyrosine kinase family. In one aspect, the activity or function of MEK1 is elevated, and the activity or function of at least one member of the Src tyrosine kinase family is elevated in a SrcTK/MEK associated cancer. Exemplary SrcTK/MEK associated cancers are discussed in more detail herein, and may include chronic myeloid leukemia (CML) and colorectal cancer.

As used herein, the term "TrkB/MEK associated cancer" refers to cancers that are associated with or otherwise affected by the activity or function of MEK1 and TrkB. In one aspect, the activity or function of MEK1 is elevated, and the activity or function of TrkB is elevated in a TrkB/MEK associated cancer. Exemplary TrkB/MEK associated cancers are also discussed in more detail herein, and may include pancreatic cancer, neural cancer, glioma, neuroblastoma and retinoblastoma.

In some embodiments, cancers that are "associated with or otherwise affected by the activity or function" of one or more protein kinases are cancers which are attributable to disregulation of protein kinase activity. In other embodiments, cancers that are "associated with or otherwise affected by the activity or function" of one or more protein kinases are cancers which are attributable to disregulation of an upstream or downstream event in a protein kinase pathway. In other embodiments, cancers that are "associated with or otherwise affected by the activity or function" of one or more protein kinases are cancers which are attributable to mutations in genes which regulate protein kinase activity. In some embodiments, cancers that are "associated with or otherwise affected by the activity or function" of one or more protein kinases are cancers which are attributable to increased or constitutive activation of one or more signal molecules. In some embodiments, cancers that are "associated with or otherwise affected by the activity or function" of one or more protein kinases are cancers which are attributable to the increased or constitutive ability of the protein kinase to phosphorylate proteins. In still other embodiments, cancers that are "associated with or otherwise affected by the activity or function" of one or more protein kinases are cancers which are attributable to alteration of binding of adenosine triphosphate (ATP) to the enzyme's binding site such that kinase activity is increased. In some embodiments, cancers that are "associated with or otherwise affected by the activity or function" of one or more protein kinases are cancers which are attributable to ligand binding to and/or dimerization of the protein kinase.

Cancers designated "SrcTK/MEK associated," "TrkB/MEK associated," "associated with B-RAF mutations" and/or "associated with FLT3 mutations" are cancers which have been chosen because of their apparent association with certain protein kinases or specific protein mutations, as described in more detail herein. Once a cancer (e.g., pancreatic cancer) is determined to be associated with MEK1, Src, TrkB, or any of the other kinases or protein mutations described herein, (e.g., in the literature or through experimentation), the skilled artisan would understand that treatment of the specific cancer is indicative of treatment of a cancer of the present invention (e.g., a TrkB/MEK associated cancer).

Compounds of formula (I) or (II) inhibit a number of protein kinases as described herein. As used herein, the term "inhibit" when used in relation to a protein kinase, refers to the ability of a compound of formula (I) or (II) to at least partially reduce the activity of the protein kinase. Without wishing to be bound by any particular theory, it is believed that an inhibitor of a protein kinase may either compete directly with ATP for the binding pocket of a specific kinase or otherwise interact with the kinase such that the binding pocket is no longer available to the ATP. The amount to which a compound will inhibit a protein kinase is ascertainable by a number of assays known in the art. For example, a compound may be diluted in an acceptable buffer (e.g., MOPS, EDTA, Brij-35, Glycerol, NaCl, BSA, HEPES, Triton X-100, or TRIS), and exposed to the protein kinase in the presence of a specific amount of [$\gamma$-$^{33}$P-ATP] and a substrate peptide. Following incubation and quenching, an aliquot will be taken to determine the amount of $^{33}$P incorporated. For example, ionizing radiation will be measured with a scintillation counter, to determine the amount of $\gamma$-$^{33}$P incorporated into the substrate which is associated with the kinase activity. This value would be compared to a suitable control, e.g., the same process without the inhibitor present. It will be appreciated that ability of a compound to inhibit kinase activity can be assessed or measured by any suitable method. For example, antibodies which bind phospho-peptide or phospho-protein substrates can be used to detect such phosphorylation products, which are indicative of kinase activity. Binding of antibody to substrate can be detected by any suitable method, such as labeled second antibody. In some embodiments, the ability of a compound to inhibit transphosphorylation of receptor tyrosine kinase subunits or to inhibit autophosphorylation of receptor tyrosine kinase can be assessed or measured. In some embodiments, the inhibitors of the present invention inhibit at least about 30% of the activity of the specified protein kinase at an inhibitor concentration of about 0.1 μM. In some embodiments, the inhibitors of the present invention inhibit at least about 45% of the activity of the specified protein kinase at an inhibitor concentration of about 0.1 μM. In some embodiments, the inhibitors of the present invention inhibit at least about 50% of the activity of the specified protein kinase at an inhibitor concentration of about 0.1 μM. In some embodiments, the inhibitors of the present invention inhibit at least about 55% of the activity of the specified protein kinase at an inhibitor concentration of about 0.1 μM. In some embodiments, the inhibitors of the present invention inhibit at least about 40% of the activity of the specified protein kinase at an inhibitor concentration of about 1.0 μM. In some embodiments, the inhibitors of the present invention inhibit at least about 50%, of the activity of the specified protein kinase at an inhibitor concentration of about 1.0 μM. In some embodiments, the inhibitors of the present invention inhibit at least about 75%, 80%, 85%, or 90% of the activity of the specified protein kinase at an inhibitor concentration of about 1.0 μM. In some embodiments, the inhibitors of the present invention inhibit about 95% of the activity of the specified protein kinase at an inhibitor concentration of about 1.0 μM. In some embodiments, the assay to determine amount of inhibition is performed in the presence of ATP. In some embodiments, the assay to determine amount of inhibition is performed in the presence of 10 μM ATP. In some embodiments, the assay to determine amount of inhibition is performed in the presence of [$\gamma$-$^{33}$P-ATP]. In some embodiments, the assay to determine amount of inhibition is performed in the presence of an amount of [$\gamma$-$^{33}$P-ATP] which affords a specific activity of about 500 cpm/pmol. In some embodiments, the assay to determine amount of inhibition is performed in the presence of trace amounts of [$\gamma$-$^{33}$P-ATP].

As used herein, the term "inhibition of a metastatic process" refers to the ability of a compound of formula (I) or (II) to inhibit not only the growth of a single tumor, but also the spread of tumors from a primary site to distant organs. Without wishing to be bound by any particular theory, it is believed that metastasis is a common cause of failure of cancer treatment. In one embodiment, inhibition of a metastatic process includes inhibiting the ability of the tumor cells to separate from its neighboring cells. In one embodiment, inhibition of a metastatic process includes inhibiting the ability of the tumor cells to pass through the extracellular matrix. In one embodiment, inhibition of a metastatic process includes inhibiting the ability of the tumor cells to secrete enzymes that break down the matrix. In one embodiment, inhibition of a metastatic process includes inhibiting the ability of the tumor cells to pass through the endothelial lining of the blood vessels. In one embodiment, inhibition of a metastatic process includes inhibiting the ability of the tumor cells to pass through the lymphatic system. In one embodiment, inhibition of a metastatic process includes inhibiting the ability of the tumor cells to survive in the circulatory system. In one embodiment, inhibition of a metastatic process includes inhibiting the ability of the tumor cells to extravasate into the surrounding tissue of the organ. It is to be understood that, when used in reference to a metastatic process, the term "inhibition" may refer to complete halting of a metastatic process in a subject or to a slowing of the metastatic process in a subject. Without wishing to be bound by any particular theory, it is believed that the ability of a compound of formula (I) or (II) to inhibit the metastatic process is due, at least in part, to the ability of the compound to inhibit a Src tyrosine kinase.

"Treatment", or "treating" as used herein, is defined as the application or administration of a therapeutic agent (e.g., specific multikinase inhibitors of the invention) to a patient, or to an isolated tissue or cell line from a patient. The patient generally has a disease or disorder, a symptom of disease or disorder or a predisposition toward a disease or disorder. The purpose of treatment is generally to cure, heal, alleviate, relieve, remedy, ameliorate, or improve such disease, disorder, symptoms or predisposition. "Treated," as used herein, refers to the disease or disorder being cured, healed, alleviated, relieved, remedied, ameliorated, or improved. For example, methods of treatment of the instant invention provide for administration of an inhibitor as described herein, such that the progression of a specific cancer or a specific class of cancer (e.g., a SrcTK/MEK associated cancer) is slowed or stopped. Methods of treatment of the instant invention further include the administration of an inhibitor, such that a specific cancer is cured.

The term "effective dose" or "effective dosage" is defined as an amount sufficient to achieve a desired effect. The term "desired effect" refers generally to any result that is anticipated by the skilled artisan when a compound or composition of formula (I) or (II) is administered to a subject. In some embodiments, the desired effect is a complete remission of the disease or disorder. In other embodiments, the desired effect is a partial treatment of a disease or disorder. In still other embodiments, the desired effect is a full or partial treatment of the symptoms of a disease or disorder. For example, in some embodiments, the desired effect is the shrinkage of a solid tumor. In another exemplary embodiment, the desired effect is the elimination of a solid tumor. The term "therapeutically effective dose" is defined as an amount sufficient to cure or at least partially arrest the disease and its complications in a subject already suffering from the disease.

The term "subject," as used herein, refers to animals such as mammals, including, but not limited to, humans, primates, cows, sheep, goats, horses, pigs, dogs, cats, rabbits, guinea pigs, rats, mice or other bovine, ovine, equine, canine, feline, rodent or murine species. In some embodiments, the subject is a human.

Numerous values and ranges are recited in connection with various embodiments of the present invention, e.g., amount of a compound of formula (I) or (II) present in a composition. It is to be understood that all values and ranges which fall between the values and ranges listed are intended to be encompassed by the present invention unless explicitly stated otherwise. The term "about" as used herein in association with parameters, ranges and amounts, means that the parameter or amount is within ±1% of the stated parameter or amount.

The term "stable", as used herein, generally refers to compounds which possess stability sufficient to allow manufacture and which maintain the integrity of the compound for a sufficient period of time to be detected. In some embodiments, stable compounds of formula (I) or (II) are those which maintain their integrity for a sufficient period of time to be useful for the purposes detailed herein. For example, a prodrug may be considered "stable" even though it is eventually metabolized in the body.

As used herein, "alkyl" groups include saturated hydrocarbons having one or more carbon atoms, including straight-chain alkyl groups (e.g., methyl, ethyl, propyl, butyl, pentyl, hexyl, etc.), cyclic alkyl groups (or "cycloalkyl" or "alicyclic" or "carbocyclic" groups) (e.g., cyclopropyl, cyclopentyl, cyclohexyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups). In certain embodiments, a straight-chain or branched-chain alkyl group may have 8 or fewer carbon atoms in its backbone, e.g., $C_1$-$C_8$ for straight-chain or $C_3$-$C_8$ for branched-chain. In certain embodiments, a straight-chain or branched-chain alkyl group may have 6 or fewer carbon atoms in its backbone, e.g., $C_1$-$C_6$ for straight-chain or $C_3$-$C_6$ for branched-chain. In still other embodiments, an alkyl group includes about 1 to 4 carbons. In other embodiments, an alkyl group includes about 1 to 3 carbons. In yet other embodiments, an alkyl group includes about 1 or 2 carbons. The term "lower alkyl" refers to alkyl groups having from 1 to 6 carbons in the chain, and to cycloalkyl groups having from 3 to 6 carbons in the ring structure. The term "$C_1$-$C_6$" as in "$C_1$-$C_6$ alkyl" means alkyl groups containing 1 to 6 carbon atoms. The terms "alkenyl" and "alkynyl" refer to unsaturated aliphatic groups analogous to alkyls, but which contain at least one double or triple carbon-carbon bond respectively.

The term "alkoxy" as used herein means an alkyl group having an oxygen atom attached thereto. In some embodiments, alkoxy groups include groups having 1 to about 8 carbon atoms. In other embodiments, alkoxy groups include groups having 1 to about 6 carbon atoms. In still other embodiments, alkoxy groups include groups having fewer than about 4 carbon atoms. Examples of alkoxy groups include, but are not limited to, methoxy, ethoxy, isopropyloxy, propoxy, butoxy, and pentoxy groups. The alkoxy groups can be straight-chain or branched.

The term "heterocyclic group" includes closed ring structures analogous to carbocyclic groups in which one or more of the carbon atoms in the ring is an element other than carbon, for example, nitrogen, sulfur, or oxygen. Heterocyclic groups may be saturated or unsaturated. Additionally, heterocyclic groups (such as pyrrolyl, pyridyl, isoquinolyl, quinolyl, purinyl, and furyl) may have aromatic character, in which case they may be referred to as "heteroaryl" or "heteroaromatic" groups. Exemplary heterocyclic groups include, but are not limited to imidazolyl, e.g.,

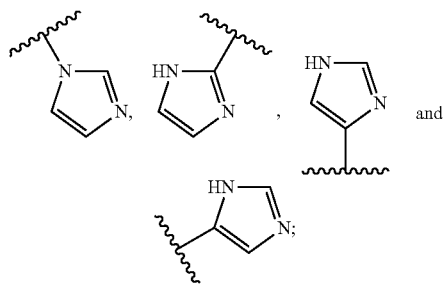

morpholinyl, e.g.

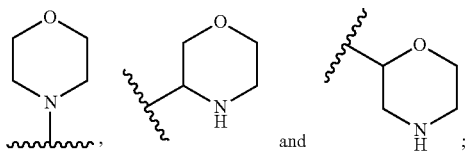 [SMILES: *N1CCOCC1 ; *C1COCCN1 ; *C1CNCCO1]

piperidinyl, e.g.,

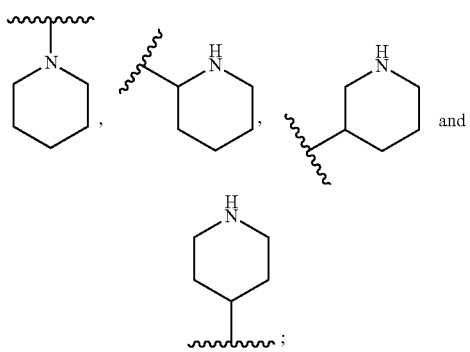

pyrrolidinyl, e.g., and

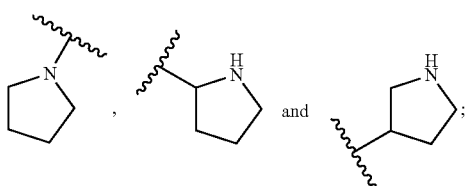 [SMILES: *N1CCCC1 ; *C1CCCN1 ; *C1CCNC1]

piperazinyl, e.g.,

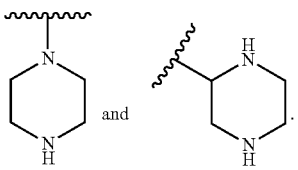 [SMILES: *N1CCNCC1 ; *C1CNCCN1]

The term "amine" or "amino," as used herein, refers to an unsubstituted or substituted moiety of the formula —$NR^aR^b$, in which $R^a$ and $R^b$ are each independently hydrogen, alkyl, aryl, or heterocyclyl, or $R^a$ and $R^b$, taken together with the nitrogen atom to which they are attached, form a cyclic moiety having from 3 to 8 atoms in the ring. Thus, the term amino includes cyclic amino moieties such as piperidinyl or pyrrolidinyl groups, unless otherwise stated.

Regarding connectivity, an "arylalkyl" group, for example, is an alkyl group substituted with an aryl group (e.g., phenylmethyl (i.e., benzyl)). An "alkylaryl" moiety is an aryl group substituted with an alkyl group (e.g., p-methylphenyl (i.e., p-tolyl)). Thus, the term imidazolyl-alkyl refers to an alkyl group substituted with an imidazolyl moiety.

When specified, the chemical moieties of the compounds of formula (I) or (II), including those groups discussed above, may be "substituted or unsubstituted." In some embodiments, the term "substituted" means that the moiety has substituents placed on the moiety other than hydrogen (i.e., in most cases, replacing a hydrogen), which allow the molecule to perform its intended function. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, permissible substituents include acyclic and cyclic, branched and unbranched, carbocyclic and heterocyclic, aromatic and nonaromatic substituents of organic compounds. The compounds of formula (I) or (II) may have one or more substitutions, as described herein.

As used in the description and drawings herein, an optional double/triple bond is represented by two solid lines together with a third dashed line, and refers to a covalent linkage between two carbon atoms which can be either a double bond or a triple bond. For example, the structure:

can represent either butene or butyne.

When compounded chemical names, e.g., "alkylaryl," "aryloxy," and the like, are used herein, they are understood to have a specific connectivity to the core of the chemical structure. The moiety listed farthest to the right (e.g., aryl in "alkylaryl"), is the moiety which is directly connected to the core. That is, for example, in a structure V—$CH_2CH_2CH_3$, when the variable "V" is an alkylaryl, the structure is understood to be alkyl-aryl-$CH_2CH_2CH_3$.

As used herein, the term "compound" is intended to mean a substance made up of molecules that further consist of atoms. A compound may be any natural or non-natural material, for example, peptide or polypeptide sequences, organic or inorganic molecules or compositions, nucleic acid molecules, carbohydrates, lipids or combinations thereof. A compound generally refers to a chemical entity, whether in the solid, liquid or gaseous phase, and whether in a crude mixture or purified and isolated. Compounds encompass the chemical compound itself as well as, where applicable: amorphous and crystalline forms of the compound, including polymorphic forms, said forms in mixture or in isolation; free acid and free base forms of the compound; isomers of the compound, including geometric isomers, optical isomers, and tautomeric isomers, said optical isomers to include enantiomers and diastereomers, chiral isomers and non-chiral isomers, said optical isomers to include isolated optical isomers or mixtures of optical isomers including racemic and non-racemic mixtures; said geometric isomers to include transoid and cisoid forms, where an isomer may be in isolated form or in admixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, including acid addition salts and base addition salts, including organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different.

In some embodiments, the term "compound" explicitly refers to small molecules. As used herein, the term "small molecule," as used herein, refers to a compound that is not itself the product of gene transcription or translation (e.g., protein, RNA, or DNA) and preferably has a low molecular weight, e.g., organic molecules having a molecular weight of less than about 2,000 daltons (Da). In some embodiments, small molecules have a molecular weight of less than about 1,500 Da. In other embodiments, small molecules have a molecular weight of less than about 1,000 Da. In still other embodiments, small molecules have a molecular weight of less than about 750 Da. In yet other embodiments, small molecules have a molecular weight of less than about 500 Da.

The phrase, "pharmaceutically acceptable prodrugs" as used herein, refers to derivatives of a compound, usually with significantly reduced pharmacological activity, which contain an additional moiety, which are susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention.

As used herein the term "ester" refers to a group having the formula R'—COOR, where one of R' or R is, for example, an alkyl group, a haloalkyl group or an aromatic group, and the other of R' or R is the active moiety. A "pharmaceutically acceptable ester" refers to an ester which acts as a prodrug, e.g., an ester which is subject to at least partial removal (e.g., by hydrolysis or other cleavage) from the core structure in vivo.

The term "protecting group" as used herein (e.g., with regard to the synthesis of compounds of formula (I) or (II)), refers to a particular functional moiety, e.g., O, S, or N, being temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction.

The term "amine" or "amino," as used herein, refers to an unsubstituted or substituted moiety of the formula —$NR^aR^b$, in which $R^a$ and $R^b$ are each independently, for example, hydrogen, alkyl, aryl, or heterocyclyl, or $R^a$ and $R^b$, taken together with the nitrogen atom to which they are attached, form a cyclic moiety having from 3 to 8 atoms in the ring.

Compounds of Formula (I) and (II)

The invention includes compounds of formula (I):

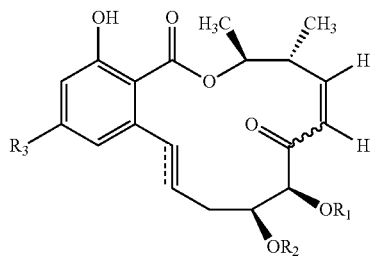

(I)

wherein:

$R_1$ is H $R_2$ is a moiety selected from the group consisting of H and trifluoromethylcarbonyl; or $R_1$ and $R_2$ are taken together with the core structure to form a heterocyclydiyl moiety of formula (a):

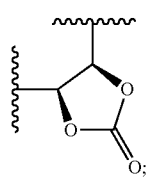

(a)

$R_3$ is a moiety selected from the group consisting of —$OR_a$ and —$NR_bR_c$;

$R_a$ is a $C_{1-4}$ alkyl group optionally substituted with an imidazolyl;

$R_b$ is a moiety selected from the group consisting of a $C_{1-4}$ alkyl group and a $C_{1-4}$ alkoxy group, wherein $R_b$ is substituted with 0, 1 or 2 groups each independently selected from the group consisting of —$OCH_3$, —C(O)OH, —C(O)NR'R", —NH($C_{1-3}$ alkyl), —NH($CH_2CH_2O)_nCH_3$, wherein n is 2-4, piperazinyl, N-methylpiperazinyl, piperidinyl, N-methylpiperidinyl, N-morpholinyl, imidazolyl, pyrrolidinyl, —$OPO_3H_2$ and hydroxyl; wherein the —NH($C_{1-3}$ alkyl) group is substituted with 0, 1 or 2 hydroxyl moieties and wherein R' and R" are each independently selected from —H or —$CH_3$; and $R_c$ is H, or $R_b$ and $R_c$ are taken together with the nitrogen to which they are attached to form a heterocyclyl moiety selected from the group consisting of formula (b) and formula (c):

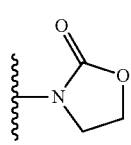

(b)

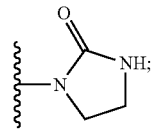

(c)

or a pharmaceutically acceptable salt or ester thereof.

In some embodiments, represents a double bond. In some embodiments, represents a triple bond. In some embodiments, $R_2$ is H. In some embodiments, $R_3$ is —$NR_bR_c$, where $R_b$ is an unsubstituted $C_{1-4}$ alkyl. In some embodiments, $R_b$ is methyl. In some embodiments, $R_b$ is ethyl. In some embodiments, $R_3$ is —$NR_bR_c$, where $R_b$ is a $C_{1-4}$ alkyl, substituted with 1 or 2 —OH groups. In some embodiments, $R_b$ is 2-hydroxyethyl. In some embodiments, $R_b$ is 2,3-dihydroxypropyl. In some embodiments, $R_3$ is —$OR_a$, where $R_a$ is a $C_{2-3}$ alkyl substituted with an imidazolyl group.

Exemplary imidazolyl groups include, but are not limited to,

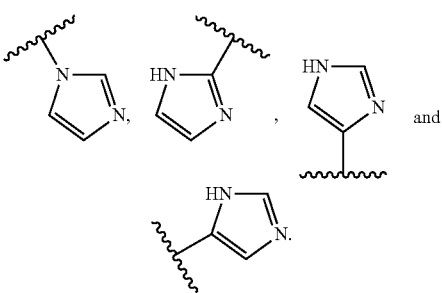

and

In some embodiments, the imidazolyl group is

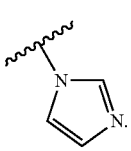 [SMILES: *n1ccnc1]

Exemplary morpholinyl groups include, but are not limited to,

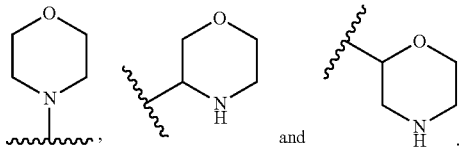 [SMILES: *N1CCOCC1 ; *C1COCCN1 ; *C1CNCCO1]

In some embodiments, the morpholinyl group is

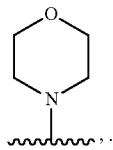

Exemplary piperidinyl groups include, but are not limited to,

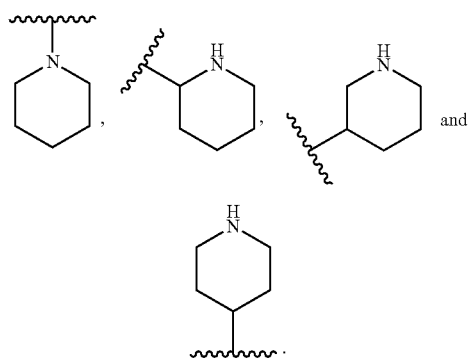

In some embodiments, the piperidinyl group is

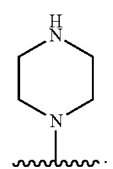

Exemplary N-methylpiperidinyl groups include, but are not limited to,

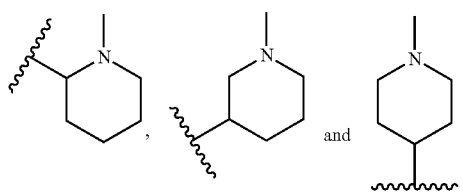

In some embodiments, the N-methylpiperidinyl group is

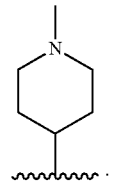

Exemplary pyrrolidinyl groups include, but are not limited to,

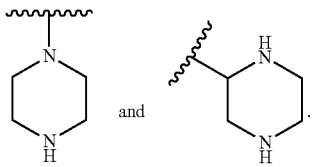 [SMILES: *N1CCNCC1 ; *C1CNCCN1]

In some embodiments, the pyrrolidinyl group is

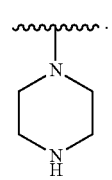

Exemplary piperazinyl groups include, but are not limited to,

In some embodiments, the piperazinyl group is

Exemplary N-methylpiperazinyl groups include, but are not limited to,

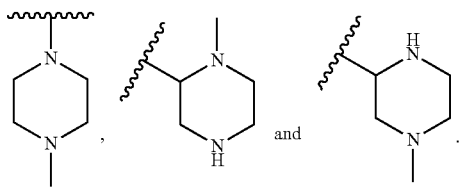

In some embodiments, the N-methylpiperazinyl group is

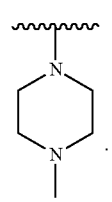

In other embodiments, compounds of formula (I) or (II) include the compounds listed hereinbelow:

(Compound 013)
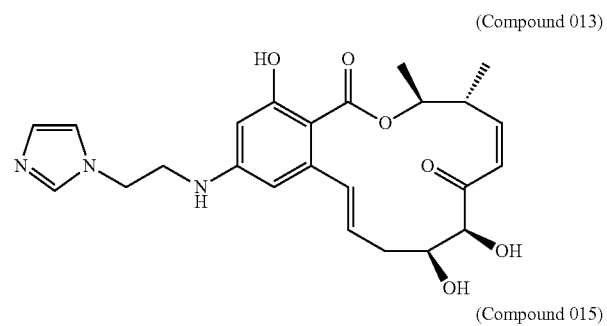
(Compound 014)
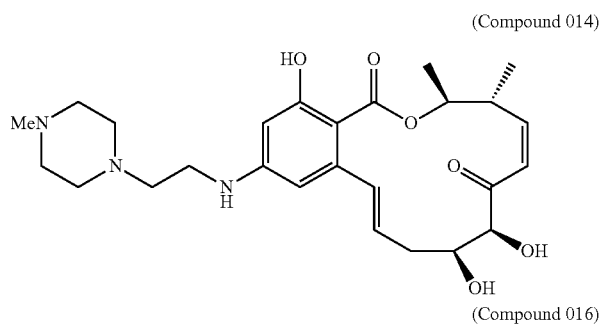
(Compound 015)
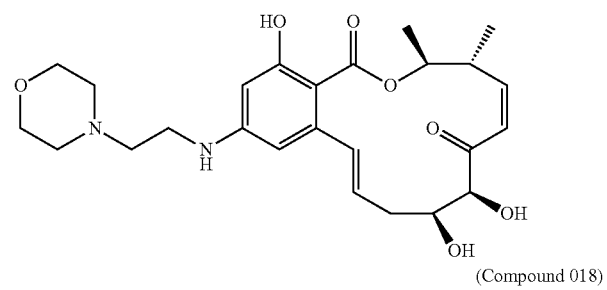
(Compound 016)
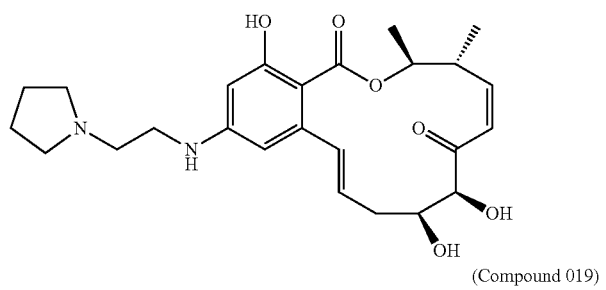
(Compound 018)
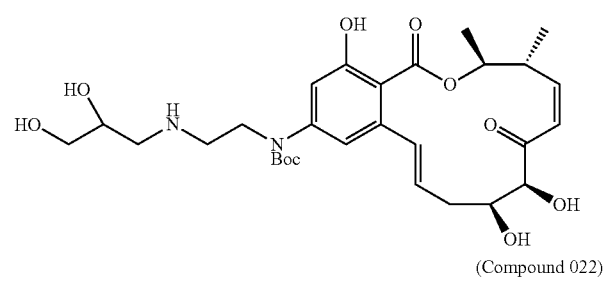
(Compound 019)
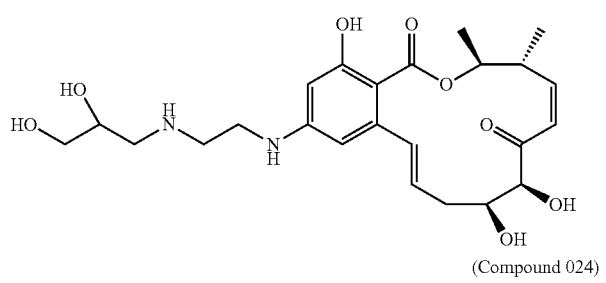
(Compound 022)
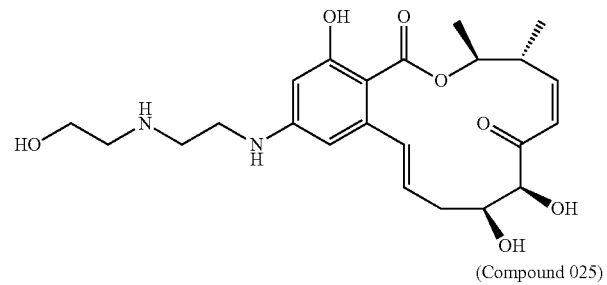
(Compound 024)
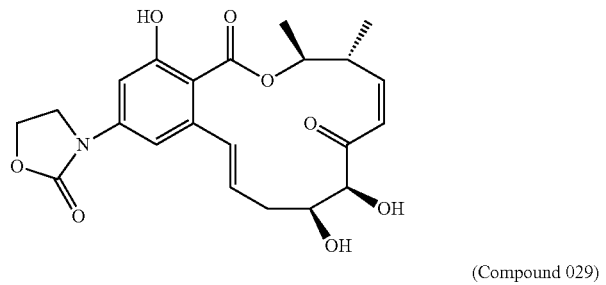
(Compound 025)
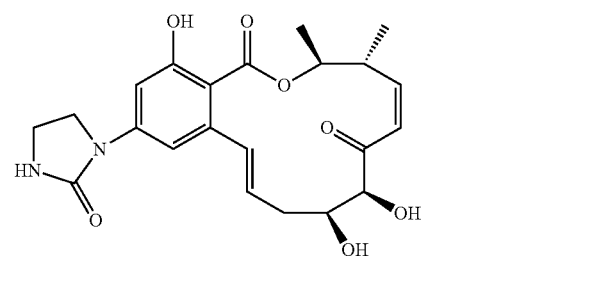
(Compound 029)
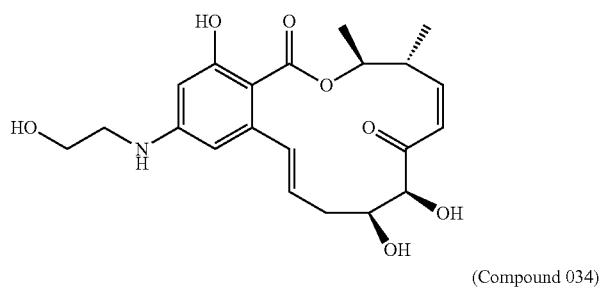
(Compound 034)
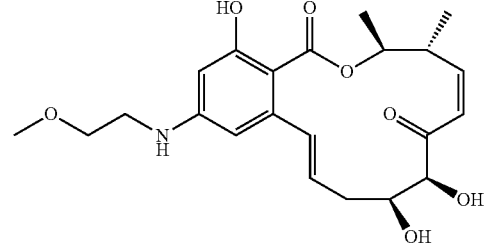

-continued
(Compound 141)
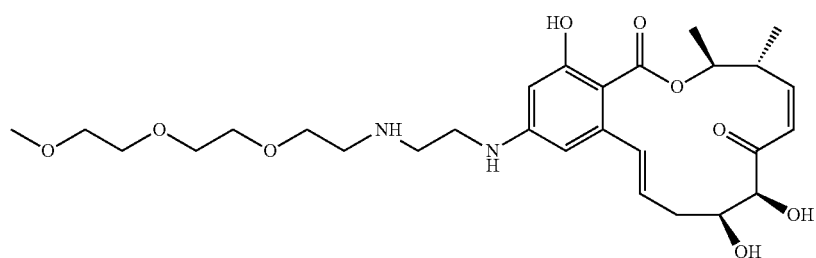
(Compound 045)
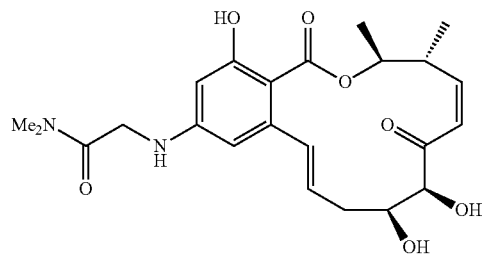
(Compound 046)
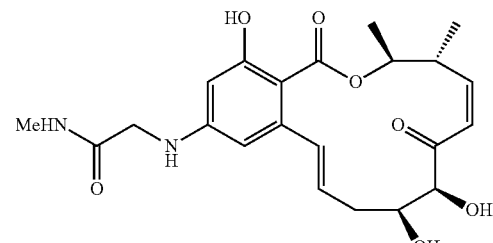
(Compound 047)
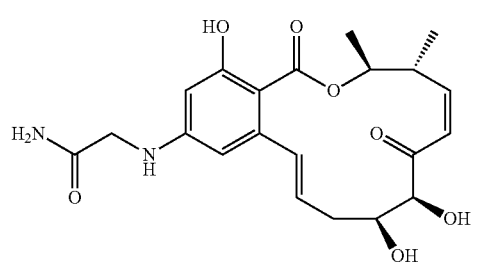
(Compound 048)
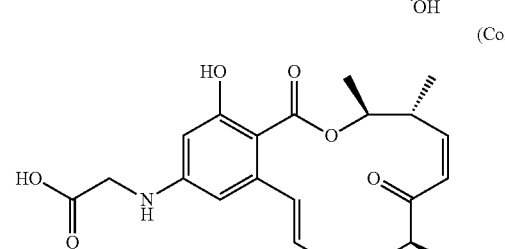
(Compound 054)
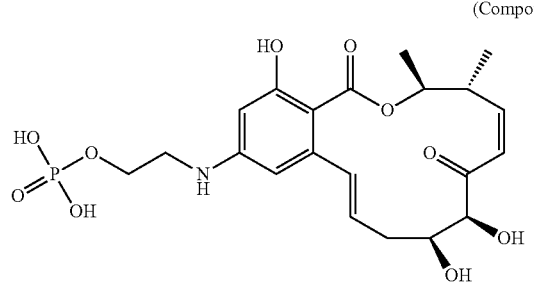
(Compound 065)
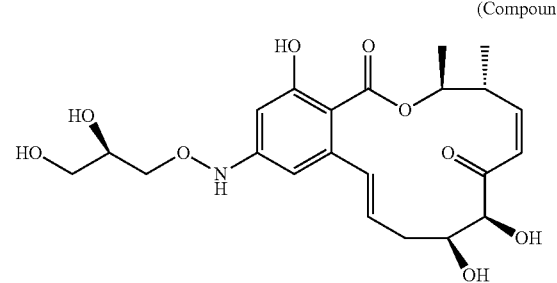
(Compound 069)
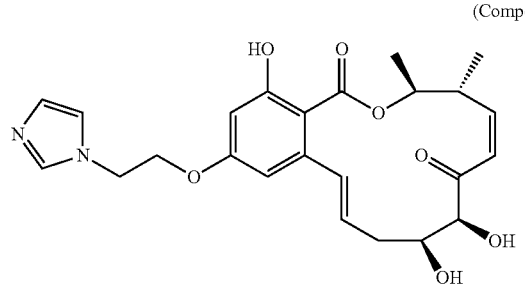
(Compound 076)
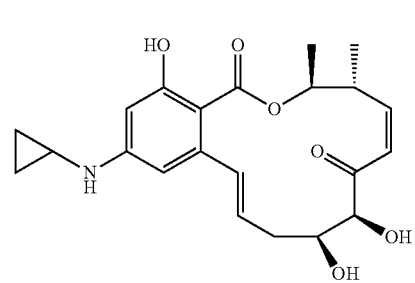
(Compound 091)
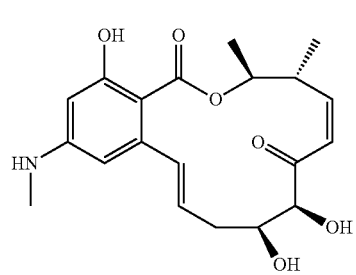
(Compound 092)
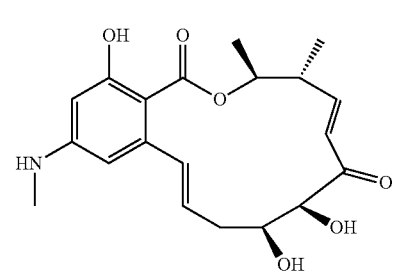

(Compound 106)
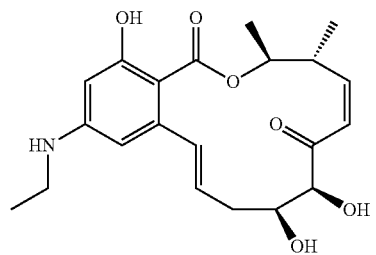
(Compound 114)
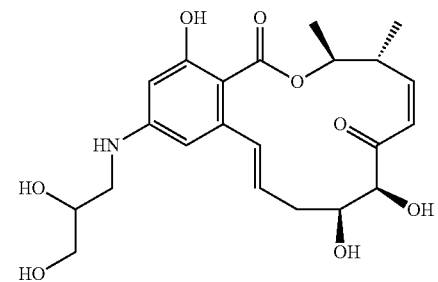
(Compound 122)
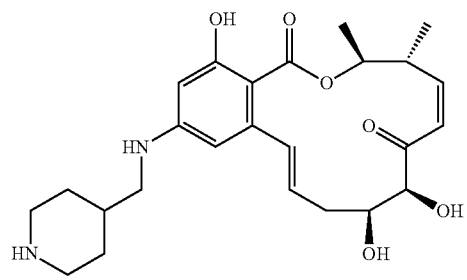
(Compound 127)
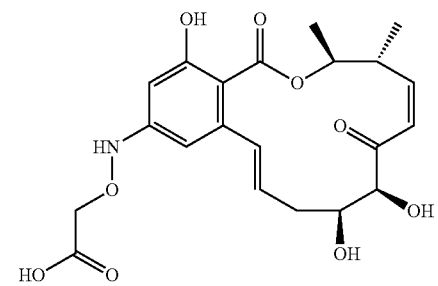
(Compound 137)
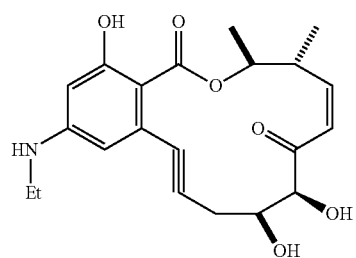
(Compound 144)
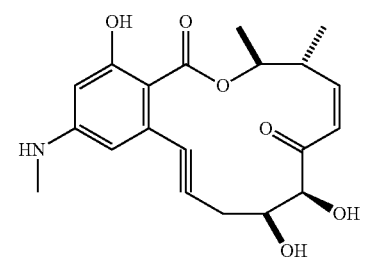
(Compound 155)
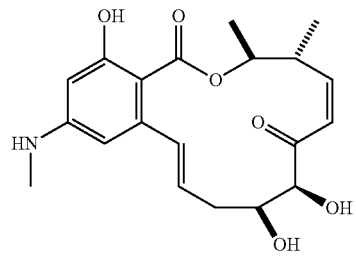
(Compound 156)
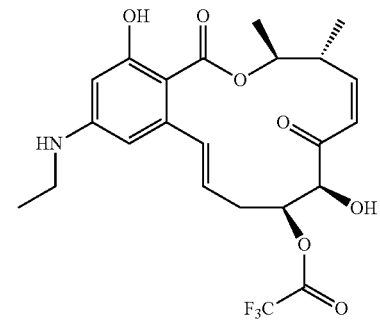
(Compound 157)
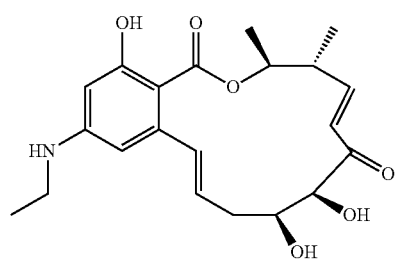
(Compound 158)
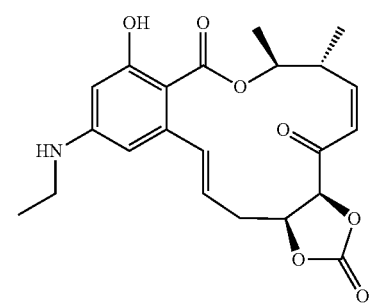
and pharmaceutically acceptable salts or esters thereof.

In some embodiments, the compound is at least one compound selected from the group consisting of:

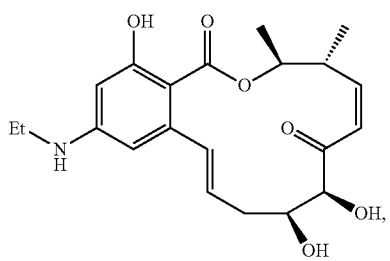
(Compound 013)

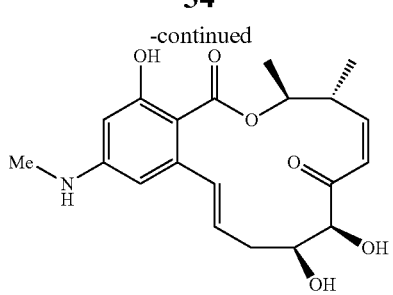

and pharmaceutically acceptable salts or esters thereof.

In at least one embodiment, the compound of formula (I) or (II) is not compound 029, compound 069, compound 091 or compound 106. In at least one embodiment, the compound of formula (I) or (II) is not a specific compound listed in US Application Publication No. 2004/0224936.

In some aspects, the present invention is directed to novel compounds of formula (I). All novel compounds of formula (I) described herein are included in the invention as compounds. In some embodiments, the present invention is directed to one or more of the compounds listed hereinbelow:

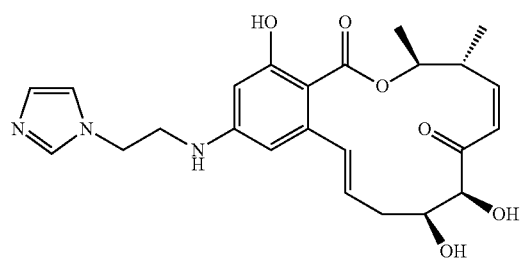
(Compound 015)

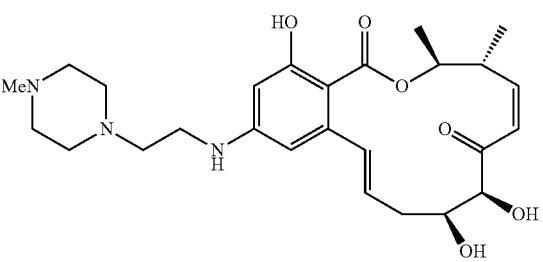 [SMILES: C[C@@H]1/C=C\C(=O)[C@@H](O)[C@@H](O)C/C=C/c2cc(NCCN3CCN(C)CC3)cc(O)c2C(=O)O[C@H]1C]
(Compound 016)

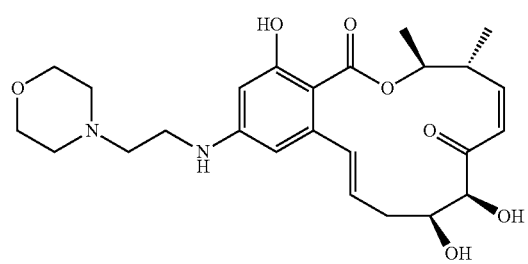 [SMILES: C[C@@H]1/C=C\C(=O)[C@@H](O)[C@@H](O)C/C=C/c2cc(NCCN3CCOCC3)cc(O)c2C(=O)O[C@H]1C]
(Compound 018)

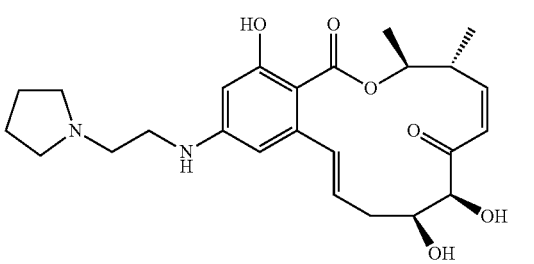 [SMILES: C[C@@H]1/C=C\C(=O)[C@@H](O)[C@@H](O)C/C=C/c2cc(NCCN3CCCC3)cc(O)c2C(=O)O[C@H]1C]
(Compound 019)

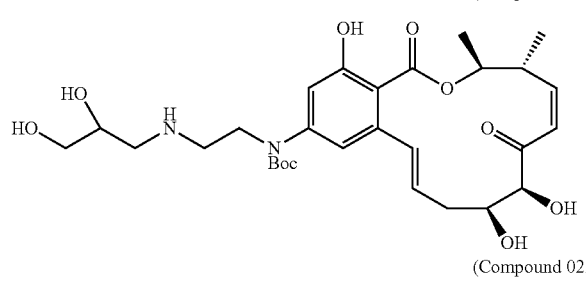
(Compound 022)

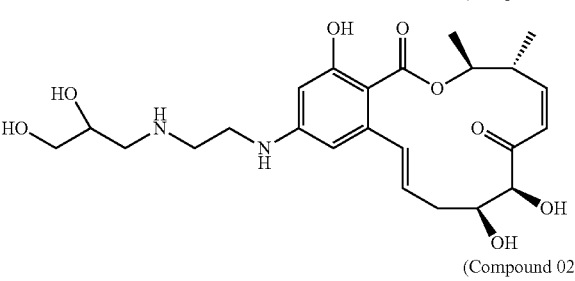
(Compound 024)

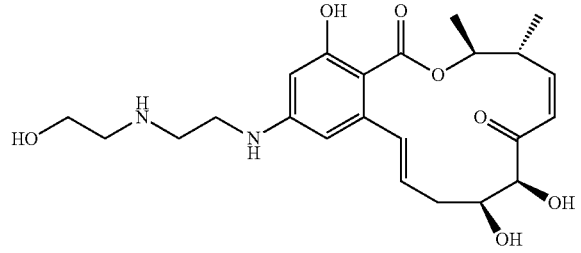

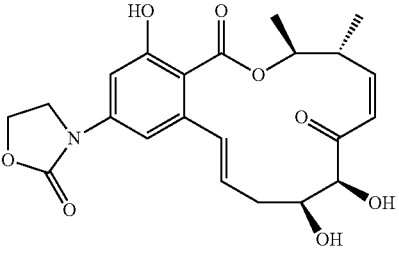

-continued
(Compound 025)
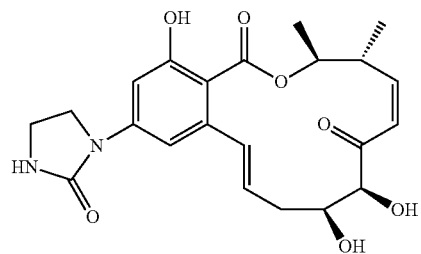 [SMILES: C[C@@H]1/C=C\C(=O)[C@@H](O)[C@@H](O)C/C=C/c2cc(N3CCNC3=O)cc(O)c2C(=O)O[C@H]1C]
(Compound 034)
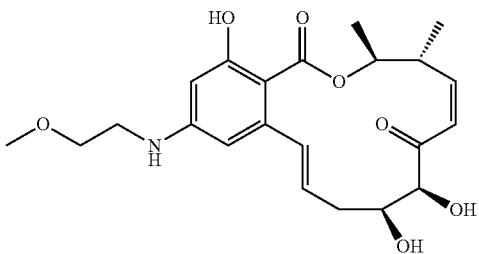
(Compound 041)
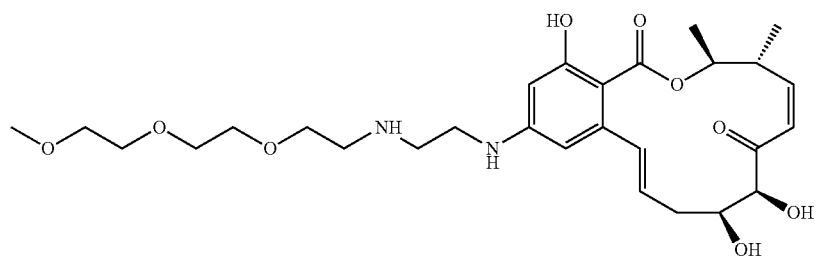
(Compound 045)
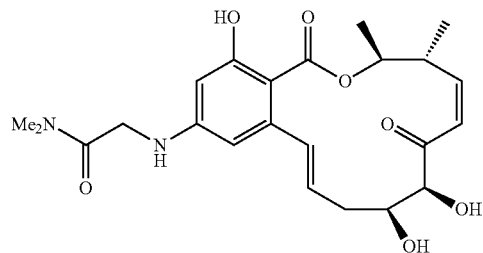
(Compound 046)
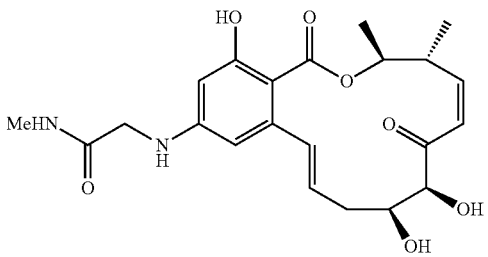
(Compound 047)
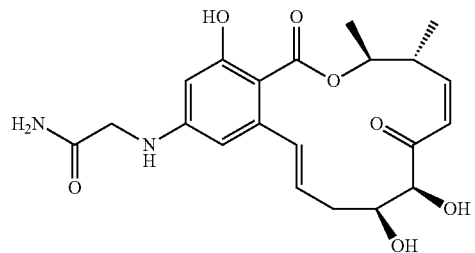
(Compound 048)
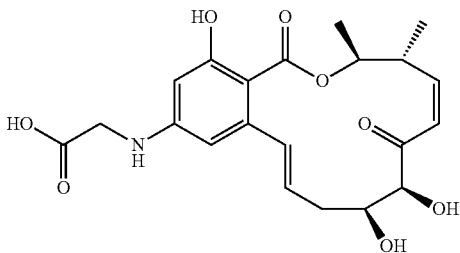
(Compound 054)
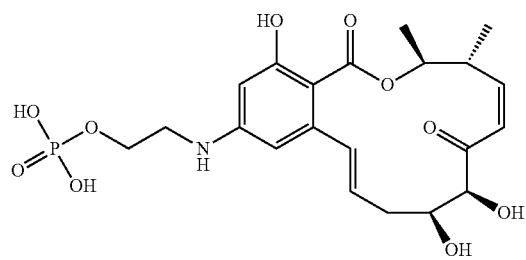
(Compound 065)
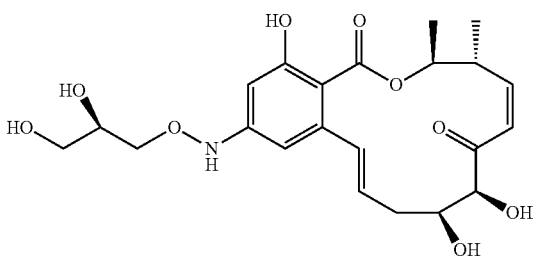

(Compound 076)
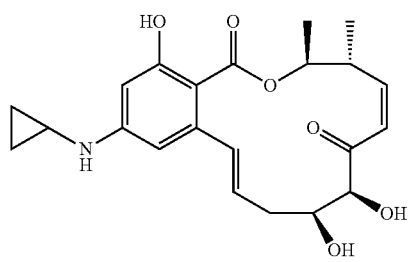
(Compound 114)
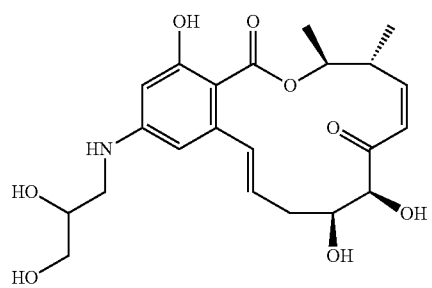
(Compound 122)
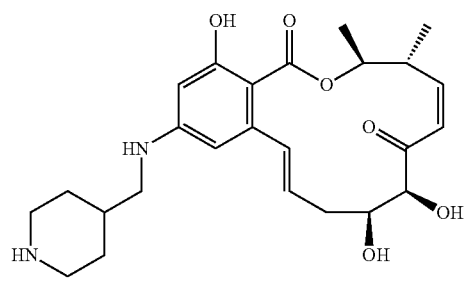
(Compound 127)
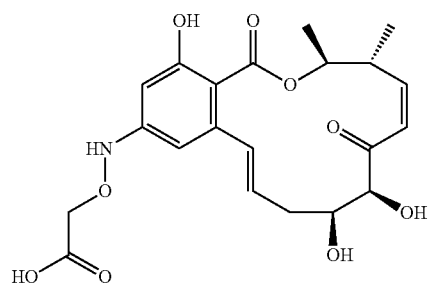
(Compound 137)
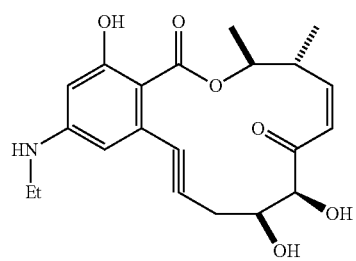
(Compound 144)
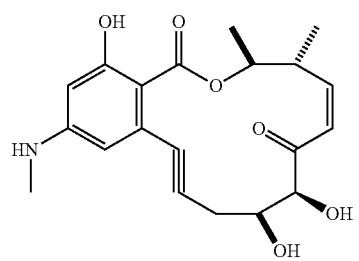
(Compound 155)
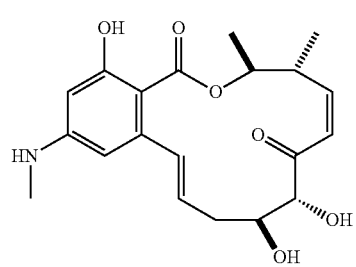
(Compound 156)
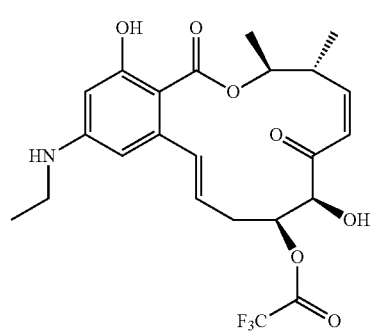
(Compound 157)
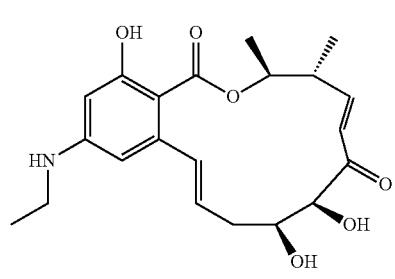
(Compound 158)
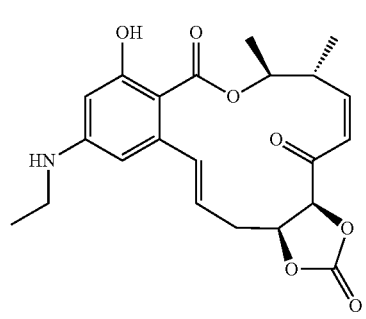
and pharmaceutically acceptable salts or esters thereof.

In some embodiments, the compounds of formula (I) include compounds of formula (II):

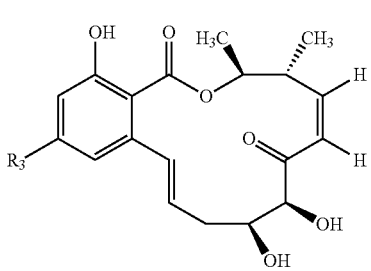
(II)

wherein
$R_3$ is —$NHR_b$, and $R_b$ is $C_1$-$C_3$ alkyl substituted with 0, 1, or 2 hydroxyl moieties; or a pharmaceutically acceptable salt or ester thereof.

In some embodiments, $R_3$ is an unsubstituted $C_{1-3}$ alkyl-amino. In some embodiments, $R_3$ is methylamino. In other embodiments, $R_3$ is ethylamino. In some embodiments, $R_3$ is a $C_{1-3}$ alkyl-amino substituted with one hydroxyl moiety. In some embodiments, $R_3$ is a $C_{1-3}$ alkyl-amino substituted with two hydroxyl moieties. The hydroxyl moieties can be on any of the carbons in the $C_{1-3}$ alkyl chain. Additionally, more than one hydroxyl moiety can be on a single carbon of the $C_{1-3}$ alkyl chain. In some embodiments, there is a hydroxyl moiety on the 2-carbon of the alkyl chain. In some embodiments, $R_3$ is hydroxyethylamino, e.g., 2-hydroxyethylamino. In other embodiments, $R_3$ is dihydroxypropylamino, e.g., 2,3-dihydroxypropylamino. In some embodiments, the $C_{1-3}$ alkyl is an acyclic $C_{1-3}$ alkyl chain.

In some embodiments, the compound is at least one compound selected from the group consisting of:

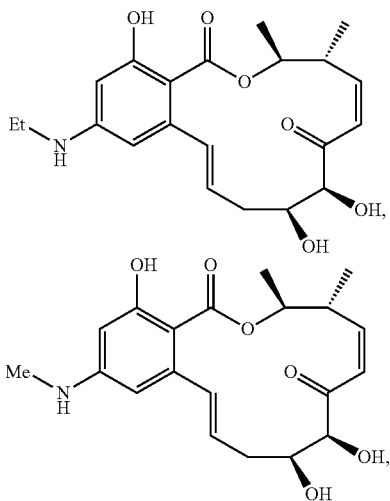

and pharmaceutically acceptable salts or esters thereof.

In at least one embodiment, the compound of formula (I) or (II) is not compound 029, compound 069, compound 091 or compound 106. In at least one embodiment, the compound of formula (I) or (II) is not a specific compound listed in US Application Publication No. 2004/0224936.

In some aspects, the present invention is directed to novel compounds of formula (I). All novel compounds of formula (I) described herein are included in the invention as compounds. In some embodiments, the present invention is directed to one or more of the compounds listed hereinbelow:

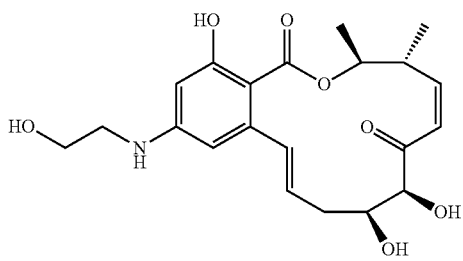
(Compound 029)

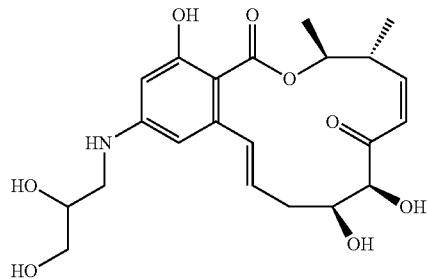
(Compound 114)

and pharmaceutically acceptable salts or estersprodrugs thereof.

In at least one embodiment, the compound of formula (I) or (II) is not compound 029, compound 091 or compound 106. In at least one embodiment, the compound of formula (I) or (II) is not a specific compound listed in US Application Publication No. 2004/0224936.

The compounds of formula (I) or (II) may include one or more asymmetric centers, and thus can exist in various isomeric forms, e.g., stereoisomers and/or diastereomers. Thus, compounds and pharmaceutical compositions of formula (I) or (II) may be in the form of an individual enantiomer, diastereomer or geometric isomer, or may be in the form of a mixture of stereoisomers. In certain embodiments, the compounds of formula (I) or (II) are enantiopure compounds. In certain other embodiments, mixtures of stereoisomers or diastereomers are provided.

Compounds of formula (I) or (II) may also have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers.

The compounds of formula (I) or (II) may further exist as one or a combination of crystalline forms, e.g., polymorphs, solvates or hydrates of compounds of formula (I) or (II). Various crystalline forms may be identified and/or prepared using different solvents, or different mixtures of solvents for recrystallization; by performing crystallizations at different temperatures; or by using various modes of cooling, ranging from very fast to very slow cooling during crystallizations. Different crystalline forms may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques.

Synthetic Methodology

Guidance for preparing compounds useful for practicing the present invention can be found, for example, in WO 05/023792 on pages 32-38 and WO 03/076424 on pages 28-36, as well as in the Examples presented therein. The contents of these applications are incorporated herein in their entireties by this reference. These references in combination with the information contained herein and the additional body of knowledge with regard to macrolide chemistry provides a person of skill in the art with guidance on synthetic strategies, protecting groups, and other materials and methods useful for the synthesis of the compounds of formula (I) or (II). For example, the above references provide background information on preparing compounds similar to the compounds described herein or relevant intermediates, as well as information on formulation, uses, and administration of such compounds.

Specific guidance and examples are also provided herein relating to various exemplary compounds and intermediates thereof. Accordingly, compounds of formula (I) or (II) and their preparation can be understood further by the examples herein, which illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

Starting materials and reagents useful in synthesizing the compounds of formula (I) or (II) are either commonly available from commercial suppliers or can be prepared by methods known to a person of ordinary skill in the art. The starting materials, intermediates, and compounds of formula (I) or (II) may be isolated and purified using conventional techniques, including filtration, distillation, crystallization, chromatography, and the like. They may be characterized using conventional methods, including physical constants and spectral data.

Exemplary syntheses of the compounds of formula (I) or (II) are provided in the Exemplification. It will be appreciated that the methods as described herein can be applied to each of the compounds as disclosed herein and equivalents thereof. Additionally, the reagents and starting materials are well known to those skilled in the art. Although the schemes described in the above-cited references depict certain exemplary compounds, it will be appreciated that the use of alternate starting materials will yield other analogs of formula (I) or (II).

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g., ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

On occasions where triphenylphosphine oxide was a major byproduct of the reaction, the reaction mixture was added directly to a large volume of well-stirred hexane. The resultant precipitate of triphenylphosphine oxide was removed by filtration and the filtrate processed in the usual manner.

Unless mentioned specifically, chromatographic purification was used. Chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. If solid, final products were submitted for biological testing in their solid form. If freeze-drying was desired or necessary, final compounds were generally dissolved in 50% aqueous acetonitrile or other appropriate solvent or mixture of solvents, filtered and transferred to vials, then freeze-dried under high vacuum before submission for biological testing.

Pharmaceutical Compositions

In another aspect of the present invention, pharmaceutical compositions are provided, which comprise any one of the compounds described herein (or a pharmaceutically acceptable salt or ester thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an anticancer agent approved for the treatment of cancer, as discussed in more detail herein, or it may be any one of a number of agents undergoing approval in the Food and Drug Administration that ultimately obtain approval for the treatment of cancer. It will also be appreciated that certain of the compounds of present invention can exist in free form for treatment, or where appropriate, as a pharmaceutically acceptable salt or ester thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of formula (I) or (II), or separately by reacting a free base or free acid function with a suitable reagent, as described generally below. For example, a free base function can be reacted with a suitable acid. Furthermore, where the compounds of formula (I) or (II) carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

As described above, the pharmaceutical compositions comprising compounds of formula (I) or (II) may additionally comprise a pharmaceutically acceptable carrier, which, as used herein, may include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of formula (I) or (II), such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Compositions comprising compounds of formula (I) or (II) may be formulated to have any concentration desired. In some embodiments, the composition is formulated such that it comprises at least a therapeutically effective amount. In some embodiments, the composition is formulated such that it comprises an amount that would not cause one or more unwanted side effects. In certain embodiments, compositions are formulated so that the compound is present at a concentration of between about 1 mg/mL and about 20 mg/mL; between about 1 mg/mL and about 15 mg/mL; between about 1 mg/mL and about 10 mg/mL; between about 2 mg/mL and about 9 mg/mL; between about 3 mg/mL and about 8 mg/mL; between about 4 mg/mL and about 7 mg/mL; between about 4 mg/mL and about 6 mg/mL. In certain embodiments, compositions are formulated such that the compound is present at a concentration of about 5 mg/mL.

Methods of Treatment

As discussed above, compounds of formula (I) or (II) exhibit a unique kinase inhibition profile. In some embodiments, based at least in part on this unique kinase inhibition profile, the compounds of formula (I) or (II) are useful for treating and/or preventing a variety of cancers, as discussed in further detail herein. Exemplary cancers include solid tumors, leukemias, lymphomas and myelomas such as multiple myeloma, neural cancer (e.g., glioma, neuroblastoma or retinoblastoma), leukemia (e.g., chronic myeloid leukemia, acute myeloid leukemia and/or acute lymphoblastic leukemia (ALL)), melanoma, pancreatic cancer, colorectal, thyroid and/or breast cancer. Accordingly, in some aspects, the present invention is directed to methods for the treatment and/or prevention of a cancer in a subject. For example, in some embodiments, the present invention is directed to methods for the treatment a SrcTK/MEK associated cancer in a subject. In other embodiments, the present invention is directed to methods for the treatment a TrkB/MEK associated cancer in a subject.

The methods of the present invention generally include administering an effective amount of a composition comprising a selected multikinase inhibitor to the subject, such that the cancer is treated. The selected multikinase inhibitor is chosen such that it has a unique multikinase inhibition profile, which targets or is otherwise associated with the cancer. For example, in some embodiments, the methods for treating a SrcTK/MEK associated cancer include administering a SrcTK/MEK inhibitor or another compound of formula (I) or (II) to a subject in need thereof. In other embodiments, the methods for treating a TrkB/MEK associated cancer include administering a TrkB/MEK inhibitor or another compound of formula (I) or (II) to a subject in need thereof.

Compounds of formula (I) or (II) have a unique multikinase inhibitory profile. For example, in some embodiments, compounds of formula (I) or (II) have inhibitory activity against a number of protein kinases including the Src tyrosine kinase family, MEK1, MEKK1, TrkB, BCR-ABL, FLT-3 and KDR kinases. Such compounds include, for example compounds 106 and 091, synthesis and certain biological properties of which are characterized in the Examples and Figures herein. This unique kinase inhibition profile suggests that compounds of formula (I) or (II) may have a broader therapeutic spectrum than selective MEK1 inhibitors.

In some embodiments, compounds of formula (I) or (II) include those which exhibit activity as inhibitors of MEK1; inhibitors of members of the Src family (e.g., Src, Lyn, Fyn, Lck, Yes); inhibitors of the NF-κB pathway through MEKK1 inhibition; inhibitors of TrkB; inhibitors of Bcr-Abl; inhibitors of FLT-3; and/or inhibitors of KDR.

In some embodiments, compounds of formula (I) or (II) include those which exhibit activity as inhibitors of MEK1. Accordingly, in some embodiments, an inhibitor of the present invention inhibits the activity of MEK1 by at least about 50% at a concentration of about 0.1 µM. In some embodiments, an inhibitor of the present invention inhibits the activity of MEK1 by at least about 51% at a concentration of about 0.1 µM. In some embodiments, an inhibitor of the present invention inhibits the activity of MEK1 by at least about 52% at a concentration of about 0.1 µM. In some embodiments, an inhibitor of the present invention inhibits the activity of MEK1 by at least about 53%, 54%, 55%, 56%, 57%, 58%, 59% or even 60% at a concentration of about 0.1 µM. In further embodiments, an inhibitor of the present invention inhibits the activity of MEK1 by at least about 85% at a concentration of about 1.0 µM. In still further embodiments, an inhibitor of the present invention inhibits the activity of MEK1 by at least about 86% at a concentration of about 1.0 µM. In other embodiments, an inhibitor of the present invention inhibits the activity of MEK1 by at least about 87%, 88%, 89%, 90%, 91%, 92%, 93%, 94%, or even 95% at a concentration of about 1.0 µM.

In some embodiments, the compounds of formula (I) or (II) inhibit MEK1. For example, in some embodiments, compounds of formula (I) or (II) exhibit $IC_{50}$ values less than 10 µM. In certain other embodiments, compounds of formula (I) or (II) exhibit $IC_{50}$ values less than 7.5 µM. In certain embodiments, compounds of formula (I) or (II) exhibit $IC_{50}$ values less than 5 µM. In certain other embodiments, compounds of formula (I) or (II) exhibit $IC_{50}$ values less than 2.5 µM, less than 1 µM, less than 0.75 µM, less than 0.5 µM, less than 0.25 µM, less than 0.1 µM, less than 75 nM or less than 50 nM. All ranges and values between the listed values are meant to be encompassed by the present invention.

The RAS-MAPK signaling pathway is also viewed as an important pathway for anticancer therapies, based upon its central role in regulating the growth and survival of cells from a broad spectrum of human tumors (FIG. 1). MEK1 is downstream of RAS and RAF proteins, which are often mutated and abnormally active in cancer. Tumors with elevated MEK signaling based on B-RAF mutations are thus attractive targets for using the compositions and methods of the present invention.

It is believed that the Ras/Raf/MEK/ERK signal transduction pathway regulates cell proliferation in diverse types of cells. Mutations in this pathway are often observed in transformed cell lines and frequently linked with human cancer. Davies et al. (*Nature* 417, 949-954, 2002), for example, identified B-RAF (an isoform of Raf) somatic missense mutations in 67% of malignant melanomas and 12% of colorectal cancers. All mutations were within the kinase domain with a single substitution, such as V600E (V599E), which accounts for 90% of these mutations. Mutated B-RAF proteins have elevated kinase activity, leading to constitutive activation of MEK, which then triggers ERK phosphorylation, and activates downstream pathway. It is believed that B-RAF mutated cancers, including melanoma, are attractive therapeutic targets for MEK inhibitors. The frequency of B-RAF mutations in melanoma and colorectal cancers, and the relative lack of effective therapies for advanced stages of these diseases suggest that inhibition of B-RAF activity may be an important new strategy in these cancer types. Moreover, in certain embodiments, B-RAF mutation can be used as molecular marker for "patient enrichment strategies" (i.e., for targeting B-RAF mutation carrying patients that will benefit from compositions and methods of the invention).

It was discovered by the present inventors that that compounds of formula (I) or (II) are potent inhibitors of B-RAF mutated cancer cell growth, and thus may selectively target B-RAF mutated cancers. As used herein, the term "B-RAF mutated cancer" refers to cancers that are associated with a particular point mutation of B-RAF. Accordingly, in some embodiments, the present invention provides compositions and methods for the treatment of B-RAF mutated cancers. Compounds of formula (I) or (II) include compounds which exhibit an antiproliferative activity against B-RAF mutated cancers; exhibit an antiproliferative effect on suitable cell lines maintained in vitro, or in animal studies using a scientifically acceptable model; and/or exhibit a favorable therapeutic profile (e.g., safety, efficacy, and stability).

In certain embodiments, compounds of formula (I) or (II) are useful for treating and/or preventing tumors with elevated MEK signaling, including, but not limited to, those with B-RAF mutations. A number of proteins have received attention as targets for elevated MEK signaling (see Table 1 below, modified from Table 1 in Nature Reviews Cancer: 4:937-947, 2004). Mutations in these proteins could lead to activation of MEK-ERK pathway. Specifically, ovarian cancer, thyroid cancer, colorectal cancer and melanoma show high frequencies of B-RAF mutations.

TABLE 1

| Tumor type | Pathway mutations in patient tumors |
| --- | --- |
| Colon | KRAS (45%), B-RAF (12%) |
| Pancreatic | KRAS (90%) |
| Ovarian | B-RAF (30%) |
| Melanoma | NRAS(15%), B-RAF (67%) |
| Non-small-cell lung | KRAS (35%) |
| Papillary thyroid | HRAS, KRAS and NRAS (60%); B-RAF (30-70%) |
| ALL, AML | NRAS (30%) |

Accordingly, in certain embodiments, the methods of the present invention include methods for treating and/or preventing tumors with elevated MEK signaling, including, but not limited to, those with B-RAF mutations. In certain embodiments, compounds of formula (I) or (II) are useful for treating and/or preventing melanoma, colorectal cancer, ovarian cancer and/or thyroid cancer. Accordingly, in certain embodiments, the methods of the present invention include methods for treating and/or preventing a B-RAF mutated cancer. In certain embodiments, compounds of formula (I) or (II) are useful for treating and/or preventing cancers carrying a a B-RAF mutation (e.g., a V600E mutation). In certain embodiments, the methods of the present invention include methods for treating and/or preventing a B-RAF mutated cancer carrying a V600E mutation.

In some embodiments, compounds of formula (I) or (II) include those which exhibit activity as inhibitors of a number of members of the Src tyrosine kinase family. Accordingly, in some embodiments, an inhibitor of the present invention inhibits the activity of at least five members of the Src tyrosine kinase family by at least about 40% at a concentration of about 0.1 µM. In other embodiments, an inhibitor of the present invention inhibits the activity of at least five members of the Src tyrosine kinase family by at least about 45% at a concentration of about 0.1 µM. In still other embodiments, an inhibitor of the present invention inhibits the activity of at least five members of the Src tyrosine kinase family by at least about 46%, 47%, 48%, 49%, 50%, 51%, 52%, 53%, 54%, or even 55% at a concentration of about 0.1 µM. In still other embodiments, an inhibitor of the present invention inhibits the activity of at least five members of the Src tyrosine kinase family by at least about 85% at a concentration of about 1.0 µM. In other embodiments, an inhibitor of the present invention inhibits the activity of at least five members of the Src tyrosine kinase family by at least about 90% at a concentration of about 1.0 µM. In still other embodiments, an inhibitor of the present invention inhibits the activity of at least five members of the Src tyrosine kinase family by at least about 91%, 92%, 93%, 94%, or even 95% at a concentration of about 1.0 µM. Exemplary members of the Src tyrosine kinase family include, but are not limited to cSrc, Fyn, Lyn, Lck and Yes.

In some embodiments, an inhibitor of the present invention inhibits the activity of at least four members of the Src tyrosine kinase family by at least about 40% at a concentration of about 0.1 µM. In other embodiments, an inhibitor of the present invention inhibits the activity of at least four members of the Src tyrosine kinase family by at least about 45% at a concentration of about 0.1 µM. In still other embodiments, an inhibitor of the present invention inhibits the activity of at least four members of the Src tyrosine kinase family by at least about 46%, 47%, 48%, 49%, 50%, 51%, 52%, 53%, 54%, or even 55% at a concentration of about 0.1 µM. In still other embodiments, an inhibitor of the present invention inhibits the activity of at least four members of the Src tyrosine kinase family by at least about 90% at a concentration of about 1.0 µM. In still other embodiments, an inhibitor of the present invention inhibits the activity of at least four members of the Src tyrosine kinase family by at least about 91%, 92%, 93%, 94%, 95%, 96%, or even 97% at a concentration of about 1.0 µM. In some embodiments, the four members of the Src tyrosine kinase family which are inhibited by the inhibitors, e.g., SrcTK/MEK inhibitors, of the present invention are cSrc, Fyn, Lyn and Lck.

In some embodiments, an inhibitor of the present invention inhibits the activity of at least three members of the Src tyrosine kinase family by at least about 55% at a concentration of about 0.1 µM. In other embodiments, an inhibitor of the present invention inhibits the activity of at least three members of the Src tyrosine kinase family by at least about 60% at a concentration of about 0.1 µM. In still other embodiments, an inhibitor of the present invention inhibits the activity of at least three members of the Src tyrosine kinase family by at least about 61%, 62%, 63%, 64%, 65%, 66%, 67%, 68% or even 69% at a concentration of about 0.1 µM. In still other embodiments, an inhibitor of the present invention inhibits the activity of at least three members of the Src tyrosine kinase family by at least about 93% at a concentration of about 1.0 µM. In still other embodiments, an inhibitor of the present invention inhibits the activity of at least three members of the Src tyrosine kinase family by at least about 94%, 95%, 96%, 97% or even 98% at a concentration of about 1.0 µM. In some embodiments, the three members of the Src tyrosine kinase family which are inhibited by the inhibitors, e.g., SrcTK/MEK inhibitors, of the present invention are selected from cSrc, Fyn, Lyn and Lck. For example, in some embodiments, the three members of the Src tyrosine kinase family which are inhibited by the compounds and/or inhibitors of the present invention are Fyn, Lyn and Lck. For example, in other embodiments, the three members of the Src tyrosine kinase family which are inhibited by the inhibitors of the present invention are cSrc, Fyn and Lck.

In some embodiments, an inhibitor of the present invention inhibits the activity of at least two members of the Src tyrosine kinase family by at least about 65% at a concentration of about 0.1 µM. In other embodiments, an inhibitor of the present invention inhibits the activity of at least two members of the Src tyrosine kinase family by at least about 70% at a concentration of about 0.1 µM. In still other embodiments, an inhibitor of the present invention inhibits the activity of at least two members of the Src tyrosine kinase family by at least about 71%, 72%, 73%, 74%, 75%, 76%, 77%, 78% or even 79% at a concentration of about 0.1 µM. In still other embodiments, an inhibitor of the present invention inhibits the activity of at least two members of the Src tyrosine kinase family by at least about 95% at a concentration of about 1.0 µM. In still other embodiments, an inhibitor of the present invention inhibits the activity of at least two members of the Src tyrosine kinase family by at least about 96%, 97%, 98% or even 99% at a concentration of about 1.0 µM. In some embodiments, the two members of the Src tyrosine kinase family which are inhibited by the compounds and/or inhibitors, e.g., SrcTK/MEK inhibitors, of the present invention are Fyn and Lck.

In some embodiments, an inhibitor of the present invention inhibits the activity of at least one member of the Src tyrosine kinase family by at least about 70% at a concentration of about 0.1 µM. In other embodiments, an inhibitor of the present invention inhibits the activity of at least one member of the Src tyrosine kinase family by at least about 75% at a concentration of about 0.1 µM. In still other embodiments, an inhibitor of the present invention inhibits the activity of at least one member of the Src tyrosine kinase family by at least about 76%, 77%, 78%, 79%, 80%, 81%, 82%, 83%, 84% or even 85% at a concentration of about 0.1 µM. In still other embodiments, an inhibitor of the present invention inhibits the activity of at least one member of the Src tyrosine kinase family by at least about 97% at a concentration of about 1.0 µM. In still other embodiments, an inhibitor of the present invention inhibits the activity of at least one member of the Src tyrosine kinase family by at least about 98%, 99% or even 100% at a concentration of about 1.0 µM. In some embodiments, the one member of the Src tyrosine kinase family which is inhibited by the compounds and/or inhibitors, e.g., SrcTK/MEK inhibitors, of the present invention is selected from Fyn and Lck.

The skilled artisan would understand that any or all of the above-indicated Src tyrosine kinase profiles can be accurate with regard to one single compound. That is, a single inhibitor of the present invention at a concentration of about 0.1 µM can inhibit five members of the Src tyrosine kinase family by at least about 45%, four members by at least about 50%, three members by at least about 60%, two members by at least about 70% and one member by at least about 75%. It is also understood that, in the foregoing scenario, the one member of the Src tyrosine kinase family which is inhibited by at least 75% may also be one of the five members which are inhibited by at least 45%. Thus, in an exemplary case, a compound of formula (I) or (II) may have the following profile at a concentration of about 0.1 µM: 50% inhibition of cSrc, 31% inhibition of Fyn, 42% inhibition of Lyn, 73% inhibition of Lck and 56% inhibition of Yes.

Without wishing to be bound by any particular theory, it is also believed that members of the Src tyrosine kinase family may also be useful in inhibition of the metastatic process. For example, Src has been associated with the establishment of metastasis through cell motility and invasion. Accordingly, in some embodiments, the methods of the present invention include methods for inhibition of a metastatic process in a subject.

Recently, it has also been shown that Lyn, a Src tyrosine kinase family member, plays an important role in the mechanism of imatinib mesylate resistance. Without wishing to be bound to any particular theory, it is also believed that certain members of the Src tyrosine kinase family are associated with chronic myeloid leukemia and/or colorectal cancer. Accordingly, in some embodiments, the present invention is directed to methods for treating chronic myeloid leukemia and/or colorectal cancer. Moreover, certain members of the Src tyrosine kinase family have been associated with imatinib mesylate resistance, e.g., in chronic myeloid leukemia. Accordingly, the present invention is directed to methods for treating cancers which are resistant to imatinib and pharmaceutically acceptable salts and esters thereof, e.g., imatinib mesylate. In some embodiments, the present invention is directed to imatinib mesylate resistant chronic myeloid leukemia.

As used herein, the term "resistance" refers to the occasion where a subject becomes less responsive to a therapeutic agent over time. Accordingly, in some embodiments, resistance to a therapeutic agent refers to a subject's complete non-responsiveness to the agent (e.g., where rate of growth of a tumor is not inhibited) as compared to the absence of administration of the agent. In some embodiments, resistance to a therapeutic agent refers to a subject's partial non-responsiveness to the agent (e.g., where rate of growth of a tumor is inhibited only to a very low degree) as compared to the absence of administration of the agent. The quality of being resistant to a therapeutic agent is a highly variable one, with different tumors exhibiting different levels of "resistance" to a given therapeutic agent, under different conditions. In other embodiments, resistance to a therapeutic agent refers to a subject's complete or partial non-responsiveness to the agent as compared to a previous administration of the agent. In still other embodiments, resistance to a therapeutic agent refers to a subject who is being administered the agent, and desires additional therapy.

In some embodiments, compounds of formula (I) or (II) include those which exhibit activity as inhibitors of TrkB. Accordingly, in some embodiments, an inhibitor of the present invention inhibits the activity of TrkB by at least about 65% at a concentration of about 0.1 µM. In some embodiments, an inhibitor of the present invention inhibits the activity of TrkB by at least about 70% at a concentration of about 0.1 µM. In some embodiments, an inhibitor of the present invention inhibits the activity of TrkB by at least about 75% at a concentration of about 0.1 µM. In some embodiments, an inhibitor of the present invention inhibits the activity of TrkB by at least about 76%, 78%, 80%, 82%, 84%, 86% or even 88% at a concentration of about 0.1 µM. In further embodiments, an inhibitor of the present invention inhibits the activity of TrkB by at least about 85% at a concentration of about 1.0 µM. In still further embodiments, an inhibitor of the present invention inhibits the activity of TrkB by at least about 90% at a concentration of about 1.0 µM. In other embodiments, a compound or inhibitor of the present invention inhibits the activity of TrkB by at least about 91%, 92%, 93%, 94%, 95%, 96%, 97%, or even 98% at a concentration of about 1.0 µM.

Without wishing to be bound by any particular theory, it is believed that TrkB, the nerve derived growth factor (NDGF) receptor, may play important roles in proliferation and survival of neural cancers such as glioma, retinoblastoma and neuroblastoma. Moreover, it is also believed that TrkB activity may be associated with pancreatic cancer. For example, signal transduction through TrkB may cause severe pain in patients with pancreatic cancer. Accordingly, in some embodiments, the methods of the present invention include methods for treating and/or preventing glioma, retinoblastoma and neuroblastoma. In other embodiments, the methods of the present invention include methods for treating and/or preventing pancreatic cancer.

In certain embodiments, compounds of formula (I) or (II) or active metabolites thereof exhibit high penetration through the blood brain barrier (BBB). When used with regard to the amount which crosses the BBB, the term "a compound of formula (I) or (II)" is intended to include active metabolites thereof. Accordingly, in some embodiments, the methods of the present invention include methods for treating a central nervous system tumor in a subject in need thereof. The method generally includes administration of a composition as described herein (including a compound of formula (I) or (II)) such that at least a portion of the compound of formula (I) or (II) penetrates the blood brain barrier, as demonstrated in a suitable animal. In some embodiments, at least about 20% of the compound of formula (I) or (II) penetrates the blood brain barrier, based upon a ratio of amount of a compound of formula (I) or (II) in the brain to amount of a compound of formula (I) or (II) in the plasma, as demonstrated in a suitable animal. In some embodiments, at least about 40% of the compound of formula (I) or (II) penetrates the blood brain barrier, based upon a ratio of amount of the compound in the brain to amount of a compound of formula (I) or (II) in the plasma, as demonstrated in a suitable animal. In other embodiments, at least about 50% of the compound of formula (I) or (II) penetrates the blood brain barrier, as demonstrated in a suitable animal. In still other embodiments, at least about 55%, 60%, 65%, 70%, 75%, 80%, 85%, 90%, 95% or even 100% of the compound of formula (I) or (II) penetrates the blood brain barrier, as demonstrated in a suitable animal. Thus, whether a compound of formula (I) or (II) penetrates the blood brain barrier of a subject (e.g., a human) can be determined in a suitable animal (e.g., a rodent, such as a mouse). It is to be noted that the percentages are calculated based upon the area under the concentration-time curve for a given time period ($AUC_{0-t}$) in the brain versus the plasma. Accordingly, the percentages represent a ratio of concentrations. That is, if ($AUC_{0-24h}$) for a compound is 20 ng/mL in the brain and 80 ng/mL in the plasma, then the percentage of the compound that penetrates the blood brain barrier is 20% (20 ng/ml in the brain divided by the total concentration of (20 ng/mL+80 ng/mL)). In some embodiments, the percentages are calculated based upon the area under the concentration-time curve for the time period from t=0 (time of dosing) to the last quantifiable concentration point, i.e., ($AUC_{0-last}$). Exemplary central nervous system tumors include, but are not limited to, brain tumors, glioma and neuroblastoma.

In some embodiments, the inhibitors of the present invention inhibit Bcr-Abl and/or FLT-3. Bcr-Abl and FLT-3 are known targets for leukemia treatment. Accordingly, in certain embodiments, the methods of the present invention include methods for treating and/or preventing leukemia. In some embodiments, an inhibitor of the present invention inhibits the activity of Bcr-Abl by at least about 40% at a concentration of about 0.1 µM. In some embodiments, an inhibitor of the present invention inhibits the activity of Bcr-Abl by at least about 45% at a concentration of about 0.1 µM. In some embodiments, an inhibitor of the present invention inhibits the activity of Bcr-Abl by at least about 46%, 47%, 48%, 49%, 50%, 52% or even 54% at a concentration of about 0.1 µM. In further embodiments, an inhibitor of the present invention inhibits the activity of Bcr-Abl by at least about 75% at a concentration of about 1.0 µM. In still further embodiments, an inhibitor of the present invention inhibits the activity of Bcr-Abl by at least about 80% at a concentration of about 1.0 µM. In other embodiments, an inhibitor of the present invention inhibits the activity of Bcr-Abl by at least about 81%, 82%, 83%, 84%, 85%, 86%, 88%, or even 90% at a concentration of about 1.0 µM. In some embodiments, an inhibitor of the present invention inhibits the activity of FLT-3 by at least about 45% at a concentration of about 0.1 µM. In some embodiments, an inhibitor of the present invention inhibits the activity of FLT-3 by at least about 50% at a concentration of about 0.1 µM. In some embodiments, an inhibitor of the present invention inhibits the activity of FLT-3 by at least about 52%, 54%, 56%, 58%, 60%, 65% or even 70% at a concentration of about 0.1 µM. In further embodiments, an inhibitor of the present invention inhibits the activity of FLT-3 by at least about 85% at a concentration of about 1.0 µM. In still further embodiments, an inhibitor of the present invention inhibits the activity of FLT-3 by at least about 90% at a concentration of about 1.0 µM. In other embodiments, an inhibitor of the present invention inhibits the activity of FLT-3 by at least about 91%, 92%, 93%, 94%, 95% or even 96% at a concentration of about 1.0 µm.

Compounds and compositions of formula (I) or (II) are useful for treating a FLT3 mutated cancer in a subject. As used herein, FLT3 mutated cancers are cancers associated with activation mutations in FLT3 which activate the kinase function of the encoded protein.

The FMS-like tyrosine kinase 3 gene (FLT3 or FLT-3) encodes a member of the type III platelet-derived growth factor family of receptor tyrosine kinases. FLT3 is expressed in many hematological malignancies, and its signaling cascade has been implicated in multiple tumorigenic pathways. For example, FLT3 mutations can lead to activation of the STATS and Ras/MAPK pathways. (Parcells et al., *Stem Cells,* 24(5); 1174-1184 (2006))

Activation mutations of FLT3 have been reported in leukemia patients. For example, the two most frequent types of FLT3 mutations associated with adult cytogenetically normal acute myeloid leukemia (CN-AML) are: (1) internal tandem duplications (ITD) in the juxtamembrane domain (present in approximately 30% of CN-AML patients); and (2) mutations in the second tyrosine kinase domain (TKD) (present in approximately 7% of CN-AML patients). Common TKD mutations include nucleotide substitutions, deletions, or insertions affecting amino acid residues D835 and/or I836 in the activation loop (A-loop) of the TKD. The D835Y substitution constitutes approximately 50% of TKD mutations reported. Y842C, K663Q, and V592A mutations have also been observed. FLT3 proteins with these ITD or TKD mutations exhibit ligand-independent FLT3 dimerization and constitutive activation through autophosphorylation. (Whitman et al., *Blood,* 111(3):1552-1559 (2008); see also, Parcells et al., *Stem Cells,* 24(5); 1174-1184 (2006)) Activation mutations of FLT3 have been associated with an inferior prognosis. (Stone, *Blood,* 1041: 915-916 (2004))

In some embodiments, the compounds of formula (I) or (II) can inhibit FLT3 mutated cancer cell growth. In certain embodiments, the compounds can exhibit antiproliferative activity against FLT3 mutated cancers; an antiproliferative effect on suitable cell lines maintained in vitro or in animal models (e.g., comprising an activation mutation of FLT3); and/or a favorable therapeutic profile (e.g., safety, efficacy, and stability).

Accordingly, the invention provides a method of treating a FLT3 mutated cancer in a subject in need thereof, comprising administering a therapeutically effective amount of a compound or composition of formula (I) or (II) to said subject. In certain embodiments of the method, a compound of formula (I) or (II) or a composition comprising same is used for treating cancers carrying a FLT3 mutation. In certain embodiments of the method, the FLT3 mutated cancer carries an internal tandem duplication (ITD) in the juxtamembrane domain. In certain embodiments of the method, the FLT3 mutated cancer carries a mutation in the second tyrosine kinase domain, for example, in the activation loop. In certain embodiments of the method, the FLT3 mutated cancer carries a mutation of residue D835 and/or a mutation of residue I836, for example, a D835Y mutation. In certain embodiments of the method, the FLT3 mutated cancer carries a Y842C, K663Q or V592A mutation. Moreover, in certain embodiments, FLT3 mutation can be used as molecular marker for "patient enrichment strategies" in order to identify patients for treatment.

As noted above, activation mutations of FLT3 have been reported in leukemia patients, and the invention provides a method of treating leukemia in a subject, comprising administering a therapeutically effective amount of a compound or composition of formula (I) or (II) to the subject. In one embodiment of the method the leukemia is acute myeloid leukemia (AML).

Without wishing to be bound by any particular theory, it is believed that the unique multikinase inhibition profiles of the compounds of formula (I) or (II) indicates that such compounds can be useful in targeting hematological malignancies as well as solid tumors. (See, e.g., Warmuth, M et al. *Ann Hematol.* 78(2):49-64 (1999) and Harder, K W et al. *Immunity.* 15(4):603-15 (2001).) In certain embodiments, compounds of formula (I) or (II) exhibit anticancer activity with evidence of apoptosis in B-cell non-Hodgkin's lymphoma, possibly by inhibition of MEKK1, an upstream molecule for NF-κB activation, which leads to chemoresistance to apoptosis. Accordingly, in certain embodiments, the methods of the present invention include methods for treating and/or preventing hematologic malignant cancer cell growth such as multiple myeloma and B-cell lymphomas.

In still other embodiments, the compounds of formula (I) or (II) inhibit the growth of tumor cell lines in vitro. For example, in some embodiments, compounds of formula (I) or (II) exhibit $IC_{50}$ values less than 10 µM. In certain other embodiments, compounds of formula (I) or (II) exhibit $IC_{50}$ values less than 7.5 µM. In certain embodiments, compounds of formula (I) or (II) exhibit $IC_{50}$ values less than 5 µM. In certain other embodiments, compounds of formula (I) or (II) exhibit $IC_{50}$ values less than 2.5 µM, less than 1 µM, less than 0.75 µM, less than 0.5 µM, less than 0.25 µM, less than 0.1 µM, less than 75 nM or less than 50 nM. All ranges and values between the listed values are meant to be encompassed by the present invention.

In some embodiments, compounds of formula (I) or (II) cause tumor regression in vivo. In certain exemplary embodiments, compounds of formula (I) or (II) cause tumor regression in vivo in suitable mouse tumor xenograft models. As demonstrated in the Examples herein, certain compounds of formula (I) or (II) have strong in vivo efficacy in multiple xenografts by i.v. dosing. In certain embodiments, compounds of formula (I) or (II) cause reduction of tumor size to below 70% of the size at the start of compound administration in a suitable cancer cell xenograft model. In certain embodiments, compounds of formula (I) or (II) cause reduction of tumor size to below 65% of the size at the start of compound administration in a suitable cancer cell xenograft model. In certain embodiments, compounds of formula (I) or (II) cause reduction of tumor size to below 60% below 55% or below 50% of the size at the start of compound administration in a suitable cancer cell xenograft model. All values and ranges between the listed values are intended to be encompassed by the present invention.

In certain embodiments, compounds of formula (I) or (II) cause inhibition of tumor growth in vivo. For example, in some embodiments, compounds of formula (I) or (II) cause significant inhibition of tumor growth in suitable cancer cell xenograft models. In certain embodiments, compounds of formula (I) or (II) cause inhibition of tumor growth in treated animals by >50% compared to that of control animals (i.e., "treated" tumor size<50% "control" tumor size; or T/C value<50%) in suitable cancer cell xenograft models. In certain embodiments, compounds of formula (I) or (II) have T/C values<70%. In certain embodiments, compounds of formula (I) or (II) have T/C values<65%, <60%, or <55%. All values and ranges between the listed values are intended to be encompassed by the present invention.

Exemplary compounds, including F152 (natural product), were tested for their growth inhibitory activity in MDA-MB-435 and other cancer cell lines. Several compounds were shown to have remarkable cancer cell growth inhibitory activities (e.g., with nM $IC_{50}$ values). Based on biological characterization in various relevant assays (See Examples and Figures), it is believed that certain compounds of formula (I) or (II) exhibit potent cell growth inhibition especially toward B-RAF mutated cells; possess a multikinase inhibitory profile, including MEK1, MEKK1, Src kinase family tyrosine kinase, TrkB, FLT-3, and Bcr-Abl; have potent in vivo antitumor activity in multiple tumor xenografts including "major tumor types" without significant body weight loss; have projecting efficacy in Q4D and/or Q7D iv dosing in subjects; have signs of better efficacy than certain MEK1 inhibitors known in the art in combination therapy; be able to penetrate the blood-brain barrier, which renders the compounds potentially useful for treating/preventing brain tumors; be potentially useful for targeted therapy based on possible biomarkers for specific cancers.

In some embodiments, compounds of formula (I) or (II) are natural product-based multikinase inhibitors that are highly effective against cancer-relevant kinases including the Src family (Src, Lyn, Fyn, Lck, Yes), NF-kB pathway through MEKK1 inhibition, TrkB, Bcr-Abl, FLT-3 and KDR, as well as B-RAF mutated cancer cells. This unique profile may offer the compounds of formula (I) or (II) a competitive advantage in the clinic, for example low levels of cytotoxicity against non-dividing cells, and therefore potentially good therapeutic margin.

In certain embodiments, compounds of formula (I) or (II) exhibit synergy in combination therapy with another anticancer agent. In certain exemplary embodiments, compounds of formula (I) or (II) exhibit synergy in combination therapy with SN-38 (active metabolite of CPT-11). In some embodiments, compounds of formula (I) or (II) are more effective in tumor cell killing when used in combination with another anticancer agent (e.g., SN-38, an active metabolite of CPT-11—see, e.g., Example 9).

In certain embodiments, compounds of formula (I) or (II) exhibit inhibitory activity against NF-κB. As such, they are useful for treating and/or preventing cancers related to NF-κB activity. In certain embodiments, compounds of formula (I) or (II) are useful for treating and/or preventing hematologic malignancies such as multiple myeloma and/or B cell lymphomas. In some embodiments, compounds of formula (I) or (II) are beneficial for cancer patients showing resistance in conventional chemotherapy via NF-κB activation.

According to the present invention, the inventive compounds may be assayed in any of the available assays known in the art for identifying compounds having, for example, MEK1 inhibitory activity, protein kinase inhibitory activity, NF-κB activation inhibitory activity and cancer cell growth inhibitory activity. For example, the assay may be cellular or non-cellular, in vivo or in vitro, high- or low-throughput format, etc.

Dosages and Modes of Administration

It will be appreciated that the compounds and compositions, according to the method of the present invention, may be administered using any amount and any route of administration effective for the treatment of cancer. Thus, the expression "effective amount" as used herein, refers to a sufficient amount of agent to inhibit the growth of tumor cells, or refers to a sufficient amount to reduce the effects of cancer. The exact amount required will vary from subject to subject, depending on the species, age, and general condition of the subject, the severity of the diseases, the particular anticancer agent, its mode of administration, and the like. The compounds of formula (I) or (II) are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of formula (I) or (II) will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

In certain embodiments, the compounds or compositions are administered systemically. As used herein, "systemic administration" refers to any means by which a compound of formula (I) or (II) can be made systemically available. For example, systemic administration encompasses enteral (e.g., oral and rectal) and parenteral methods of administration. In certain embodiments, systemic administration encompasses intravenous administration, intraperitoneal administration, intramuscular administration, intracoronary administration, intraarterial administration (e.g., into a carotid artery), intradermal administration, subcutaneous administration, transdermal delivery, intratracheal administration, subcutaneous administration, intraarticular administration, intraventricular administration, inhalation (e.g., aerosol), intracerebral, nasal, naval, oral, intraocular, pulmonary administration, impregnation of a catheter, by suppository and direct injection into a tissue, or systemically absorbed topical or mucosal administration. Mucosal administration includes administration to the respiratory tissue, e.g., by inhalation, nasal drops, ocular drop, etc.; anal or vaginal routes of administration, e.g., by suppositories; and the like. In certain exemplary embodiments, the compositions of formula (I) or (II) are administered intravenously.

It will be appreciated that the inventive compound may be administered systemically in dosage forms, formulations or e.g. suitable delivery devices or implants containing conventional, non-toxic pharmaceutically acceptable carriers and adjuvants such that the compound effectiveness is optimized. For example, the inventive compound may be formulated together with appropriate excipients into a pharmaceutical composition, which, upon administration of the composition to the subject, systemically releases the active substance in a controlled manner. Alternatively, or additionally, compound dosage form designs may be optimized so as to increase the compound effectiveness upon administration. The above strategies (i.e., dosage form design and rate control of drug input), when used alone or in combination, can result in a significant increase in compound effectiveness and are considered part of the invention.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, creams or drops), bucally, as an oral or nasal spray, or the like. In certain embodiments, the compounds of formula (I) or (II) may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally. In certain embodiments, administration is conducted by intermittent dosing one to three times a week.

In certain embodiments, the compounds of formula (I) or (II) may be administered at dosage levels of about 1-500 mg/m$^2$; e.g., about 5-400 mg/m$^2$; about 10-250 mg/m$^2$ one or more times a week to obtain the desired therapeutic effect. Specific ranges and values which fall between the listed ranges are also contemplated by the present invention.

In certain embodiments, the compounds of formula (I) or (II) may be administered intravenously one to three times a week. In certain embodiments, the compounds of formula (I) or (II) may be administered intravenously once a week. In certain embodiments, the compounds of formula (I) or (II) may be administered intravenously twice a week.

Administration of the compounds of formula (I) or (II) can be continuous over a specified period of time, can be intermittent or can be in a bolus. For example, in one embodiment, the compounds of formula (I) or (II) are formulated for intravenous use and can be administered to patients as a slow injection, e.g., over about 30 minutes to about 3 hours. In another embodiment, the compounds of formula (I) or (II) are formulated for intravenous use and can be administered to patients as a bolus injection, also referred to as IV (intravenous) push. In still another embodiment, the compounds of formula (I) or (II) are formulated for intravenous use and can be administered to patients in any number of discreet injections that are separated by time periods which may or may not be equivalent.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions, which can be used, include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of formula (I) or (II) by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of formula (I) or (II) and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

In certain exemplary embodiments, pharmaceutically acceptable topical formulations of the invention are contained in a patch that is applied adjacent to the area of skin to be treated. As used herein a "patch" comprises at least a topical formulation and a covering layer, such that, the patch can be placed over an area of skin. Any patch known in the art can be used in conjunction with the compositions and methods of the present invention.

In certain exemplary embodiments, the inventive compounds may be used as coating for stents. Guidance for using compounds of formula (I) or (II) in this capacity can be found, for example, in WO 05/023792.

Coadministration

It will also be appreciated that the compounds and pharmaceutical compositions of formula (I) or (II) can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive compounds of formula (I) or (II) include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Other anticancer agents that may be used in combination with compounds or compositions of formula (I) or (II), include a therapeutic antibody or antibody fragment, such as a human, humanized, chimeric, and/or single-chain antibody or antibody fragment (e.g., Fv, Fab, Fab', F(ab')$_2$, dAb) or the like (e.g., Trastuzumab, Bevacizumab, Cetuximab, Rituximab). For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe—See Appendix A).

In certain embodiments, the pharmaceutical compositions comprising compounds of formula (I) or (II) further comprise one or more additional therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Treatment Kits

In some aspects, the present invention provides a kit for carrying out the methods in accordance with the present invention. In general, the pharmaceutical pack or kit comprises one or more of the ingredients of the pharmaceutical compositions of formula (I) or (II). For example, the kit may include one or more containers filled (completely or partially) with a compound or composition of formula (I) or (II). Such kits are suited for, e.g., the delivery of solid oral forms such as tablets or capsules. In some embodiments, the kit includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. In some embodiments, the kit includes instructions or directions for the use of the other components of the kit. In some embodiments, the kit comprises a composition comprising a compound of formula (I) or (II) and a second therapeutic agent, with instructions on coadministration of the two agents. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The contents of all references, patents, and patent applications cited throughout this application are hereby incorporated by reference.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

The schemes listed herein are merely illustrative of some methods by which the compounds of this invention can be synthesized, and it is to be understood that various modifications to these schemes can be made.

Example 1

Synthesis of Compounds

General Reaction Procedures:

Unless mentioned specifically, reaction mixtures were stirred using a magnetically driven stirrer bar. An inert atmosphere generally refers to either dry argon or dry nitrogen. Reactions were monitored either by thin layer chromatography, by proton nuclear magnetic resonance (NMR) or by high-pressure liquid chromatography (HPLC), of a suitable sample of the reaction mixture.

Common abbreviations include m-CPBA: meta-chloroperbenzoic acid; DDQ: 2,3-Dichloro-5,6-dicyano-1,4-benzoquinone; DEAD Diethyl azodicarboxylate; DIBAL-H: Diisobutyl aluminum hydride; DMAP: N,N-Dimethylaminopyridine; DMF: N,N-Dimethylformamide; HMPA: Hexamethylphosphoramide; LDA: Lithium diisopropyl amide; LiHMDS: Lithium bis(trimethylsilyl)amide; PCC: Pyridinium chlorochromate; TBAF: Tetrabutylammonium fluoride; THF: Tetrahydrofuran; CH$_2$Cl$_2$ or DCM: methylene chloride; MPM: para-methoxy benzyl; Boc: tert-butyl oxy carbamate; TfOH: trifluoromethane sulfonic acid; Tf2O: trifluoromethane sulfonic acid anhydride; TFA: trifluoroacetic acid; and TFAA: trifluoroacetic acid anhydride.

Synthesis of a Common Starting Material
Compound 003:

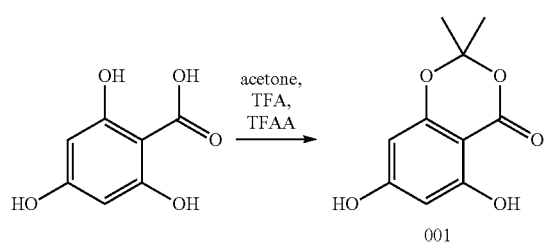

To a solution of trihydroxy-benzoic acid (120 g) in 350 mL of acetone, 500 mL of TFA (trifluoro acetic acid) was added at 40° C. under stirring. After 1 h at 40° C., 300 mL of TFAA (trifluoro acetic anhydride) was added. The mixture was heated for 3 days. The mixture was distilled under house vacuum at 50° C. to remove solvents. The crude product was then diluted with 4 L of CH$_2$Cl$_2$, washed with water, sat. NaHCO$_3$, dried and concentrated to give 85 g of semi pure solid 001. The solid was crystallized in EtOH (1 g/2 mL) to give 20 g of pure crystal. The mother liquor was then purified by silica gel with CH$_2$Cl$_2$ to 5% MeOH/CH$_2$Cl$_2$ to give 55 g of additional product 001.

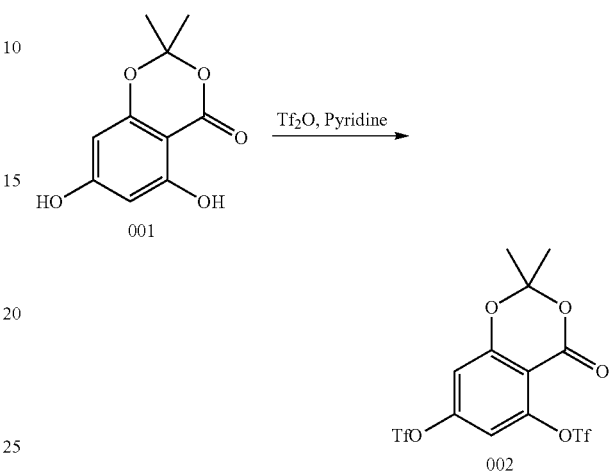

To a solution of 001 (50 g, 238 mmol) in 156 mL of pyridine, Tf$_2$O (100 mL, 595 mmol, 2.5 eq.) was added at 0° C. in 3 h. Then it was warmed to room temperature and stirred for 2 h. The reaction mixture was diluted with water. The mixture was filtered, and the solid on the filter was washed with water, dried under vacuum to give 100 g of solid 002.

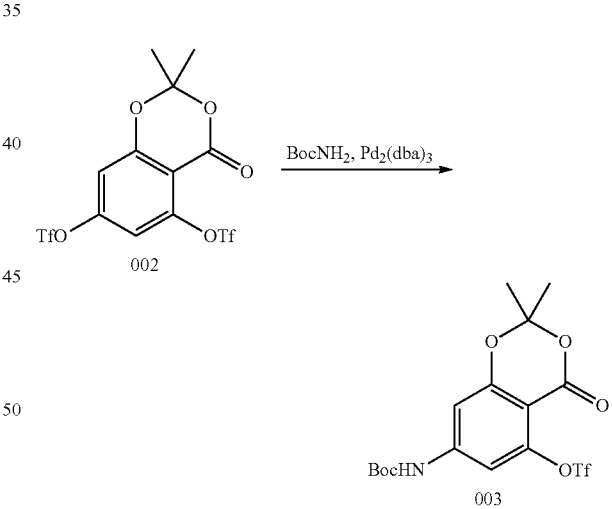

Ditriflate 002 (45.35 g), BocNH$_2$ (17.22 g), Pd$_2$(dba)$_3$ (4.38 g) and Pt-Bu$_3$ (4.38 g) were mixed in 150 mL of toluene. Tri-ethylamine (26.92 mL) was added to this mixture and the reaction was heated under inert atmosphere at 80° C. for 4 h. The crude reaction mixture was cooled and filtered through a pad of celite. The filtrates were concentrated and purified on silica gel with Hex/EtOAc, 9:1, 4:1 to give 28.3 g of desired product, compound 003.

Synthesis of Common Intermediates

Intermediates 009 and 010 were synthesized as illustrated in Scheme 1.

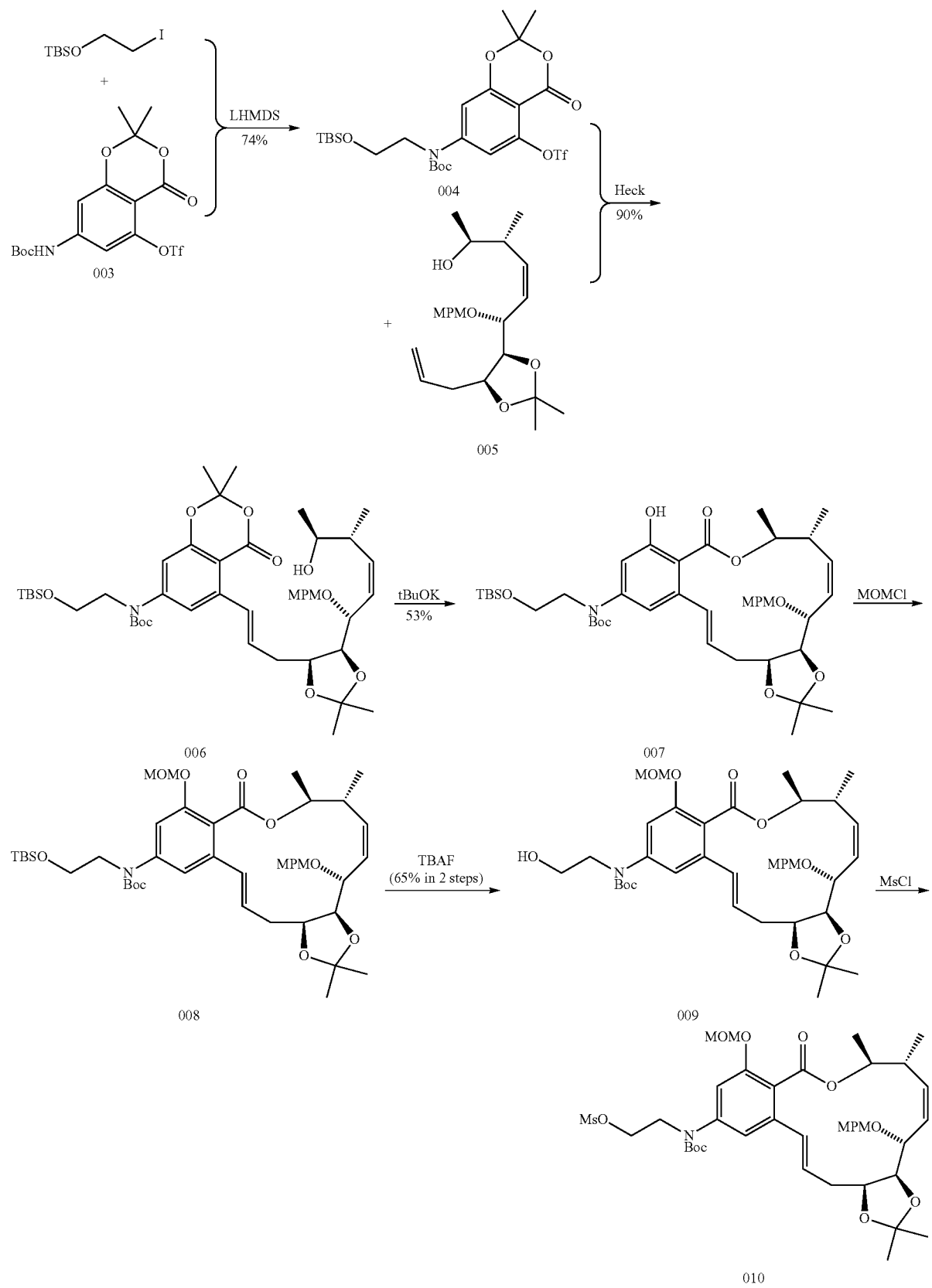
Scheme 1

Compound 004:

Compound 003 (18.6 g, 42.1 mmol) in DMPU (42 ml) was cooled to 0° C. A solution of lithium hexamethyldisilylamide in THF (1.0 M, 47 ml, 47 mmol) was added slowly using a syringe pump maintaining internal temperature below 5° C. The resulting dark red-brown solution was stirred at 0° C. for an additional 1 hr 20 min. TBSO-ethyliodide (16.0 g, 55.9 mmol) was added via canula over 10 min, while maintaining internal temperature below 3° C. The reaction mixture was stirred at 0° C. for an additional 10 min and subsequently stirred at room temperature over night. The reaction was quenched with saturated sodium bicarbonate (30 ml) and the solvent was removed under reduced pressure. The residue was purified by flash chromatography eluting with 5% EtOAc/Hexanes to obtain 18.5 g (74%) pure desired product, compound 004. $^1$H-NMR (400 MHz, C6D6) δ: 7.20 (d, J=2.0 Hz, 1H), 3.59 (t, J=5.2 Hz, 2H), 3.41 (d, J=5.2 Hz, 2H), 1.29 (s, 9H), 1.18 (s, 6H), 0.82 (s, 9H), −0.07 (s, 6H); MS m/e: (M+23)=622.

Compound 006:

To 005 (13.0 g, 33.4 mmol) and 004 (18.6 g, 31.0 mmol) were added N-methylpyrrolidinone (30 mL), dicyclohexylmethylamine (8 ml, 37.4 mmol) and $Pd_2(DBA)_3$ (8.51 g, 9.29 mmol). The mixture was heated at 100° C. for 2.5 hr and then at 110° C. for 10 hr. The solvents were then removed under reduced pressure with heating. The residue was purified by flash chromatography eluting with a 10-17% gradient solvent of EtOAc/Hexanes to yield 24.7 g (90%) of the compound 006. $^1$H-NMR (400 MHz, C6D6) δ: 8.10 (d, J=16.0 Hz, 1H), 7.45 (d, J=2.0 Hz, 1H), 7.30 (d, J=8.8 Hz, 2H), 7.05 (d, J=2.0 Hz, 1H), 6.92 (d, J=8.8 Hz, 2H), 6.57-6.49 (m, 1H), 5.62-5.48 (m, 2H), 4.6 (d, 1H), 4.48 (m, 1H), 4.38-4.32 (m, 1H), 4.22 (d, 1H), 4.17-4.13 (m, 1H), 3.68 (m, 2H), 3.58 (m, 2H), 3.49-3.45 (m, 1H), 3.34 (s, 3H), 2.85-2.77 (m, 1H), 2.73-2.67 (m, 1H), 2.63-2.56 (m, 1H), 1.44 (s, 3H), 1.37 (s, 9H), 1.24 (s, 6H), 1.20 (s, 3H), 1.13 (d, J=6.0 Hz, 3H), 1.03 (d, J=6.8 Hz, 3H), 0.88 (s, 9H), −0.02 (s, 6H); MS m/e: (M+23)=862.

Compound 007:

To 006 (12.0 g, 14.3 mmol) in THF (1.48 L) was added potassium hexamethyldisilylamide in toluene (0.5M, 30 mL, 6.0 mmol) slowly at room temperature via a syringe pump down wall over a period of 1.5 hr. The reaction was quenched with aqueous ammonium chloride solution (800 ml). The layers were separated and the aqueous layer was back extracted three times with MTBE (3×400 mL) and three times with ethyl acetate (3×400 mL). The combined extracts were dried with sodium sulfate and concentrated. The residue was purified by flash chromatography eluting with 5% then 10% EtOAc/Hexanes to give 5.99 g (54%) of compound 007 and 2.32 g (19%) of recovered starting material 006. $^1$H-NMR of 007 (400 MHz, C6D6) δ: 7.29 (d, J=2.4 Hz, 1H), 7.19 (d, J=15.6 Hz, 1H), 7.14 (d, J=2.4 Hz, 1H), 6.93 (d, J=8.4 Hz, 1H), 6.78 (d, J=8.4 Hz, 1H), 5.93-5.86 (m, 1H), 5.67 (dd, J=8.8 and 9.2 Hz, 1H), 5.46 (dd, J=10.4 and 8.8 Hz, 1H), 5.22 (dd, J=9.6 and 10.4 Hz, 1H), 4.88-4.82 (m, 1H), 4.42-4.36 (m, 1H), 4.25-4.19 (m, 2H), 3.80-3.76 (m, 1H), 3.72-3.60 (m, 4H), 3.29 (s, 3H), 3.11-3.02 (m, 1H), 2.83-2.74 (m, 1H), 2.64-2.57 (m, 1H), 1.42 (s, 3H), 1.35 (s, 9H), 1.23 (s, 3H), 1.04 (d, J=6.4 Hz, 3H), 0.90 (s, 9H), 0.77 (d, J=7.2 Hz, 3H), 0.01 (s, 6H); MS m/e: (M+23)=804.

Compound 008:

To 007 (5.94 g, 7.60 mmol) in THF cooled at 0° C. (ice/water bath) were added DBU (4.9 mL, 33 mmol) then methoxylmethylchloride (2.3 mL, 30.3 mmol) in portions down wall. After stirring for 3 hr, the reaction mixture was washed three times with aqueous ammonium chloride solution, water and brine. The aqueous layers were back extracted three times with MTBE. The combined extracts were dried with sodium sulfate and concentrated to get 6.27 g (99%) of a white foam crude product which was clean and directly used for the next desilylation reaction. A small amount of crude product was purified by prep-TLC (eluting with 30% EtOAc/Hexanes) to verify the desired product, 008. $^1$H-NMR (400 MHz, C6D6) δ: 7.32 (d, J=8.8 Hz, 1H), 7.16 (br s, Hz, 1H), 7.06 (s, 1H), 7.86 (d, J=8.4 Hz, 2H), 6.82 (d, J=18.0 Hz, 1H), 6.49-6.41 (m, 1H), 5.52-5.46 (m, 2H), 5.33 (dd, J=10.4 and 10 Hz, 1H), 4.98 (dd, J=8.8 and 8.8 Hz, 1H), 4.82 (s, 2H), 4.74 (d, J=10.8 Hz, 1H), 4.58 (d, J=11.2 Hz, 1H), 4.37 (dd, J=6.4 and 6.4 Hz, 1H), 4.17 (dd, J=9.6 and 7.2 Hz, 1H), 3.75-3.63 (m, 4H), 3.26 (s, 3H), 3.23-3.16 (m, 1H), 3.09 (s, 3H), 2.67-2.59 (m, 2H), 1.35 (s, 9H), 1.30 (d, J=6.8 Hz, 3H), 1.27 (s, 3H), 1.11 (s, 3H), 0.95 (d, J=6.4 Hz, 3H), 0.90 (s, 9H), 0.01 (s, 3H), 0.00 (s, 3H); MS m/e: (M+23)=848.

Compound 009:

Compound 008 (6.27 g) was dissolved in THF (230 ml) in 1 L round bottom flask and cooled to 0° C. To this was added buffered TBAF (1.0 M TBAF and 0.5M imidazole/HCl in THF, 15.2 ml) via a syringe pump over 26 min. After completion of addition, the mixture was stirred at room temperature for 12 hr. The reaction mixture was washed with saturated aqueous bicarbonate solution, water and brine sequentially. Aqueous phases were extracted with MTBE. The combined organic extracts were dried with sodium sulfate and purified by chromatography to afford 5.08 g (94%) of 009 as a colorless oil. $^1$H NMR (400 MHz, $CDCl_3$) δ 7.34-6.85 (m, 6H), 6.78 (d, J=16.0 Hz, 1H), 6.43 (m, 1H), 5.52-5.46 (m, 2H), 5.33 (dd, J=10.4, and 10.0 Hz, 1H), 4.96 (t, J=10.0 Hz, 1H), 4.75 (s, 2H), 5.25 (d, J=11.2 Hz, 1H), 4.57 (d, J=11.2 Hz, 1H), 4.37 (dd, J=6.4, and 6.4 Hz, 1H), 4.20-4.15 (m, 1H), 3.56-3.40 (m, 4H), 3.25 (s, 3H), 3.22-3.16 (m, 1H), 3.07 (s, 3H), 2.66-2.50 (m, 2H), 1.30 (d, J=7.2 Hz, 3H), 1.29 (s, 9H), 1.27 (s, 3H), 1.11 (s, 3H), 0.94 (d, J=6.8 Hz, 3H); MS, m/e (m+23)=734. 113 mg (2%) of side product, Compound 023, was also isolated and was used to synthesize Compound 024.

Compound 010:

Into a round bottom flask were added 009 (500 mg, 0.702 mmol) and methylene chloride (14.0 mL) and the mixture was cooled to 0° C. Triethylamine (0.29 mL, 2.10 mmol) was added, then methanesulfonyl chloride (0.082 mL, 1.00 mmol) was added slowly. After 2 hrs, TLC and MS check indicated the reaction was complete, clean and desired product was observed. The reaction mixture was poured into a saturated sodium bicarbonate solution, and extracted with DCM three times. The extracts were combined and dried over sodium sulfate, concentrated and then azeotroped with toluene. The colorless oil crude product, 010, was reasonably clean and generally directly subjected to the nucleophiles in next step reaction without purification. Yield 555 mg (100%). $^1$H NMR (400 MHz, $CDCl_3$) δ 7.38-6.90 (m, 6H), 6.83 (d, J=16.4 Hz, 1H), 6.53 (m, 1H), 5.57-5.50 (m, 2H), 5.38 (dd, J=10.0, and 10.4 Hz, 1H), 5.00 (t, J=8.8 Hz, 1H), 4.88 (AB, 2H), 4.78 (d, J=11.2 Hz, 1H), 4.61 (d, J=11.2 Hz, 1H), 4.42 (dd, J=6.8, and 6.4 Hz, 1H), 4.24-4.20 (m, 1H), 4.02 (t, J=5.6 Hz, 2H), 3.51 (t, J=5.6 Hz, 2H), 3.30 (s, 3H), 3.25-3.21 (m, 1H), 3.12 (s, 3H), 2.70-2.53 (m, 2H), 2.20 (s, 3H), 1.38-1.33 (s and d overlapped, 12H), 1.33 (s, 3H), 1.16 (s, 3H), 0.98 (d, J=6.8 Hz, 3H); MS, m/e (M+23=812).

Synthesis of Selected Compounds
Compound 011:

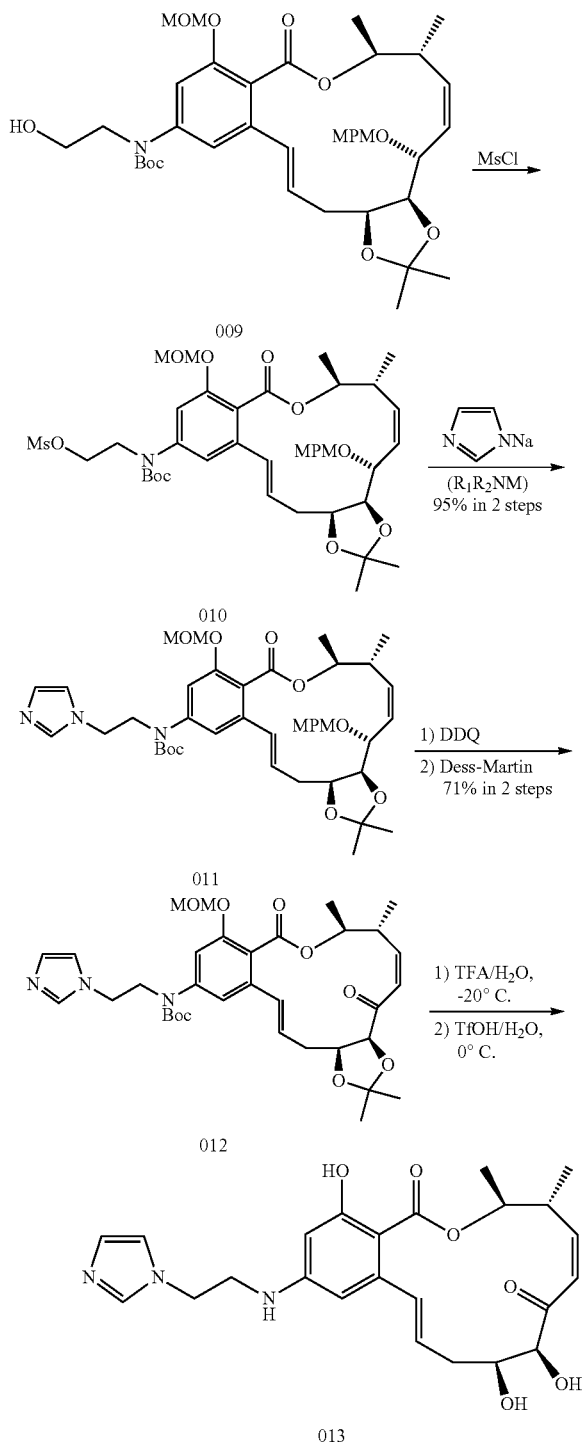

To 010 (554 mg, 0.702 mmol) prepared as described above was added DMF (5.44 mL) and imidazole sodium derivative (1.26 g, 14.0 mmol). The mixture was stirred over night at room temperature. A check via TLC indicated that the reaction was complete. The solvent was removed under reduced pressure and the residue was partitioned between dichloromethane (DCM) and aqueous bicarbonate. The mixture was extracted with DCM (3×100 ml) and the combined organic extracts were dried over sodium sulfate and concentrated. The residue was purified by flash chromatography eluting with 10-50% gradient of EtOAc/Hexanes and 0-7% MeOH/DCM to obtain 531 mg (100%) of 011 as a white foam.

Compound 011 was then subjected to the sequential treatment of DDQ, Dess-Martin oxidation, to give compound 012 and TFA/water, and TfOH/water, similar to the synthesis of compound 091, below, to obtain analog 013 as a white powder. Yield: 41 mg (55%). $^1$H NMR (400 MHz, 10% CD$_3$OD/CDCl$_3$) δ: 1.07 (d, 3H, J=8 Hz), 1.29 (d, 3H, J=8 Hz), 1.97 (m, 1H), 2.06 (m, 1H), 3.42 (m, 3H, J=4 Hz), 3.85 (br s, 2H), 3.93 (m, 1H), 4.05 (t, 2H, 8 Hz), 4.39 (d, 1H J=3 Hz), 4.78 (m, 1H, J=3 Hz), 5.82 (m, 1H, 3 Hz), 5.89 (d, 1H, J=3 Hz), 5.92 (d, 1H, J=3 Hz), 6.02 (dd, 1H, J=12 Hz), 6.13 (d, 1H, J=12 Hz), 6.73 (d, 1H, J=16 Hz), 6.88 (d, 1H, J=16 Hz), 7.38 (s, 1H). MS m/e: (m+1) 456 (5%), (m+23) 478 (100%).

Compound 014:

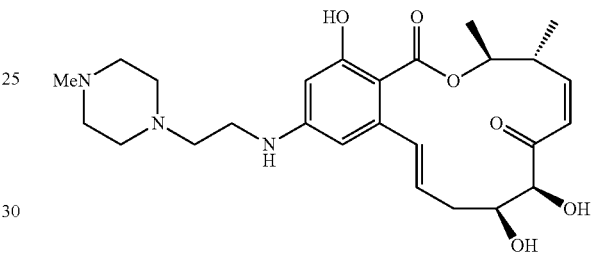

Compound 014 was synthesized from compound 010 following the same procedures as the synthesis of compound 013, except N-methylpiperidine was used in place of sodium imidazole. Yield 18 mg (30%). $^1$H NMR (400 MHz, CD$_3$OD) δ: 1.15 (d, 2H, J=6 Hz), 1.36 (d, 2H, J=6 Hz), 1.45 (t, 2H, J=6 Hz), 1.97 (s, 1H), 2.08 (m, 1H), 2.70 (t, 2H, J=6 Hz), 2.79 (s, 3H) 3.30 (m, 2H), 3.48 (m, 2H), 4.05 (m, 1H), 4.48 (d, 1H, J=4 Hz), 5.95 (m, 2H), 6.12 (dd, 2H, J=8 Hz), 6.32 (d, 1H, J=8 Hz), 6.88 (d, 1H, J=16 Hz). MS m/e: (m+1) 488 (100%).

Compound 015:

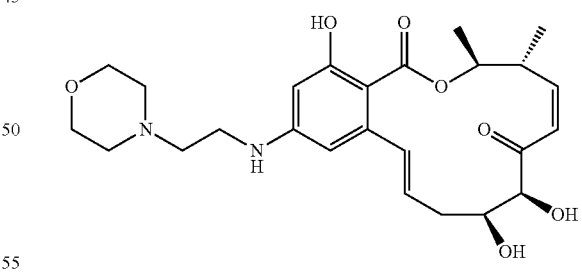

Compound 015 was synthesized from compound 010 following the same procedures as the synthesis of compound 013, except morpholine was used in place of sodium imidazole. The yield was a white powder, 80 mg (76%). $^1$H NMR (400 MHz, C6D6) δ: 0.78 (d, 3H, J=8 Hz), 0.93 (t, 3H, J=8 Hz), 1.00 (d, 3H, J=8 Hz), 1.94 (m, 6H), 2.13 (m, 2H), 2.61 (q, 2H, J=4 Hz), 3.46 (t, 4H, J=4 Hz), 3.94 (m, 1H), 4.30 (d, 1H, J=3 Hz), 4.66 (m, 2H), 5.41 (t, 1H, J=8 Hz), 5.55 (d, 1H, J=12 Hz), 5.97 (m, 1H), 6.02 (d, 1H, J=4 Hz), 6.22 (d, 1H, J=3 Hz), 6.94 (d, 1H, J=16 Hz). MS m/e: (m+1) 475 (100%), (m+23) 497 (9%).

Compound 016:

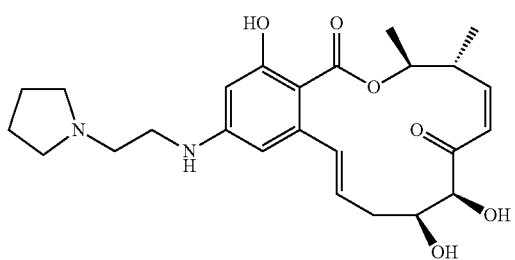

Compound 016 was synthesized from compound 010 following the same procedures as the synthesis of compound 013, except pyrrolidine was used in place of sodium imidazole. Yield 14.6 mg (47%). $^1$H NMR (400 MHz, CD$_3$OD) δ: 1.14 (d, 3H, J=3 Hz), 1.27 (s, 2H), 1.34 (d, 3H, J=3 Hz), 1.85, (m, 4H, J=3 Hz), 2.08 (m, 2H), 2.72 (m, 4H), 2.79 (t, 2H, J=8 Hz), 3.31 (t, 2H, J=8 Hz), 3.46 (m, 1H), 4.04 (m, 1H), 4.48 (d, 1H, 3 Hz), 5.95 (m, 1H) 5.97 (d, 1H, J=4 Hz), 6.09 (d, 1H, J=12 Hz), 6.14 (d, 1H, J=4 Hz), 6.30 (d, 1H, J=12 Hz), 6.87 (d, 1H, J=16 Hz). MS m/e: (m$^{+1}$) 459 (100).

Compounds 018 and 019:

treatment with DDQ, PCC and TFA to obtain compound 018. Yield 32 mg. MS m/e: (m$^{+1}$) 579.

Compound 018 was then treated with TfOH, in the same manner as the synthesis of compound 013 to yield compound 019 (9.2 mg, 23%). $^1$H-NMR (400 MHz, CD$_3$OD) δ: 1.16 (d, 3H, J=6.73 Hz), 1.36 (d, 3H, J=6 Hz), 2.09 (m, 2H), 2.65 (s, 1H), 3.07 (m, 1H), 3.23 (m, 2H), 3.30 (m, 2H), 3.40 (m, 4H), 3.54 (m, 1H), 3.9 (m, 2H), 4.04 (m, 2H), 4.48 (d, 1H, J=2.4 Hz), 5.58 (m, 1H), 6.06 (d, 1H, J=2.4 Hz), 6.12 (m, 2H), 6.19 (d, 1H, J=2.4 Hz), 6.32 (d, 2H, J=11.5 Hz), 6.9 (d, 1H, J=16 Hz). MS, m/e: (m+23) 479 (100%).

Compound 022:

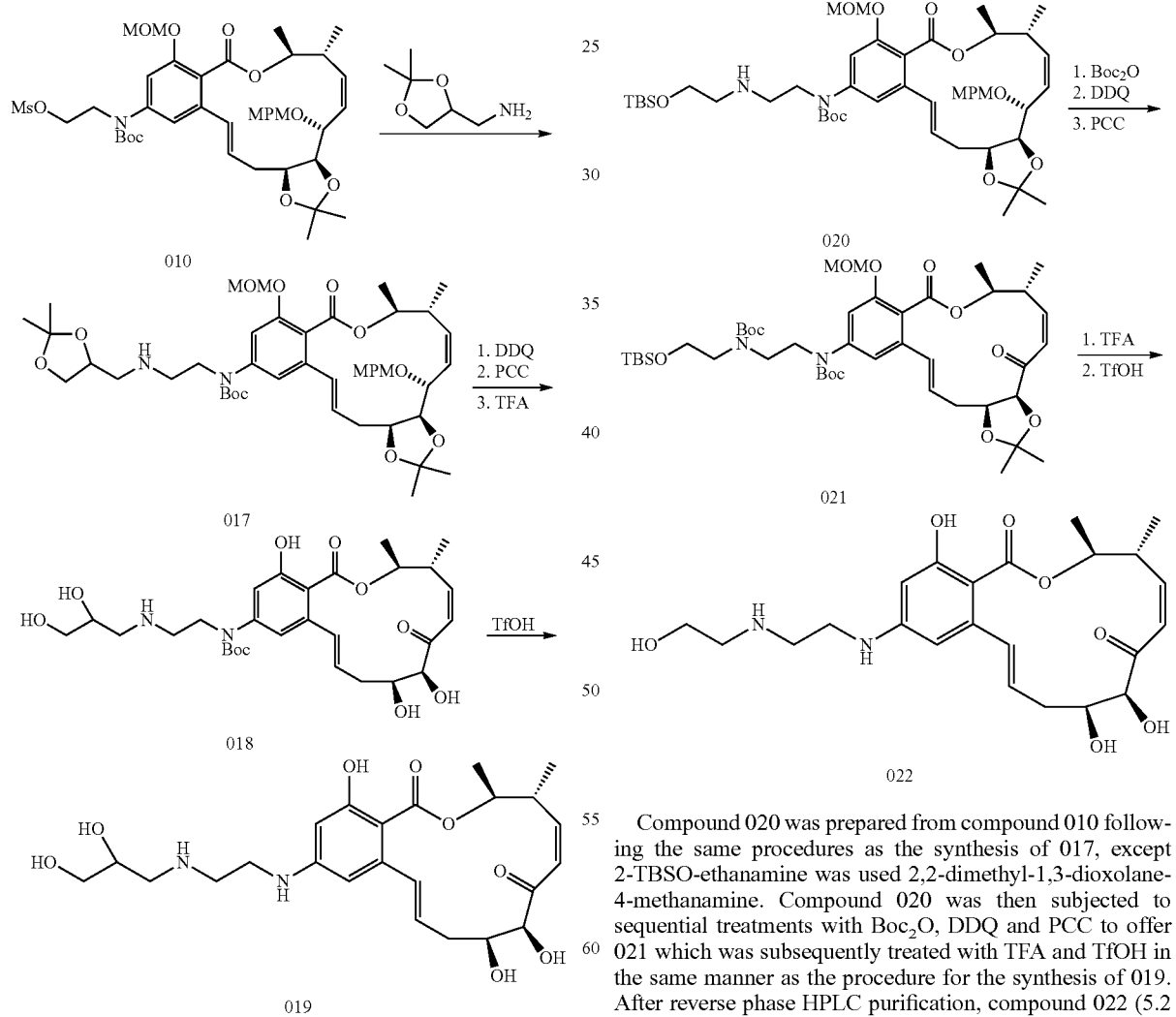

Compound 017 was prepared from compound 010 following the same procedures as the synthesis of compound 013, except 2,2-dimethyl-1,3-dioxolane-4-methanamine was used in place of sodium imidazole. 017 was subjected to sequential Compound 020 was prepared from compound 010 following the same procedures as the synthesis of 017, except 2-TBSO-ethanamine was used 2,2-dimethyl-1,3-dioxolane-4-methanamine. Compound 020 was then subjected to sequential treatments with Boc$_2$O, DDQ and PCC to offer 021 which was subsequently treated with TFA and TfOH in the same manner as the procedure for the synthesis of 019. After reverse phase HPLC purification, compound 022 (5.2 mg) was obtained as a TFA salt form. $^1$H-NMR (400 MHz, CD$_3$OD) δ: 1.18 (d, 3H, J=6.75 Hz), 1.41 (d, 3H, J=6.15 Hz), 2.1 (m, 2H), 2.65 (s, 1H), 3.15 (t, 2H, J=5.25 Hz), 3.22 (t, 2H, J=6.75 Hz), 3.50 (m, 2H), 3.56 (m, 2H), 3.63 (m, 2H), 3.77 (m, 2H), 3.91 (s, 1H), 4.02 (m, 1H), 4.49 (t, 1H, J=2.4 Hz), 4.93 (m, 1H), 6.01 (m, 1H), 6.13 (m, 2H), 6.23 (s, 1H), 6.32 (d, 1H, J=11.5 Hz), 6.92 (d, 1H, J=15.85 Hz). MS, m/e (m+1) 445 (100).

Compound 024:

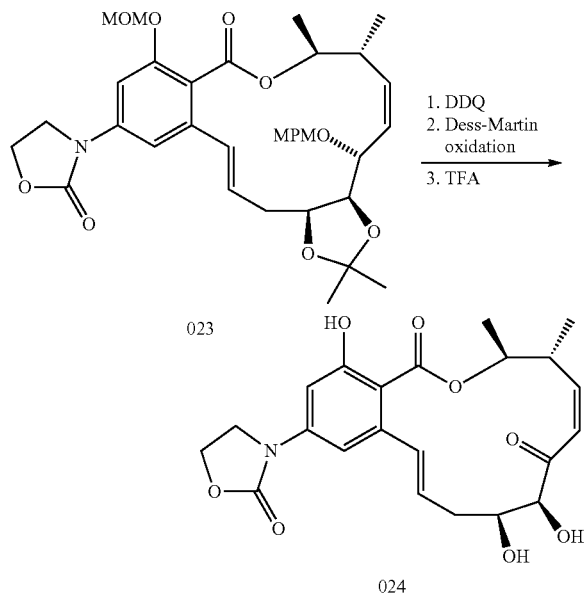

Compound 023 (113 mg) was obtained as a side product during the synthesis of 009. Compound 023 was then subjected to the same process as the synthesis of compound 013 to obtain analog compound 024. Yield 16.8 mg (30% in 3 steps). ¹H-NMR (400 MHz, CDCl₃) δ 7.18 (d, J=2.4 Hz, 1H), 7.05 (d, J=2.4 Hz, 1H), 6.96 (d, J=15.2 Hz, 1H), 6.34 (d, J=11.2 Hz, 1H), 6.17 (d, J=10.4 Hz, 1H), 6.10 (m, 1H), 5.05-4.94 (m, 1H), 4.50-4.46 (m, 3H), 4.10-4.05 (m, 3H), 3.56-3.49 (m, 1H), 2.16-2.10 (m, 1H), 1.40 (d, J=6.4 Hz, 3H), 1.17 (d, J=6.4 Hz, 3H); MS, m/e (M+23)=454, (M−1)=430.

Compound 025

To compound 010 (220 mg, 0.28 mmol) was added ammonia solution in methanol (2M, 100 ml) and concentrated ammonia aqueous solution (22 ml). The mixture was stirred at room temperature over night. The reaction mixture was poured into saturated bicarbonate solution (500 ml) and extracted four times with DCM and once with ethyl acetate. The combined extracts were concentrated and the residue was purified by chromatography to obtain 100 mg of urea compound (60%).

The urea compound was then subjected to the same process as in the synthesis of compound 013, except PCC oxidation was applied in place of Dess-Martin oxidation. Compound 025 was obtained in 91% yield (49 mg). ¹H-NMR (400 MHz, CD₃OD) δ: 1.14 (d, 3H, J=8 Hz), 1.38 (d, 3H, J=6 Hz), 2.07 (m, 2H), 2.17 (m, 2H), 2.82 (s, 2H), 3.18 (s, 1H), 3.60 (m, 1H), 4.02 (m, 2H), 4.07 (m, 2H), 4.52 (m, 2H), 4.95 (m, 1H), 5.33 (s, 1H), 6.12 (m, 2H), 6.25 (d, 1H, J=12 Hz), 6.89 (s, 1H), 6.93 (d, 1H, J=3 Hz), 7.25 (d, 1H, J=3 Hz). MS, m/e (m+23) 453 (100%).

Compound 029:

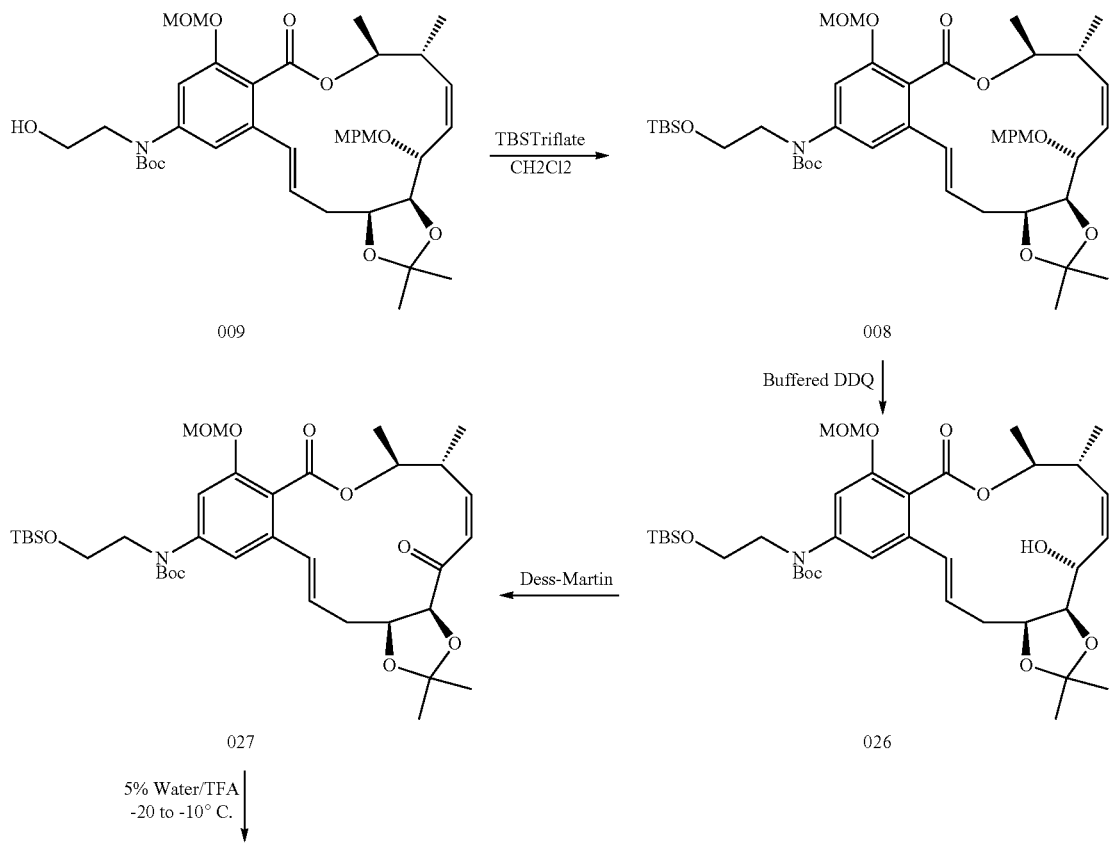

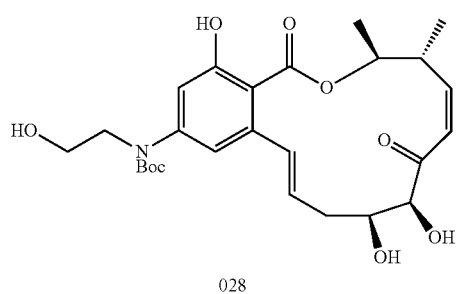

73

028

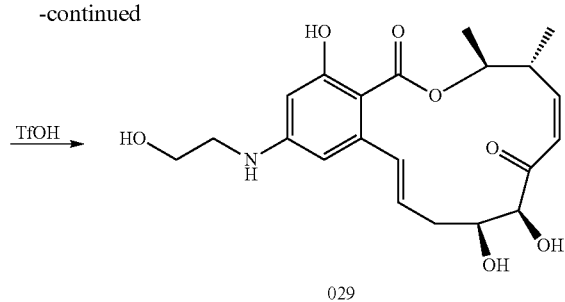

74

029

Compound 029 was synthesized from 008. Compound 008 was subjected to the sequential treatment of DDQ, Dess-Martin oxidation, to give 027. Similar to the synthesis of 013, 027 was then treated with TFA/water and TfOH/water, to obtain analog 029 as a white powder. Yield: 40.1 mg (45%). $^1$H-NMR (400 MHz, CDCl$_3$) δ: 1.16 (d, 3H, J=8 Hz), 1.20 (d, 1H, J=4 Hz), 1.12 (s, 1H), 1.25 (t, 8H, J=8 Hz), 1.39 (d, 3H, J=8 Hz), 2.04 (s, 8H), 3.31 (t, 2H, J=4 Hz), 3.54 (m, 1H), 3.82 (t, 2H, 4 Hz), 3.91 (m, 1H), 4.04 (m, 1H), 4.48 (s, 1H), 4.86 (m, 1H), 5.30 (s, 1H), 5.94 (m 1H), 6.03 (d, 1H, J=4 Hz), 6.09 (d, 1H, J=4 Hz), 6.16 (q, 2H, J=8 Hz). 6.83 (d, 1H, J=16 Hz). MS m/e: (m+23) 428 (100%).

Compound 034:

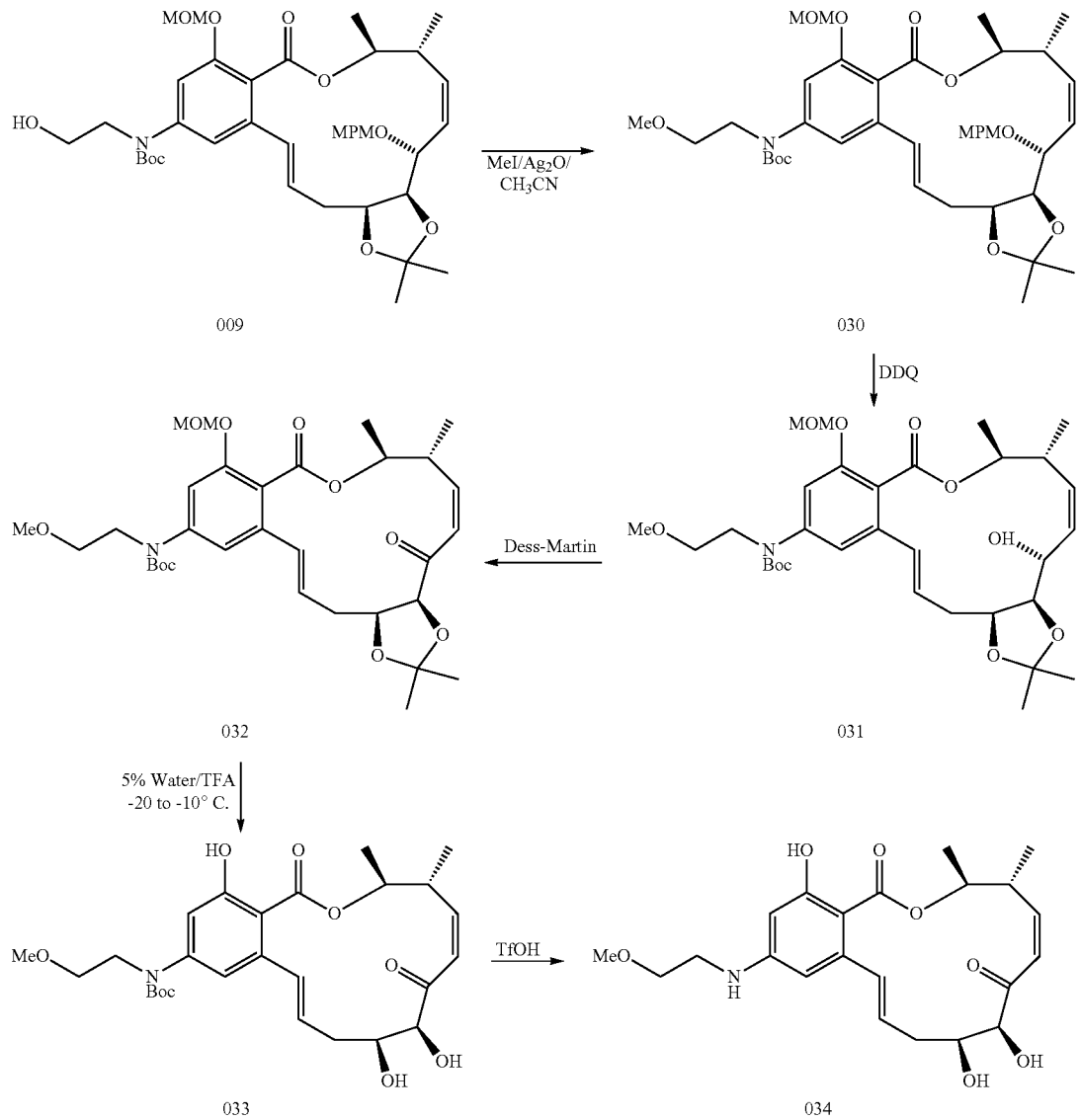

Compound 009 (310.0 mg, 0.0004355 mol), silver (I) oxide (202 mg, 0.000871 mol), and methyl iodide (542.2 μl, 0.008710 mol) were mixed in anhydrous acetonitrile (1.581 mL, 0.03027 mol) and the mixture was heated by microwaves in a sealed tube for 5 min intervals. Reaction was complete as shown by TLC (5% MeOH/DCM). The reaction mixture was filtered through celite 545 and the residue was purified by chromatography: 12 g Redi-Sep pack Si-Gel column using 0-5% acetone/DCM, resulted in incomplete separation, it was necessary to repurify on 2 mm Prep Plate X2 using 5% acetone/DCM. This process was repeated to remove all of the side product, from our desired product. EtOAc/Hexane co-solvent helped remove all impurities from the desired product, 030. Yield: 160 mg (51%). Then, following the same procedures as the synthesis of 013, compound 034 was obtained. Yield: 25 mg (47%). $^1$H-NMR (400 MHz, CDCl$_3$) δ: 1.17 (d, 3H, J=8 Hz), 1.26 (t, 1H, J=8 Hz), 1.40 (d, 3H, J=8 Hz), 2.05 (s, 1H), 2.14 (m, 2H), 2.62 (d, 1H, J=3 Hz) 3.31 (t, 2H, J=3 Hz), 3.38 (s, 3H), 3.58 (t, 3H, J=4 Hz), 3.86 (d, 1H, J=4 Hz), 4.01 (s, 1H), 4.12 (q, 1H, J=4 Hz), 4.49 (m, 1H) 4.53 (br s, 1H), 4.88 (m 1H), 5.94 (m, 1H), 6.03 (d, 1H, J=4 Hz), 6.09 (d, 1H, J=4 Hz), 6.17 (m 2H), 6.84 (d, 1H, J=16 Hz). MS m/e: (m+1) 420 (30%), (m+23) 442 (100%).

Compound 041:

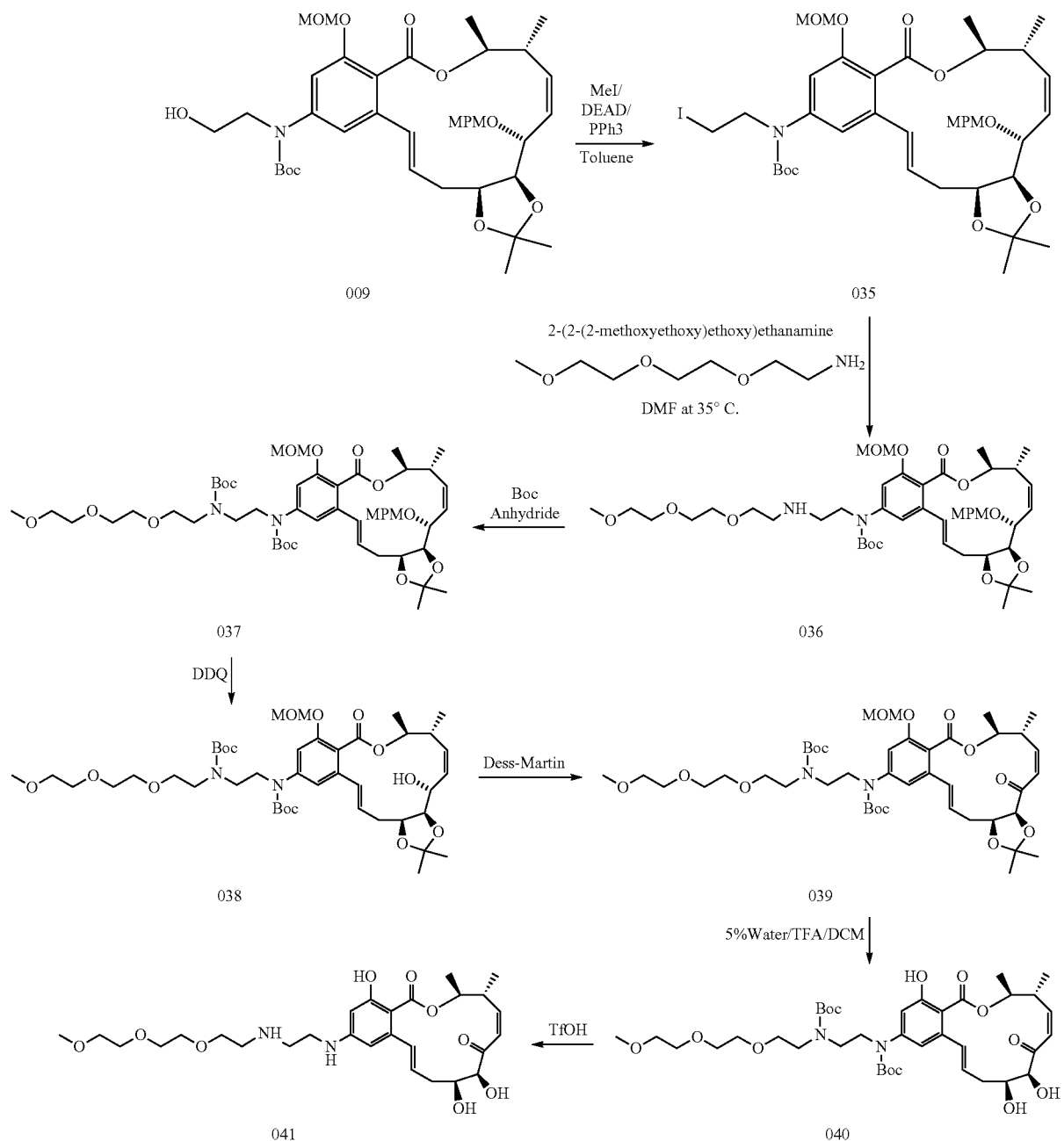

009 (26.9 mg, 0.0378 mmol) and triphenylphosphine (16.8 mg, 0.0642 mmol) were dissolved in toluene (0.40 mL, 3.78 mmol). Methyl iodide (3.06 μl, 0.049 mmol) and diethyl azodicarboxylate (6.54 µl, 0.0416 mmol) was added at the same time in one shot. Reaction mixture was stirred for 1.5 hrs and monitored by TLC at 15 min intervals. Reaction was allowed to stir over night. TLC (50% EtOAc/hexane) the next morning showed a 1:1 mixture of product to starting material, this was confirmed by MS. Additional triphenylphosphine (16.8 mg, 0.0642 mmol), followed by methyl iodide (3.06 µl, 0.0491 mmol) and diethyl azodicarboxylate (6.54 µl, 0.0416 mmol) were added simultaneously. The reaction was monitored at 10 min intervals, and still showed substantial amount final polyether product 041. Yield: 43.2 mg (80%). $^1$H-NMR (400 MHz, CDCl$_3$) δ: 1.15 (d, 3H, J=7 Hz), 1.37 (d, 3H, J=7 Hz), 2.05 (s, 1H), 2.07 (m, 2H), 3.05 (t, 2H, J=3 Hz), 3.08 (t, 2H, J=3 Hz), 3.36 (s, 3H), 3.38 (m, 2H), 3.54 (m, 2H), 3.64 (m, 8H), 3.69 (m, 2H), 4.03 (s, 1H), 4.18 (q, 1H, J=7.1 Hz), 4.47 (d, 1H, J=3 Hz), 4.84 (m, 1H), 5.40 (s, 1H), 5.99 (m, 1H), 6.00 (d, 1H, J=3 Hz), 6.12 (m, 4H), 6.79 (d, 1H, J=16 Hz). MS m/e: (m+1) 551 (100%), (m+23) 573 (10%).
Compound 042

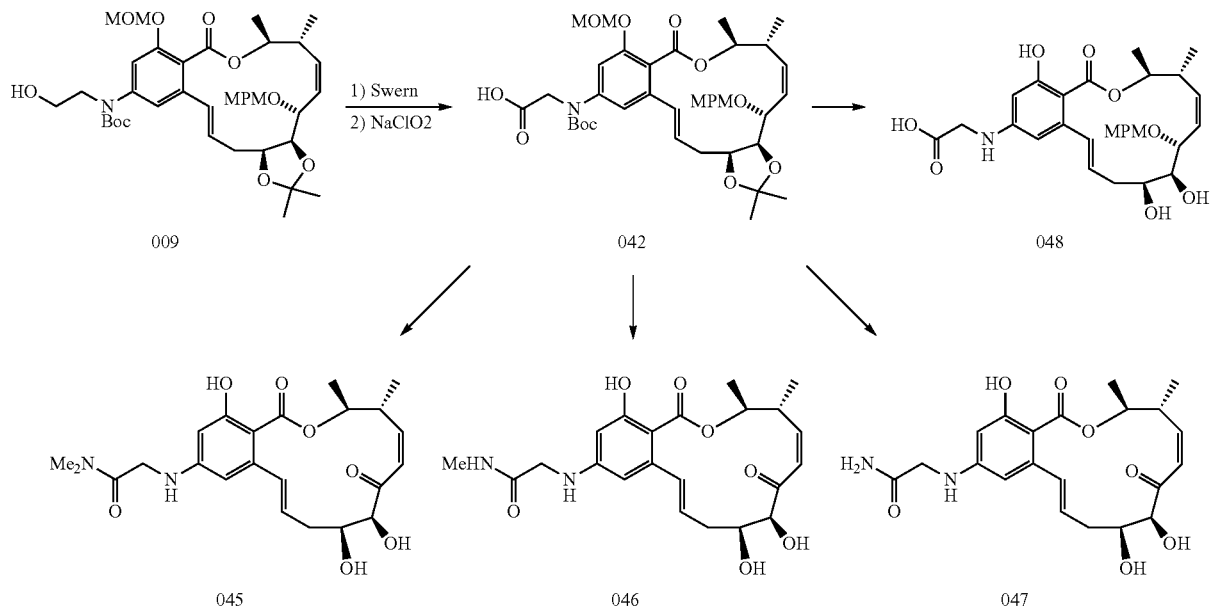

of starting material. Additional triphenylphosphine (16.8 mg, 0.0642 mmol), followed by methyl iodide (3.06 µl, 0.0491 mmol) and diethyl azodicarboxylate (6.54 µl, 0.0416 mmol) were added simultaneously. The reaction was monitored at 10 min intervals by TLC, and showed that it went to completion. Aqueous workup was performed and extracted with MTBE. The organic extracts were dried over sodium sulfate and concentrated. The residue was loaded onto a 4 g Redi-sep column, and eluted with 10% Ethanol/Hexanes. Compound 035 was isolated as a clear oil confirmed by TLC, MS and NMR. Yield: 31 mg (100%)

An amino-polyether fragment was added to 035 to produce compound 036 using the same procedures as used in the synthesis of compound 013. The product structure was verified by NMR, MS, and TLC. Yield: 150.2 mg (61%).

Into an oven dried round bottom flask was added the 036 (174.5 mg, 0.0002036 mol), followed by tetrahydrofuran (1.651 mL, 20.36 mmol) and di-tert-butyldicarbonate (222.2 mg, 1.018 mmol) and 4-dimethylaminopyridine (4.97 mg, 0.0407 mmol) under an atmosphere of nitrogen. The reaction was the stirred for 1 hour, and determined to be complete by TLC and MS. The reaction mixture was diluted with water and extracted with MTBE, dried over sodium sulfate and concentrated. The residue, compound 037, was purified on red-sep column eluting with 0-5% MeOH/DCM. Yield: 162.3 mg (83%).

The same procedures as used in the synthesis of compound 013 were performed with compound 037 in order to give the To a 250 ml round bottom flask were added dichloromethane (4 ml) and oxalyl chloride solution in dichloromethane (2.0M, 2.1 ml). The solution was cooled to −78° C. and DMSO was added. After stirring for 5 min, 009 in dichloromethane (0.05M, 55 ml, 2.75 mmol) was added. After stirring additional 30 min, triethylamine (2.3 ml) was added and the reaction mixture was allowed to warm up to 0° C. over 45 min. The mixture was poured into saturated aqueous sodium bicarbonate solution. The layers were separated and the aqueous layer was back extracted three times using dichloromethane. The combined organic extracts were dried with sodium sulfate and concentrated.

The above crude aldehyde product (1.95 g) was mixed with t-butyl alcohol (52 ml) in a 200 ml round bottom flask. To this were added 2-methyl-2-butene via a syringe and needle, sodium chlorite (2.5 g), potassium hydrogen phosphate (1.8 g) and water (25 ml). The reaction mixture was stirred at room temperature for 1 hour. Aqueous sodium thiosulfate solution (150 ml) and ethyl acetate (150 ml) were added and the mixture was stirred for 1 hour. The layers were separated, and the aqueous layer was cooled to 0° C., acidified to a pH of about 3 using 1N HCl. and back extracted three time using ethyl acetate. The combined organic extracts were washed three times with distilled water, dried with sodium sulfate and concentrated to obtain 1.8 g (90%) over 2 steps. Four analogs were synthesized from 042 as shown in the scheme above.

Compound 045:

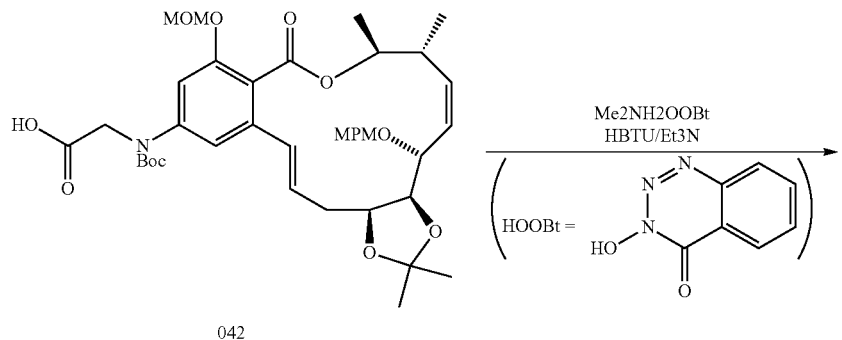

042

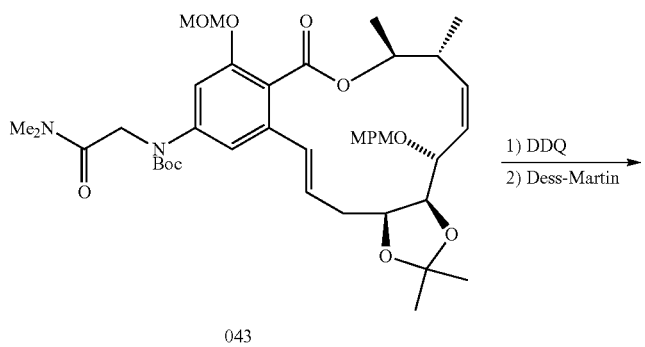

043

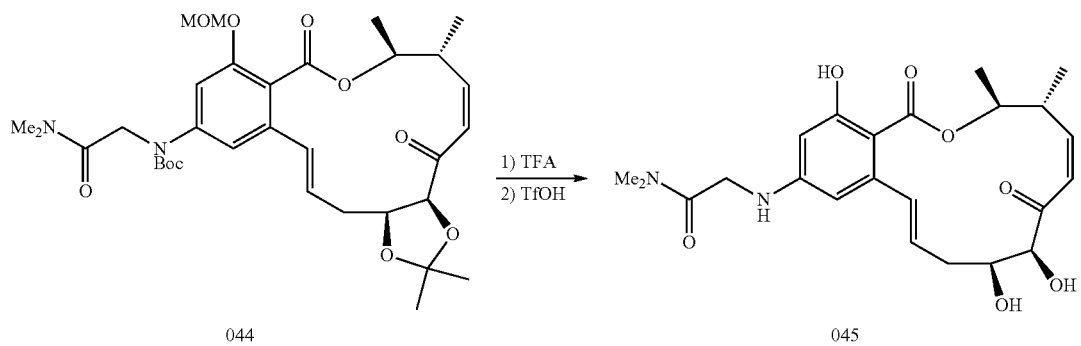

044       045

Compound 042 (316 mg), dimethylammonium-OOBt salt (370 mg), HBTU (672 mg), triethyl amine (0.43 ml) and dichloromethane (3 ml) were added to a 10 ml round bottom flask and the mixture was stirred at room temperature over night. The reaction mixture was poured into a saturated aqueous sodium bicarbonate solution and extracted three times using dichloromethane. The combined extracts were dried with sodium sulfate and purified by Biotage chromatography to obtain 320 mg (98%) of 043. Compound 043 was then subjected to the same procedures as the synthesis of compound 013 to obtain compound 045. $^1$H-NMR (400 MHz, CD$_3$OD) δ: 6.88 (d, J=15.2 Hz, 1H), 6.32 (d, J=11.6 Hz, 1H), 6.19 (d, J=2.4 Hz, 1H), 6.12 (dd, J=11.6 and 10.0 Hz, 1H), 6.02-5.95 (m, 1H), 5.96 (d, J=2.4 Hz, 1H), 4.48 (d, J=2.0 Hz, 1H), 4.06-4.03 (m, 1H), 3.99 (s, 2H), 3.50-3.43 (m, 1H), 3.07 (s, 3H), 2.97 (s, 3H), 2.16-2.02 (m, 2H), 1.36 (d, J=6.4 Hz, 3H), 1.15 (d, J=7.2 Hz, 3H); MS m/e: (M+23)=469.

Compound 046:

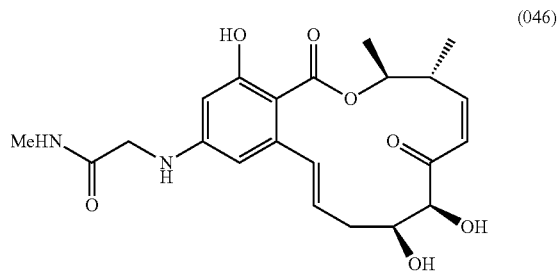 [SMILES: CNC(=O)CNc1cc(O)c2c(c1)/C=C/C[C@H](O)[C@H](O)C(=O)/C=C\[C@@H](C)[C@H](C)OC2=O]

(046)

The synthesis of compound 046 was the same as the synthesis 045 except methylammonium-OOBt salt was used in place of dimethylammonium-OOBt. MS m/e: (M+23)=455.

Compound 047:

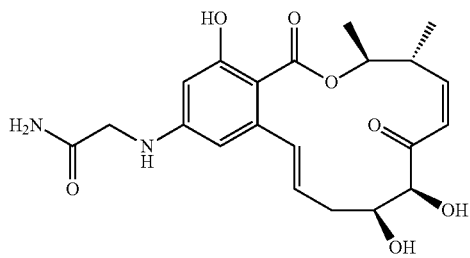
(047)

The synthesis of compound 047 was the same as the synthesis of 045 except ammonium-OOBt salt was used in place of dimethylammonium-OOBt and pyridiniumchlorochromate (PCC) was used in place of Dess-Martin reagent. $^1$H-NMR (400 MHz, CD$_3$OD) δ: 6.89 (d, J=15.2 Hz, 1H), 6.31 (d, J=11.2 Hz, 1H), 6.16 (d, J=2.4 Hz, 1H), 6.12 (dd, J=11.2 and 9.6 Hz, 1H), 6.02-5.94 (m, 1H), 5.92 (d, J=2.4 Hz, 1H), 4.48 (d, J=2.0 Hz, 1H), 4.06-4.03 (m, 1H), 3.77 (s, 2H), 3.50-3.43 (m, 1H), 2.16-2.02 (m, 2H), 1.35 (d, J=6.0 Hz, 3H), 1.15 (d, J=7.2 Hz, 3H); MS m/e: (M+23)=441.

Compound 048:

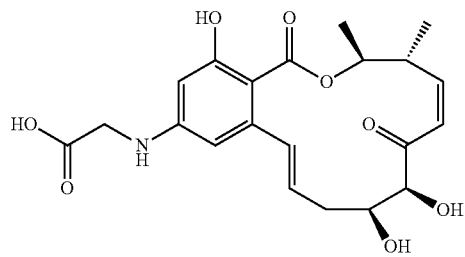
(048)

Compound 042 was subjected to the same procedure as for the synthesis of compound 013 to yield 8.5 mg (58%) of compound 048. $^1$H-NMR (400 MHz, CD$_3$OD) δ: 1.16 (d, 3H, J=6.75 Hz), 1.36 (d, 3H, J=5.86 Hz), 2.0 (s, 2H), 2.10 (m, 2H), 3.3 (m, 1H), 3.47 (m, 1H), 3.64 (s, 1H), 3.87 (s, 2H), 4.05 (m, 1H), 4.09 (d, 1H, J=7 Hz), 4.12 (m, 1H), 4.48 (d, 1H, J=2.40 Hz), 5.91 (d, 1H, J=2.40 Hz), 5.97 (m, 1H), 6.10 (m, 1H), 6.12 (m, 1H), 6.16 (d, 1H, J=3 Hz), 6.32 (d, 1H, J=12 Hz), 6.89 (d, 1H, J=15.5 Hz). MS m/e: (m−1) 418 (100%).

Compound 054:

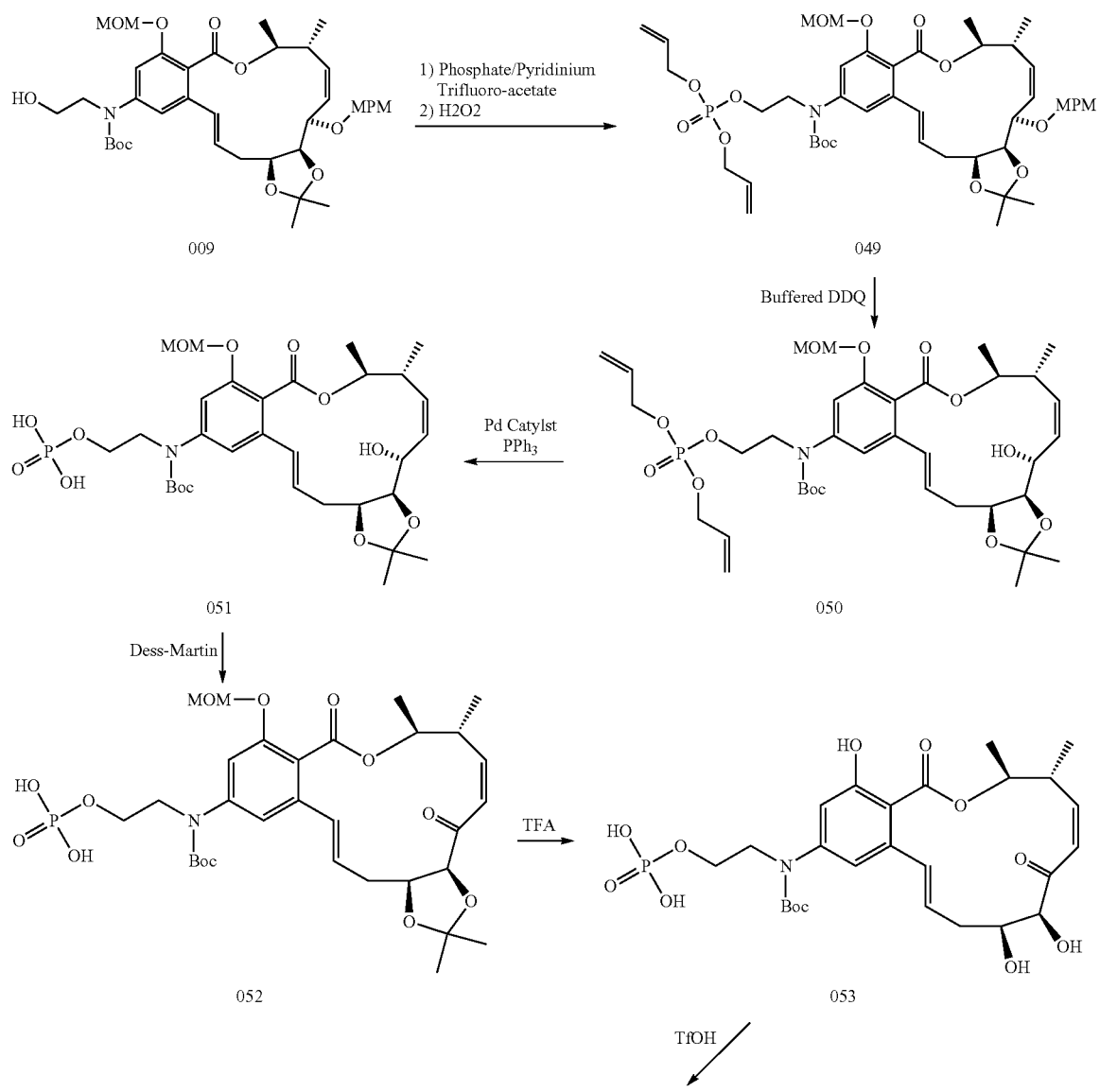

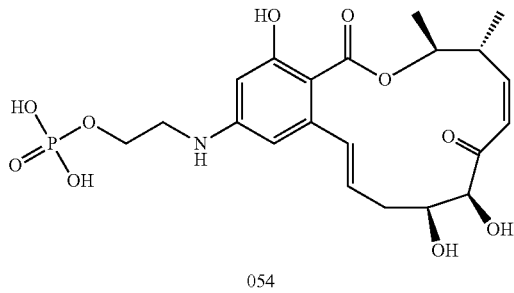

054

Compound 009 (200 mg, 0.00028 mol) was dissolved in methylene chloride (1.44 mL, 0.0225 mol). The diallyldiisopropylphosphoramidite (172 mg, 0.000702 mol), and pyridinium trifluoroacetate (136 mg, 0.000702 mol) was added. The reaction mixture was stirred at 20-25° C. The reaction was the cooled to about 0-5° C. and 30% $H_2O_2$ in water (3:7, $H_2O_2$:water, 0.14 mL) was added. After 15 min TLC (MTBE) showed disappearance of intermediate. Into the reaction was added water (1.98 mL, 0.1101 mol) and the product was extracted three times with MTBE. The organic phase was dried and then concentrated on rotavap to a crude colorless film. The product, compound 049, was purified on a 4 g redi-sep column eluting with 0-10% acetone/DCM. Yield: 242 mg (99%). DDQ Deprotection of 049 was the same as in the synthesis of compound 013 affording 201 mg (97%) of compound 050.

Into a round bottom flask under an atmosphere of nitrogen, compound 050 (100.5 mg, 0.134 mmol) was dissolved in tetrahydrofuran (4 mL) was added, followed by the addition of tetrakis(triphenylphosphine) palladium(0) (31 mg, 0.027 mmol), silane, phenyl-(99.0 µL, 0.000802 mol) and triphenylphosphine (42 mg, 0.00016 mol). The mixture was stirred for 60 minutes, and the reaction was monitored at 15 minute intervals until TLC (1:1 Maigic) showed that the reaction was complete. Solvent was removed under vacuum.

The residue was dissolved in 2:3:1 solvent system and loaded onto DEAE resin in a 1" diameter column. The resin was flushed with the 2:3:1 solvent system to remove all catalyst and non-polar materials. After the filtrate turned clear, 0.04 M ammonium acetate was used to continue washing the resin and elute the product, compound 051. The concentration of ammonium acetate was increased to 0.1M to drive off the remaining product from the resin. Fractions containing the product were collected and concentrated to a residue; the flask was placed under high vacuum and heated to 40° C. to remove all traces of ammonium acetate. Yield: 94.3 mg (100%).

The remainder of the procedure for the synthesis of compound 054 was similar to the analog compound 013, except that the workup and purification for 054 was accomplished with the DEAE Resin as shown above for compound 051. $^1$H-NMR, $^{31}$P-NMR, and MS verify structure. Product 054 submitted in free form. Yield 7.0 mg (30%); $^1$H-NMR (400 MHz, $CD_3OD$) δ: 1.15 (d, 3H, J=6.75 Hz), 1.36 (d, 3H, J=5.9 Hz), 2.10 (m, 2H), 3.3 (m, 2H), 3.45 (m, 1H), 4.01 (q, 2H, J=6 Hz), 4.06 (m, 2H), 4.48 (d, 1H, J=3 Hz), 5.93 (d, 1H, J=3 Hz), 5.98 (m, 1H),), 6.12 (m, 1H), 6.18 (d, 1H, J=3 Hz), 6.32 (s, 1H, J=12 Hz), 6.87 (s, 1H, J=16 Hz). $^{31}$P NMR (400 MHz, $CD_3OD$) δ: 2.60 (s, 1P). MS m/e: $(m^{-1})$ 484

Compound 065:

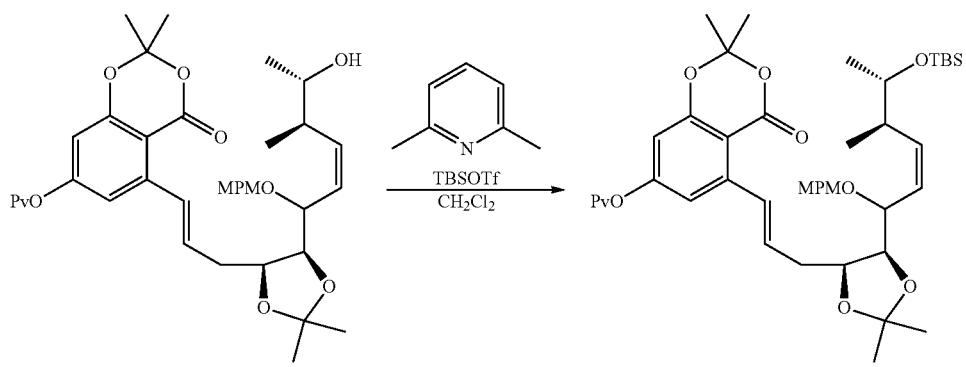

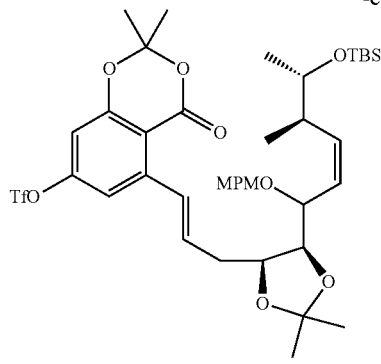

058

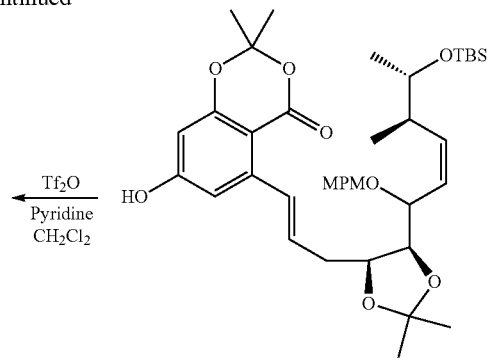

057

Compound 055 was synthesized in a manner similar to the synthesis of compound 006, shown above. To a solution of 055 (5.3 g, 7.95 mmol) and 2,6-lutidine (2.3 ml, 19.87 mmol) was added TBSOTf (2.19 ml, 9.54 mmol) dropwise at room temperature. The reaction mixture was quenched with aqueous sodium bicarbonate and the aqueous was extracted with ethyl acetate. The organics were combined and dried over $Na_2SO_4$. The dried solution was filtered and concentrated in vacuo. Purification of the residue by flash column chromatography on $SiO_2$ eluted with 5-10% ethyl acetate in hexane gave 5.26 g of desired product, compound 056.

To 056 (5.26 g, 6.73 mmol) in methanol (100 ml) was added $K_2CO_3$ (1.86 g) at room temperature. The reaction mixture was stirred for 2 hours and concentrated in vacuo. Purification of the residue by flash column chromatography on $SiO_2$ eluted with 10% ethyl acetate in hexane gave 2.48 g of desired product 057.

To 057 (2.48 g, 3.56 mmol) and pyridine (0.86 ml) in methylene chloride (20 ml) was added $Tf_2O$ (0.72 ml) dropwise at 0° C. The reaction mixture was allowed to warm to room temperature and stirred for 2 hours. The reaction was quenched with aqueous $NaHCO_3$. The aqueous layer was extracted with ethyl acetate and dried with $MgSO_4$. The dried solution was filtered and concentrated in vacuo. Purification of the residue by flash column chromatography on $SiO_2$ eluted with 5-10% ethyl acetate in hexane gave 2.77 g of desired product 058.

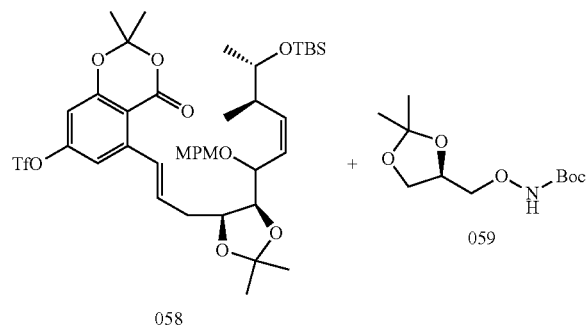

058      059      060

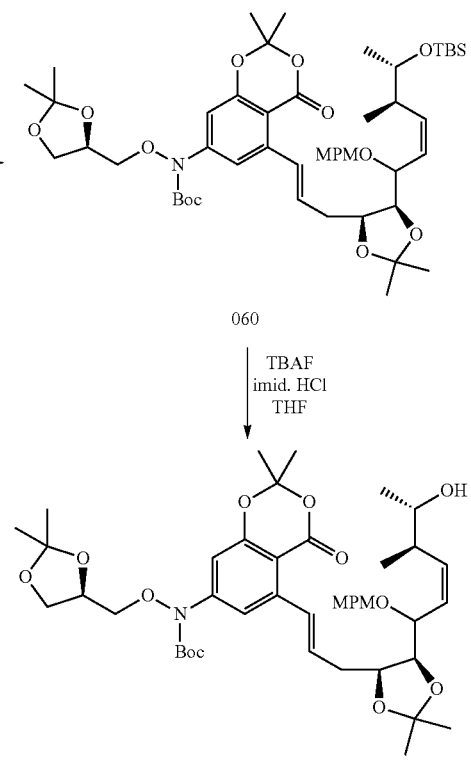

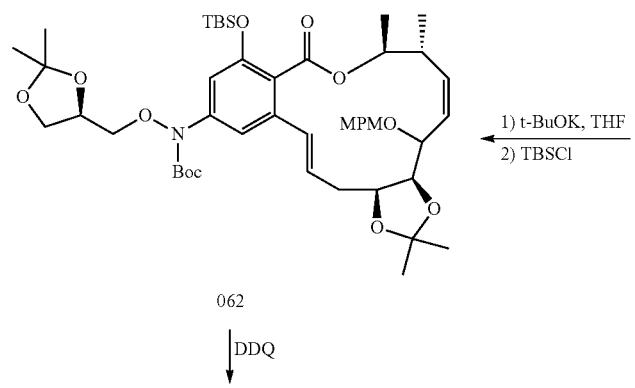

062      061

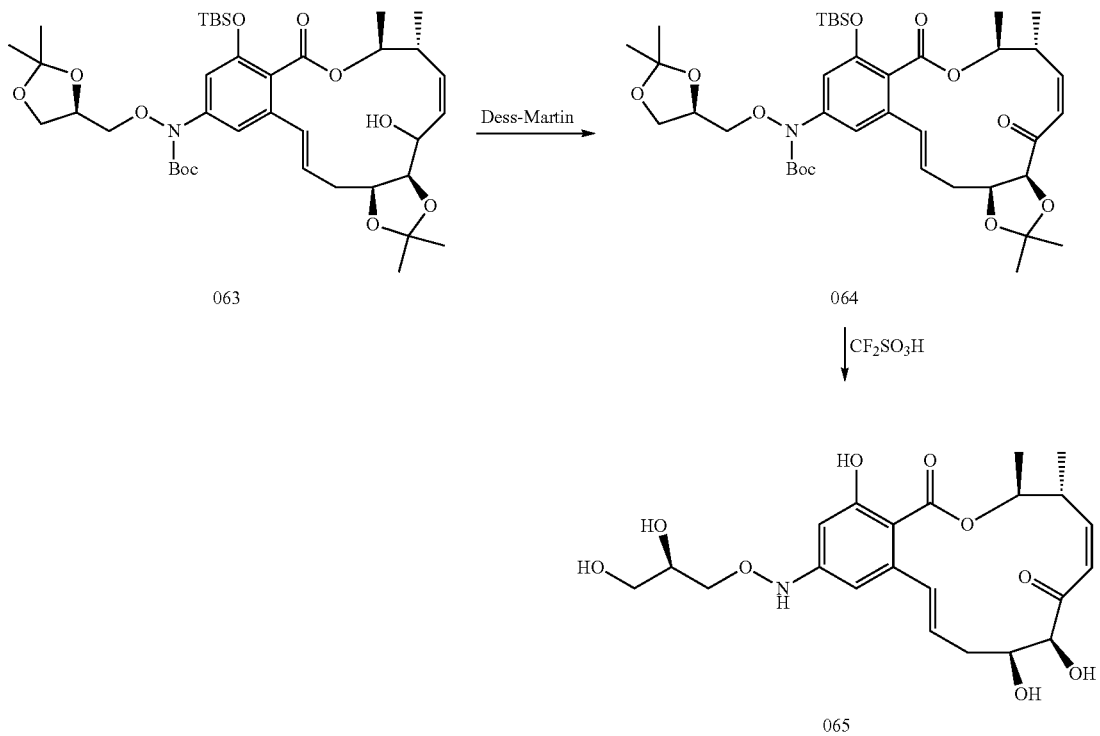

Compound 058 (1.74 g, 2.1 mmol), compound 059 (0.62 g) and (rac)-BINAP (196.1 mg) were weighed into a 100 ml round bottom reaction flask and azeotropically dried with toluene. Pd(OAc)$_2$ (47.1 mg) and Cs$_2$CO$_3$ (821.1 mg) were weighed in dry box to the reaction flask. The flask was removed from dry box and added de-gassed toluene (20 ml). The reaction mixture was heated to 80° C. for 15 hours and concentrated in vacuo. Purification of the residue by flash column chromatography on SiO$_2$ eluted with 5-10% ethyl acetate in hexane gave 1.64 g of desired product 060.

The buffered TBAF was prepared by dissolving imidazole HCl (659.0 mg) in TBAF (1.0 M in THF, 12.6 ml). The solution of 060 (1.67 g) in buffered TBAF was heated to 60° C. and stirred for 60 hours. The reaction was quenched by aqueous NH$_4$Cl. The aqueous was extracted with ether. The organics was combined and dried with Na$_2$SO$_4$. The dried solution was filtered and concentrated in vacuo. Purification of the residue by flash column chromatography on SiO$_2$ eluted with 10-30% ethyl acetate in hexane gave 0.80 g of desired product 061.

To the solution of t-BuOK (1.31 ml, 1.0 M in THF) in THF (9 ml) was added compound 061 (710 mg, 0.87 mmol) in THF (3 ml) slowly at 0° C. and then rinsed with 2 ml of THF. After the addition of starting material was completed, TBSCl (138.7 mg) in THF (2 ml) was added at 0° C. The reaction was quenched in 20 min and the aqueous was extracted with AcOEt. The organics was combined and dried over Na$_2$SO$_4$. The dried solution was filtered and concentrated in vacuo. Purification of the residue by flash column chromatography on SiO$_2$ eluted with 10% ethyl acetate in hexane gave 401.3 mg of desired product, compound 062.

To 062 (401.3 mg, 0.46 mmol) in methylene chloride and water (10 ml, 4:1 mixture) was added DDQ (128.0 mg) and stirred at room temperature for 2 hours. The reaction was quenched with aqueous Na$_2$SO$_3$ and NaHCO$_3$. The aqueous material was extracted with AcOEt. The organics were combined and dried over Na$_2$SO$_4$. The dried solution was filtered and concentrated in vacuo. Purification of the residue by flash column chromatography on SiO$_2$ eluted with 10% ethyl acetate in hexane gave 335.4 mg of desired product 063.

To 063 (335.4 mg, 0.45 mmol) and pyridine (54.4 μl) in methylene chloride (8 ml) was added Dess-Martin periodinane (259.2 mg) at room temperature. The reaction mixture was stirred for 1 hour and quenched with aqueous NaHCO$_3$. The aqueous material was extracted with AcOEt. The organics were combined and dried over Na$_2$SO$_4$. The dried solution was filtered and concentrated in vacuo. Purification of the residue by flash column chromatography on SiO$_2$ eluted with 10% ethyl acetate in hexane gave 232.5 mg of desired product 064.

To 064 (47.1 mg, 0.063 mmol) in toluene/water (1 ml/0.035 ml) was added CF$_3$SO$_3$H (16.8 μl) at 0° C. The reaction mixture was stirred for 1.5 hours and warmed to room temperature. Additional TfOH (16.8 μl) was added and the reaction was quenched in 5 minutes with saturated aqueous NaHCO$_3$. The aqueous was extracted with AcOEt. The organics was combined and dried over Na$_2$SO$_4$. The dried solution was filtered and concentrated in vacuo. Purification of the residue by flash column chromatography on SiO$_2$ eluted with 10% methanol in methylene chloride gave 7.4 mg of desired product 065. $^1$HNMR (CD$_3$OD): 6.92, (d, J=15.6 Hz, 1H), 6.36, (s, 1H), 6.35 (s, 1H), 6.34 (d, J=11.6 Hz, 1H), 6.32 (d, J=15.2 Hz), 6.13 (dd, J=11.6, 10.0 Hz, 1H), 6.04-5.96 (m, 1H), 4.96-4.86 (m, 1H), 4.48 (d, J=2.0 Hz, 1H). 4.08-4.02 (m, 1H), 3.95-3.87 (m, 2H), 3.86-3.79 (m, 1H), 3.64-3.53 (m, 2H), 3.52-3.43 (m, 1H), 2.18-2.02 (m, 2H), 1.38 (d, J=6.4 Hz, 3H), 1.16 (d, J=7.2 Hz. 3H).

Compound 069:

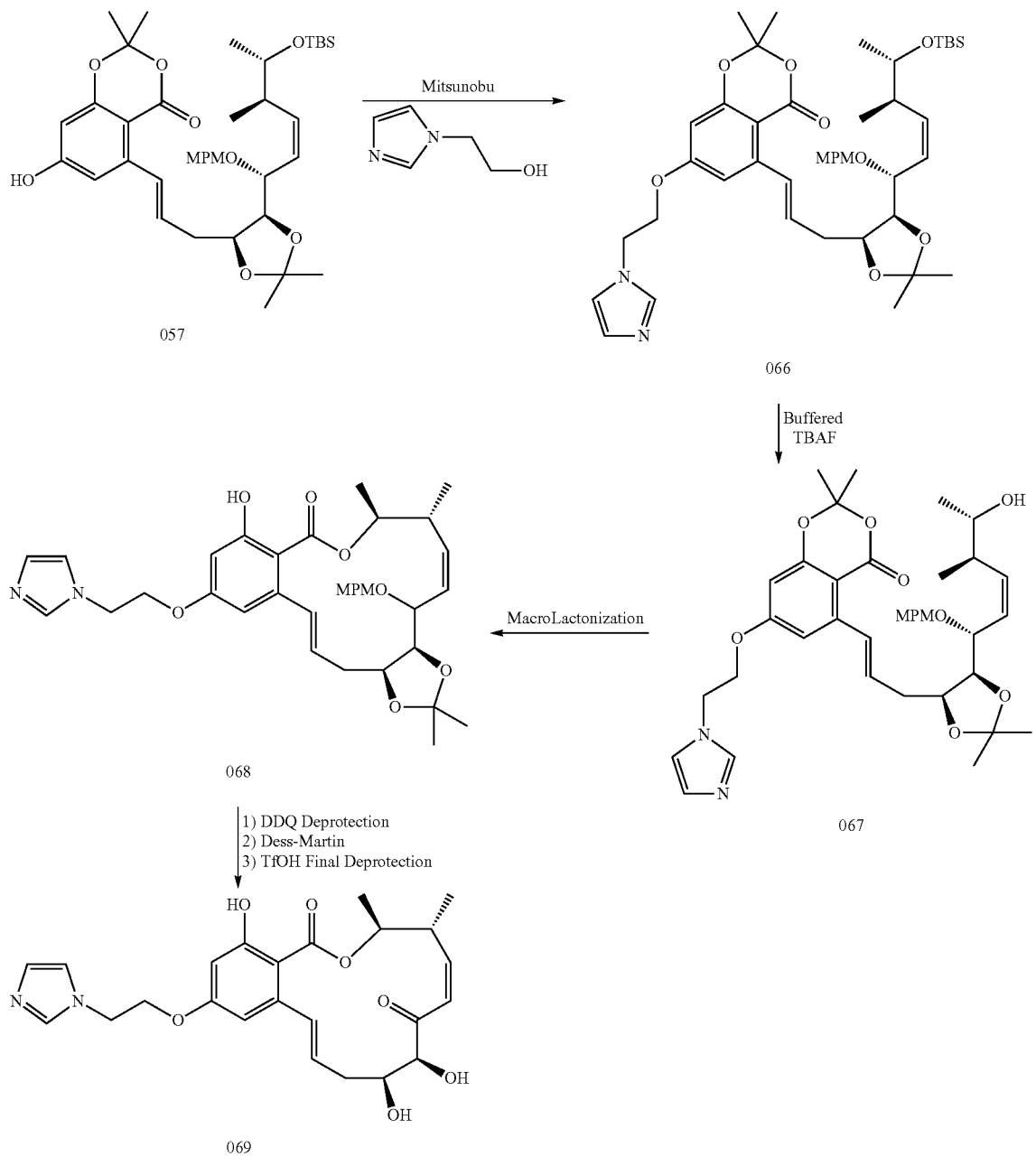

Into a round bottom flask was added 057 (2.331 g, 0.003345 mol), triphenylphosphine (1.14 g, 0.00435 mol) and tetrahydrofuran (13.6 mL, 0.167 mol). The mixture was cooled to 0° C. under a nitrogen atmosphere. Imidazole ethanol fragment (0.450 g, 0.00401 mol) was added, followed by addition on diethyl azodicarboxylate (0.685 mL, 0.00435 mol). The reaction was allowed to warm slowly to room temperature while stirring. A TLC test revealed an intense product spot together with some unreacted starting material. The reaction was cooled to 0° C. and an additional 0.2 eq of the amine, triphenylphosphine, and DEAD were added. The ice bath was removed and reaction was allowed to warm to room temperature. After 30 min, TLC showed the reaction was complete and all starting material was consumed. All solvent was removed under high vacuum. The residue was dissolved in MTBE, the mixture was cooled in an ice bath and some of the triphenyl phosphate was filtered off. The residue was purified on 40 g column, using 0-5% MeOH/DCM. Product fractions containing compound 066 were combined and concentrated down to a residue. Yield: 3.65 g (100%).

The TBS protecting group was removed using buffered TBAF with imidazole hydrochloride, for a total compound 067 yield of ~2.0 g (90%).

Compound 068 was produced from 067 using the same procedure as used in the synthesis of compound 007. Combining all batches, the total yield was 467 mg (50%).

The intermediate compound 068 was deprotected with DDQ, then oxidized with Dess-martin reagent and deprotected with TfOH to give the product, compound 069 (100 mg). ¹H-NMR (400 MHz, CDCl₃) d 1.19 (d, J=7.2 Hz, 3H), 1.43 (d, J=6.0 Hz, 3H), 2.10-2.25 (m, 2H), 3.58-3.65 (m, 1H), 4.00-4.03 (m, 1H), 4.22 (t, J=5.2 Hz, 2H), 4.34 (t, J=5.2 Hz, 2H), 4.50 (d, J=2.4, 1H), 4.88-4.95 (m, 1H), 5.96-6.03 (m, 1H), 6.14 (dd, J=9.6, 11.2 Hz, 1H), 6.22 (d, J=11.6, 1H), 6.33 (d, J=2.4 Hz, 1H), 6.37 (d, J=2.8 Hz), 6.86 (d, J=15.6 Hz, 1H), 7.03 (s, 1H), 7.08 (s, 1H), 12.17 (s, 1H).
Compound 076:

Buffered TBAF was prepared by dissolving imidazole HCl (108.3 mg) in TBAF (1.0 M in THF, 2.1 ml). The solution of 071 (247.5 mg, 0.3 mmol) in buffered TBAF was heated to 60° C. and stirred for 36 hours. The reaction was quenched by aqueous NH₄Cl. The aqueous material was extracted with ether. The organics were combined and dried with Na₂SO₄. The dried solution was filtered and concentrated in vacuo. Purification of the residue by flash column chromatography

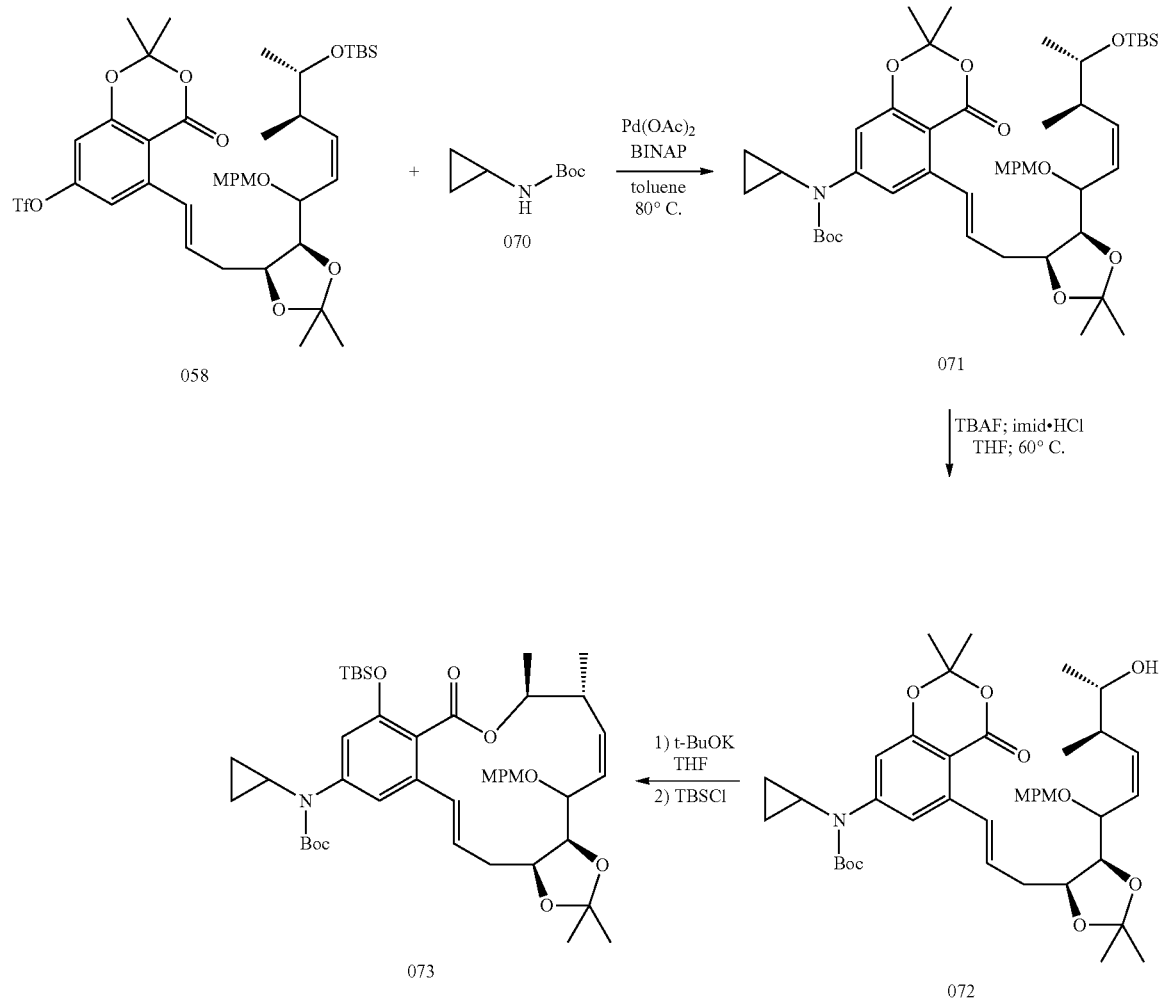

on SiO₂ eluted with 10-20% ethyl acetate in hexane gave 116.6 mg of desired product, compound 072.

To a solution of t-BuOK (0.24 ml, 1.0 M in THF) in THF (2 ml) was added 072 (116.6 mg, 0.16 mmol) in THF (1 ml) slowly at 0° C. and rinsed with 2 ml of THF. After the addition of starting material was completed, TBSCl (25.6 mg) in THF (2 ml) was added at 0° C. The reaction was quenched in 20 min and the aqueous material was extracted with AcOEt. The organics were combined and dried over Na₂SO₄. The dried solution was filtered and concentrated in vacuo. Purification of the residue by pTLC developed with 30% ethyl acetate in hexane gave 40.0 mg of desired product, compound 073.

Compound 058 as synthesized above (459.7 mg, 0.55 mmol), compound 070 (104.6 mg) and (rac)-BINAP (51.8 mg) were weighed into a 25 ml round bottom reaction flask and azeotropically dried with toluene. Pd(OAc)₂ (12.4 mg) and Cs₂CO₃ (216.8 mg) were weighed in dry box to the reaction flask. The flask was removed from dry box and added de-gassed toluene (3 ml). The reaction mixture was heated to 80° C. for 60 hours and concentrated in vacuo. Purification of the residue by flash column chromatography on SiO₂ eluted with 5-10% ethyl acetate in hexane gave 247.5 mg of desired product, compound 071.

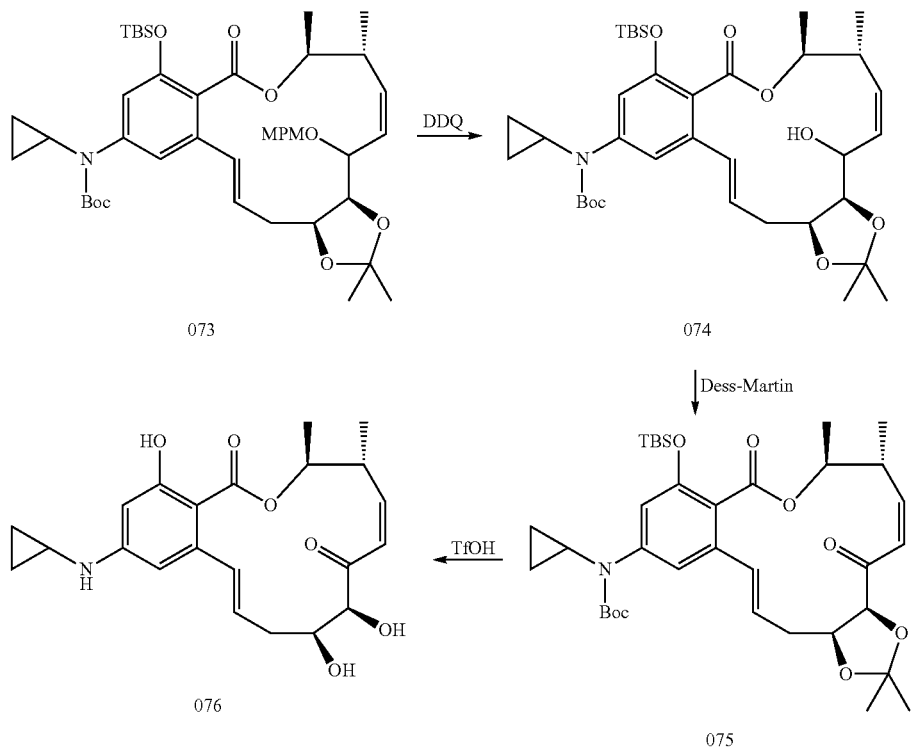

To compound 073 (40.0 mg, 0.051 mmol) in methylene chloride and water (2 ml, 4:1 mixture) was added DDQ (14.2 mg) and stirred at room temperature overnight. The reaction was quenched with aqueous $Na_2SO_3$ and $NaHCO_3$. The aqueous was extracted with AcOEt. The organics was combined and dried over $Na_2SO_4$. The dried solution was filtered and concentrated in vacuo. Purification of the residue by pTLC developed with 20% ethyl acetate in hexane gave 25.0 mg of desired product, compound 074.

To compound 074 (25.0 mg, 0.038 mmol) and pyridine (6.1 μl) in methylene chloride (2 ml) was added Dess-Martin periodinane (31.0 mg) at room temperature. The reaction mixture was shred for 5 h and quenched with aqueous $NaHCO_3$. The aqueous was extracted with AcOEt. The organics was combined and dried over $Na_2SO_4$. The dried solution was filtered and concentrated in vacuo. Purification of the residue by pTLC developed with 30% ethyl acetate in hexane gave 24.0 mg of desired product, compound 075.

To compound 075 (24.0 mg, 0.037 mmol) in toluene/water (1 ml/0.035 ml) was added $CF_3SO_3H$ (19.4 μl) at 0° C. The reaction mixture was stirred for 10 min and warmed to room temperature. The reaction was quenched in 1 h with saturated aqueous $NaHCO_3$. The aqueous material was extracted with AcOEt. The organics were combined and dried over $Na_2SO_4$. The dried solution was filtered and concentrated in vacuo. Purification of the residue by pTLC developed with 10% methanol in methylene chloride gave 2.4 mg of desired product, compound 076. $^1$HNMR ($CDCl_3$): 6.86 (d, J=15.2 Hz, 1H), 6.29 (d, J=2.8 Hz, 1H), 6.26-6.12 (m, 3H), 5.99-5.90 (m, 1H), 4.94-4.84 (m, 1H), 4.56-4.46 (m, 2H), 4.06-3.98 (m, 1H), 3.84 (d, J=5.6 Hz, 1H), 3.65-3.54 (m, 1H), 2.50-2.42 (m, 2H), 2.24-2.08 (m, 2H), 1.42 (d, J=6.0 Hz, 3H), 1.26 (t, J=7.2 Hz, 1H), 1.18 (d, J=6.8 Hz, 3H), 0.82-0.76 (m, 2H), 0.56-0.51 (m, 2H).

Compound 081:

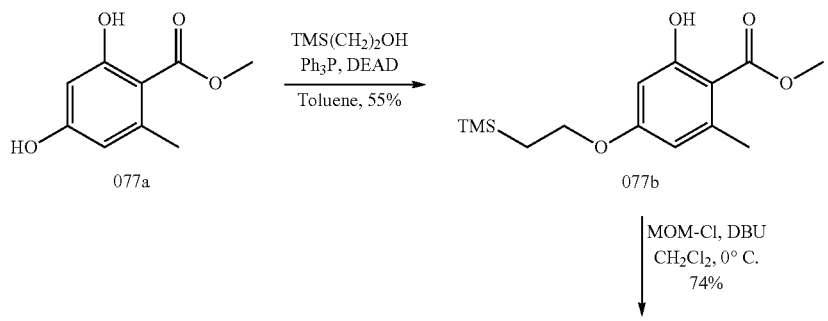

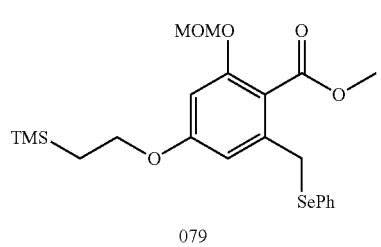 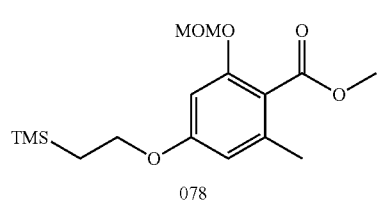

DEAD was added to a solution of compound 077a, Ph₃P and 2-TMS-ethanol in toluene at 0° C. The mixture was stirred at room temperature for 1 hour before it was quenched with aqueous NaHCO₃. The organic phase was dried (Na₂SO₄), concentrated and purified by silica gel chromatography to afford 077b.

MOM-Cl (2.8 mL, 37 mmol) was added to a solution of 077b (2.1 g, 7.4 mmol) and DBU (7.1 mL, 48 mmol) in 10 mL of CH₂Cl₂ at 0° C. The mixture was stirred at room temperature for 15 minutes before the organic phase was washed with NaHCO₃, concentrated and purified by silica gel chromatography to furnish compound 078 (1.8 g, 5.5 mmol) from a silica gel plug in 74% yield.

2.5 M n-BuLi in hexanes was introduced drop wise to the stirring solution of diisopropylamine in of THF at −5° C. The solution was stirred at 0° C. for 30 minutes before it was cooled to −78° C. Compound 078 in THF was added to the cold LDA slowly so that the internal temperature was kept below −78° C. The mixture was stirred at −78° C. for 45 minutes, and then (PhSe)₂ in THF was added slowly so that the internal temperature was kept below −60° C. The reaction mixture was stirred for 40 minutes before it was quenched with aqueous NH₄Cl at −78° C. EtOAc was added to the mixture at room temperature. After separation, the organic layer was dried (Na₂SO₄) and concentrated. 5% EtOAc in toluene was used to elute 079 from a silica gel column.

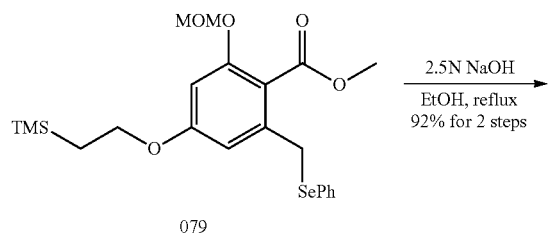

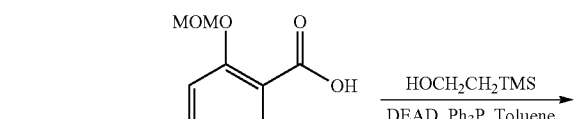

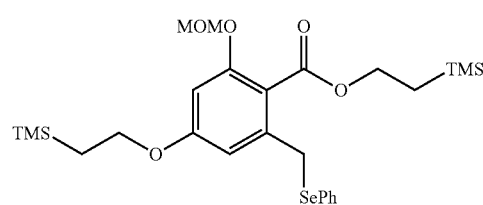

2.5 N NaOH was added to 079 in EtOH. The mixture was refluxed for 12 hours before it was acidified and extracted with EtOAc. Organic phase was dried (Na₂SO₄) and concentrated to afford solid 080. DEAD was added to a solution of 080, Ph₃P and 2-TMS-ethanol in toluene at 0° C. The mixture was stirred at room temperature for 1 hour before it was quenched with aqueous NaHCO₃. The organic phase was dried (Na₂SO₄), concentrated and purified by silica gel chromatography to afford compound 081.

Compound 087:

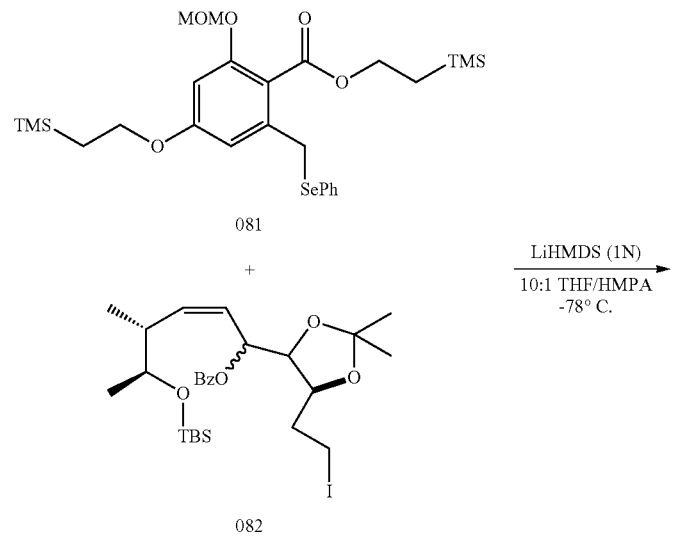

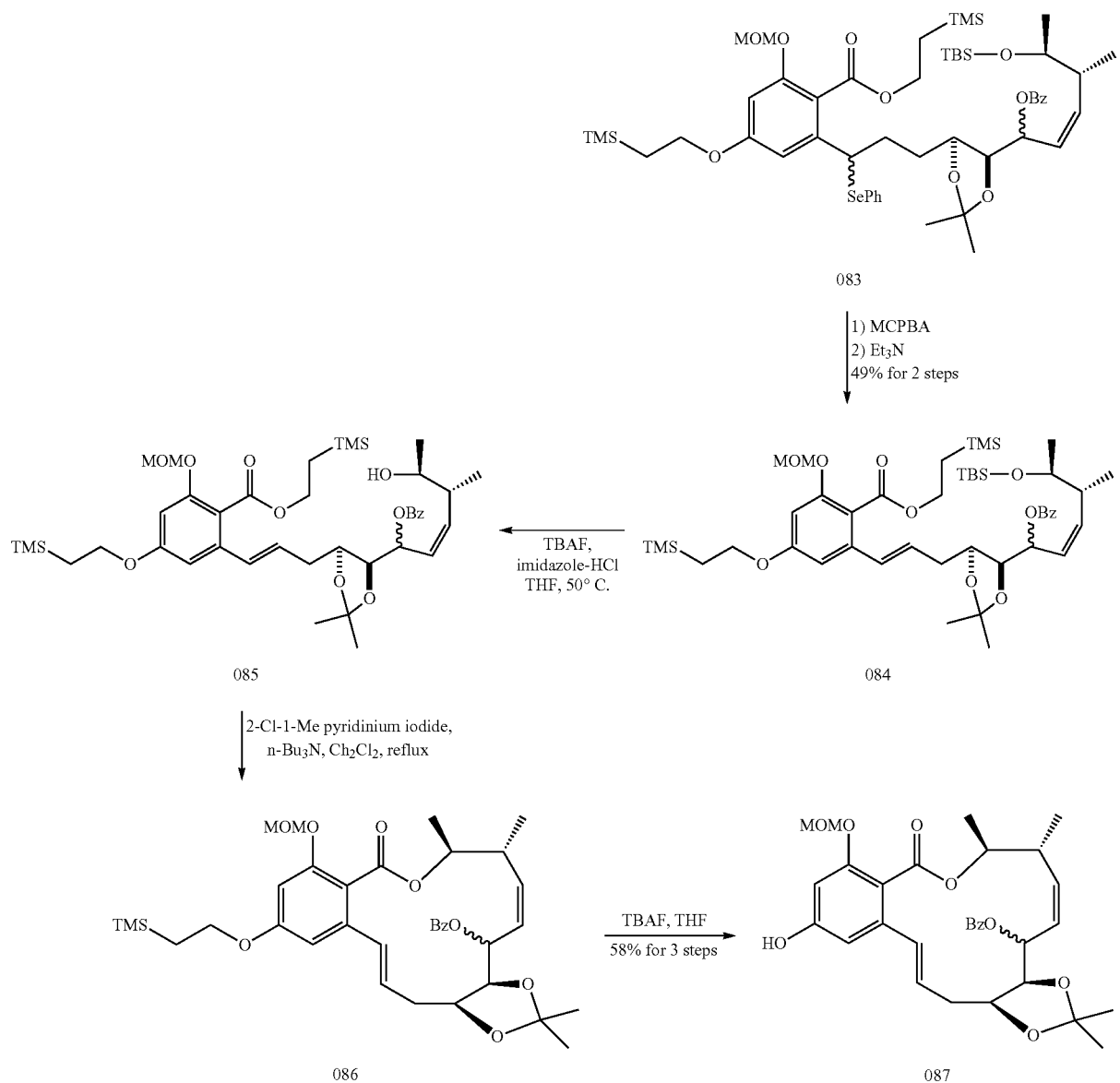

LiHMDS in THF was introduced drop wise into a cold (−78° C.) solution of compounds 081 and 082 in 10:1 THF-HMPA. The internal temperature was kept below −70° C. during the addition. The mixture was stirred at −78° C. for about 30 minutes before it was quenched with aqueous NH$_4$Cl and diluted with EtOAc. Organic phase was dried (Na$_2$SO$_4$), concentrated and purified by silica gel chromatography to afford 083 (1.9 g, 1.6 mmol) in 82% yield.

m-CPBA (1.0 g, 4.2 mmol) was added in three portions into a cold (0° C.) solution of 083 in CH$_2$Cl$_2$. The mixture was stirred at 0° C. for 1 hour before the addition of Et$_3$N. After the reaction mixture was stirred at room temperature for 1 hour, it was quenched with aqueous Na$_2$S$_2$O$_3$ and diluted with aqueous NaHCO$_3$. The organic phase was dried (Na$_2$SO$_4$), concentrated and purified by silica gel chromatography to afford compound 084.

In a solution of TBAF buffered with 0.33 mole equivalent of imidazole.HCl was introduced to the solution of 084 in THF. The mixture was stirred at 50° C. for 12 hours before it was diluted with Et$_2$O and washed with aqueous NH$_4$Cl. Organic phase was dried (Na$_2$SO$_4$) and concentrated to furnish crude 085, which was dissolved in CH$_2$Cl$_2$ and was added drop wise to a refluxing mixture of 2-chloro-1-methylpyridinium iodide and n-Bu$_3$N in of CH$_2$Cl$_2$. The mixture was refluxed for 2 hours before it was diluted with Et$_2$O and washed with 0.05 N HCl, H$_2$O and NaHCO$_3$. Organic phase was dried (Na$_2$SO$_4$), concentrated and purified by silica gel chromatography to afford compound 086.

TBAF in THF (7.0 mL, 7.0 mmol) was introduced to the solution of 086 (0.87 g, 1.3 mmol) in 7 mL of THF. The mixture was stirred at room temperature for 4 hours before it was diluted with Et$_2$O and washed with brine. Organic phase was dried (Na$_2$SO$_4$), concentrated and purified by silica gel chromatography to afford compound 087 (0.43 g, 0.78 mmol) in 58% yield over 3 steps.

Compound 091:

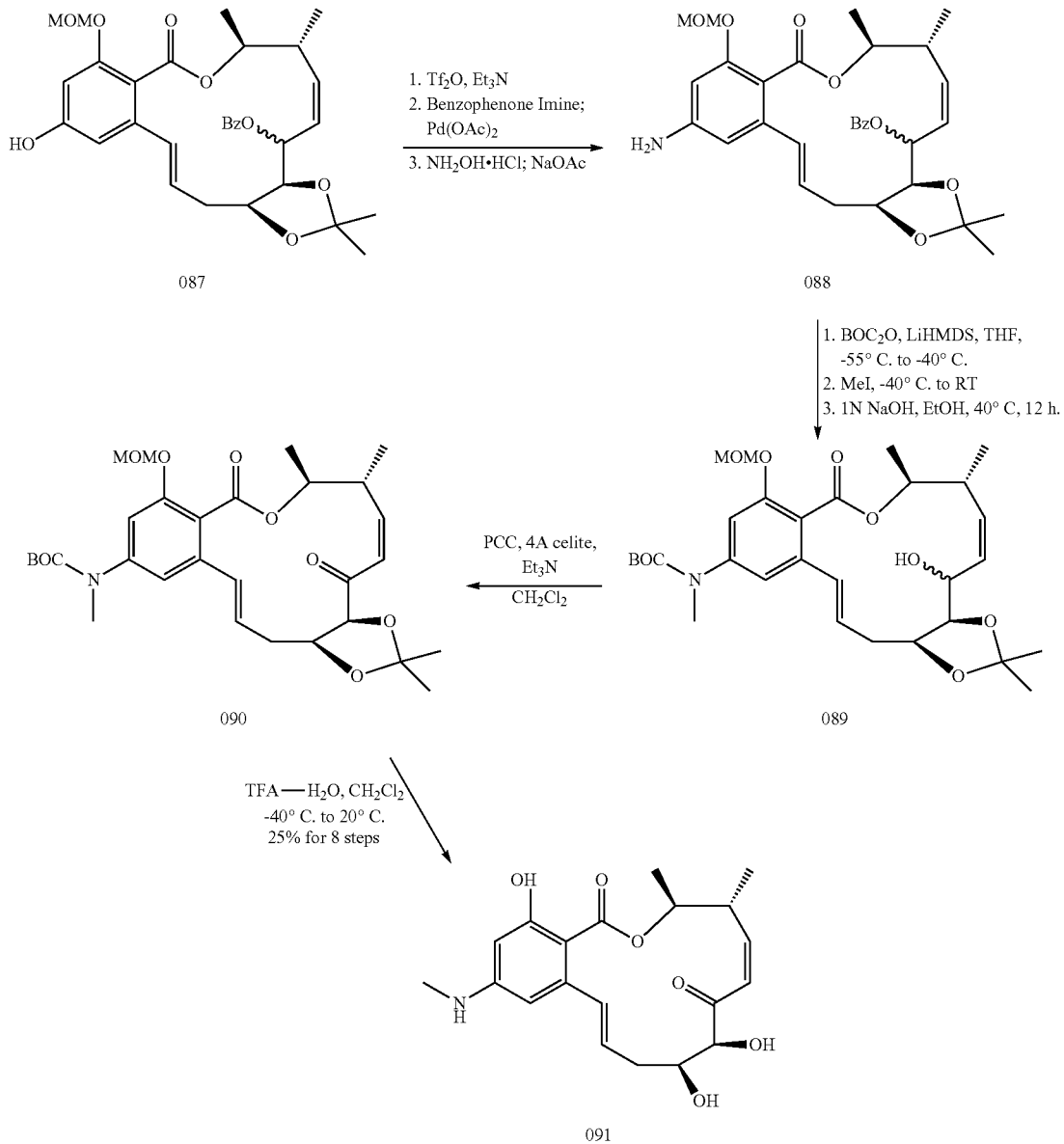

Tf₂O (0.42 ML, 2.5 mmole) was added to a solution of 087 (0.95 g, 1.7 mmole) and Et₃N (0.58 ML, 4.2 mmole) in 20 ML of CH₂Cl₂ at 0° C. The mixture was stirred for 10 min before the addition of aqueous NaHCO₃. The aqueous layer was extracted twice with CH₂Cl₂. The organic phase was concentrated and passed through a short plug of silica gel (20% EtOAc/Hex).

The triflate thus obtained was added Pd(OAc)₂ (19 mg, 0.08 mmole), BINAP (64 mg, 0.10 mmole) and Cs₂CO₃ (0.66 g, 2.0 mmole) in a dry box. Benzophenone imine (0.32 ML, 1.9 mmole) and 30 mL of toluene was added under nitrogen before the mixture was heated at 90° C. for 14 h. The mixture was then diluted with EtOAc and brine. The organic layer was dried (Na₂SO₄) and concentrated.

The resultant crude material was dissovled in 8 mL of MeOH and 5 mL of THF before the addition of NaOAc (0.56 g, 6.8 mmole) and NH₂OH.HCl (0.24 g, 3.4 mmole) at room temperature. After 50 min, EtOAc and brine was added. The organic layer was dried (Na₂SO₄), concentrated and purified with silica gel (30 EtOAc/Hex) to produce crystalline compound 088 (0.88 g, 1.6 mmole).

LiHMDS (1N in THF, 8.0 mmole) was added slowly to a solution of 088 (0.88 g, 1.6 mmole) in 16 mL of THF at −55 to −50° C. The mixture was stirred at −45° C. for 5 min before the addition of BOC₂O (0.38 mL, 1.8 mmole). After the mixture was stirred at −40° C. for 30 min, MeI (0.60 mL, 9.6 mmole) was added. After 10 minutes, the mixture was warmed up to room temperature for 2 hours. The mixture was recooled to −35° C. and 72 mL of 1N NaOH and 48 mL of EtOH were added. After it was heated at 45° C. for 12 hours, the mixture was diluted with 100 mL of water and 150 mL of CH₂Cl₂. The aqueous layer was extracted twice with 50 mL of CH₂Cl₂. The organic layer was concentrated and purified by silica gel chromatography (30% EtOAc/Hex) to furnish colorless gel 089 (0.58 g, 1.0 mmole).

A suspension of compound 089 (0.40 g, 0.71 mmole), PCC (0.46 g, 2.1 mmole), 4 Å molecular sieves (0.50 g), and celite (0.50 g) in 8 ML of $CH_2Cl_2$ was stirred at room temperature for 2.5 h before the addition of $Et_3N$ (0.29 ML, 2.1 mmole). After 5 min, 30 mL of $Et_2O$ was added and the mixture was filtered. The filtrate was concentrated and passed through a short silica gel plug (75% EtOAc/Hex) to provide colorless crystalline 090 (0.35 g, 0.63 mmole).

TFA (5% water, 6 ML) was added slowly to the solution of compound 090 (0.35 g, 0.63 mmole) in $CH_2Cl_2$ at −35° C. The mixture was stirred at −20° C. for 1 hour before the addition of saturated aq. $NaHCO_3$ (PH ~8) and $CH_2Cl_2$. The aqueous layer was extracted twice with $CH_2Cl_2$. The organic layer was dried ($Na_2SO_4$), concentrated and purified by silica gel chromatography (75% EtOAc/Hex) to afford compound 091 (124 mg, 0.33 mmole) in 25% overall yield over 8 steps. NMR: $^1$H-NMR 8 (Benzene-$d_6$) 0.80 (d, J=6.8 Hz, 3H, C4-$CH_3$), 1.02 (d, J=6.0 Hz, 3H, C3-$CH_3$), 2.07 (d, J=5.1 Hz, 3H, $NCH_3$), 2.11 (m, 2H, 10-$CH_2$), 2.26 (d, J=11.3 Hz, 1H, C9-OH), 3.06 (m, 1H, NH), 3.44 (m, 1H, 4-CH), 3.82 (d, J=5.1 Hz, 1H, C8-OH), 3.89 (ddt, J1=11.3 Hz, J2=2.8 Hz, J3=7.0 Hz, 1H, 9-CH), 4.22 (dd, J1=2.6 Hz, J2=5.1 Hz, 1H, 8-CH), 4.67 (dq, J1=6.0 Hz, J2=10.4 Hz, 1H, 3-CH), 5.40 (dd, J1=9.6 Hz, J2=11.3 Hz, 1H, 5-CH), 5.48 (d, J=11.3 Hz, 1H, 6-CH), 5.85 (d, J=2.3 Hz, 1H, aromatic CH), 6.00 (dt, J1=15.2 Hz, J2=7.5 Hz, 1H, 11-CH), 6.13 (d, J=2.3 Hz, 1H, aromatic CH), 6.98 (d, J=15.4 Hz, 1H, 12-CH), 13.03 (s, 1H, phenol). MS: 398 ($M^+Na$, 100%).

Compound 092:

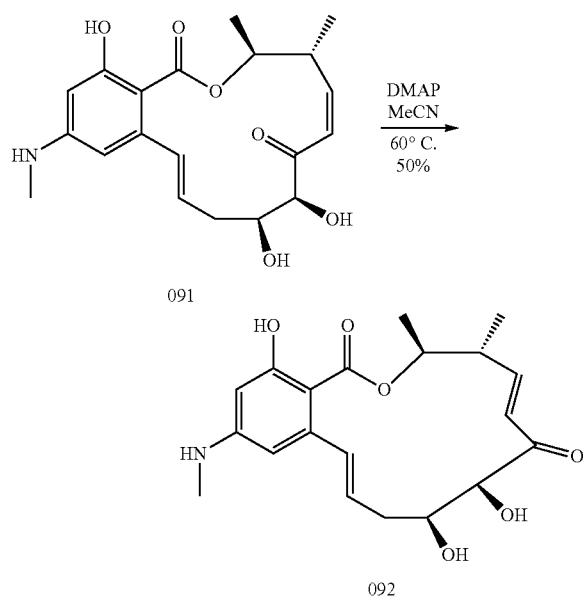

To a solution of compound 091 (16 mg) in $CH_3CN$ was added DMAP (20 mg). The solution was then stirred at 60° C. for 3 hours and then at room temperature for 12 hours. The crude mixture was purified on Silica gel and desired product 092 (13 mg) was eluted with 60% EtOAc/Hexanes. $^1$HNMR (Benzene-$d^6$): 6.79 (2H, dd, $J_1$=16.0 Hz, $J_2$=5.95 Hz); 6.09 (1H, d, J=2.3 Hz); 5.92 (1H, dd, $J_1$=16.0 Hz, $J_2$=1.4 Hz); 5.82 (1H, m); 5.81 (1H, d, J=2.3 Hz); 4.98 (1H, m); 4.42 (1H, m); 3.97 (1H, m); 3.80 (1H, d, J=5.7 Hz); 3.04 (1H, m); 2.37 (2H, m); 2.04 (3H, d, J=5.7 Hz); 2.04 (1H, m); 1.67 (1H, m); 0.86 (3H, d, J=7.1 Hz); 0.56 (3H, d, J=7.1 Hz). Note that the coupling constants of the 2 enone olefin hydrogens changed from 11 Hz in 091 to 16 Hz in 092.

Compound 106:

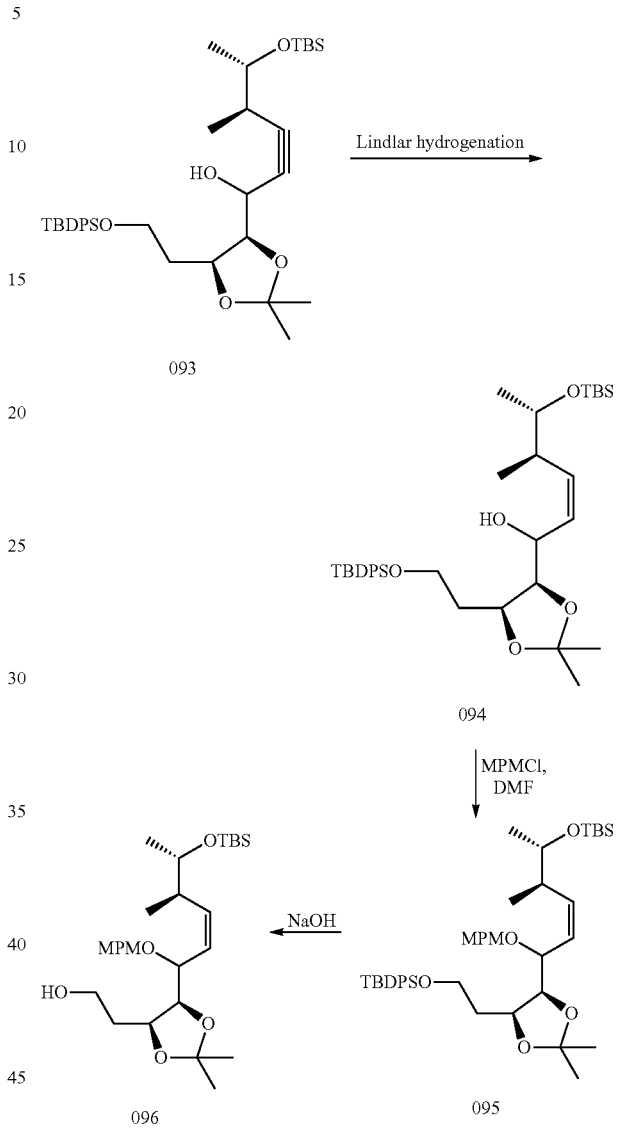

To a solution of 093 (165.9 g, 265 mmol) in 2.65 L of Hexanes, quinoline (2.65 mL) and Lindlar catalyst (28.2 g, 13.3 mmol, 0.05 eq.) were added. The mixture was degassed repeatedly under vacuum and recharged with nitrogen (3×) and hydrogen (3×). The intake of hydrogen on hydrogenator was set to 0.114 mol and the reaction was monitored by MS/$^1$H NMR. After the reaction proceeded overnight, the suspension was filtered and recharged with catalyst and hydrogen. After 3 days, the reaction was filtered through celite. The filtrates were concentrated and purified on silica gel to give 104 g of 094 as an oil.

To a solution of 094 (67.4 g, 107 mmol), MPMCl (21.9 mL, 161 mmol, 1.5 eq.) and a 1M solution of NaHMDS in THF (140 mL, 140 mmol, 1.3 eq.) was added slowly with syringe pump over 2 hours at 0° C. After the mixture was stirred for 1.5 hours at 0° C., it was quenched with saturated $NH_4Cl$ at 0° C. and warmed to room temperature. The mixture was extracted three times with EtOAc, and the extracts were washed with water and brine, and then dried and concentrated. The crude product was purified on silica gel to give 095 quantitatively.

095 (119.6 g, 160 mmol) was dissolved in a mixture of 10% NaOH in methanol (3.2 L, v/v) and 3.5 mL of water. The reaction was heated at 45° C. for 48 h. After cooled, it was diluted with 9 L of $CH_2Cl_2$, washed twice with water, once with saturated $NH_4Cl$, and once with brine, and then dried and concentrated. The crude product was purified on silica gel with 10%-25-35% of EtOAc/Hexanes to give 096 (78 g, 96% yield).

and once with brine, and then dried and concentrated. The crude product 097 was used directly for next step.

To a suspension of $Ph_3PCH_3Br$ (115.8 mL, 324.3 mmol, 2.2 eq.) in a mixture of THF (870 mL) and DMSO (433.6 mL), n-BuLi (184.3 mL of 1.6 M solution, 294.8 mmol, 2 eq.) was added at 0° C. After stirred for 1 h, a solution of 097 (74.7 g in 175 mL of THF, 147.4 mmol) was added at 0° C. After 30 min, it was warmed to room temperature. After 2 hours, it was quenched with 1.1 L of saturated $NHCl_4$ and extracted three times with EtOAc. The extracts were washed with water and brine and then dried and concentrated. The crude product was

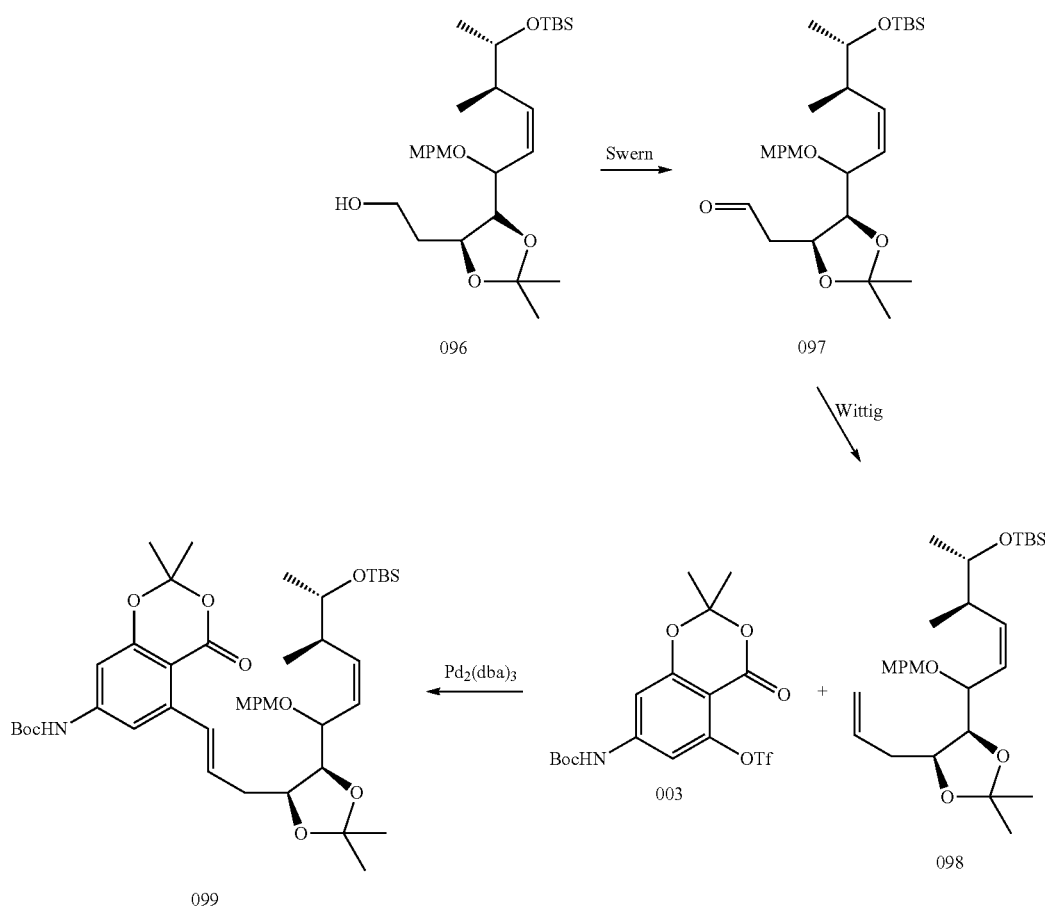

To a solution of $(COCl)_2$ (25 mL, 295 mmol, 2 eq.) in $CH_2Cl_2$ (870 mL), DMSO (41.85 mL, 590 mmol, 4 eq.) was slowly added at −78° C. After stirring for 30 min at −78° C., a solution of 096 (75 g, 147.4 mmol) in $CH_2Cl_2$ (160 mL) was added over 45 minutes. After the mixture was stirred at −78° C. for 45 min, $Et_3N$ (82.2 mL, 590 mmol, 4 eq.) was added at the same temperature. After the reaction is further stirred for 30 min, it was warmed to 0° C. for 1.5 h. The reaction was quenched with 750 mL of saturated $NH_4Cl$ and extracted three times with EtOAc. The extracts were dried and concentrated. The crude product was re-suspended with 2.5 L of 1:1 solution of EtOAc/Hexanes, washed three times with water purified on silica gel with 5-10% EtOAc/Hexanes to give 66.5 g of 098 as an oil (89% yield).

To a mixture of 098 (2.5 g, 4.95 mmol) and triflate 003 (2.7 g, 6.4 mmol, 1.3 eq.), $Pd_2(dba)_3$ (1.36 g, 1.48 mmol, 0.3 eq.) was added in the dry box. After the mixture was moved out of dry box, it was suspended in 8.3 mL of dioxane and N-methyl N-dicyclohexane amine (2.1 mL, 9.9 mmol, 2 eq.) was added. The reaction was heated at 100° C. for 12 hours with vigorous stirring. After cooled, 6 g of celite was added and diluted with EtOAc. The mixture was filtered through a celite plug and rinsed with EtOAc. The filtrates were concentrated. The crude product was purified on silica gel with 10-20% EtOAc/Hexanes to give 3 g of pure 099 (76% yield).

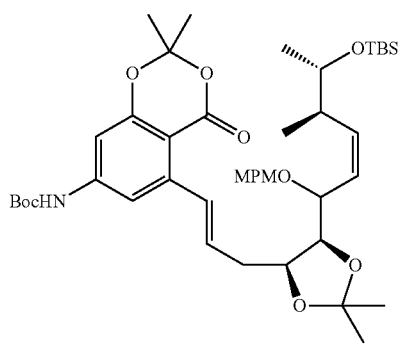

099

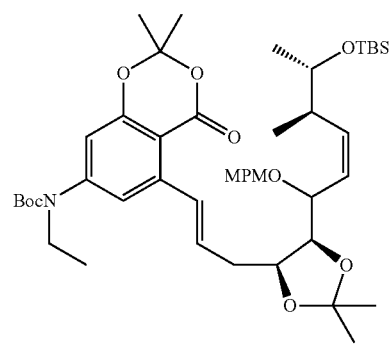

100

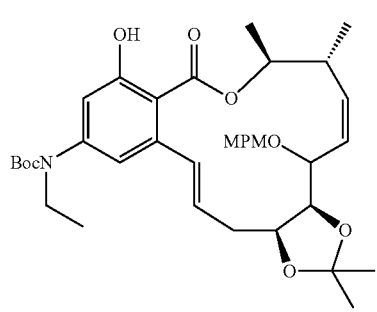

102

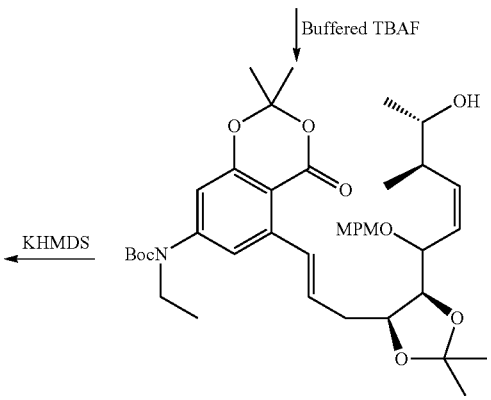

101

To a solution of 099 (46.3 g, 58.16 mmol) in DMPU (291 mL), LiHMDS (116 mL of 1M solution in THF, 116.3 mmol, 2 eq.) was added at 0° C. After the mixture was stirred for 40 minutes at the same temperature, EtI (27.9 mL, 349 mmol, 6 eq.) was added. After 5 minutes, the mixture was warmed to room temperature. After the mixture was stirred for 3 hours, it was quenched with 1 L of Sat. NHCl$_4$ at 0° C. The mixture was extracted with MTBE/Hexanes (1:1). The extracts were washed with brine, and then dried and concentrated. The crude product was purified on silica gel with 15-20% EtOAc/Hexanes to give 40 g of desired product, 100 (84% yield).

To a solution of 100 (48 g, 58.2 mmol) in 230 mL, a solution of TBAF (407 mL of 1M solution, 407 mmol, 7 eq.) and imidazole.HCl (21.3 g, 203.9 mmol, 3.5 eq.) was added. The reaction was heated at 60° C. for 72 hours. After the mixture was cooled to room temperature, it was quenched with saturated NH$_4$Cl and was extracted three times with ether. The organic layers were washed with water and brine, and then dried and concentrated. The crude product was purified on silica gel with 20-30% EtOAc/Hexanes to give 31.4 g (76% yield) of 101.

To a solution of 101 (20.3 g, 28.6 g) in 3 L of THF, 0.5M KHMDS solution (60 mL, 30 mmol, 1.05 eq.) was added slowly by syringe pump over 120 minutes. After the mixture was stirred for 5 minutes, it was quenched with 1.5 L of sat. NH$_4$Cl. The mixture was extracted three times with ether. The extracts were washed with brine, and then dried and concentrated. The crude product was purified on silica gel with 10-20%-50% EtOAc/Hexanes to give 14.2 g of 102 (76% yield).

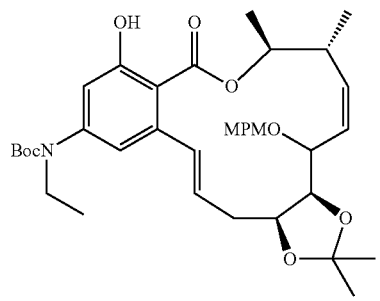

102

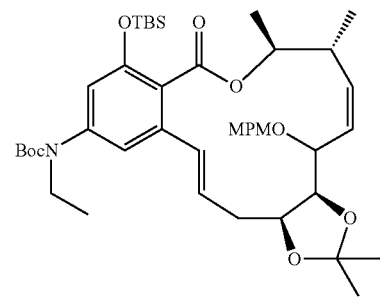

103

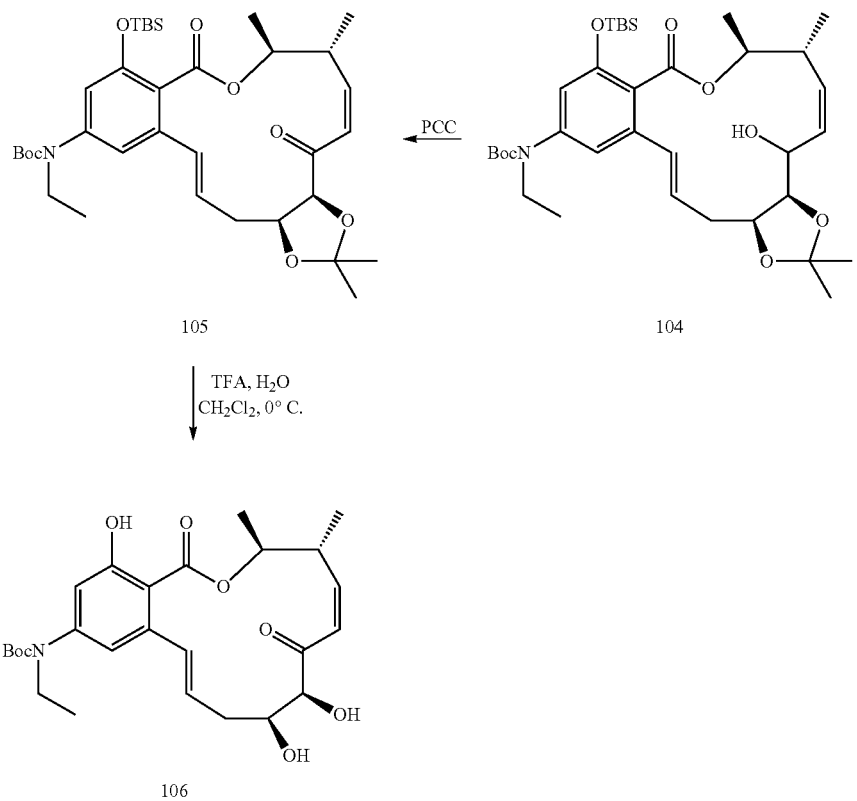

To a solution of 102 (19 g, 29.15 mmol) in DMF (194 mL), imidazole (4 g, 58.3 mmol, 2 eq.) and TBSCl (5.27 g, 35 mmol, 1.2 eq.) were added. After the mixture was stirred overnight, it was quenched with a saturated solution of NaHCO₃ and water. The mixture was extracted with EtOAc. The organic layer was washed with water and brine, and then dried and concentrated. The crude product was purified on silica gel column to give 22 g (99% yield) of 103.

To a solution of 103 (22 g, 28.7 mmol) in a mixture of $CH_2Cl_2$ (230 mL) and $H_2O$ (57.4 mL), DDQ (9.78 g, 43 mmol, 1.5 eq.) was added at 0° C. After the mixture was stirred for 2 hours, it was quenched with 1 L of a 1:1 mixture of aqueous saturated NaHCO₃ and 10% aqueous $Na_2S_2O_3$. The mixture was extracted three times, each with of ether. The extracts were washed with brine, and then dried and concentrated. The crude product was purified on silica gel to give 18.1 g of 104.

To a solution of 104 (18 g, 27.9 mmol) in 279 mL of $CH_2Cl_2$, dried 4 Å molecular sieves (18 g) and PCC (18 g) were added. After the mixture was stirred for 90 min, it was quenched with Et₃N (19.45 mL). The reaction mixture was filtered through a plug of celite and the plug was rinsed with 75% EtOAc in hexanes (900 mL). The filtrates were concentrated. The crude product was purified on silica gel column with 10-15-20% EtOAc/Hexanes to give 14.6 g (81%) of 105.

In a 2 L flask, 105 (8.5 g, 13.2 mmol) was dissolved in $CH_2Cl_2$ (82.5 mL) and the mixture was cooled to 0° C. A solution of 5% $H_2O$/TFA (4.1/78.1 mL) was added slowly (~30 min) and the mixture was stirred at 0° C. for 14.5 hours. The reaction was monitored by TLC. The reaction mixture was diluted with $CH_2Cl_2$ at 0° C. The reaction was then quenched with a solution of NaHCO₃ in water (~1.2 eq compared to TFA). The reaction was cooled to room temperature and extracted three times with $CH_2Cl_2$, dried with $Na_2SO_4$. The solution was then filtered and concentrated. Chromatography on Si-Gel, 50-60-75% EtOAc/hexane gave 106: 4.8 g, 93% yield. NMR: $^1$H-NMR δ (Benzene-d₆) 0.65 (t, J=7.2 Hz, 3H, NCH₂$\underline{CH_3}$), 0.81 (d, J=7.0 Hz, 3H, C4-CH₃), 1.03 (d, J=6.0 Hz, 3H, C3-CH₃), 2.12 (m, 2H, 10-CH₂), 2.35 (d, J=10.9 Hz, 1H, C9-OH), 2.52 (dt, J1=5.3 Hz, J2=7.2 Hz, 2H, N$\underline{CH_2}$CH₃), 3.22 (t, J=5.1 Hz, 1H, NH), 3.44 (m, 1H, 4-CH), 3.89 (m, 2H, 9-CH and C8-OH), 4.24 (dd, J1=2.4 Hz, J2=4.8 Hz, 1H, 8-CH), 4.67 (dq, J1=6.0 Hz, J2=10.4 Hz, 1H, 3-CH), 5.40 (dd, J1=9.7 Hz, J2=11.4 Hz, 1H, 5-CH), 5.49 (d, J=11.5 Hz, 1H, 6-CH), 5.84 (d, J=2.3 Hz, 1H, aromatic CH), 6.01 (m, 1H, 11-CH), 6.17 (d, J=2.5 Hz, 1H, aromatic CH), 6.97 (d, J=15.2 Hz, 1H, 12-CH), 13.05 (s, 1H, phenol).

Compound 114:

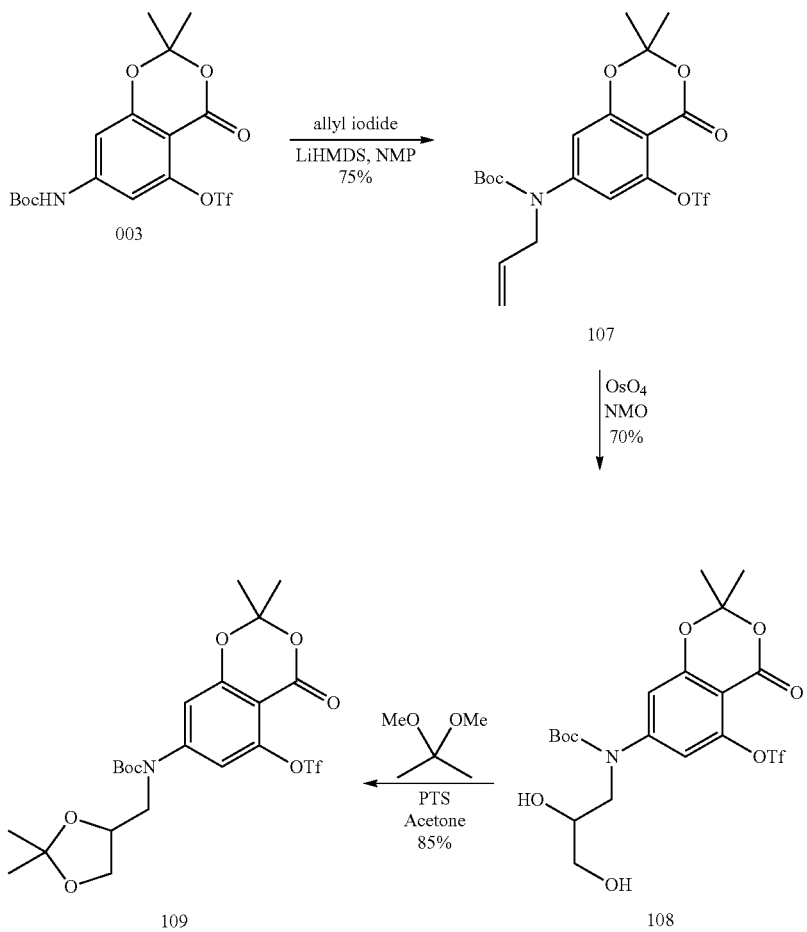

To a solution of 003 (2.914 g, 6.60 mmol) in 1,3-Dimethyl-3,4,5,6-tetrahydro-2(1H)-pyrimidinone (20.0 mL, 0.166 mol) at 0 to −5° C. was added lithium hexamethyldisilazide (8.0 mL, 1.0M in THF). After the reaction mixture was stirred at cold for 30 minutes, to the solution was added 3-Iodo-1-Propene (0.74 mL, 7.9 mmol). The resulting solution was warmed up to room temperature and stirred for 4 hours. The reaction mixture was diluted with ether, added 10.0 ml of 1.0N HCl, extracted with ether. The combined ether solution was washed with saturated bicarbonate (30 mL), and brine (20 mL), and dried with MgSO$_4$. Chromatography purification with 10, 15% EtOAc/Hexane gave compound 107 (2.4 g, 75%) as white solid.

To a solution of compound 107 in t-BuOH:THF:water (100.0 mL, t-BuOH:THF:water=10:3:1) at room temperature was added N-Methylmorpholine N-oxide (0.79 g, 6.7 mmol) and Osmium tetraoxide (1.70 g, 0.167 mmol). After the reaction mixture was stirred at room temperature for two hours, reaction progressed slowly. To the reaction mixture was added additional osmium tetraoxide (4.71 g, 0.463 mmol). The reaction mixture was stirred at room temperature over night. The reaction mixture was diluted with EtOAc (250 mL), and was added sodium thiosulfate (10%, 150 mL). The reaction mixture was extracted the aqueous with EtOAc (2×250 ml), dried and concentrated. Evaporation of the solvent gave compound 108 (1.8 g, 70%).

To a solution of 108 in acetone (20 mL) was added 2,2-Dimethoxypropane (2.0 mL, 0.016 mol) and PTS (110 mg). The reaction mixture was stirred at room temperature for 30 minutes. The reaction mixture was then diluted with EtOAc (50 mL), washed with 5% NaOH (40 mL). The aqueous was extracted with EtOAc (3×50 mL). The combined organic solvent was concentrated. Chromatography purification (20-30% EtOAc/hexane) gave compound 109 (1.63 g, 84%) as oil.

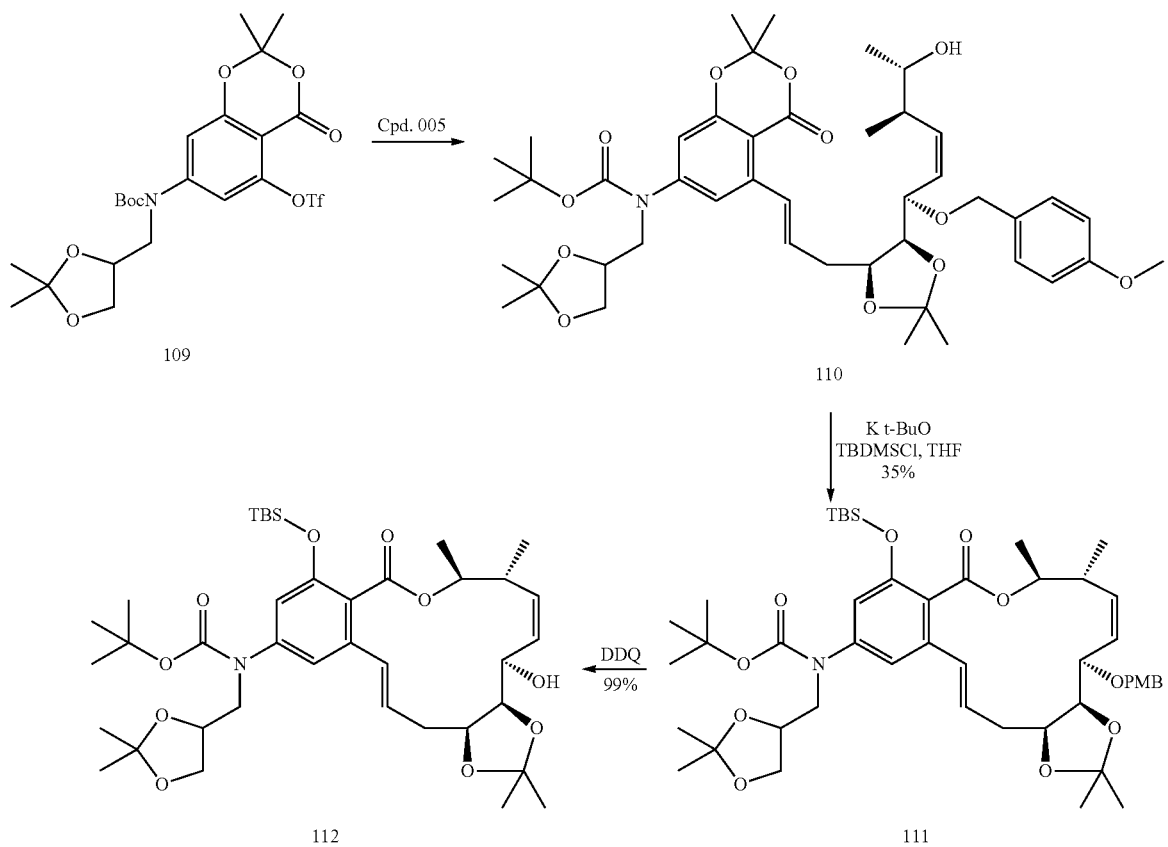

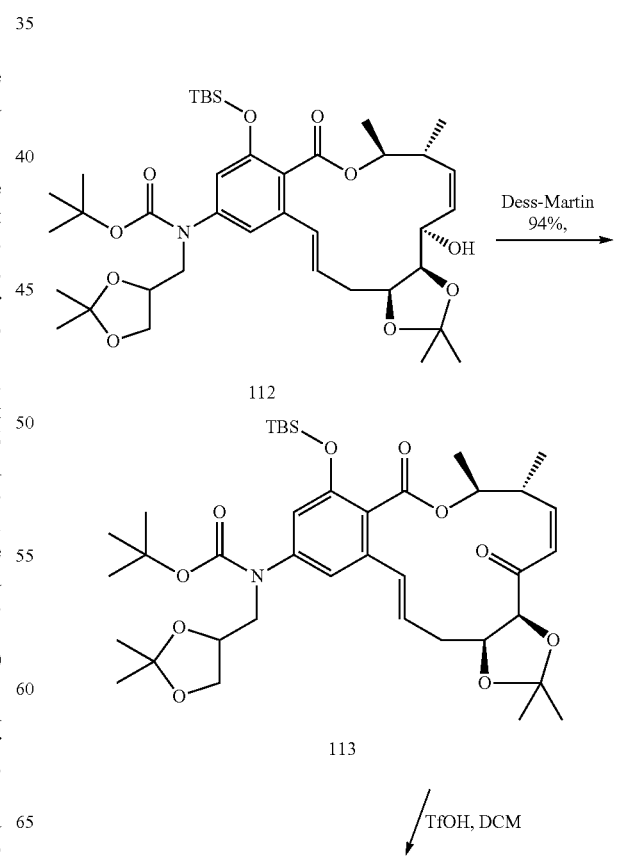

To a 10 ml flask was added compound 005 (0.9624 g, 0.002464 mol) and 109 (1.45 g, 0.00261 mol), the mixture was dried under high vacuum. To the mixture was added Tris(dibenzylideneacetone)dipalladium(0) (0.677 g, 0.000739 mol), and N-Methylpyrrolidinone (2.50 mL, 0.0259 mol) and N-cyclohexyl-N-methyl-cyclohexanamine (1.06 mL, 0.00493 mol). The reaction mixture was stirred at 80° C. over night. The reaction was cooled to room temperature, and was diluted with TBME. The organic solution was washed with 1N HCl, brine, and was concentrated under reduced pressure. Chromatography purification (20% EtOAc/Hexane) gave compound 110 (1.73 g, 88%).

To a solution of 1.0M potassium tert-Butoxide (3.2 mL, 3.2 mmol) in THF (10.0 mL) in a 50 mL round bottomed flask at 0° C. was added a solution of compound 110 (1.72 g, 2.16 mmol) in THF (5.0 mL) via syringe pump. The reaction mixture was stirred for 10 minutes after the addition of compound 110 and was quenched with tert-butyldimethylsilyl chloride (490 mg, 0.0032 mol) in THF (5.0 mL) at 0° C. The reaction mixture was diluted with water and was extracted with EtOAc. Chromatography purification (20% EtOAc/hexane) gave compound 111 (0.64 g, 35%).

To a solution of 111 (0.65 g, 0.00076 mol) in DCM (8.0 mL) at 0° C. was added water (2.0 mL) and 2,3-Dichloro-5,6-dicyanohydroquinone (0.245 g, 0.00106 mol). The reaction mixture was stirred at room temperature for 3 hours. After checking TLC (30% EtOAc/hexane), the reaction was quenched with sodium thiosulfate in saturated bicarbonate. The reaction mixture was extracted with TBME, dried and concentrated. Chromatography purification (20%-40% EtOAc/hexane) gave compound 112 (0.557 g, 100%).

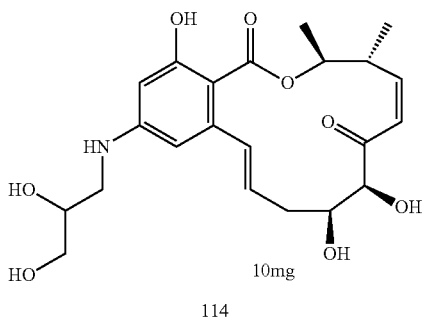

114

To a solution of compound 112 (111.2 mg, 0.0001519 mol) in DCM (1.0 mL) was added Pyridine (18 μl, 0.00023 mol) and Dess-Martin periodinane (0.077 g, 0.00018 mol) at 0° C. The reaction mixture was stirred for 30 minutes at 0° C., still some starting material was detected by TLC. The reaction mixture was then allowed to warm to room temperature and stirred for 30 minutes. The reaction mixture was then diluted with 30% EtOAc/hexane, the resulting solution was filtered through a silicon plug, and washed with 30% EtOAc/hexane. Chromatography purification (30% EtOAc/hexane) gave compound 113 (103.8 mg, 94%).

To a solution of 113 (101.5 mg, 0.0001390 mol) in DCM (1.0 mL) was added water (20 micro liter) and Trifluoromethanesulfonic acid (61.5 μl, 0.000695 mol) at 0° C. The reaction mixture was stirred for 20 minutes at 0° C., and was allowed to warm to room temperature and was stirred for another 30 minutes. The reaction mixture was quenched with saturated sodium bicarbonate, and was extracted with DCM. Chromatography purification (5% MeOH/DCM) gave compound 114 (42.0 mg, 69.4%). $^1$HNMR (CD$_3$OD): 6.86 (d, J=15.6 Hz, 1H), 6.30 (d, J=11.6 Hz, 1H), 6.10-6.18 (m, 2H), 5.93-6.00 (m, 2H), 4.47 (d, J=2.0 Hz 1H), 4.04 (t, J=2.8 Hz, 1H), 3.78 (m, 1H), 3.55 (m, 2H), 3.43 (m, 1H), 3.30 (m, 3H), 3.08 (m, 1H), 2.08 (m, 2H), 1.35 (d, J=5.6 Hz, 3H), 1.14 (d, J=7.2 Hz, 3H). Mass 457.95 observed.

Compound 122:

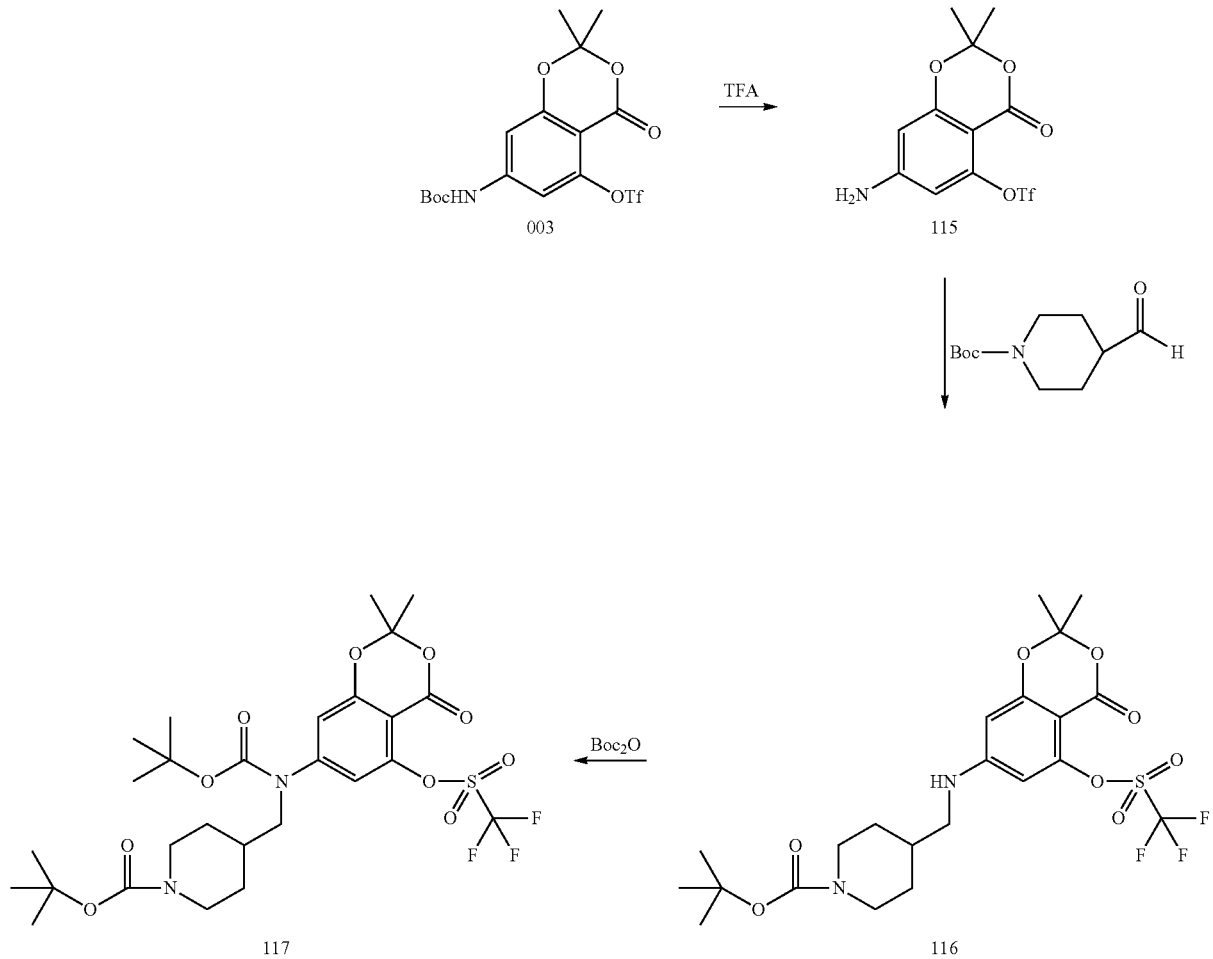

Triethylsilane (510 µl, 0.0032 mol) and Trifluoroacetic Acid (75 µl, 0.97 mmol) were added to a solution of 003 (176 mg, 0.399 mmol) in DCM (3.0 mL) at 0° C. The reaction mixture was stirred at 0° C. for 1 hour, still a lot starting material left after checking TLC (30% EtOAc/Hex). The reaction mixture was warmed up to room temperature and stirred at ambient temperature over night. There was not much progress by checking TLC. To the reaction mixture was added additional TFA (1.0 mL) at 0° C. The reaction mixture was stirred at room temperature for 30 minutes. There was no starting material by TLC. The reaction mixture was poured into saturate bicarbonate, extracted with EtOAc (3×20 mL). The combined organic layer was dried and filtered. The mixture was concentrated and purified on preparative TLC (30% EtOAc/hexane) gave compound 115 (0.107 g, 79%).

Sodium triacetoxyborohydride (0.57 g, 0.0027 mol) was added to a solution of N-tert-butoxycarbonyl piperadine-1-carboxylate (448.1 mg, 0.002101 mol), compound 115 (348.0 mg, 0.001020 mol), and acetic acid (1300 µl, 0.023 mol) in THF (10.0 mL) at room temperature. The reaction mixture was stirred at room temperature for 5 hours. The reaction mixture was then concentrated without aqueous workup. Purification using preparative TLC (35% EtOAc/hexane) gave compound 116 (0.4164 g, 76%).

Di-tert-Butyldicarbonate (0.0251 g, 0.000115 mol) was added to a solution of compound 116 (31.0 mg, 0.0000576 mol) in DCM (1.0 mL). To the reaction mixture was added 4-Dimethylaminopyridine (0.00703 g, 0.0000576 mol) and triethylamine (8.02 µl, 0.0000576 mol). The reaction mixture was then stirred at ambient temperature over night. Preparative TLC purification (30% EtOAc/hexane) gave compound 117 (16.4 mg, 45%).

Compounds 117 (0.3916 g, 0.0006132 mol) and 005 (0.2422 g, 0.0006202 mol) were combined in a reaction flask and was dried under high vacuum. Tris(dibenzylideneacetone)dipalladium(0) (0.17 g, 0.00019 mol) was added to the above mixture in a drybox. N-Methylpyrrolidinone (2.0 mL, 0.021 mol) and Cyclohexanamine, N-cyclohexyl-N-methyl- (268 µl, 0.00125 mol) was added to the reaction flask. The reaction mixture was stirred at 80° C. in an oil bath for 20 hours. The mixture was diluted with MTBE, and washed with 1.0 M hydrochloric acid. The aqueous was extracted with MTBE and was concentrated. Chromatography purification (20-40% EtOAc/hexane) gave compound 118 (0.373 g, 69%).

Compound 118 (0.37 g, 0.00042 mol) in THF (7.2 mL) was added to a solution of potassium tert-Butoxide in tetrahydrofuran (0.716 mL, 1.00M) in tetrahydrofuran (7.20 mL, 0.0888 mol) at 0° C. over 5 minutes. No starting material was observed (TLC, 30% EtOAc/hexane) after the reaction mixture was stirred for 10 minutes. The reaction was quenched with tert-Butyldimethylsilyl chloride (0.108 g, 0.000716 mol) in THF (1.0 mL) at 0° C. and was stirred for 10 minutes. Chromatography purification (20% EtOAc/hexane) gave compound 119 (0.182 g, 46%).

Water (2.0 mL) and Dichlorodicyanoquinone (57.3 mg, 0.000252 mol) was added to a solution of compound 119 (181.6 mg, 0.0001942 mol) in DCM (8.0 mL) at 0° C. The reaction mixture was then warmed to ambient temperature and was stirred for 3 hours. The reaction was quenched with 1:1 10% sodium thiosulfate/saturated bicarbonate after no starting material was detected (TLC, 30% EtOAc/hexane). The aqueous was extracted with TBME. Chromatography purification (20%-40% EtOAc/hexane) gave compound 120 (0.1461 g, 92%).

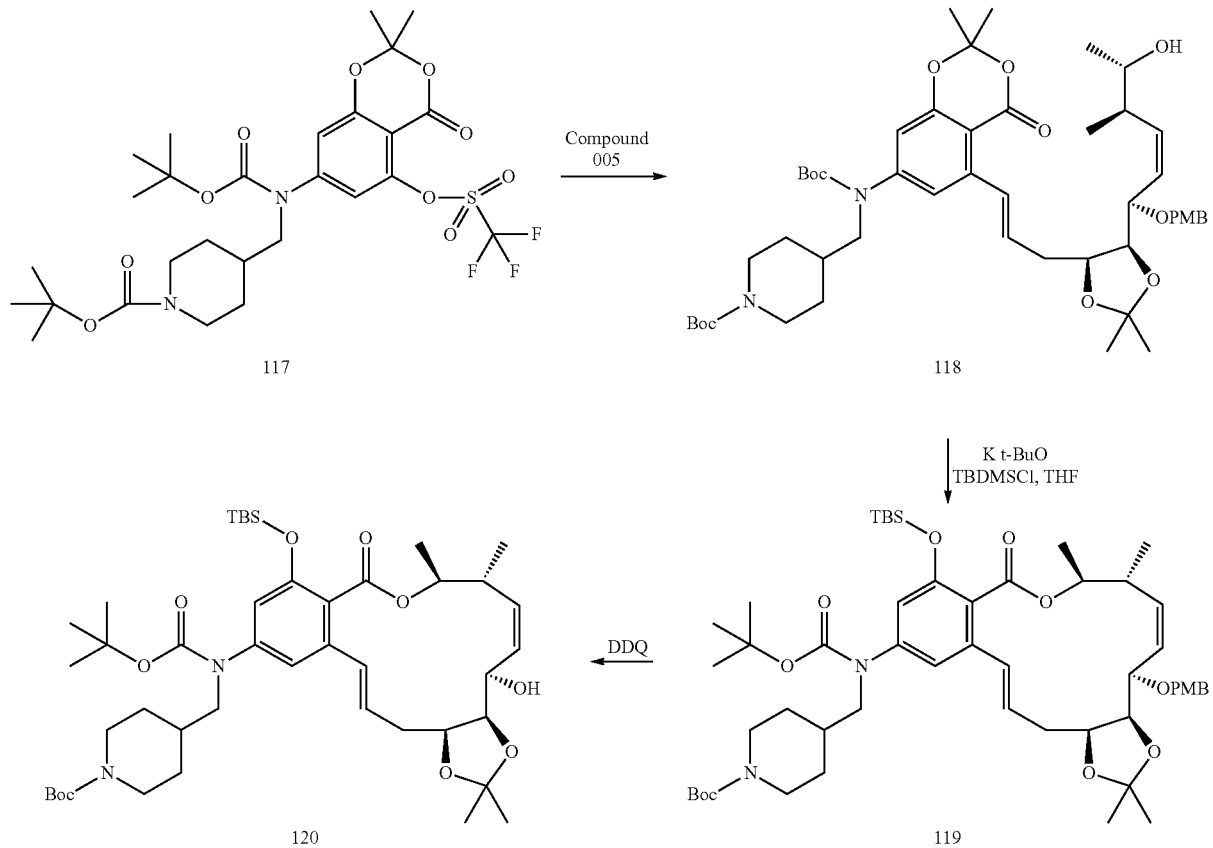

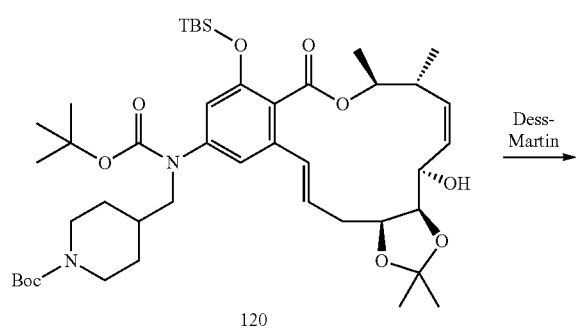

120

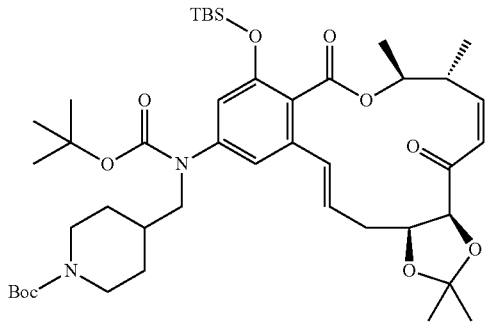

121

|TfOH

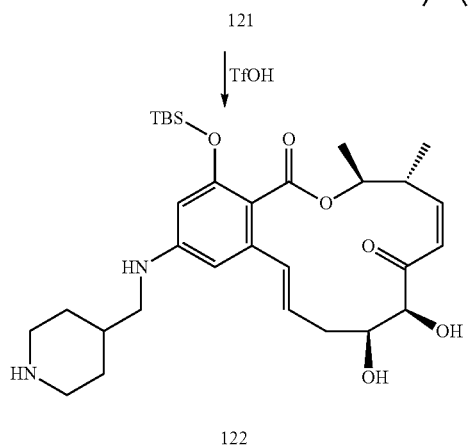

122

To a solution of compound 120 (146.1 mg, 0.179 mmol) in DCM (1.0 mL) was added Pyridine and Dess-Martin periodinane (0.099 g, 0.23 mmol) at 0° C. The reaction mixture was stirred for 30 minutes at 0° C., still some starting material was detected by TLC. The reaction mixture was then allowed to warm to room temperature and stirred at ambient temperature until all the starting material was consumed. The reaction mixture was then diluted with 30% EtOAc/hexane, the resulting solution was filtered through a silicon plug, and washed with 30% EtOAc/hexane. Chromatography purification (30% EtOAc/hexane) gave compound 121 (107.4 mg, 74%).

To a solution of compound 121 (107.4 mg, 0.0001321 mol) in Methylene chloride (1.50 mL, 0.0234 mol) was added Water (22.4 µl, 0.00124 mol) and Trifluoromethanesulfonic acid (55.0 µl, 0.000622 mol) at 0° C. The reaction mixture was stirred at 0° C. for 90 minutes. Still some starting material was not consumed (TLC, 10% $NH_4OH$/EtOH). The reaction mixture was stirred for another 30 minutes at room temperature and was diluted with 20 ml TBME. To the reaction mixture was added saturated sodium bicarbonate, extracted with EtOAc (3×20 mL), the aqueous was further extracted with EtOAc (3×20 mL). The combined organic solvent was dried with sodium sulfate, and filtered. The crude material was loaded onto preparative TLC, and was eluted with 10% $NH_4OH$/EtOH(Rf 0.1). The desired band was collected, and was rinsed with 10% $NH_4OH$/EtOH to give compound 122 (46.8 mg, 77%). $^1$HNMR ($CD_3OD$): 6.85 (d, J=15.2 Hz, 1H), 6.29 (d, J=12.0 Hz, 1H), 6.08-6.11 (m, 2H), 5.91-5.98 (m, 2H), 4.47 (d, J=2.4 Hz, 1H), 4.04 (m, 1H), 3.46 (m, 1H), 3.02 (d, J=12.0 Hz, 2H), 2.97 (d, J=6.4 Hz, 2H), 2.56 (m, 2H), 2.09 (m, 2H), 1.71 (m, 4H), 1.34 (d, J=6.0 Hz, 3H), 1.22, (m, 2H), 1.14 (d, J=6.8 Hz, 3H).

Compound 127:

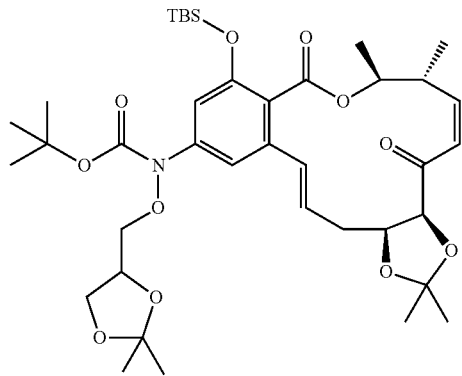

123

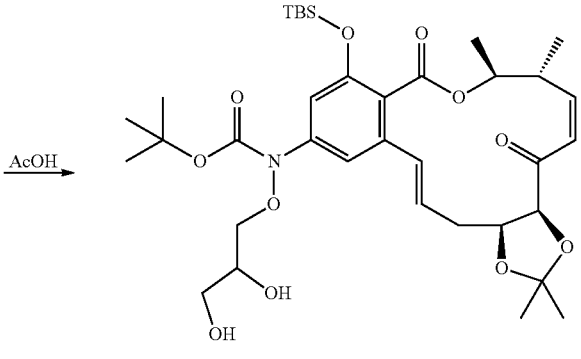

124

| Lead Tetraacetate

-continued

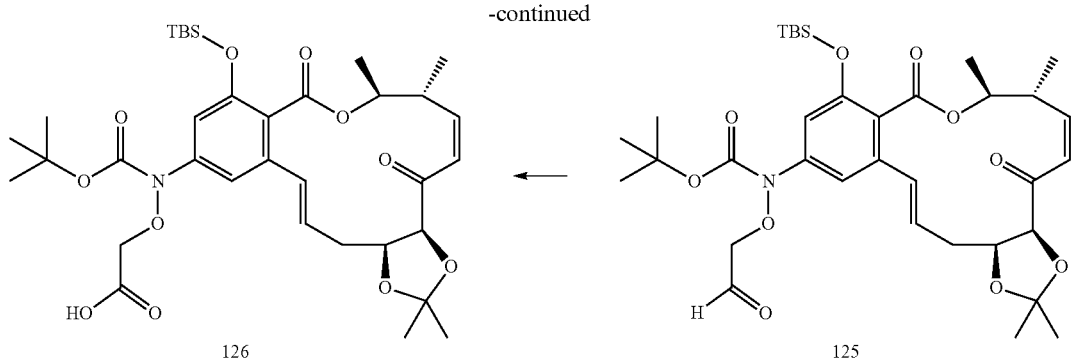

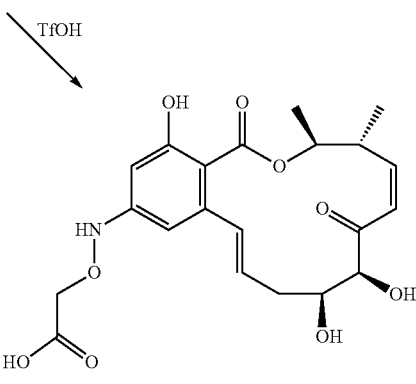

A solution of acetic acid/water (4.0 mL, Acetic acid:water=4:1) at 0° C. was added to compound 123 (prepared in the same manner as compound 064) (195.2 mg, 0.0002617 mol). The reaction mixture was kept at 0° C. for 30 minutes and then was warmed up to ambient temperature. After being stirred over night at ambient temperature, the reaction mixture was diluted with sodium bicarbonate, and was extracted with EtOAc. Preparative TLC (75% EtOAc/Hexane) gave compound 124 (0.1686 g, 91%).

To a solution of compound 124 (168.6 mg, 0.0002388 mol) in Toluene (3.0 mL, 0.028 mol) and DCM (1.0 mL) was added Lead tetraacetate (0.127 g, 0.000287 mol). The reaction mixture was stirred for 20 to 30 minutes at ambient temperature, and was filtered through celite. The celite was washed with DCM. Preparative TLC (50% EtOAc/hexane) gave compound 125 (106.1 mg, 66%).

To a solution of compound 125 (106.0 mg, 0.0001573 mol) in tetrahydrofuran (0.50 mL, 0.0062 mol), tert-Butyl alcohol (1.50 mL, 0.0157 mol), 2-Methylbut-2-ene (0.50 mL, 0.0047 mol) was added a solution of sodium chlorite (88.9 mg, 0.000786 mol) and potassium phosphate monobasic (100 mg, 0.0007 mol) in 0.6 ml of water at ambient temperature. The reaction mixture was stirred at ambient temperature for 2 hours, and was concentrated. The residue was diluted with water, acidified to pH 2 with dilute HCl. The aqueous was extracted with EtOAc. Preparative TLC gave compound 126 (66.1 mg, 61%).

To a solution of compound 126 (32.5 mg, 0.0471 mmol) in methylene chloride (1.0 mL, 0.016 mol) and water (1.7 μl, 0.094 mmol) at 0° C. was added trifluoromethanesulfonic acid (17 μl, 0.00019 mol). The reaction mixture was stirred at 0° C. for 60 minutes and at ambient temperature for 60 minutes. The reaction mixture was quenched with saturated sodium bicarbonate. The aqueous phase was extracted with DCM (2×20 mLl). No desired product appeared in a TLC of the DCM solution. The aqueous phase was then acidified to pH 3, and was extracted with EtOAc (3×10 mL). Preparative TLC gave compound 127 (10.2 mg, 50%).

Compound 137:

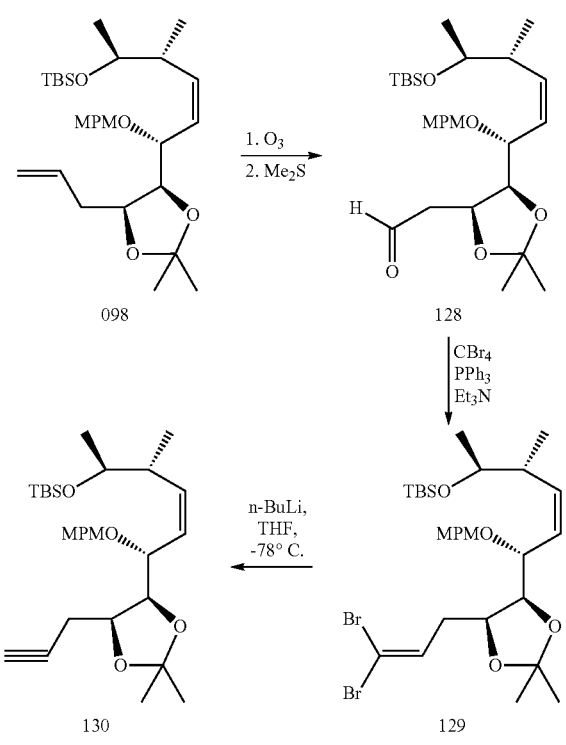

To a solution of compound 098 (1.0 g, 1.98 mmol) in MeOH/CH$_2$Cl$_2$ (5 ml/5 ml) at −78° C. was bubbled O$_3$. After 7 min, N$_2$ was bubbled through for 10 min and 2 pipettes of Me$_2$S were added. The reaction mixture was warmed up to room temperature and solvents were removed by evaporation. Purification by silica gel chromatography gave compound 128 (735 mg, 73%).

To a reaction flask containing CBr$_4$ (969 mg, 2.90 mmol) and PPh$_3$ (15.2 g 5.80 mmol) in 10 ml of CH$_2$Cl$_2$ was added a solution of compound 128 (734 mg, 1.45 mmol) and Et$_3$N (202 μl, 1.45 mmol) in 5 ml of CH$_2$Cl$_2$ at 0° C. The ice bath was removed and the reaction mixture was stirred at room temperature for 1 hour. After titration with Hexane, purification by silica gel chromatography gave compound 129 (557 g, 58%).

To a solution of compound 129 (557 mg, 0.84 mmol) in THF (5 ml) at −78° C. was added n-BuLi (840 μl, 2.5M in Hexane). After 1 hr the reaction was quenched with saturated aqueous NH$_4$Cl. The aqueous layer was extracted with MTBE. Purification by silica gel chromatography gave compound 130 (360 mg, 85%).

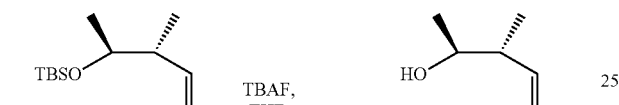

130      131

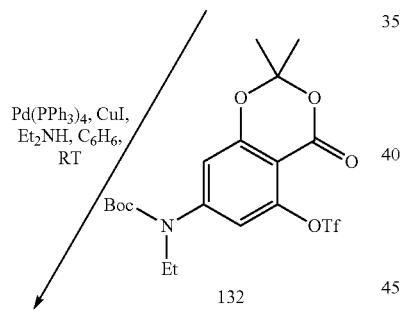

132

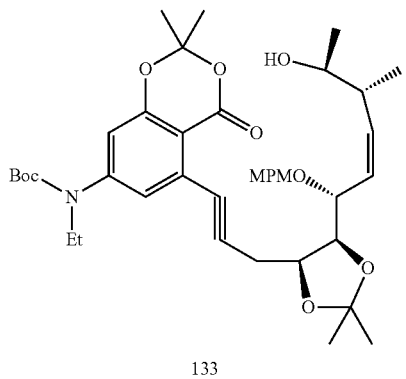

133

To a solution of compound 130 (358 mg, 0.71 mmol) in THF (5 ml) at room temperature was added TBAF (1.1 ml, 1.0M in THF). The reaction mixture was heated at 50° C. for 4 hours. The mixture was then diluted with MTBE, washed with water and brine. Purification by silica gel chromatography gave compound 131 (277 mg, 100%).

To a solution of compound 131 (263.8 mg, 0.678 mmol) and compound 132 (637.4 mg, 1.356 mmol) in benzene (1.8 ml) and Et$_2$NH (1.2 ml) at room temperature was added Pd(PPh$_3$)$_4$ (39.2 mg, 0.034 mmol) and CuI (12.9 mg, 0.068 mmol). The reaction mixture was stirred for 5 hours. The mixture was then diluted with MTBE, washed with saturated NH$_4$Cl, saturated NaHCO$_3$ and brine. Purification by silica gel chromatography gave compound 133 (251.5 mg, 52%).

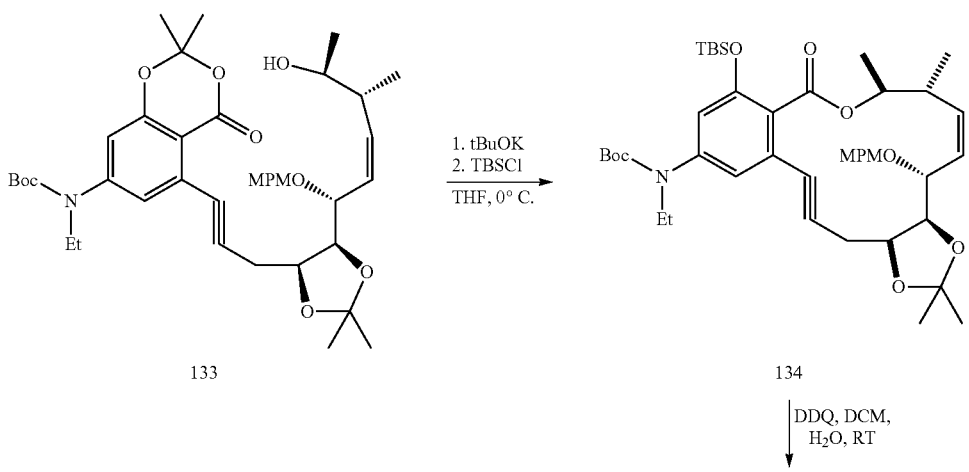

133      134

| DDQ, DCM, H$_2$O, RT

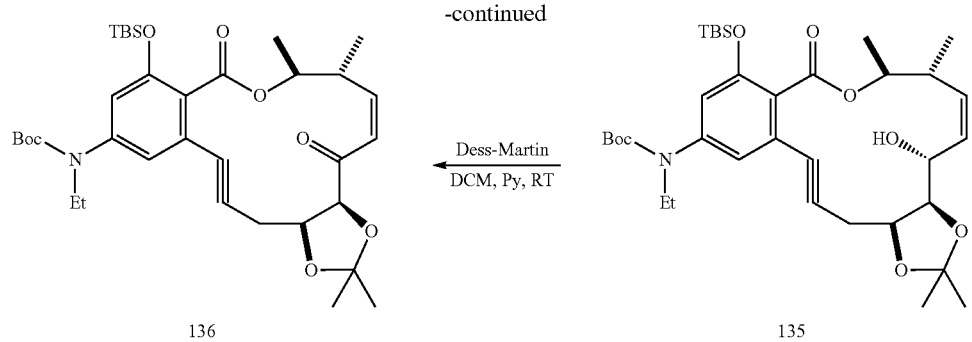

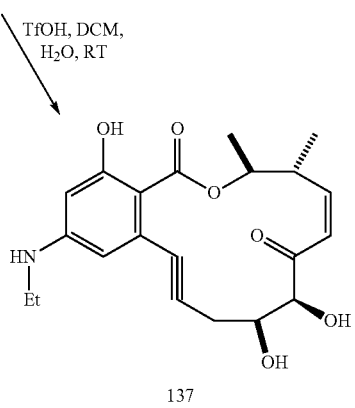

To a solution of t-BuOK (565 μl, 1.0M in THF) in THF (13.0 ml) at 0° C. was added the solution of compound 133 (200.0 mg, 0.28 mmol) in THF (8.0 ml) at rate of 0.1 ml/min. After 1 hour, TBSCl (169 mg, 0.56 mmol) was added. After 5 minutes, the reaction mixture was quenched with saturated NaHCO$_3$, diluted with water and extracted with MTBE. Purification by silica gel chromatography gave compound 134 (175.4 mg, 82%).

To a solution of compound 134 (200.0 mg, 0.28 mmol) in DCM 4.0 ml) and water (1.0 ml) at room temperature was added DDQ (96.2 mg, 0.42 mmol). After 2 hours, the reaction was quenched with 10% Na$_2$S$_2$O$_3$ in a saturated NaHCO$_3$ aqueous solution and extracted with MTBE. Purification by silica gel chromatography gave compound 135 (133.1 mg, 74%).

To a solution of compound 135 (133.0 mg, 0.207 mmol) in DCM (3.0 ml) at room temperature was added pyridine (42.0 μl, 0.518 mmol) and Dess-Martin reagent (175.0 mg, 0.414 mmol). After 1 hour, the reaction was quenched with 10% Na$_2$S$_2$O$_3$ in saturated NaHCO$_3$ aqueous solution and extracted with DCM. Purification by silica gel chromatography gave compound 136 (114.8 mg, 86%).

To a solution of compound 136 (113.0 mg, 0.176 mmol) in DCM (2.0 ml) at 0° C. was added water (19.0 μl, 1.056 mmol) and TfOH (46.0 μl, 0.528 mmol). The reaction was allowed to warm up to room temperature. After 30 minutes, the reaction was quenched with saturated NaHCO$_3$ and extracted with DCM. Purification by silica gel chromatography gave compound 137 (46.4 mg, 68%). $^1$H NMR (400 MHz, CDCl$_3$) δ 1.20 (d, J=6.8 Hz, 3H), 1.25 (t, J=6.8, 3H), 1.38 (d, J=6.0, 3H), 2.47-2.48 (m, 2H), 2.85 (d, J=11.2 Hz), 3.70-3.21 (m, 2H), 3.41-3.45 (m, 1H), 3.95 (d, J=5.2, 1H), 4.00-4.40 (m, 1H), 4.27-4.33 (m, 1H), 4.54-4.56 (m, 1H), 4.93-5.00 (m, 1H), 6.04 (d, J=2.4, 1H), 6.23-6.32 (m, 3H), 12.10 (s, 1H). Compound 144:

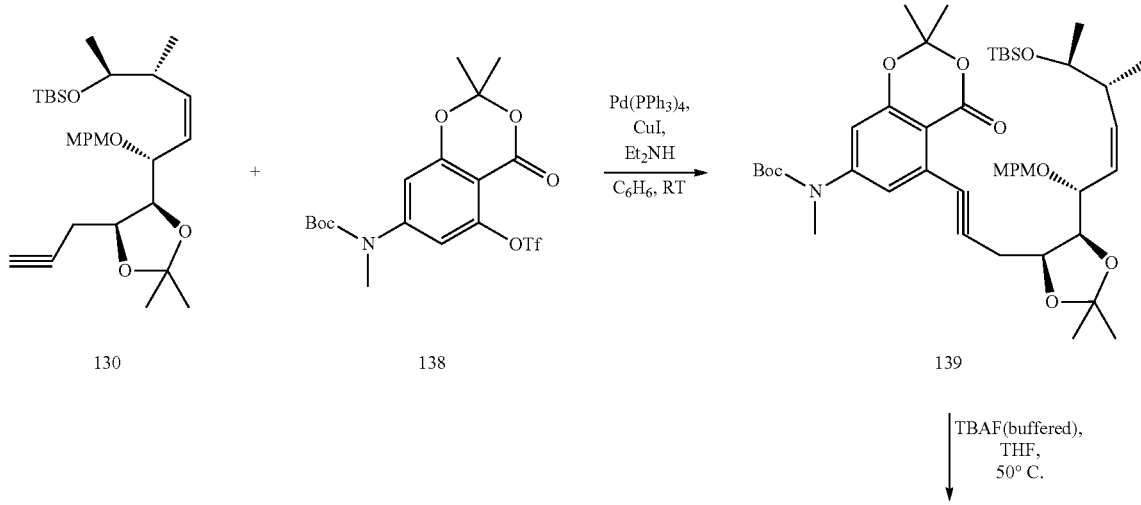

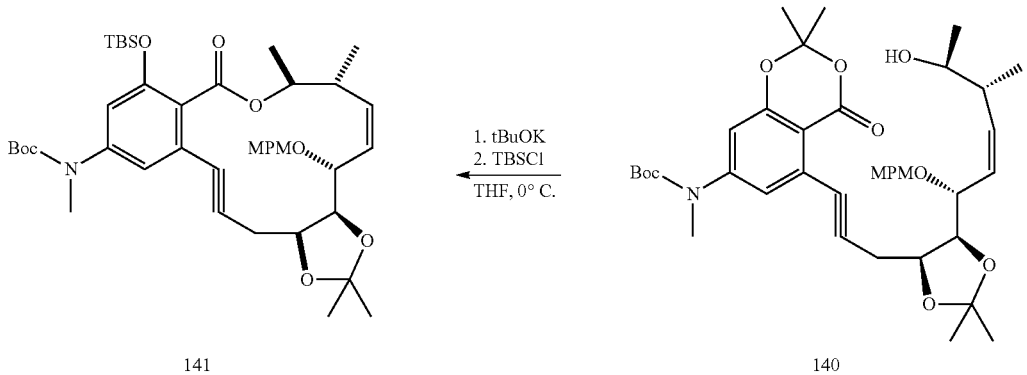

141 140

To a solution of compound 130 (475 mg, 0.944 mmol) and compound 138 (558 mg, 1.227 mmol) in benzene (2.2 ml) and Et$_2$NH (1.5 ml) at room temperature was added Pd(PPh$_3$)$_4$ (55 mg, 0.0472 mmol) and CuI (18 mg, 0.0944 mmol). The reaction mixture was stirred for 3 hours. The reaction mixture was then diluted with MTBE, washed with saturated NH$_4$Cl, saturated NaHCO$_3$ and brine. Purification by silica gel chromatography gave compound 139 (485 mg, 56%).

To a solution of compound 139 (485 mg, 0.60 mmol) in THF (5.0 ml) was added buffered TBAF (3.6 ml, 0.5N buffered with imidazole/HCl) at room temperature. The reaction mixture was heated at 50° C. for 60 hours. The reaction mixture was then diluted with MTBE and washed with water and brine. Purification by silica gel chromatography gave compound 140 (280.8 mg, 67%).

To a solution of t-BuOK (720 µl, 1.0M in THF) in THF (13.5 ml) at 0° C. was added the solution of compound 140 (250 mg, 0.36 mmol) in THF (13.5 ml). After 2 hours, TBSCl (217 mg, 1.44 mmol) was added. After 5 minutes, the reaction mixture was quenched with saturated NaHCO$_3$, diluted with water and extracted with MTBE. Purification by silica gel chromatography gave compound 141 (155 mg, 52%).

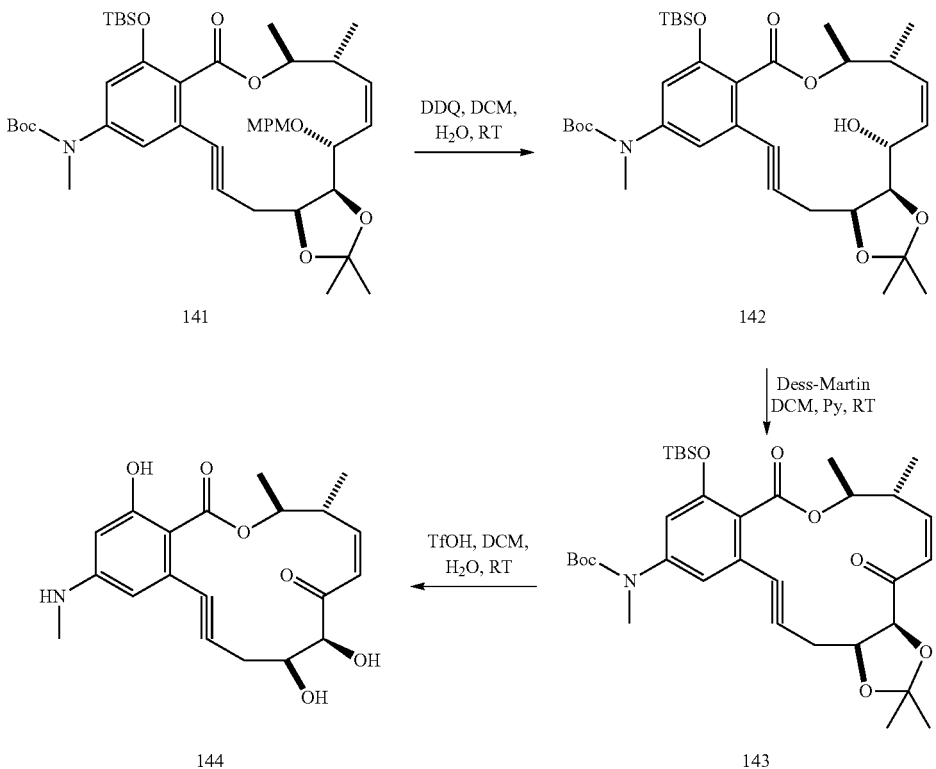

To a solution of compound 141 (153 mg, 0.204 mmol) in DCM 4.0 ml) and water (1.0 ml) at room temperature was added DDQ (69.5 mg, 0.306 mmol). After 2.5 hours, the reaction was quenched with saturated NaHCO$_3$ and extracted with MTBE. Purification by silica gel chromatography gave compound 142 (124.0 mg, 96%).

To a solution of compound 142 (124.0 mg, 0.197 mmol) in DCM (5.0 ml) at room temperature was added pyridine (40.0 µl, 0.492 mmol) and Dess-Martin reagent (167.0 mg, 0.394 mmol). After 1 hr, the reaction was quenched with 10% Na$_2$S$_2$O$_3$ in saturated NaHCO$_3$ aqueous solution and extracted with DCM. Purification by silica gel chromatography gave compound 143 (122.8 mg, 99%).

To a solution of compound 143 (54.5 mg, 0.087 mmol) in DCM (2.0 ml) at 0° C. was added water (9.4 µl, 0.522 mmol) and TfOH (23.0 µl, 0.261 mmol). The reaction was allowed to warm up to room temperature. After 30 minutes, it was quenched with saturated NaHCO$_3$ and extracted with DCM. Purification by silica gel chromatography gave compound 144 (30.0 mg, 92%). $^1$H NMR (400 MHz, CDCl$_3$) δ 1.20 (d, J=6.8 Hz, 3H), 1.38 (d, J=6.0 Hz, 3H), 2.47-2.48 (m, 2H), 2.85 (d, J=5.2 Hz, 3H), 3.40-3.50 (m, 1H), 3.94 (d, J=5.2), 4.12-4.19 (m, 1H), 4.28-4.33 (m, 1H), 4.54-4.56 (m, 1H), 4.93-5.00 (m, 1H), 6.05 (d, J=2.4 Hz, 1H), 6.30 (s, 1H), 6.33 (m, 2H), 12.11 (s, 1H).

Compound 155:

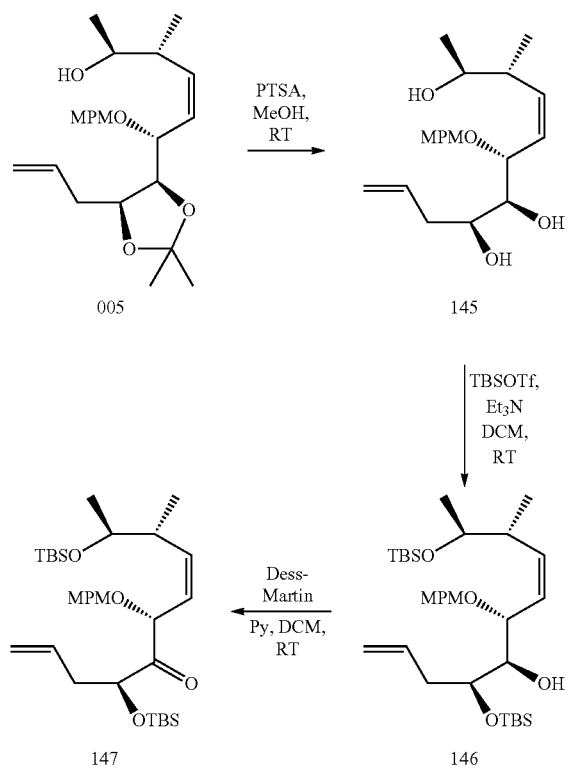

To a solution of 005 (2.46 g, 4.87 mmol) in MeOH (40 ml) at 0° C. was added p-toluenesulfonic acid (1.02 g, 5.36 mmol). The reaction was warmed up to room temperature and stirred for 18 hours. The reaction mixture was then quenched with saturated NaHCO$_3$ and extracted with MTBE. Purification by silica gel chromatography gave compound 145 (1.42 g, 64%).

To a solution of compound 145 (1.53 g, 4.37 mmol) in DCM at 0° C. was added Et$_3$N (1.83 ml, 13.11 mmol) and TBSOTf (2.10 ml, 9.18 mmol). The reaction was warmed up to room temperature and stirred for 35 minutes. The reaction mixture was then quenched with saturated NaHCO$_3$ and extracted with DCM. Purification by silica gel chromatography gave compound 146 (1.18 g, 41%).

To a solution of compound 146 (1.09 g, 1.88 mmol) in DCM (10.0 ml) at room temperature was added pyridine (303 µl, 3.76 mmol) and Dess-Martin reagent (1.20 g, 2.82 mmol). After 5 hours, the reaction was quenched with 10% Na$_2$S$_2$O$_3$ in saturated NaHCO$_3$ aqueous solution and extracted with MTBE. Purification by silica gel chromatography gave compound 147 as crude product.

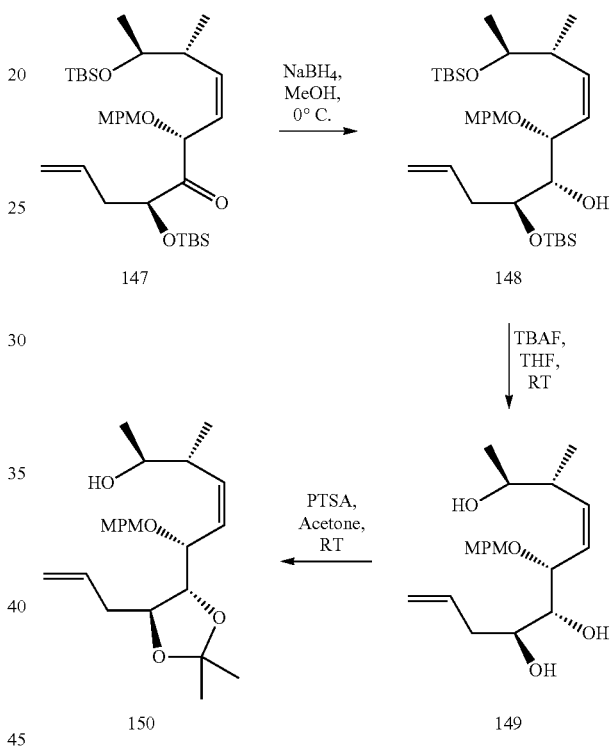

To a solution of compound 147 in MeOH (15.0 ml) at 0° C. was added NaBH$_4$ (142 mg, 3.76 mmol). After 10 minutes, the reaction was quenched with saturated NH$_4$Cl and extracted with MTBE. Purification by silica gel chromatography gave compound 148 (714 mg, 66% from 1006-216B).

To a solution of compound 148 (710 mg, 1.23 mmol) in THF (10 ml) at room temperature was added TBAF (3.7 ml, 1.0M in THF). The reaction mixture was heated at 50° C. for 17 hours. The reaction mixture was then diluted with MTBE, washed with saturated NaHCO$_3$ and brine. Purification by silica gel chromatography gave compound 149 (419 mg, 97%).

To a solution of compound 149 (400 mg, 1.14 mmol) in acetone (10 ml) at room temperature was added 2,2-dimethoxypropane (419 µl, 3.42 mmol) and PTSA (100 mg). After 20 min, it was diluted with MTBE, washed with saturated NaHCO$_3$ and brine. Purification by silica gel chromatography gave compound 150 (450 mg, 95%).

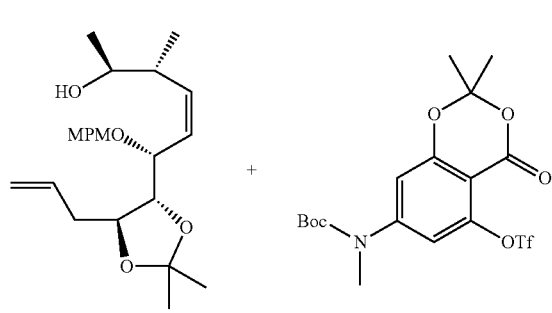
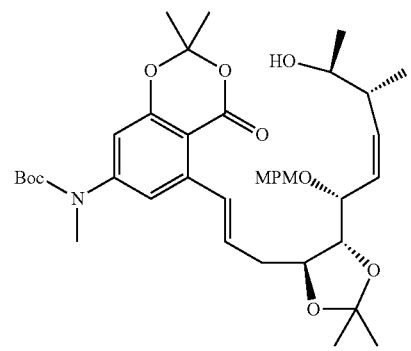

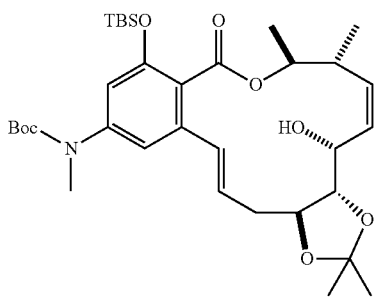
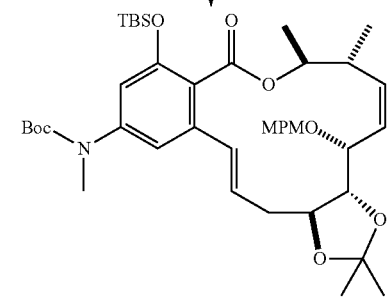

To a solution of compound 150 (384 mg, 0.98 mmol) and compound 138 (582 mg, 1.27 mmol) in NMP (2.0 ml) at room temperature was added Pd$_2$(DBA)$_3$ (90.0 mg, 0.098 mmol) and Cy$_2$NMe (272 μl, 1.27 mmol). The reaction mixture was heated at 80° C. for 24 hours. The reaction mixture was then diluted with MTBE, filtered through celite, washed with 1.0N aqueous HCl and brine. Purification by silica gel chromatography gave compound 151 (441.3 mg, 65%).

To a solution of t-BuOK (884 μl, 1.0M in THF) in THF (15.0 ml) at 0° C. was added the solution of compound 151 (410 mg, 0.59 mmol) in THF (5.0 ml). After 30 minutes, TBSCl (178 mg, 1.18 mmol) was added. After 10 minutes, the reaction mixture was quenched with saturated NaHCO$_3$, diluted with water and extracted with EtOAc. Purification by silica gel chromatography gave compound 152 (170.1 mg, 34%).

To a solution of compound 152 (170 mg, 0.226 mmol) in DCM 4.0 ml) and water (1.0 ml) at room temperature was added DDQ (77.0 mg, 0.339 mmol). After 2.5 hours, the reaction was quenched with 10% Na$_2$S$_2$O$_3$ in saturated NaHCO$_3$ and extracted with MTBE. Purification by silica gel chromatography gave compound 153 (122.6 mg, 86%).

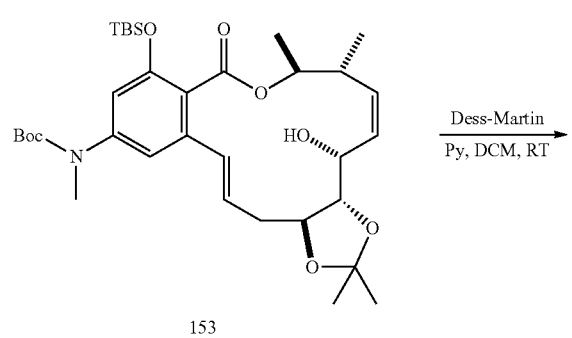
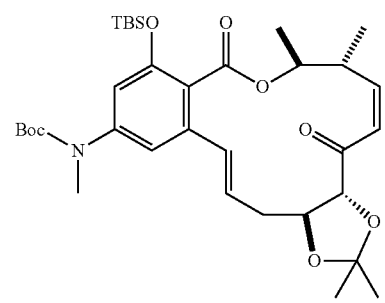

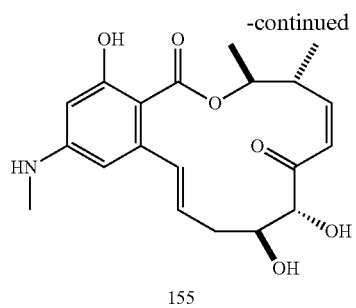

155

To a solution of compound 153 (61.0 mg, 0.097 mmol) in DCM (2.5 ml) at room temperature was added pyridine (19.6 μl, 0.243 mmol) and Dess-Martin reagent (82.0 mg, 0.194 mmol). After 1 hour, the reaction was quenched with 10% $Na_2S_2O_3$ in saturated $NaHCO_3$ aqueous solution and extracted with MTBE. Purification by silica gel chromatography gave compound 154 (46.1 mg, 76%).

To a solution of compound 154 (41.8 mg, 0.066 mmol) in DCM (2.0 ml) at 0° C. was added water (7.1 μl, 0.396 mmol) and TfOH (17.6 μl, 0.198 mmol). The reaction was allowed to warm up to room temperature. After 30 minutes, it was quenched with saturated $NaHCO_3$ and extracted with DCM. Purification by silica gel chromatography gave compound 155 (11.1 mg, 45%). $^1$H NMR (400 MHz, $CDCl_3$) δ 0.64 (d, J=6.80, 3H), 0.93 (d, J=6.0, 3H), 2.06 (d, J=3.6 Hz, 3H), 2.37-2.44 (m, 1H), 2.54-2.64 (m, 1H), 2.79 (br, 1H), 3.05-3.22 (m, 2H), 3.81-3.91 (m, 1H), 4.18-4.33 (m, 1H), 4.60-4.71 (m, 1H), 5.33 (t, J=11.6 Hz, 1H), 5.86 (d, J=2.8 Hz, 1H), 5.91-6.03 (m, 1H), 6.04 (d, J=11.6 Hz, 1H), 6.11 (d, J=2.0 Hz, 1H), 7.00 (d, J=15.6 Hz, 1H), 12.86 (s, 1H).

Compound 156:

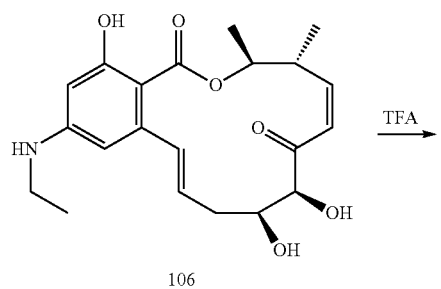

106

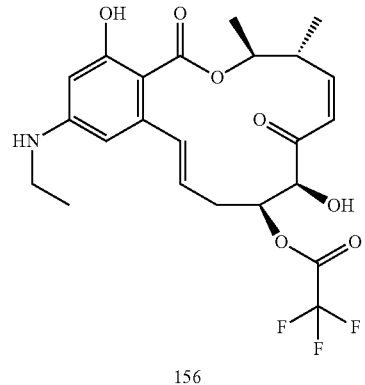

156

Compound 106 (1 wt) was dissolved in TFA (3 vols, 15 eq.) and stirred at room temperature. The progress of the reaction was monitored by TLC. After 48 h stirring, the reaction mixture was diluted with DCM (20 vols), washed with sat. aq. $NaHCO_3$, and brine. The organic layer was concentrated and purified by flash chromatography to give 156 as white solid (48.3% yield) (NMR data below). Compound 106 was also recovered (9.1% recovery rate). $^1$HNMR($C_6D_6$): δ=6.83 (d, 1H), 6.12 (s, 1H), 5.81 (dt, 1H), 5.70 (s, 1H), 5.55 (d, 1H), 5.40 (dd, 1H), 5.12 (s, 1H), 4.61 (m, 1H), 4.19 (s, 1H), 3.86 (d, 1H), 3.26 (q, 1H), 3.15 (br s, 1H), 2.48 (q, 2H), 2.30-2.35 (m, 1H), 2.12 (q, 1H), 0.99 (d, 3H), 0.75 (d, 3H), 0.60 (t, 3H), −2.00 (s, 1H)

Compound 157:

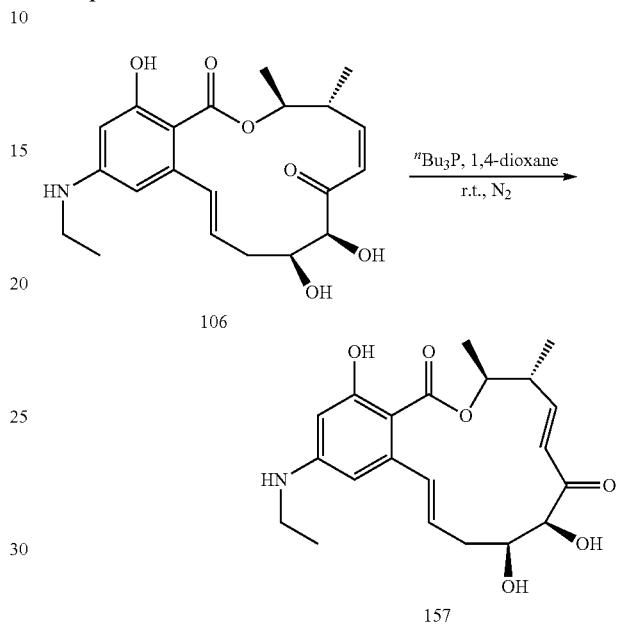

Compound 106 was dissolved in 1,4-dioxane (11 vols) and $^n$Bu$_3$P (1.2 eq.) was slowly added under $N_2$ atmosphere. The reaction mixture was stirred at room temperature, and the progress of the reaction was followed by TLC and HPLC. After 23 h stirring at r.t., the reaction mixture was diluted with TBME (100 vols), washed with water (2×10 vols) and brine (10 vols). The aqueous layers were back extracted with TBME (50 vols). The combined organic layer was dried over $Na_2SO_4$ and concentrated. The residue was purified by flash chromatography to give 157 as white solid (58.5%). MS (ES+): M+Na$^+$=412.1, M+H$^+$=390.1; MS (ES−): M−H$^+$=388.0; $^1$HNMR($C_6D_6$): δ=6.78-6.84 (m, 2H), 6.13 (d, 1H), 5.95 (d, 1H), 5.86 (m, 1H), 5.83 (d, 1H), 4.97-5.02 (m, 1H), 4.47 (br s, 1H), 4.02 (br s, 1H), 3.93 (br s, 1H), 3.26 (t, 1H), 2.64 (br s, 1H), 2.52 (m, 2H), 2.39-2.43 (m, 1H), 2.04-2.11 (m, 1H), 1.68 (m, 1H), 0.88 (d, 3H), 0.64 (t, 3H), 0.58 (d, 3H), −2.38 (s, 1H).

Compound 158:

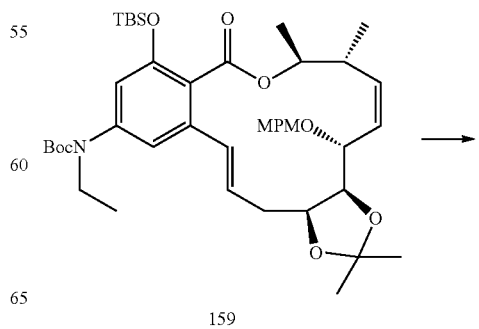

159

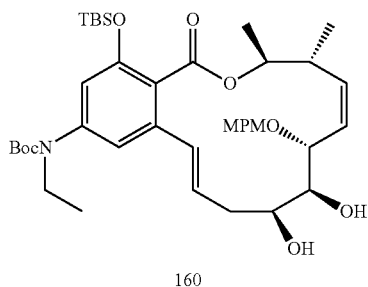

160

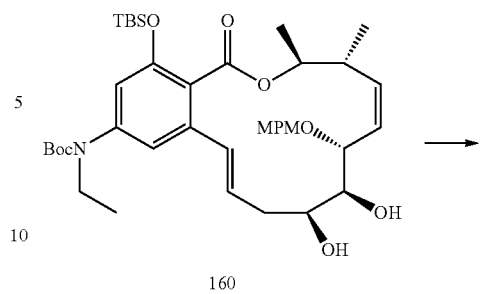

160

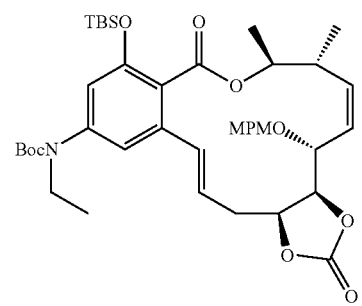

161

The starting material (159) (100.0 mg, 0.13 mmol) was dissolved in 1.0 ml of methanol at 0° C. p-Toluenesulfonic acid (49.4 mg, 0.28 mmol) was added. The reaction mixture was stirred at 0° C. for 25 min, then at room temperature over night. It was quenched with sat. aqueous sodium bicarbonate solution and extracted with ethyl acetate. After purification on silica gel column, 160 was obtained in 84% yield. The chiral starting material (159) can be obtained by separation of a racemic mixture of 094 (see preparation of 106) and carrying through the steps to achieve 103.

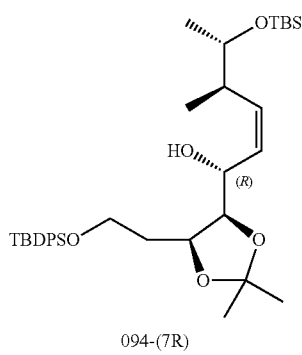

094-(7R)

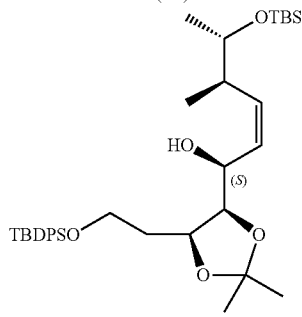

094-(7S)

The two stereoisomers of 094 (at position 7) were separated by chromatography on silica gel using a 12:1 mixture of hexane/ethyl acetate as eluent. Identification of the stereochemistry was made by NMR spectroscopy. The less polar isomer was found to have the "R" stereochemistry at position 7 while the more polar has the "S" stereochemistry. The "R" isomer, 094-(7R), was used to produce 159 with the same synthetic route that was used to produce 103 from 094 (see example compound 106 for reference).

Compound 160 (46.0 mg, 0.063 mmol) was dissolved in 2.0 ml of dichloromethane at 0° C. Pyridine (51.0 µl, 0.63 mmol) and phosgene (167.0 µl, 0.32 mmol) were added, respectively. The reaction mixture was stirred at 0° C. for 15 min, it was quenched with sat. sodium bicarbonate solution and extracted with methyl t-butyl ether. After purification on silica gel prep plate, 161 was obtained in quantitative yield.

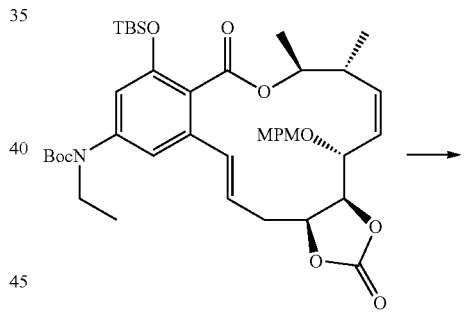

161

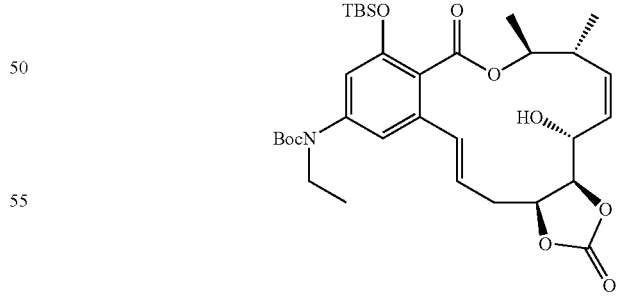

162

Compound 161 (47.4 mg, 0.063 mmol) was dissolved in the mixture of 2.0 ml dichloromethane and 0.5 ml water. 2,3-Dichloro-5,6-dicyano-1,4-benzoquinone (31.5 mg, 0.14 mmol) was added. After stirring at room temperature for 2 h, the reaction mixture was quenched with 10% sodium thiosulfate in sat. sodium bicarbonate solution and extracted with methyl t-butyl ether. After purification on silica gel prep plate, 162 was obtained in 69% yield.

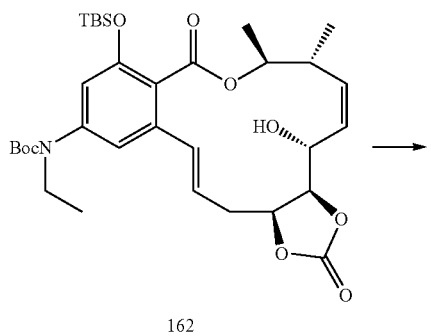

162

Compound 162 (27.6 mg, 0.044 mmol) was dissolved in dichloromethane. Pyridine (8.9 µl, 0.11 mmol) and Dess-Martin reagent (37.0 mg, 0.088 mmol) were added, respectively. The reaction mixture was stirred at room temperature for 1.5 h. It was quenched with 10% sodium thiosulfate in sat. sodium bicarbonate aqueous solution, and extracted with methyl t-butyl ether. After purification on silica gel column, 163 was obtained in 100% yield.

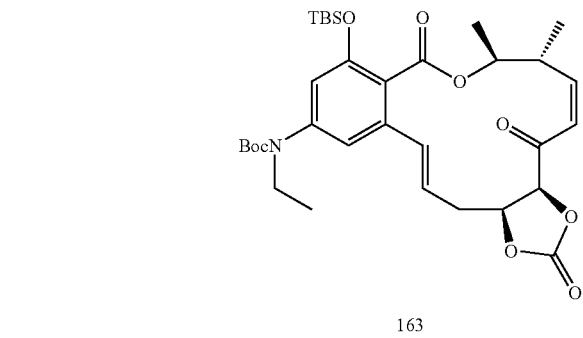

163

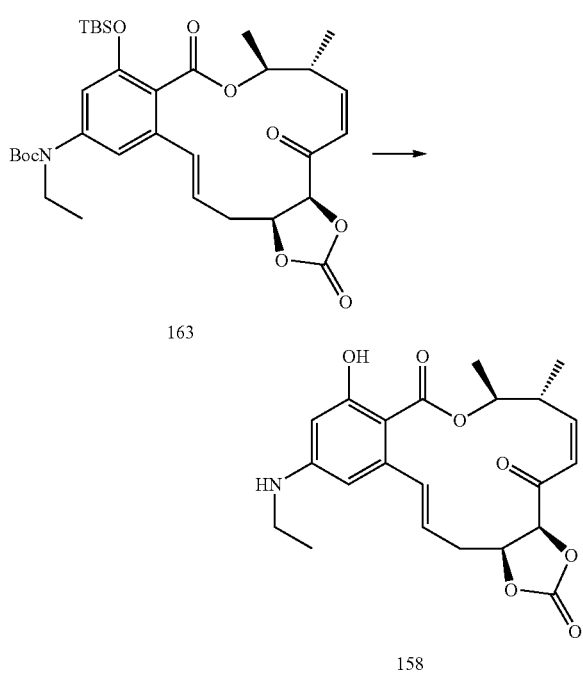

163

158

Compound 163 (27.7 mg, 0.044 mmol) was dissolved in 1.0 ml dichloromethane. Triflic acid (11.6 µl, 0.13 mmol) and water (4.8p1, 0.26 mmol) were added at 0° C. After stirring at room temperature for 1 h, the reaction mixture was quenched with sat. sodium bicarbonate solution and extracted with dichloromethane. After purification on silica gel column, 158 was obtained in 89% yield. $^1$H NMR (CDCl$_3$) δ12.10 (s, 1H), 7.08 (dd, J=15.2, 2.4 Hz, 1H), 6.11 (m, 2H), 6.03 (dd, J=13.2, 2.4 Hz, 2H), 5.53 (m, 1H), 5.14 (d, J=8.4 Hz, 1H), 5.04 (m, 1H), 4.94 (m, 1H), 4.11 (s, 1H), 3.92 (m, 1H), 3.19 (dd, J=21.6, 7.2 Hz, 2H), 2.86 (m, 1H), 2.75 (m, 1H), 1.45 (d, J=6.0 Hz, 3H), 1.26 (t, J=7.2, 3H), 1.14 (d, J=6.8 Hz, 3H).

Examples 2-12

Biological Assays

A set of thirty compounds of formula (I) or (II) was randomly selected, and each compound was tested for its growth inhibitory activity in MDA-MB-435 and HT-29 cancer cell lines. Several compounds were found to have remarkable cancer cell growth inhibitory activity (e.g., nM IC$_{50}$ values). Two compounds (herein referred to as Compounds 091 and 106) were selected for further investigation to further evaluate and characterize biological properties of the compounds of this class (i.e., F152 analogs). It is to be understood for the biological assays, e.g., the cell based assays, that results given may be exemplary of more than one set of data. In certain cases, e.g., in certain in vitro assays, a mean and standard deviation is representative of the acquired data. In other cases, e.g., in certain in vivo assays, a single representative data set is chosen from several substantially similar data sets (e.g., data sets taken from the same assay using various dosages, etc.). The representative data set is often chosen based upon the assay conditions most similar to assay conditions used in clinical studies for human dosages. The skilled artisan would understand that different assay conditions, e.g., different dosages or dosing schedules, may give different results.

Example 2

A biochemical MEK1 assay was carried out to investigate whether compounds of formula (I) or (II), e.g., compounds 029, 091, 106 and 114 are MEK1 inhibitors. Biochemical MEK1 inhibition of the compounds was assessed using an ELISA assay. All assays were performed in a 96 well format. A plate coated with ERK2, a substrate protein for MEK1 was used for biochemical MEK1 assay. In a final volume of 40 µL, MEK1 (25 ng) was incubated with 50 mmol/L HEPES, 20 mmol/L MgCl$_2$, 4 mmol/L MnCl$_2$, and 0.5 mmol/L Na$_3$VO$_4$ in the absence or presence of the test compounds. The reaction was initiated by the addition of 1 µmol/L ATP. After incubation for 40 minutes at 30° C., the reaction mixture was discarded and the plate was then washed 4 times with 0.05% Tween20/PBS. Each well was incubated with 100 µL of 1:4000 diluted phospho-ERK1/2 monoclonal antibody (Cell Signaling, MA) for 1.5 hours at room temperature. The antibody was then discarded and the plate was washed 6 times with 0.05% Tween20/PBS. Finally, 100 µL of 1:2000 diluted of HRP conjugated anti-mouse IgG antibody (Cell Signaling, MA) was added. After incubation for 90 minutes, this antibody was discarded and the plate was washed 8 times with 0.05% Tween20/PBS. Phosphorylated ERK2 was then visualized by peroxidase reaction, and read at 450 nm. FIG. 2A is a table depicting results from MEK1 assays.

The experiments confirm that compounds 091 and 106 are potent MEK1 inhibitors with low nM activity (See FIG. 2A).

Compound 091 showed more potent MEK1 inhibitory activity at a low concentration of ATP, suggesting modes of binding to MEK1 are ATP competitive.

Example 3

A study was carried out to investigate the specificity of compounds to various cancer relevant kinases in vitro. Compounds 091 and 106 were tested at the concentrations of 0.1 µM and 1 µM against a panel of 95 cancer relevant kinases including: Abl(h), Abl (T315I)(h), ALK(h), AMPK(r), Arg (m), Aurora-A(h), Axl(h), Blk(m), Bmx(h), BTK(h), CaMKII (r), CaMKIV(h), CDK1/cyclinB(h), CDK2/cyclinA(h), CDK2/cyclinE(h), CDK3/cyclinE(h), CDK5/p35(h), CDK6/cyclinD3(h), CDK7/cyclinH/MAT1(h), CHK1(h), CHK2(h), CK1δ (h), CK2(h), c-RAF(h), CSK(h), cSRC(h), EGFR(h), EphB2(h), EphB4(h), Fes(h), FGFR3(h), Flt3(h), Fms(h), Fyn(h), GSK3α(h), GSK3β(h), IGF-1R(h), IKKα(h), IKKβ (h), IR(h), JNK1α1(h), JNK2α2(h), JNK3 (h), Lck(h), Lyn (h), MAPK1(h), MAPK2(h), MAPKAP-K2(h), MEK1(h), Met(h), MKK4(m), MKK6(h), MKK7β(h), MSK1(h), MST2 (h), NEK2(h), p70S6K(h), PAK2(h), PAR-1Bα(h), PDGFRα (h), PDGFRβ(h), PDK1(h), PKA(h), PKBα(h), PKBβ(h), PKBγ(h), PKCα(h), PKCβII(h), PKCγ(h), PKCδ(h), PKCε (h), PKCη(h), PKCι(h), PKCµ(h), PKCθ(h), PKCζ(h), PKD2(h), PRAK(h), PRK2(h), ROCK-II(r), ROCK-II(h), Ros(h), Rsk1(h), Rsk2(h), Rsk3(h), SAPK2a(h), SAPK2b (h), SAPK3(h), SAPK4(h), SGK(h), Syk(h), Tie2(h), TrkB (h), Yes(h) & ZAP-70(h) (FIG. 2B).

In a final reaction volume of 25 µL, each human enzyme was incubated with appropriate buffer. The reaction was initiated by the addition of the MgATP mix with [$\gamma^{33}$P-ATP]. After incubation for 40 minutes at room temperature, the reaction was stopped by the addition of 5 µL of a phosphoric acid solution. All assays were performed at an ATP concentration of 10 µM.

10 µL of the reaction was spotted onto a P30 filtermat and washed three times for 5 minutes in a phosphoric acid solution. $^{33}$P transferred to a substrate peptide was then determined by scintillation counting. The results were expressed as a percentage of that in control incubations. The kinases (1) with >50% inhibition at the 0.1 µM concentration of compound, and (2) with concentration-response of inhibitions between 0.1 µM and 1 µM were considered as target kinases of the compounds.

Besides strong MEK1 inhibition, the compounds also inhibited members of the Src tyrosine kinase family (Lyn, Fyn, Lck, Yes, c-Src), FLT-3 and TrkB kinase activities at 0.1 µM concentration. Moreover, it appears that the compounds are highly selective for tyrosine kinases, as indicated by their lack of inhibition of a multitude of serine/threonine kinases.

Furthermore, inhibitory activities of the compounds were confirmed against six of these kinases with a full range of concentrations. Three cytoplasmic Src family kinases were studied: c-Src, Fyn and Lyn. We also studied cytoplasmic Abl kinase and two receptor tyrosine kinases: Flt3, and TrkB. A standard ATP concentration of 10 µM was used in all reactions. All experiments were conducted with duplicate measurements. As seen in FIG. 2B, six kinases showed IC$_{50}$ below 214 nM for Compound 091. TrkB and members of the Src family were the most sensitive enzymes to Compound 091 inhibition.

Example 4

In Vitro Anticancer Activity of Exemplary Compounds

Compounds 091 and 106, were extensively tested in solid cancer cell lines (shown in FIG. 3 for 18 cell lines for compound 091 and 20 cell lines for compound 106). All cell lines were introduced into 96-well plates and grown in the absence or continuous presence of 0.3-10000 nM of either compound 091 or compound 106 for 96 hours. Cell growth was assessed using a CellTiter-Glo® Luminescent Cell Viability Assay (Promega) or a methylene blue assay. IC$_{50}$ values were determined as the concentration of a substance which inhibits cell growth by 50% compared to untreated cell populations.

Cell lines which carried a B-RAF V600E mutation were very sensitive to Compounds 091 and 106 in the low-nM or sub-µM concentration range, as shown in FIG. 3.

Example 5

Figure 4:
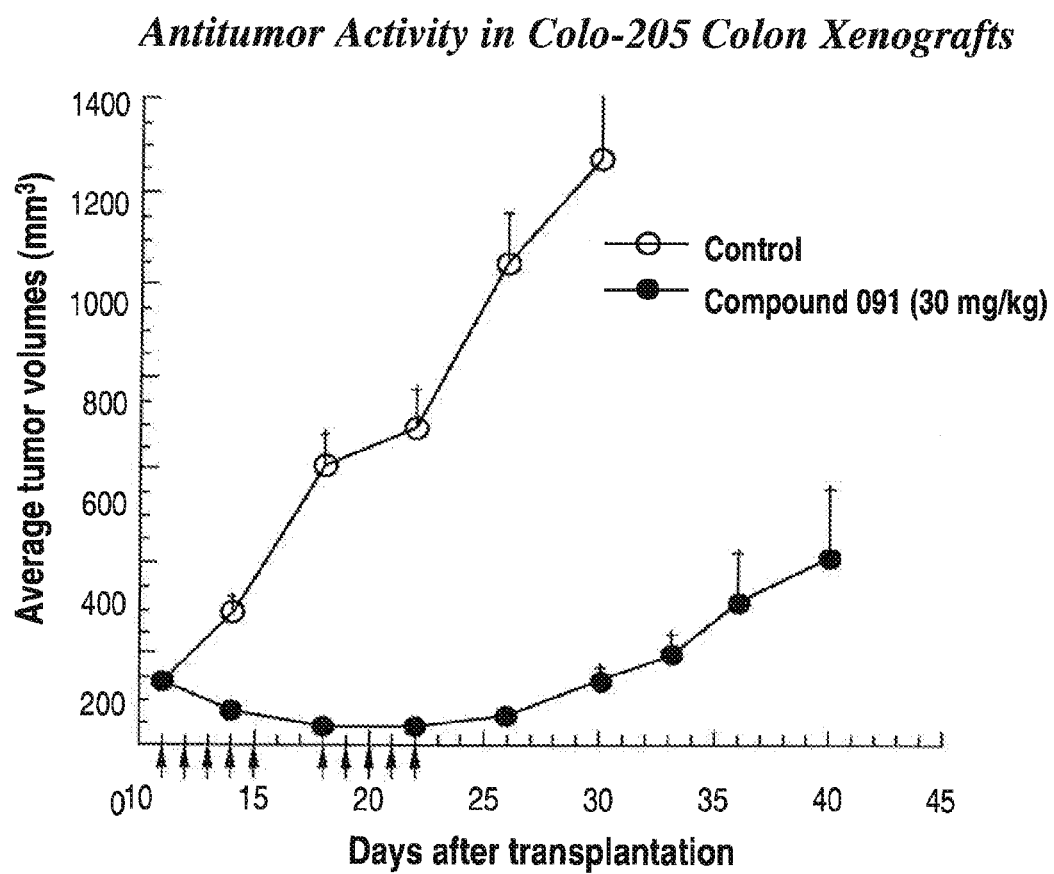
FIG. 4 includes graphs depicting results from in vivo Anti-tumor Activity of exemplary compounds of formula (I) or (II) in Colo-205 Human Colon Cancer Xenografts.

In Vivo Antitumor Activity in Colo205 Human Colon Cancer Xenografts (FIG. 4)

A study was carried out to investigate anticancer activity of compounds 091 and 106 in human Colo205 BRAF mutated colon cancer xenografts. The compounds were evaluated against subcutaneous-implanted Colo205 human colon cancer xenografts in female athymic mice.

The human colon cancer cell line, Colo205 which has B-RAF (V600E) mutation was transplanted subcutaneously into female nude mice. The experiment consisted of 6 mice per group on the first day of treatment. The compound was administered intravenously for two weekly rounds of five daily injections (q1d×5) with a two-day rest period between the rounds. Compound 091 was administered in a vehicle volume of 0.1 mL/10 g of body weight.

The general health of the mice was monitored daily. Tumor dimensions and body weights were recorded twice a week starting on the first day of treatment. Tumor weights were calculated using the equation (l×w$^2$)/2, where l and w refer to the larger and smaller dimensions collected at each measurement. When the mean tumor volume reached 140 mm$^3$, vehicle (cremophor:ethanol:5% glucose; 1:1:8) or the test compound (30 mg/kg) was administered to mice (6/group).

As can be seen from FIG. 4, compound 091 generated an approximate 70% tumor regression in COLO205 BRAF mutated colon cancer xenografts. In a similar study with a different dosing schedule, compound 106 caused 70% tumor regression from the first day of treatment in COLO205 BRAF mutated colon cancer xenografts.

Example 6

Figure 5:
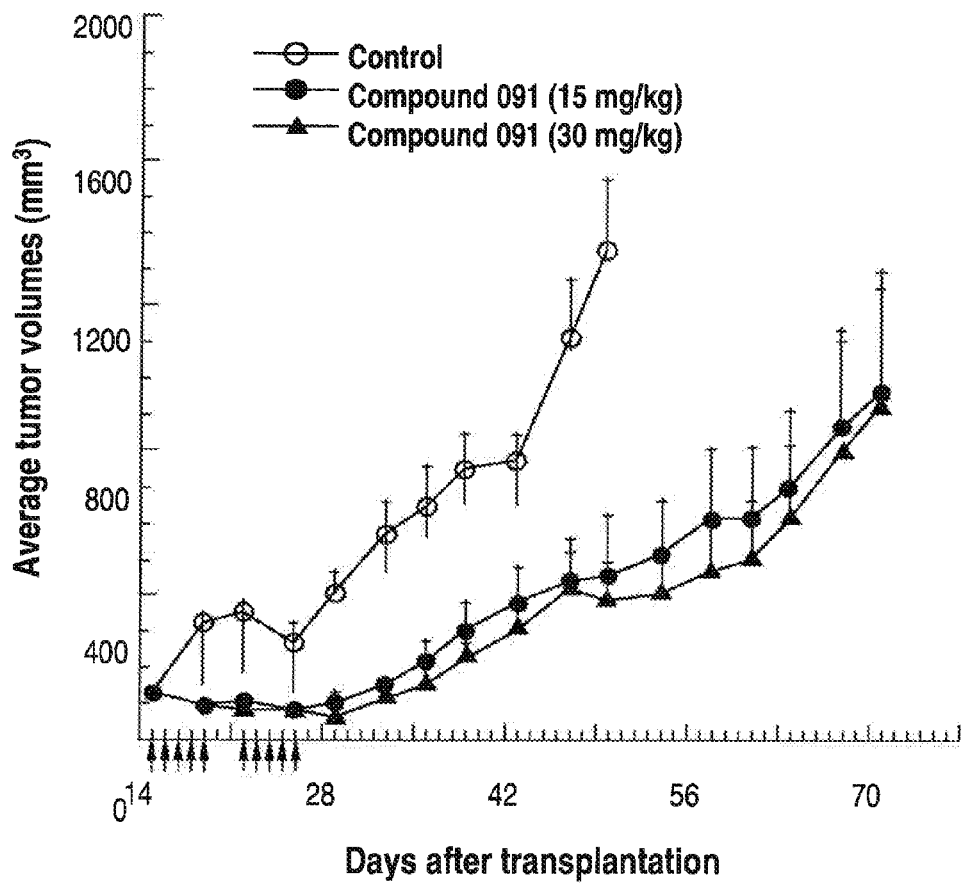
FIG. 5 includes graphs depicting results from in vivo Anti-tumor Activity of exemplary compounds of formula (I) or (II) in BxPC-3 Human Pancreatic Cancer Xenografts.

In Vivo Antitumor Activity in BxPC-3 Human Pancreatic Cancer Xenografts (FIG. 5)

A study was carried out to investigate anticancer activity of compound 091 in human BxPC-3 pancreatic cancer xenografts. The compound was evaluated against subcutaneous-implanted BxPC-3 human pancreatic cancer xenografts in female athymic mice.

The human pancreatic cancer cell line, BxPC-3-T1 (no mutations on B-RAF and Ras genes) was transplanted subcutaneously into female nude mice. The experiment consisted of 8 mice per group on the first day of treatment. The compound was administered intravenously for two weekly rounds of five daily injections (q1d×5) with a two-day rest period between the rounds. The compound was administered in a vehicle volume of 0.1 mL/10 g of body weight.

The general health of the mice was monitored daily. Tumor dimensions and body weights were recorded twice a week starting on the first day of treatment. Tumor weights were calculated using the equation (l×w$^2$)/2, where l and w refer to the larger and smaller dimensions collected at each measurement. When the mean tumor volume reached 130 mm$^3$, vehicle (cremophor:ethanol:5% glucose; 1:1:8) or the test compound (15, 30 mg/kg) was administered to mice (8/group).

As can be seen in FIG. 5, 30 mg/kg of compound 091 generated 50% tumor regression.

Example 7

Figure 6:
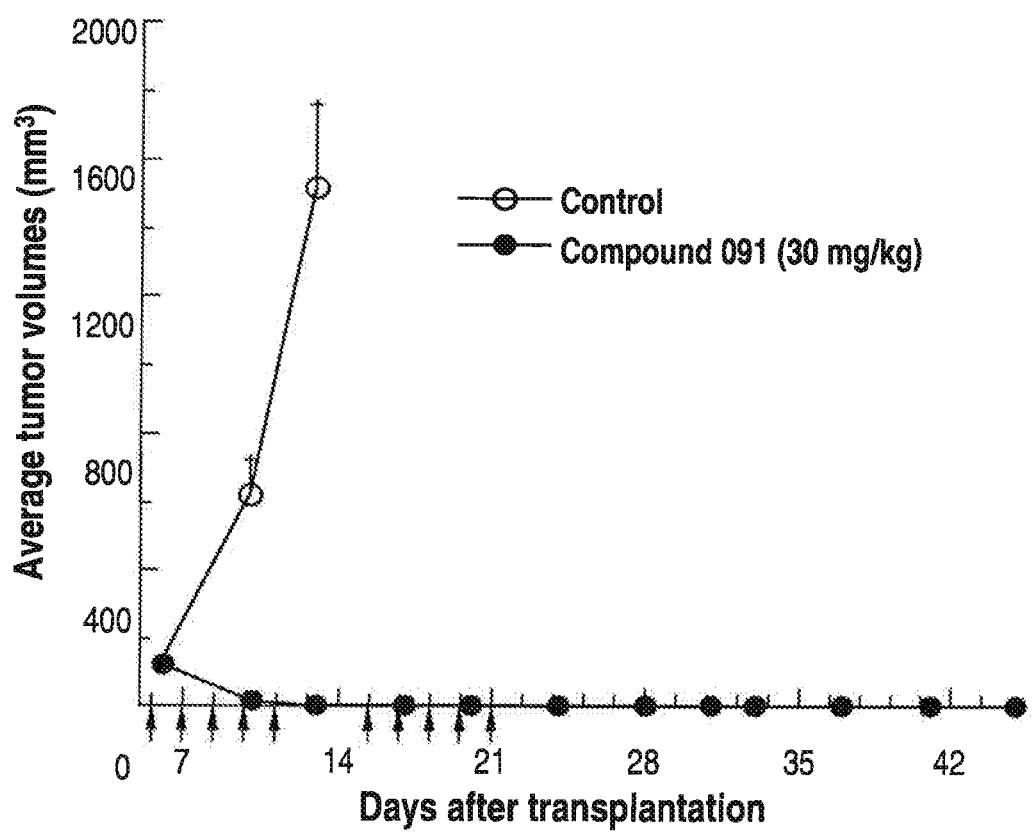
FIG. 6 includes graphs depicting results from in vivo Anti-tumor Activity of exemplary compounds of formula (I) or (II) in LOX Human Melanoma Xenografts.

In Vivo Antitumor Activity in LOX Human Melanoma Xenografts (FIG. 6)

A study was carried out to investigate anticancer activity of compounds 091 and 106 in human LOX BRAF mutated melanoma xenografts. The compounds were evaluated against subcutaneous-implanted LOX human melanoma xenografts in female athymic mice.

The human melanoma cell line, LOX which has B-RAF (V600E) mutation was transplanted subcutaneously into female nude mice. The experiment consisted of 8 mice per group on the first day of treatment. Compounds were independently administered intravenously for two weekly rounds of five daily injections (q1d×5) with a two-day rest period between the rounds. Compounds were administered in a vehicle volume of 0.1 mL/10 g of body weight.

The general health of the mice was monitored daily. Tumor dimensions and body weights were recorded twice a week starting on the first day of treatment. Tumor weights were calculated using the equation (l×w$^2$)/2, where l and w refer to the larger and smaller dimensions collected at each measurement. When the mean tumor volume reached 128 mm$^3$, vehicle (cremophor:ethanol:5% glucose; 1:1:8) or one of the test compounds (10, 20, 30, or 40 mg/kg) was administered to mice (8/group).

As can be seen in FIG. 6, 10 mg/kg Compound 091 generated 100% tumor regression for the first three weeks. Compound 091 also generated 100% tumor regression at doses of 20, 30, 40 mg/kg in all mice. Mice given 091 were tumor free at the end of the study. Moreover, administration of compound 106 at three dosages, 10, 20, and 40 mg/kg/dose, caused statistically significant anticancer activity. 10 mg/kg of 106 caused 5 out of 8 mice to be tumor free, and 20 mg/kg or 40 mg/kg both caused 8 out of 8 mice to be tumor free at the end of study.

Example 8

Inhibition of B-Cell Driven Hematological Malignant Cancer Cell Growth/Non-Hodgkin's Lymphoma (FIG. 7)

A study was carried out to investigate anticancer activity of compounds 091 and 106 in a panel of human hematologic cancer cell lines in vitro. Antiproliferative effects of compounds 091 and 106 were evaluated in 7 human cancer cell lines representing several different cancer types of hematologic malignancy. Cultured human cancer cells were placed into 96-well plates and grown in the absence or continuous presence of 0.3-1000 nM test compounds for 96 h. Cell growth was assessed using the MTT assay. IC$_{50}$ values were determined as the concentration of a substance which inhibits cell growth by 50% compared to untreated cell populations.

As indicated in FIG. 7, two cell lines derived from B-cell non-Hodgkin's lymphoma, were sensitive to Compound 091 and cell lines that were derived from leukemia, or B-cells such non-Hodgkin's lymphoma were sensitive to compound 106.

Example 9

Figure 8:
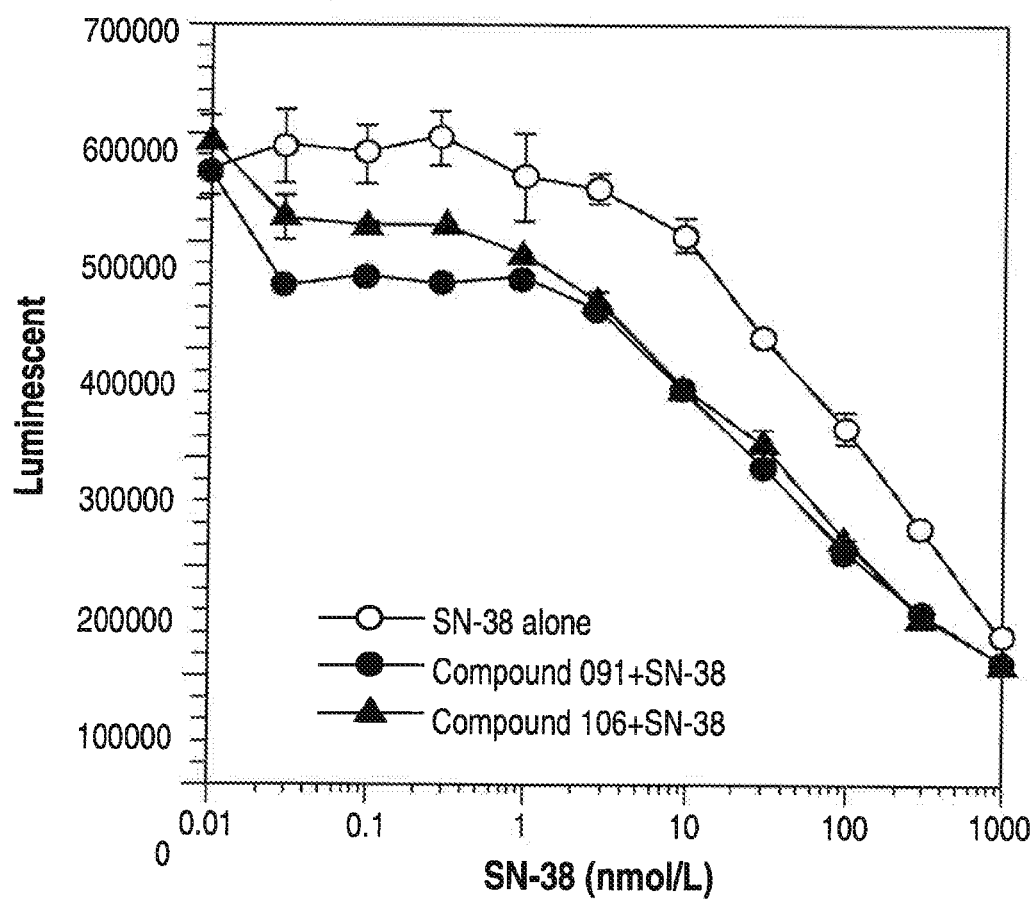
FIG. 8 describes effects of a compound on the anticancer activity of CPT-11 (SN-38) in PANC-1 Pancreatic Cancer Cells.

Enhancement of Anticancer Activity of CPT-11 (SN-38) in PANC-1 Pancreatic Cancer Cells (FIG. 8)

SN-38, active metabolite of CPT-11 is well known to increase NF-κB activity, which leads to chemo-resistance. To determine whether compounds 091 or 106 in combination with SN-38 would enhance the anticancer activity of chemotherapy due to MEKK1 inhibition, PANC-1 human pancreatic cancer cells were examined.

It is noted that 1 μM of compound 091 or compound 106 alone did not affect PANC-1 cancer cell growth in separate experiments (data not shown). Antiproliferative effects of SN-38 were evaluated in PANC-1 pancreatic cancer cells in combination with compound 091 or 106. Cultured human cancer cells were placed into 96-well plates and grown in the absence or continuous presence of 0.03-1000 nM SN-38 for 96 h with or without 1 μM of test compound. Cell growth was assessed using CellTiter-Glo® Luminescent Cell Viability Assay (Promega). IC$_{50}$ values were determined as the concentration of a substance which inhibits cell growth by 50% compared to untreated cell populations.

IC$_{50}$ values for cell growth inhibition by SN-38 alone was 82.5 nM. 1 μM of both compound 091 and compound 106 enhanced cytotoxicity of SN-38 in combination setting (e.g., with IC$_{50}$ value of 16.2 nM). Both compounds 091 and 106 enhance the anticancer activity of CPT-11 (SN-38) in this cell line in two independent experiments. These results suggest that compounds 091 and 106 block chemotherapy-induced NF-κB activation, leading to enhancement of chemo-sensitivity, although these experiments are still ongoing. Compounds 091 and 106 may enhance anticancer activity in combination setting.

Example 10

Compound 091 Penetrates Blood Brain Barrier (BBB) (FIG. 9)

Penetration of Compound 091 into the brain tissue was notably high, as measured by the brain/plasma AUC$_{0-t}$ ratio of 3.170. These data suggest that Compound 091 may be useful in treating CNS tumors including glioma via the inhibition of a combination of kinases as shown herein, e.g., the inhibition of MEK and TrkB and/or other kinases.

Example 11

Figure 10:
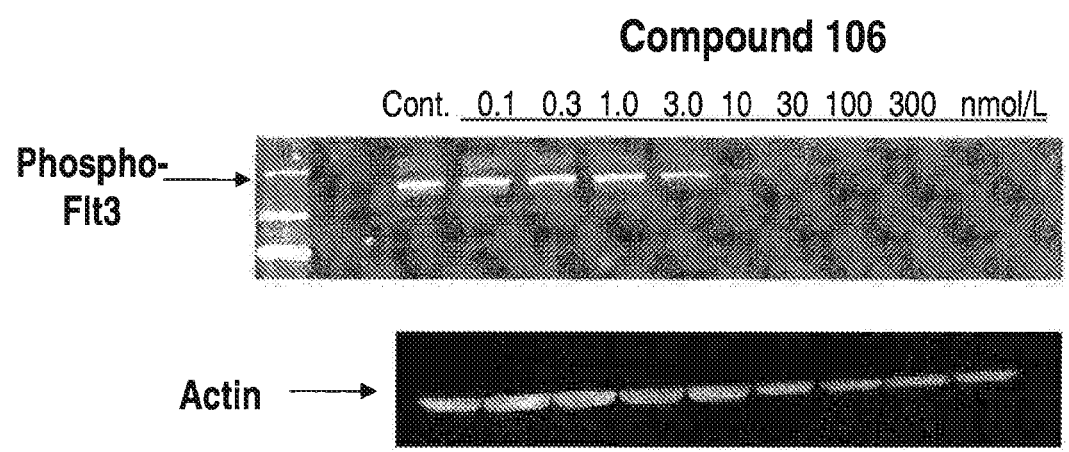
FIG. 10 describes effects of a compound on the phosphorylation of Flt-3 receptor in MV-4-11 AML cells.

Inhibition of Phosphorylation of Flt-3 Receptor Tyrosine Kinase (FLT3) (FIG. 10)

A study was carried out to investigate the ability of compound 106 to inhibit phosphorylation of Flt-3 receptor in a FLT3-mutated (AML) cell line in vitro. MV-4-11 human acute myeloid leukemia (AML) cells (Catalog #CRL-9591, ATCC, Rockville, Md.), which carry an activation mutation of Flt-3, were plated into a 25 mm$^3$ flasks and incubated for 1 day. Then, compound 106 at concentrations of 0.1 nmol/L-300 nmol/L (or culture medium) were added to each flask and cultured for 24 h. The control dish received cultured medium alone. Cells lysates were prepared using ice cold lysis buffer.

In order to detect phospho-Flt-3 protein, MV-4-11 cell lysate proteins were subjected to SDS-PAGE under reducing conditions and immunoblotted with an antibody against phospho-Flt-3 antibody (Catalog #3464, Cell Signaling Technology, Danvers, Mass.). Western blots were probed with secondary IRDye antibodies (LI-COR, Inc., Lincoln, Nebr.). Blotted proteins were visualized using the Odyssey infrared imaging system (LI-COR, Inc., Lincoln, Nebr.).

Anti-actin antibody (Catalog #sc-8432, Santa Cruz Biotechnologies, Inc., Santa Cruz, Calif.) was used as a loading control.

MV-4-11 cells showed constitutive phosphorylation of Flt-3 receptor in the absence of compound 106. The protein level of phospho-Flt-3 was decreased by compound 106 in the MV-4-11 cell line in a concentration dependent manner. 10 nmol/L compound 106 completely inhibited constitutive phosphorylation of Flt-3 receptor, showing that compound 106 is a potent inhibitor of Flt-3 receptor tyrosine kinase in whole cells.

Example 12

Figure 11:
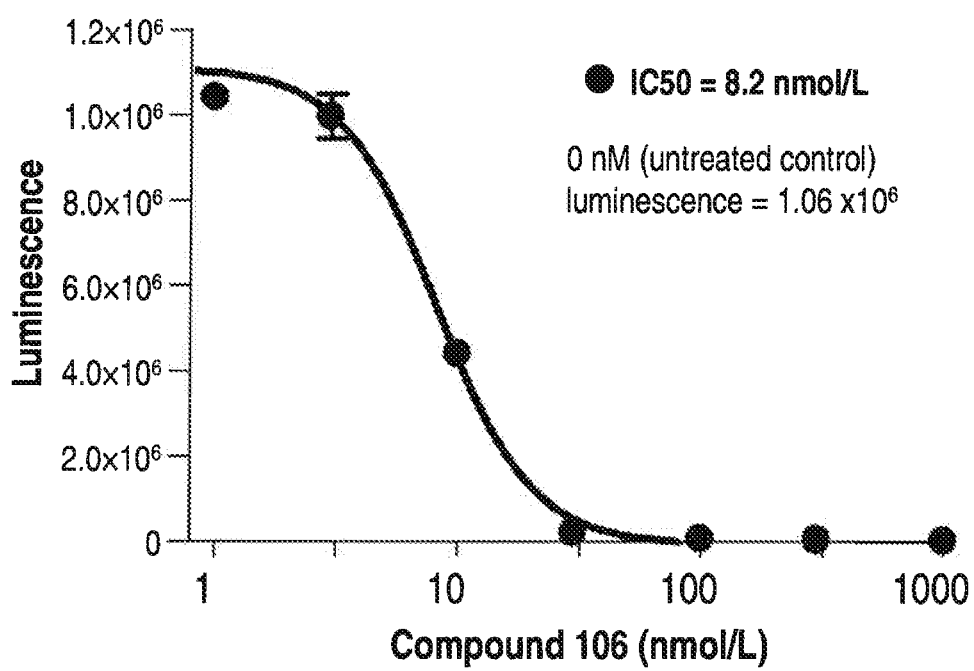
FIG. 11 is a graph which depicts inhibition of MV-4-11 cell proliferation by a compound.

Inhibition of Cell Proliferation of a FLT3-Mutated Cell Line In Vitro (FIG. 11)

A study was carried out to investigate the anticancer activity of compound 106 in a FLT-3 mutated (AML) cell line in vitro. The antiproliferative effects of compound 106 were determined in a cell proliferation assay using MV-4-11 AML cells.

MV-4-11 human acute myeloid leukemia (AML) cells, which carry an activation mutation of Flt-3, were plated into 96-well plates and grown in the absence or continuous presence of 0.03-1,000 nmol/L compound 106 for 96 h. Cell growth was assessed using CellTiter-Glo® Luminescent Cell Viability Assay (Promega, Madison, Wis.). Luminescence was read on the EnVision 2102 Multilabel Counter (Perkin-Elmer/Wallac, Waltham, Mass.). The software, Graphpad Prism (ver. 4, San Diego, Calif.) was used for determination of $IC_{50}$ values. The raw value for the untreated control represents an average from 4 wells.

MV-4-11 cells which carry an activation mutation of Flt-3 receptor tyrosine kinase were sensitive to compound 106 in the low-nmol/L concentration range. Compound 106 showed antiproliferative activity against FLT-3 mutated human cancer cells in vitro, with an $IC_{50}$ value in the low-nmol/L range.

We claim:

1. A method for treating a FLT3 mutated cancer in a subject, wherein the FLT3 mutated cancer carries a D835Y, Y842C, K663Q or V592A mutation, the method comprising:
   a) determining if the subject's cancer carries a D835Y, Y842C, K663Q or V592A mutation; and
   b) if the cancer is determined to carry a D835Y, Y842C, K663Q or V592A mutation, administering to the subject a composition comprising at least one compound of formula (I):

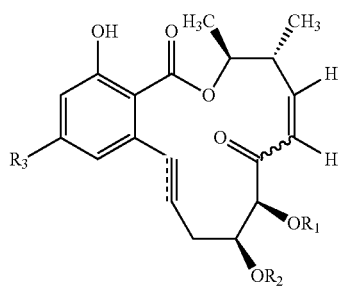

wherein:
$R_1$ is H
$R_2$ is a moiety selected from the group consisting of H and trifluoromethylcarbonyl; or $R_1$ and $R_2$ are taken together with the core structure to form a heterocyclydiyl moiety of formula (a):

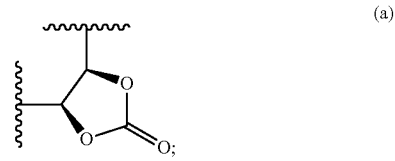 [SMILES: *[C@@H]1OC(=O)O[C@@H]1*]

$R_3$ is a moiety selected from the group consisting of —$OR_a$ and —$NR_bR_c$;
$R_a$ is a $C_{1-4}$ alkyl group optionally substituted with an imidazolyl;
$R_b$ is a moiety selected from the group consisting of a $C_{1-4}$ alkyl group and a $C_{1-4}$ alkoxy group, wherein $R_b$ is substituted with 0, 1 or 2 groups each independently selected from the group consisting of —$OCH_3$, —C(O)OH, —C(O)NR'R", —NH($C_{1-3}$ alkyl), —NH($CH_2CH_2O)_nCH_3$, wherein n is 2-4, piperazinyl, N-methylpiperazinyl, piperidinyl, N-methylpiperidinyl, N-morpholinyl, imidazolyl, pyrrolidinyl, —$OPO_3H_2$ and hydroxyl; wherein the —NH($C_{1-3}$ alkyl) group is substituted with 0, 1 or 2 hydroxyl moieties and wherein R' and R" are each independently selected from —H or —$CH_3$; and
$R_c$ is H, or $R_b$ and $R_c$ are taken together with the nitrogen to which they are attached to form a heterocyclyl moiety selected from the group consisting of formula (b) and formula (c):

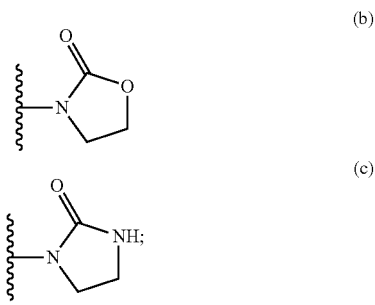

or a pharmaceutically acceptable salt or ester thereof; in an amount effective for treating the FLT3 mutated cancer.

2. The method of claim 1, wherein the FLT3 mutated cancer is a hematologic cancer.

3. The method of claim 2, wherein the hematologic cancer is a leukemia.

4. The method of claim 3, wherein the leukemia is acute myeloid leukemia.

5. The method of claim 1, wherein

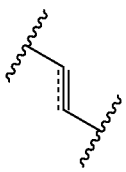

represents a double bond.

6. The method of claim 1, wherein $R_3$ is —$NR_bR_c$, and wherein $R_c$ is H and $R_b$ is an unsubstituted $C_{1-4}$ alkyl.

7. The method of claim 6, wherein $R_b$ is methyl or ethyl.

8. The method of claim 1, wherein the compound is at least one compound selected from the group consisting of:

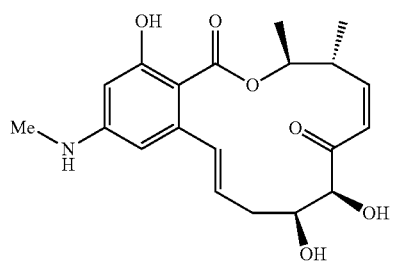
(Compound 091)

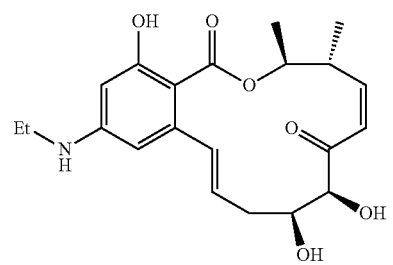
(Compound 106)

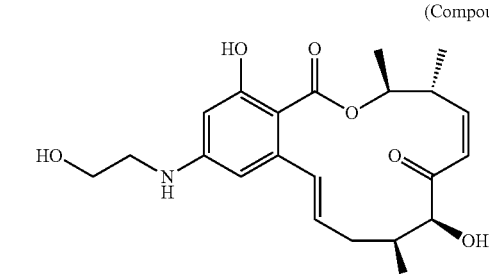
(Compound 029)

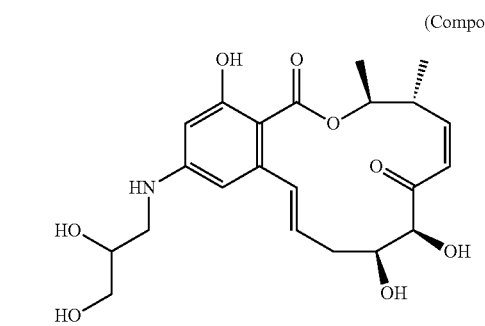
(Compound 114)

and pharmaceutically acceptable salts and esters thereof.

9. The method of claim 8, wherein the compound is at least one compound selected from the group consisting of:

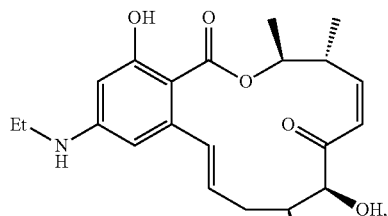

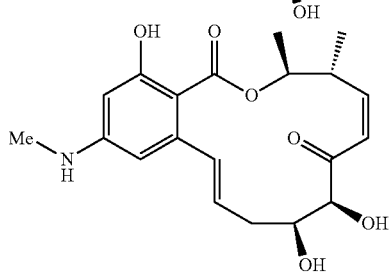

and pharmaceutically acceptable salts thereof.

10. The method of claim 9, wherein the compound is:

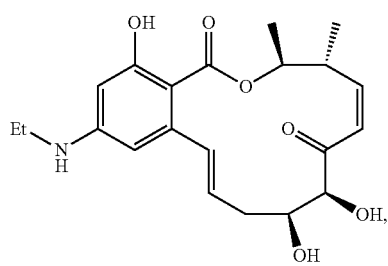 [SMILES: CCNc1cc(O)c2c(c1)/C=C/C[C@H](O)[C@H](O)C(=O)/C=C\[C@@H](C)[C@H](C)OC2=O]

or a pharmaceutically acceptable salt thereof.

11. The method of claim 10, wherein the compound is:

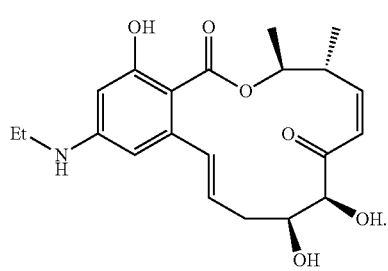 [SMILES: CCNc1cc(O)c2c(c1)/C=C/C[C@H](O)[C@H](O)C(=O)/C=C\[C@@H](C)[C@H](C)OC2=O]

12. The method of claim 1, wherein the method further comprises administration of a second chemotherapeutic drug.

13. The method of claim 1, wherein the composition comprising a compound of formula (I) is administered intravenously.

14. The method of claim 1, wherein the composition comprising a compound of formula (I) is administered at a dosage between about 0.10 mg/kg to about 25 mg/kg of body weight.

* * * * *